US008242151B2

(12) United States Patent
Yanagisawa et al.

(10) Patent No.: US 8,242,151 B2
(45) Date of Patent: Aug. 14, 2012

(54) TRICYCLIC COMPOUNDS

(75) Inventors: Arata Yanagisawa, Shizuoka (JP); Takeshi Kuboyama, Shizuoka (JP); Seiji Aratake, Shizuoka (JP); Kazuki Hemmi, Shizuoka (JP); Kimihisa Ueno, Shizuoka (JP); Michihiko Suzuki, Shizuoka (JP); Masahiro Matsubara, Shizuoka (JP); Kozo Yao, Shizuoka (JP); Akinori Hamaguchi, Shizuoka (JP); Yukihito Tsukumo, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 837 days.

(21) Appl. No.: 12/162,119

(22) PCT Filed: Feb. 7, 2008

(86) PCT No.: PCT/JP2008/052068

§ 371 (c)(1), (2), (4) Date: Jul. 24, 2008

(87) PCT Pub. No.: WO2008/096829

PCT Pub. Date: Aug. 14, 2008

(65) Prior Publication Data

US 2009/0176760 A1 Jul. 9, 2009

(30) Foreign Application Priority Data

Feb. 7, 2007 (JP) ................................ 2007-027534
Nov. 14, 2007 (JP) ................................ 2007-295224

(51) Int. Cl.

| | |
|---|---|
| ***A01N 43/82*** | (2006.01) |
| ***A01N 61/00*** | (2006.01) |
| ***A01N 43/50*** | (2006.01) |
| ***A61K 31/41*** | (2006.01) |
| ***A61K 31/00*** | (2006.01) |
| ***A61K 31/415*** | (2006.01) |

(52) U.S. Cl. .... 514/364; 514/303; 514/396; 514/211.11

(58) Field of Classification Search ........................ None
See application file for complete search history.

(56) References Cited

U.S. PATENT DOCUMENTS

| | | | |
|---|---|---|---|
| 4,687,777 | A | 8/1987 | Meguro et al. |
| 5,002,953 | A | 3/1991 | Hindley |
| 5,194,443 | A | 3/1993 | Hindley |
| 5,232,925 | A | 8/1993 | Hindley |
| 5,260,445 | A | 11/1993 | Hindley |
| 5,378,701 | A | 1/1995 | Ohshima et al. |
| 5,478,840 | A | 12/1995 | Ohshima et al. |
| 5,521,201 | A | 5/1996 | Hindley et al. |
| 5,607,955 | A | 3/1997 | Ohshima et al. |
| 5,646,169 | A | 7/1997 | Hindley et al. |
| 5,756,525 | A | 5/1998 | Hindley et al. |
| 6,288,095 | B1 | 9/2001 | Hindley et al. |
| 6,686,475 | B2 | 2/2004 | Hindley |
| 7,232,828 | B2 | 6/2007 | Pershadsingh |
| 7,411,072 | B2 | 8/2008 | Coghlan et al. |
| 2002/0049240 | A1 | 4/2002 | Hindley et al. |
| 2003/0149054 | A1 | 8/2003 | Hindley |
| 2004/0127443 | A1 | 7/2004 | Pershadsingh |
| 2005/0032854 | A1 | 2/2005 | Kawahara et al. |
| 2006/0025601 | A1 | 2/2006 | Bennani et al. |
| 2006/0063759 | A1 | 3/2006 | Coghlan et al. |
| 2006/0239999 | A1 | 10/2006 | Saki et al. |
| 2006/0252679 | A1 | 11/2006 | Saki et al. |
| 2007/0054949 | A1 | 3/2007 | Pershadsingh |
| 2007/0185070 | A1 | 8/2007 | Pershadsingh |
| 2007/0203213 | A1 | 8/2007 | Pershadsingh |
| 2008/0009536 | A1 | 1/2008 | Pershadsingh |
| 2009/0012171 | A1 | 1/2009 | Polivka |
| 2011/0201640 | A1 | 8/2011 | Yanagisawa et al. |

FOREIGN PATENT DOCUMENTS

| | | | |
|---|---|---|---|
| GB | 1043158 | | 9/1966 |
| JP | 61-267580 | A | 11/1986 |
| JP | 01-131169 | A | 5/1989 |
| JP | 6-228065 | A | 8/1994 |
| JP | 7-061983 | A | 3/1995 |
| JP | 2003-231636 | A | 8/2003 |
| JP | 2006-515566 | A | 6/2006 |

(Continued)

OTHER PUBLICATIONS

Silverman, The Organic Chemistry of Drug Design and Drug Action, 2nd ed., 2004, pp. 25-34.*

(Continued)

*Primary Examiner* — Leslie A. Royds Draper
*Assistant Examiner* — Stephanie Springer
(74) *Attorney, Agent, or Firm* — Leydig, Voit & Mayer, Ltd.

(57) ABSTRACT

The present invention provides a PPAR γ agonist comprising, as an active ingredient, a tricyclic compound represented by the formula (I)

(I)

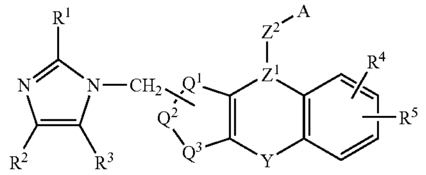

(wherein $R^1$ represents lower alkyl optionally having substituent(s) or the like, $R^2$ and $R^3$ are the same or different and each represents lower alkyl optionally having substituent(s) or the like, $R^4$ and $R^5$ are the same or different and each represents a hydrogen atom or the like, $Q^1$-$Q^2$-$Q^3$ represents CH═CH—CH═CH or the like, Y represents a single bond or the like, $Z^1$-$Z^2$ represents C═$CR^{13}$ (wherein $R^{13}$ represents a hydrogen atom or the like), or the like, and A represents —COOH or the like), or a pharmaceutically acceptable salt thereof and the like.

20 Claims, No Drawings

FOREIGN PATENT DOCUMENTS

| | | | |
|---|---|---|---|
| WO | WO 2004/017994 | A1 | 3/2004 |
| WO | WO 2004/017995 | A1 | 3/2004 |
| WO | WO 2004/052847 | A2 | 6/2004 |
| WO | WO 2005/105736 | A1 | 11/2005 |
| WO | WO 2006/107062 | A2 | 10/2006 |
| WO | WO 2007/081299 | A2 | 7/2007 |
| WO | WO 2010/016549 | A1 | 2/2011 |

OTHER PUBLICATIONS

Patani et al. "Bioisosterism: A Rational Approach in Drug Design", Chem.Rev., 1996, vol. 96, pp. 3147-3176.*

Kawai et al. "Structure-activity relationship study of novel NR2B-selective antagonists with arylamides to avoid reactive metabolites formation", Bioorg.Med.Chem.Lett., 2007, vol. 17, pp. 5537-5542.*

Benson et al., *Hypertension*, 43: 993-1002 (2004).

Kiyama et al., *Journal of Medicinal Chemistry*, 38 (14): 2728-2741 (1995).

Krovat et al., *Journal of Medicinal Chemistry*, 46(5): 716-726 (2003).

Berger et al., *Molecular Endocrinology*, 17(4): 662-676 (2003).

Copland et al., *Oncogene*, 25: 2304-2317 (2006).

Lehmann et al., *The Journal of Biological Chemistry*, 270(22): 12953-12956 (1995).

Shimazaki et al., *European Journal of Cancer*, 44: 1734-1743 (2008).

Willson et al., *J. Med. Chem.*, 39: 665-668 (1996).

Japanese Patent Office, International Search Report for PCT/JP2008/052068 (Mar. 18, 2008).

Japanese Patent Office, International Search Report for PCT/JP2009/063957 (Nov. 17, 2009).

* cited by examiner

TRICYCLIC COMPOUNDS

TECHNICAL FIELD

The present invention relates to a peroxisome proliferator-activated receptor (PPAR) γ agonist comprising a tricyclic compound as an active ingredient. In addition, the present invention relates to a tricyclic compound having a PPARγ agonist activity, which is useful as an agent for treating and/or preventing, for example, type 2 diabetes, impaired glucose tolerance, insulin resistance syndrome, hypertension, hyperlipidemia, metabolic syndrome, visceral obesity, obesity, hypertriglyceridemia, inflammatory dermatic diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis etc.), inflammatory neuropsychiatric diseases (e.g., multiple sclerosis etc.), neurodegenerative neuropsychiatric diseases (e.g., Alzheimer's disease, Parkinson's disease etc.) or the like.

BACKGROUND ART

PPARγ is a member of the nuclear hormone receptor superfamily, and plays an important role in adipocyte differentiation. Hypertrophic adipocytes secrete large amounts of a cytokine such as TNF-α, and free fatty acid which induce insulin resistance. On the other hand, thiazolinedione derivatives such as pioglitazone, rosiglitazone or the like improve insulin resistance by activating PPARγ to decrease hypertrophic adipocytes by apoptosis, and promoting differentiation of preadipocytes into small adipocytes having normal function (J. Biol. Chem., 1995, vol. 270, p. 12953; J. Med. Chem., 1996, vol. 39, p. 665 etc.). Pioglitazone and rosiglitazone, which are PPARγ agonists, have already been clinically used as therapeutic drugs for diabetes (JP-A-61-267580, JP-A-1-131169 etc.).

PPARγ agonists are also useful as agents for treating and/or preventing diseases besides diabetes, such as metabolic syndrome, obesity, impaired glucose tolerance and other insulin resistance syndrome, which are prediabetic conditions, hypertension, atherosclerosis, hyperlipidemia, inflammatory diseases such as psoriasis or the like, inflammatory bowel disease or the like.

On the other hand, angiotensin II receptors increase blood pressure by constricting blood vessels via angiotensin II receptor type 1 on the cellular membrane. Therefore, an angiotensin II receptor antagonist can be an effective agent for treating and/or preventing of cardiovascular diseases such as hypertension or the like (J. Med. Chem., 1996, vol. 39, p. 625). Angiotensin II receptor antagonists such as losartan, candesartan, telmisartan, valsartan, olmesartan or the like have already been used clinically as antihypertensive agents (JP-A-4-364171, JP-A-5-783228 etc.)

It is known that about 60% of hypertensive patients develop complications of impaired glucose tolerance or type 2 diabetes (insulin resistance). Despite the presence of various superior antihypertensive agents, the blood pressure of such patients is poorly managed and positive management of blood glucose is not practiced.

From the foregoing, a drug having a PPARγ agonist activity and an angiotensin II receptor antagonist activity in combination is considered to be useful as an agent for treating and/or preventing diseases related to these two mechanisms, such as type 2 diabetes, impaired glucose tolerance, insulin resistance syndrome, hypertension, hyperlipidemia, metabolic syndrome, visceral obesity, obesity, hypertriglyceridemia, inflammatory dermatic diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis etc.), inflammatory neuropsychiatric diseases (e.g., multiple sclerosis etc.), neurodegenerative neuropsychiatric diseases (e.g., Alzheimer's disease, Parkinson's disease etc.), cardiovascular diseases (e.g., arteriosclerosis, cardiac disease, cerebral apoplexy, renal diseases etc.), or the like; particularly type 2 diabetes, impaired glucose tolerance, insulin resistance syndrome, hypertension, hyperlipidemia, metabolic syndrome, visceral obesity, obesity, hypertriglyceridemia, or the like. While an angiotensin II receptor antagonist exhibiting an insulin sensitizing activity has already been reported, the action mechanism thereof has not been clarified (see patent references 1 and 2). In addition, a combination therapy of a thiazolidinedione derivative having a PPARγ agonist activity and an angiotensin II receptor antagonist is known to be effective for the treatment of arteriosclerosis occurring in association with hypertension, obesity associated with diabetes or the like (see patent references 3 and 4). Furthermore, angiotensin II receptor antagonists showing a PPARγ agonist activity have been reported (non-patent reference 1, patent reference 5), and a compound having a PPARγ agonist activity and an angiotensin II receptor antagonist activity in combination is expected to be usable for treating and/or preventing type 2 diabetes, metabolic syndrome and other diseases reactive with a PPARγ agonist, without increasing the risk of fluid accumulation, peripheral edema, lung edema and congestive heart failure, which are induced by PPARγ agonists (patent reference 5).

Meanwhile, a tricyclic compound represented by the following formula (A) and a derivative thereof are known to have an excellent antihypertensive action based on an angiotensin II receptor antagonistic action (see patent references 6 and 9).

(A)

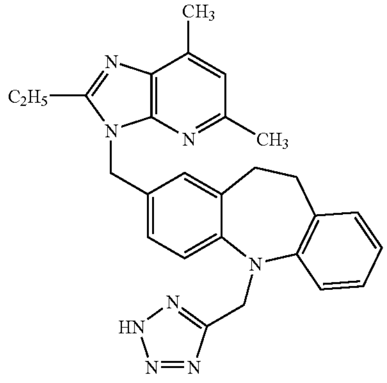

In addition, a compound represented by the following formula (B) and a derivative thereof are known as substances suppressing signal transduction of GPR4 (see patent references 7 and 8).

(B)

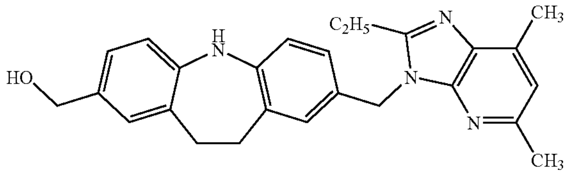

Patent reference 1: WO 2003/047573
Patent reference 2: WO 2006/107062
Patent reference 3: JP-A-9-323940
Patent reference 4: JP-A-2004-217648
Patent reference 5: WO 2004/014308
Patent reference 6: JP-B-2526005
Patent reference 7: WO 2004/017994
Patent reference 8: WO 2004/017995
Patent reference 9: JP-A-7-61983
Non-patent reference 1: “Hypertension”, 2004, vol. 43, p. 993

DISCLOSURE OF THE INVENTION

Problems to be Solved by the Invention

An object of the present invention is to provide a PPARγ agonist comprising a tricyclic compound as an active ingredient. The PPARγ agonist of the present invention preferably further has an angiotensin II receptor antagonistic action, and provides an agent for treating and/or preventing, for example, type 2 diabetes, impaired glucose tolerance, insulin resistance syndrome, hypertension, hyperlipidemia, metabolic syndrome, visceral obesity, obesity, hypertriglyceridemia, inflammatory dermatic diseases (e.g., psoriasis, atopic dermatitis, seborrheic dermatitis, solar dermatitis etc.), inflammatory diseases (e.g., rheumatoid arthritis, ulcerative colitis, Crohn’s disease, endometritis etc.), proliferative diseases (e.g., atherosclerosis, angiostenosis, restenosis etc.), inflammatory neuropsychiatric diseases (e.g., multiple sclerosis etc.), neurodegenerative neuropsychiatric diseases (e.g., Alzheimer’s disease, Parkinson’s disease etc.), cardiovascular diseases (e.g., arteriosclerosis, cardiac disease, cerebral apoplexy, renal diseases, etc.) or the like.

Another object is to provide a novel tricyclic compound having a PPARγ agonist activity or a pharmaceutically acceptable salt thereof.

Means for Solving the Problems

The present invention relates to the following (1) to (47).

(1) An agent for activating PPARγ comprising, as an active ingredient, a tricyclic compound represented by the formula (I)

(I)

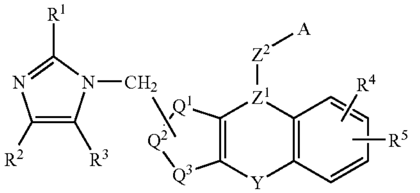

<wherein $R^1$ represents lower alkyl optionally having substituent(s), cycloalkyl optionally having substituent(s), lower alkoxy optionally having substituent(s) or lower alkylsulfanyl optionally having substituent(s), $R^2$ and $R^3$ are the same or different and each represents a hydrogen atom, lower alkyl optionally having substituent(s), lower alkenyl optionally having substituent(s), lower alkanoyl optionally having substituent(s), lower alkoxycarbonyl optionally having substituent(s), lower alkylcarbamoyl optionally having substituent(s), di-lower alkylcarbamoyl optionally having substituent(s) or aliphatic heterocyclecarbonyl optionally having substituent(s), or a group

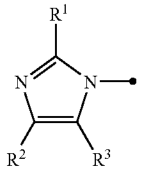

in the formula (I) is selected from the group consisting of the following formulas (a1) to (a20)

(a1)

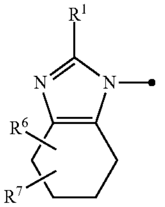

(a2)

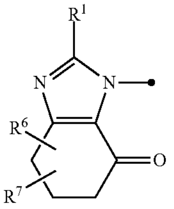

(a3)

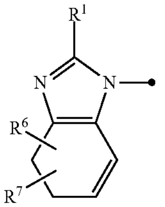

(a4)

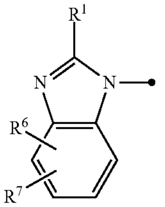

-continued
(a5)
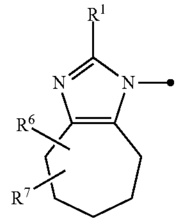
(a6)
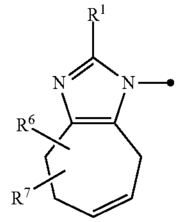
(a7)
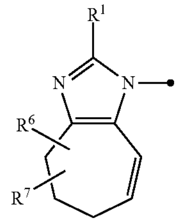
(a8)
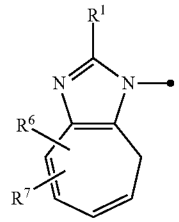
(a9)
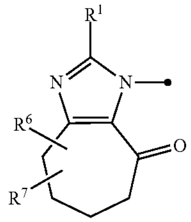
(a10)
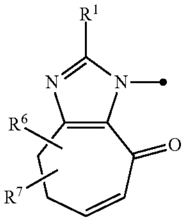
(a11)
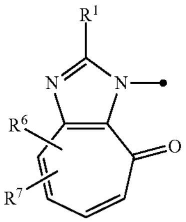
-continued
(a12)
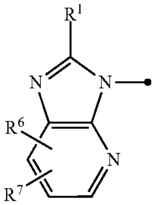
(a13)
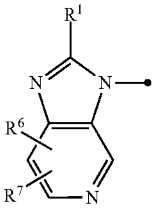
(a14)
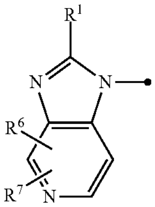
(a15)
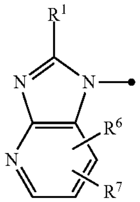
(a16)
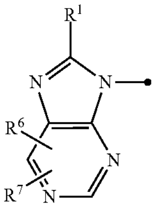
(a17)
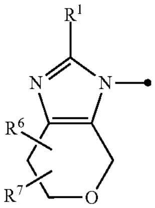
(a18)
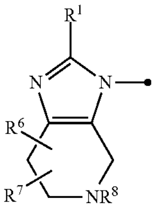

-continued (a19)

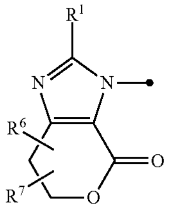

(a20)

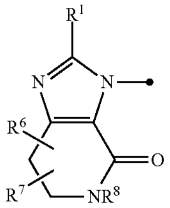

[wherein $R^1$ is as defined above, $R^6$ and $R^7$ are the same or different and each represents a hydrogen atom, halogen, nitro, cyano, formyl, oxo, hydroxy, lower alkoxy optionally having substituent(s), lower alkanoyloxy optionally having substituent(s), lower alkyl optionally having substituent(s), lower alkenyl optionally having substituent(s), lower alkanoyl optionally having substituent(s), lower alkoxycarbonyl optionally having substituent(s), —$NR^9R^{10}$ (wherein $R^9$ and $R^{10}$ are the same or different and each represents a hydrogen atom, lower alkyl optionally having substituent(s), lower alkanoyl optionally having substituent(s), lower alkoxycarbonyl optionally having substituent(s) or aralkyl optionally having substituent(s), or $R^9$ and $R^{10}$ form, together with the adjacent nitrogen atom thereto, a nitrogen-containing heterocyclic group optionally having substituent(s)), —$CONR^{11}R^{12}$ (wherein $R^{11}$ and $R^{12}$ are the same or different and each represents a hydrogen atom, lower alkyl optionally having substituent(s), lower alkanoyl optionally having substituent(s), lower alkoxycarbonyl optionally having substituent(s) or aralkyl optionally having substituent(s), or $R^{11}$ and $R^{12}$ form, together with the adjacent nitrogen atom thereto, a nitrogen-containing heterocyclic group optionally having substituent(s)), aryl optionally having substituent(s), aralkyl optionally having substituent(s), an aromatic heterocyclic group optionally having substituent(s) or an aliphatic heterocyclic group optionally having substituent(s), and $R^8$ represents a hydrogen atom or lower alkyl optionally having substituent(s)], $R^4$ and $R^5$ are the same or different and each represents a hydrogen atom, halogen, hydroxy, lower alkoxy or lower alkyl, $Q^1$-$Q^2$-$Q^3$ represents CH═CH—CH═CH, S—CH═CH or CH═CH—S, Y represents a single bond, $CH_2$, $CH_2CH_2$, CH═CH, O, S, $CH_2O$, $OCH_2$, $CH_2S$ or $SCH_2$, $Z^1$-$Z^2$ represents C═$CR^{13}$ (wherein $R^{13}$ represents a hydrogen atom or lower alkyl optionally having substituent(s)), CH—$CR^{14}R^{15}$ (wherein $R^{14}$ and $R^{15}$ are the same or different and each represents a hydrogen atom or lower alkyl optionally having substituent(s)), or N—$CR^{16}R^{17}$ (wherein $R^{16}$ and $R^{17}$ are the same or different and each represents a hydrogen atom or lower alkyl optionally having substituent(s)), and A represents a group selected from the group consisting of the following formulas (b1) to (b6)

(b1)

(b2)

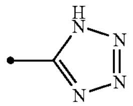

(b3)

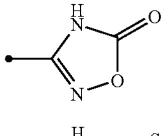

(b4)

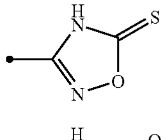

(b5)

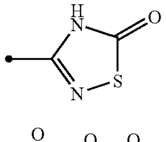

(b6)

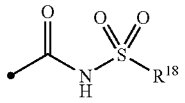

(wherein $R^{18}$ represents lower alkyl optionally having substituent(s) or aryl optionally having substituent(s))>, or a pharmaceutically acceptable salt thereof.

(2) An agent having a PPARγ agonistic action and an angiotensin II receptor antagonistic action in combination, which comprises the tricyclic compound or the pharmaceutically acceptable salt thereof recited in (1), as an active ingredient.

(3) The agent according to (1) or (2), wherein the agent is an agent for treating and/or preventing a disease related to PPARγ.

(4) The agent according to (3), wherein the disease related to PPARγ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

(5) A tricyclic compound represented by the formula (IA)

(IA)

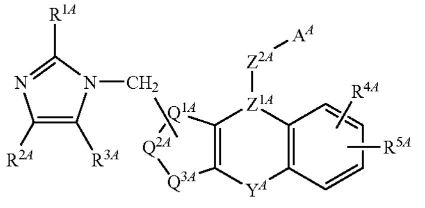

<wherein $R^{1A}$ represents lower alkyl optionally having substituent(s), cycloalkyl optionally having substituent(s), lower alkoxy optionally having substituent(s) or lower alkylsulfanyl optionally having substituent(s), $R^{2A}$ and $R^{3A}$ are the same or different and each represents a hydrogen atom, lower alkyl optionally having substituent(s), lower alkenyl optionally having substituent(s), lower alkanoyl optionally having substituent(s), lower alkoxycarbonyl optionally having substituent(s), lower alkylcarbamoyl optionally having substituent(s), di-lower alkylcarbamoyl optionally having substituent(s) or aliphatic heterocycle-carbonyl optionally having substituent(s), or
a group
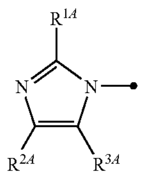
in the formula (IA) is selected from the group consisting of the following formulas (A1) to (A20)
(A1)
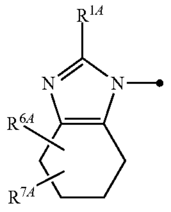
(A2)
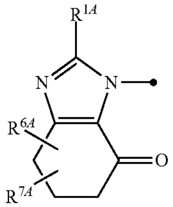
(A3)
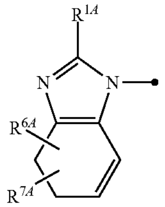
(A4)
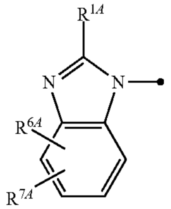
(A5)
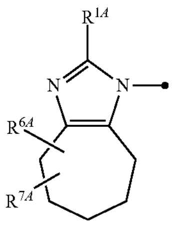
-continued
(A6)
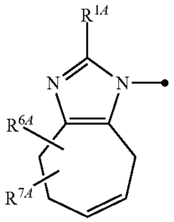
(A7)
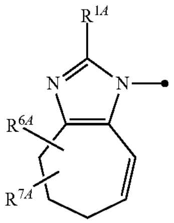
(A8)
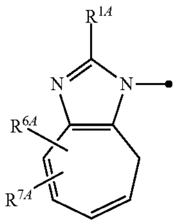
(A9)
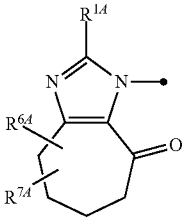
(A10)
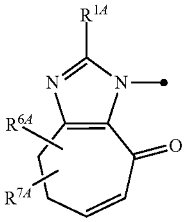
(A11)
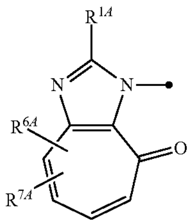
(A12)
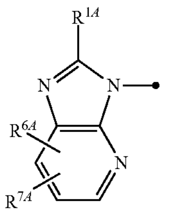

-continued (A13)

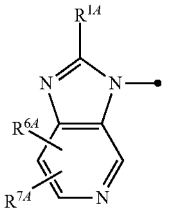

(A14)

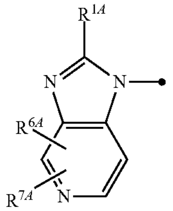

(A15)

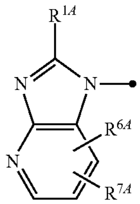

(A16)

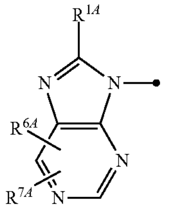

(A17)

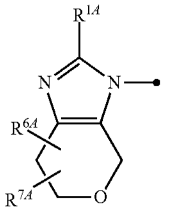

(A18)

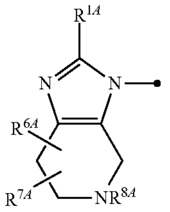

(A19)

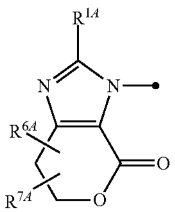

-continued (A20)

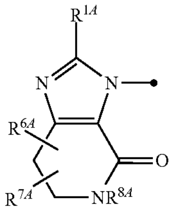

[wherein $R^{1A}$ is as defined above, $R^{6A}$ and $R^{7A}$ are the same or different and each represents a hydrogen atom, halogen, nitro, cyano, formyl, oxo, hydroxy, lower alkoxy optionally having substituent(s), lower alkanoyloxy optionally having substituent(s), lower alkyl optionally having substituent(s), lower alkenyl optionally having substituent(s), lower alkanoyl optionally having substituent(s), lower alkoxycarbonyl optionally having substituent(s), —$NR^{9A}R^{10A}$ (wherein $R^{9A}$ and $R^{10A}$ are the same or different and each represents a hydrogen atom, lower alkyl optionally having substituent(s), lower alkanoyl optionally having substituent(s), lower alkoxycarbonyl optionally having substituent(s) or aralkyl optionally having substituent(s), or $R^{9A}$ and $R^{10A}$ form, together with the adjacent nitrogen atom thereto, a nitrogen-containing heterocyclic group optionally having substituent(s)), —$CONR^{11A}R^{12A}$ (wherein $R^{11A}$ and $R^{12A}$ are the same or different and each represents a hydrogen atom, lower alkyl optionally having substituent(s), lower alkanoyl optionally having substituent(s), lower alkoxycarbonyl optionally having substituent(s) or aralkyl optionally having substituent(s), or $R^{11A}$ and $R^{12A}$ form, together with the adjacent nitrogen atom thereto, a nitrogen-containing heterocyclic group optionally having substituent(s)), aryl optionally having substituent(s), aralkyl optionally having substituent(s), an aromatic heterocyclic group optionally having substituent(s) or an aliphatic heterocyclic group optionally having substituent(s), and $R^{8A}$ represents a hydrogen atom or lower alkyl optionally having substituent(s)], $R^{4A}$ and $R^{5A}$ are the same or different and each represents a hydrogen atom, halogen, hydroxy, lower alkoxy or lower alkyl, $Q^{1A}$-$Q^{2A}$-$Q^{3A}$ represents CH═CH—CH═CH, S—CH═CH or CH═CH—S, $Y^A$ represents a single bond, $CH_2$, $CH_2CH_2$, CH═CH, O, S, $CH_2O$, $OCH_2$, $CH_2S$ or $SCH_2$, $Z^{1A}$-$Z^{2A}$ represents C═$CR^{13A}$ (wherein $R^{13A}$ represents a hydrogen atom or lower alkyl optionally having substituent(s)), CH—$CR^{14A}R^{15A}$ (wherein $R^{14A}$ and $R^{15A}$ are the same or different and each represents a hydrogen atom or lower alkyl optionally having substituent(s)), or N—$CR^{16A}R^{17A}$ (wherein $R^{16A}$ and $R^{17A}$ are the same or different and each represents a hydrogen atom or lower alkyl optionally having substituent(s)), and (i) when $Z^{1A}$-$Z^{2A}$ is C═$CR^{13AA}$ (wherein $R^{13AA}$ represents lower alkyl optionally having substituent(s)), CH—$CR^{14A}R^{15AA}$ (wherein $R^{14A}$ is as defined above, and $R^{15AA}$ represents lower alkyl optionally having substituent(s)), or N—$CR^{16AA}R^{17A}$ (wherein $R^{16AA}$ is lower alkyl optionally having substituent(s) and $R^{17A}$ is as defined above), $A^{4}$ represents a group selected from the group consisting of the following formulas (B1) to (B6)

(B1)

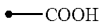

(B2)

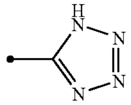

(B3)

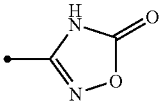

(B4)

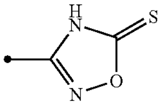

(B5)

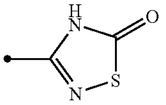

(B6)

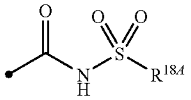

(wherein $R^{18A}$ represents lower alkyl optionally having substituent(s) or aryl optionally having substituent(s)), and (ii) when $Z^{1A}$-$Z^{2A}$ is C═$CR^{13AB}$ (wherein $R^{13AB}$ represents a hydrogen atom), CH—$CR^{14AB}R^{15AB}$ (wherein both of $R^{14AB}$ and $R^{15AB}$ represent a hydrogen atom), or N—$CR^{16AB}R^{17AB}$ (wherein both of $R^{16AB}$ and $R^{17AB}$ represent a hydrogen atom), $A^{4}$ represents a group selected from the group consisting of the following formulas (B3) to (B6)

(B3)

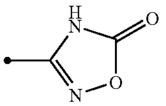

(B4)

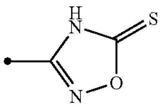

(B5)

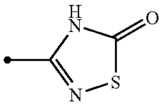

(B6)

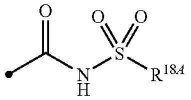

(wherein $R^{18A}$ is as defined above)>, or a pharmaceutically acceptable salt thereof.

(6) The tricyclic compound or the pharmaceutically acceptable salt thereof according to (5), wherein the group

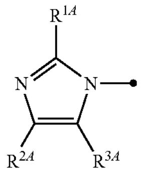

in the formula (IA) is a group selected from the group consisting of the aforementioned formulas (A1) to (A20).

(7) The tricyclic compound or the pharmaceutically acceptable salt thereof according to (5), wherein

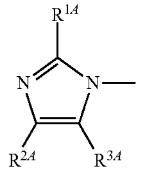

in the formula (IA) is a group selected from the group consisting of the following formulas (A4), (A9), (A11) and (A12)

(A4)

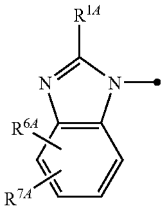

(A9)

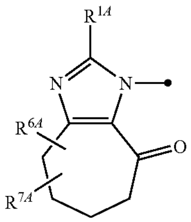

(A11)

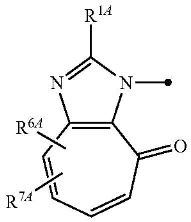

(A12)

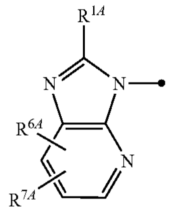

(wherein $R^{1A}$, $R^{6A}$ and $R^{7A}$ are as defined above, respectively).

(8) The tricyclic compound or the pharmaceutically acceptable salt thereof according to (5), wherein

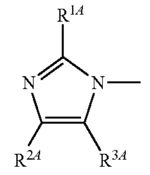

in the formula (IA) is a group represented by the following formula (A4)

(A4)

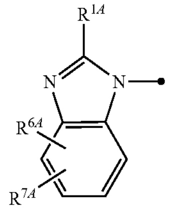

(wherein $R^{1A}$, $R^{6A}$ and $R^{7A}$ are as defined above, respectively).

(9) The tricyclic compound or the pharmaceutically acceptable salt thereof according to (5), wherein

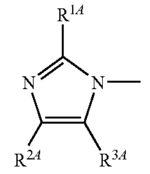

in the formula (IA) is a group represented by the following formula (A12)

(A12)

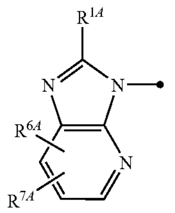

(wherein $R^{1A}$, $R^{6A}$ and $R^{7A}$ are as defined above, respectively).

(10) The tricyclic compound or the pharmaceutically acceptable salt thereof according to any of (5) to (9), wherein $Z^{1A}$-$Z^{2A}$ is C═$CR^{13AA}$ (wherein $R^{13AA}$ is as defined above), CH—$CHR^{15AA}$ (wherein $R^{15AA}$ is as defined above), or N—$CR^{16AA}R^{17A}$ (wherein $R^{16AA}$ and $R^{17A}$ are as defined above, respectively).

(11) The tricyclic compound or the pharmaceutically acceptable salt thereof according to any of (5) to (10), wherein AA is the following formula (B3)

(B3)

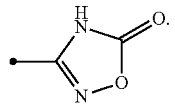

(12) The tricyclic compound or the pharmaceutically acceptable salt thereof according to any of (5) to (11), wherein $Q^{1A}$-$Q^{2A}$-$Q^{3A}$ is CH═CH—CH═CH.

(13) The tricyclic compound or the pharmaceutically acceptable salt thereof according to any of (5) to (12), wherein $Y^{A}$ is $CH_2CH_2$ or $CH_2O$.

(14) A pharmaceutical composition comprising the tricyclic compound or the pharmaceutically acceptable salt thereof recited in any of (5) to (13) as an active ingredient.

(15) A PPARγ agonist comprising the tricyclic compound or the pharmaceutically acceptable salt thereof recited in any of (5) to (13) as an active ingredient.

(16) An agent having a PPARγ agonistic action and an angiotensin II receptor antagonistic action in combination, which comprises the tricyclic compound or the pharmaceutically acceptable salt thereof recited in any of (5) to (13) as an active ingredient.

(17) An agent for treating and/or preventing a disease related to PPARγ, which comprises the tricyclic compound or the pharmaceutically acceptable salt thereof recited in any of (5) to (13) as an active ingredient.

(18) The agent according to (17), wherein the disease related to PPARγ is a disease further related to an angiotensin II receptor.

(19) The agent according to (17) or (18), wherein the disease related to PPARγ is selected from the group consisting of type 2 diabetes, impaired glucose tolerance, insulin resistance syndrome, hypertension, hyperlipidemia, metabolic syndrome, visceral obesity, obesity and hypertriglyceridemia.

(20) An angiotensin II receptor antagonist comprising the tricyclic compound or the pharmaceutically acceptable salt thereof recited in any of (5) to (13) as an active ingredient.

(21) An agent for treating and/or preventing a disease related to an angiotensin II receptor, which comprises the tricyclic compound or the pharmaceutically acceptable salt thereof recited in any of (5) to (13) as an active ingredient.

(22) An antihypertensive agent which comprises the tricyclic compound or the pharmaceutically acceptable salt thereof recited in any of (5) to (13) as an active ingredient.

(23) A method of activating PPARγ, which comprises administering an effective amount of the tricyclic compound or the pharmaceutically acceptable salt thereof recited in (1).

(24) A method of activating PPARγ and antagonizing an angiotensin II receptor, which comprises administering an effective amount of the tricyclic compound or the pharmaceutically acceptable salt thereof recited in (1).

(25) The method according to (23) or (24), wherein the method of activating PPARγ is a method for treating and/or preventing a disease related to PPARγ.

(26) The method according to (25), wherein the disease related to PPARγ is a disease further related to an angiotensin II receptor.

(27) The method according to (25) or (26), wherein the disease related to PPARγ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

(28) A method of activating PPARγ, which comprises administering an effective amount of the tricyclic compound or the pharmaceutically acceptable salt thereof recited in any of (5) to (13).

(29) A method of activating PPARγ and antagonizing an angiotensin II receptor, which comprises administering an effective amount of the tricyclic compound or the pharmaceutically acceptable salt thereof recited in any of (5) to (13).

(30) The method according to (28) or (29), wherein the method of activating PPARγ is a method for treating and/or preventing a disease related to PPARγ.

(31) The method according to (30), wherein the treating the disease related to PPARγ is a disease further related to an angiotensin II receptor.

(32) The method according to (30) or (31), wherein the disease related to PPARγ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

(33) A method of antagonizing an angiotensin II receptor, which comprises administering an effective amount of the tricyclic compound or the pharmaceutically acceptable salt thereof recited in any of (5) to (13).

(34) The method according to any of (29) to (33), wherein the method of antagonizing an angiotensin II receptor is a method for treating and/or preventing a disease related to an angiotensin II receptor.

(35) The method according to (34), wherein the method for treating and/or preventing a disease related to an angiotensin II receptor is a method for treating and/or preventing hypertension.

(36) Use of the tricyclic compound or the pharmaceutically acceptable salt thereof recited in (1) for the production of a PPARγ agonist.

(37) Use of the tricyclic compound or the pharmaceutically acceptable salt thereof recited in (1) for the production of an agent having a PPARγ agonistic action and an angiotensin II receptor antagonistic action in combination.

(38) Use of the tricyclic compound or the pharmaceutically acceptable salt thereof recited in (1) for the production of an agent for treating and/or preventing a disease related to PPARγ.

(39) Use according to (38), wherein the disease related to PPARγ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

(40) Use of the tricyclic compound or the pharmaceutically acceptable salt thereof recited in any of (5) to (13) for the production of a PPARγ agonist.

(41) Use of the tricyclic compound or the pharmaceutically acceptable salt thereof recited in any of (5) to (13) for the production of an agent having a PPARγ agonistic action and an angiotensin II receptor antagonistic action in combination.

(42) Use of the tricyclic compound or the pharmaceutically acceptable salt thereof recited in any of (5) to (13) for the production of an agent for treating and/or preventing a disease related to PPARγ.

(43) Use according to (42), wherein the disease related to PPARγ is a disease further related to an angiotensin II receptor.

(44) Use according to (42) or (43), wherein the disease related to PPARγ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

(45) Use of the tricyclic compound or the pharmaceutically acceptable salt thereof recited in any of (5) to (13) for the production of an angiotensin II receptor antagonist.

(46) Use of the tricyclic compound or the pharmaceutically acceptable salt thereof recited in any of (5) to (13) for the production of an agent for treating and/or preventing a disease related to an angiotensin II receptor.

(47) Use of the tricyclic compound or the pharmaceutically acceptable salt thereof recited in any of (5) to (13) for the production of an antihypertensive agent.

Effect of the Invention

The present invention provides a PPARγ agonist comprising a tricyclic compound as an active ingredient, which is useful as an agent for treating and/or preventing, for example, type 2 diabetes, impaired glucose tolerance, insulin resistance syndrome, hypertension, hyperlipidemia, metabolic syndrome, visceral obesity, obesity, hypertriglyceridemia, inflammatory dermatic diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis etc.), inflammatory neuropsychiatric diseases (e.g., multiple sclerosis etc.), neurodegenerative neuropsychiatric diseases (e.g., Alzheimer's disease, Parkinson's disease etc.) or the like. The PPARγ agonist provided by the present invention preferably further has an angiotensin II receptor antagonistic action, and is useful as an agent for treating and/or preventing, for example, cardiovascular diseases such as arteriosclerosis, cardiac disease, cerebral apoplexy, renal diseases, etc. or the like, in addition to the above-mentioned diseases.

In addition, a novel tricyclic compound or a pharmaceutically acceptable salt thereof having a PPARγ agonist activity, which is useful as an agent for treating and/or preventing, for example, type 2 diabetes, impaired glucose tolerance, insulin resistance syndrome, hypertension, hyperlipidemia, metabolic syndrome, visceral obesity, obesity, hypertriglyceridemia, inflammatory dermatic diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis etc.), inflammatory neuropsychiatric diseases (e.g., multiple sclerosis etc.), neurodegenerative neuropsychiatric diseases (e.g., Alzheimer's disease, Parkinson's disease etc.) or the like is provided. The tricyclic compound or a pharmaceutically acceptable salt thereof provided by the present invention preferably further has an angiotensin II receptor antagonistic action, and is useful as an agent for treating and/or preventing, for example, cardiovascular diseases such as arteriosclerosis, cardiac disease, cerebral apoplexy, renal diseases, or the like, in addition to the above-mentioned diseases.

BEST MODE FOR CARRYING OUT THE INVENTION

Hereinafter a compound represented by the formula (I) is referred to as compound (I). The same applies to the compounds of other formula numbers.

In the definition of each group of the formulas (I) and (IA), examples of lower alkyl, and the lower alkyl moiety of lower alkoxy, lower alkylsulfanyl, lower alkanoyloxy, lower alkanoyl, lower alkoxycarbonyl, lower alkylcarbamoyl and di-lower alkylcarbamoyl include straight chain or branched alkyl having 1 to 10 carbon atoms, and more specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl and the like. Two lower alkyl moieties of di-lower alkylcarbamoyl may be the same or different.

Examples of the lower alkenyl include straight chain or branched alkenyl having 2 to 10 carbon atoms, and more specific examples thereof include vinyl, allyl, 1-propenyl, butenyl, pentenyl, hexenyl, heptenyl, octenyl, nonenyl, decenyl and the like.

Examples of the cycloalkyl include cycloalkyl having 3 to 8 carbon atoms, and more specific examples thereof include cyclopropyl, cyclobutyl, cyclopentyl, cyclohexyl, cycloheptyl, cyclooctyl and the like.

Examples of the aralkyl include aralkyl having 7 to 16 carbon atoms, and more specific examples thereof include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl and the like.

Examples of the aryl include aryl having 6 to 14 carbon atoms, and more specific examples thereof include phenyl, naphthyl, azulenyl, anthryl and the like.

Examples of the aliphatic heterocyclic group and the aliphatic heterocyclic group moiety of aliphatic heterocycle-carbonyl include a 5-membered or 6-membered monocyclic aliphatic heterocyclic group comprising at least one atom selected from a nitrogen atom, an oxygen atom and a sulfur atom, a bicyclic or tricyclic condensed aliphatic heterocyclic group containing at least one atom selected from a nitrogen atom, an oxygen atom and a sulfur atom, wherein 3- to 8-membered rings are condensed, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl and the like.

Examples of the aromatic heterocyclic group include a 5-membered or 6-membered monocyclic aromatic heterocyclic group containing at least one atom selected from a nitrogen atom, an oxygen atom and a sulfur atom, a bicyclic or tricyclic condensed aromatic heterocyclic group containing at least one atom selected from a nitrogen atom, an oxygen atom and a sulfur atom, wherein 3- to 8-membered rings are condensed, and the like, and more specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl and the like.

Examples of the nitrogen-containing heterocyclic group formed together with the adjacent nitrogen atom thereto include a 5-membered or 6-membered monocyclic heterocyclic group containing at least one nitrogen atom (said monocyclic heterocyclic group may contain other nitrogen atom, oxygen atom or sulfur atom), a bicyclic or tricyclic condensed heterocyclic group containing at least one nitrogen atom (said condensed heterocyclic group may contain other nitrogen atom, oxygen atom or sulfur atom), wherein 3- to 8-membered rings are condensed, and the like, and more specific examples thereof include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl and the like.

Halogen means each atom of fluorine, chlorine, bromine or iodine.

The substituent(s) of lower alkyl optionally having substituent(s), lower alkenyl optionally having substituent(s), lower alkoxy optionally having substituent(s), lower alkylsulfanyl optionally having substituent(s), lower alkanoyloxy optionally having substituent(s), lower alkanoyl optionally having substituent(s), lower alkoxycarbonyl optionally having substituent(s), lower alkylcarbamoyl optionally having substituent(s) and di-lower alkylcarbamoyl optionally having substituent(s) are the same or different and examples thereof include 1 to 3 substituents selected from the group consisting of halogen, hydroxy, sulfanyl, nitro, cyano, carbamoyl, $C_{3-8}$ cycloalkyl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ are the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl and the like.

The substituents of aryl optionally having substituent(s), aralkyl optionally having substituent(s) and an aromatic heterocyclic group optionally having substituent(s) are the same or different and examples thereof include 1 to 3 substituents selected from the group consisting of halogen, hydroxy, sulfanyl, nitro, cyano, carbamoyl, $C_{1-10}$ alkyl, trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ are the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl and the like.

The substituents of cycloalkyl optionally having substituent(s), an aliphatic heterocyclic group optionally having substituent(s), aliphatic heterocycle-carbonyl optionally having substituent(s) and a nitrogen-containing heterocyclic group optionally having substituent(s), which is formed together with the adjacent nitrogen atom thereto, are the same or different and examples thereof include 1 to 3 substituents selected from the group consisting of oxo, halogen, hydroxy, sulfanyl, nitro, cyano, carbamoyl, $C_{1-10}$ alkyl, trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylsulfanyl, —$NR^XR^Y$ (wherein $R^X$ and $R^Y$ are the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl or $C_{7-16}$ aralkyloxycarbonyl), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl and the like.

Examples of $C_{1-10}$ alkyl and the $C_{1-10}$ alkyl moiety of $C_{1-10}$ alkoxy, $C_{2-11}$ alkanoyloxy, $C_{1-10}$ alkylsulfanyl, $C_{2-11}$ alkanoyl, $C_{1-10}$ alkoxycarbonyl, $C_{1-10}$ alkylcarbamoyl and di-$C_{1-10}$ alkylcarbamoyl shown here include the groups recited as examples of the aforementioned lower alkyl. Two $C_{1-10}$ alkyl in di-$C_{1-10}$ alkylcarbamoyl may be the same or different.

Examples of $C_{3-8}$ cycloalkyl and the cycloalkyl moiety of $C_{3-8}$ cycloalkoxy include the groups recited as examples of the aforementioned cycloalkyl.

Examples of $C_{6-14}$ aryl and the aryl moiety of $C_{6-14}$ aryloxy, $C_{7-15}$ aroyl, $C_{7-15}$ aroyloxy and $C_{6-14}$ aryloxycarbonyl include the groups recited as examples of the aforementioned aryl.

Examples of $C_{7-16}$ aralkyl and the $C_{7-16}$ aralkyl moiety of $C_{7-16}$ aralkyloxy and $C_{7-16}$ aralkyloxycarbonyl include the groups recited as examples of the aforementioned aralkyl.

Examples of the aliphatic heterocyclic group, the aromatic heterocyclic group and halogen include the groups recited as examples of the aforementioned aliphatic heterocyclic group, the aforementioned aromatic heterocyclic group and the aforementioned halogen, respectively.

As compounds (1) and (IA), the compounds described in the aforementioned (6) to (13) are more preferable. More specifically, compounds represented by the formulas (IA-A) or (IA-B), (IA-A)

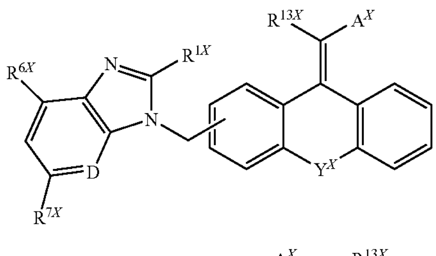

(IA-B)

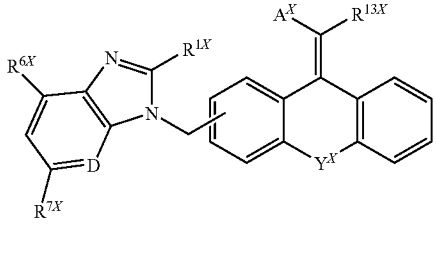

(wherein D represents CH or N, $R^{1X}$ represents $C_{1-6}$ alkyl, $C_{3-8}$ cycloalkyl or $C_{1-6}$ alkoxy, $R^{6X}$ represents a hydrogen atom, halogen, trifluoromethyl or $C_{1-6}$ alkyl, $R^{7X}$ represents a hydrogen atom, halogen or $C_{1-6}$ alkyl, $Y^X$ represents $CH_2CH_2$, $CH_2O$ or $OCH_2$, $R^{13X}$ represents a hydrogen atom or $C_{1-6}$ alkyl, and $A^X$ represents the following formula (b2) or (b3), (b2)

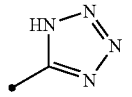

(b3)

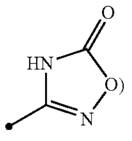

are preferable, and compounds represented by the formulas (IA-C) or (IA-D), (IA-C)

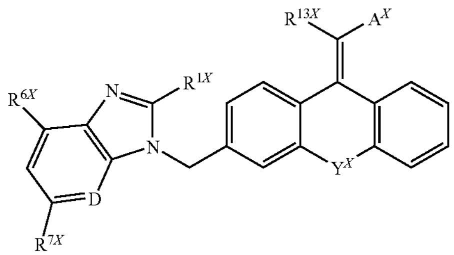

(IA-D)

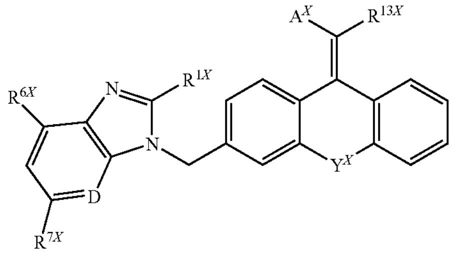

(wherein D, $R^{1X}$, $R^{6X}$, $R^{7X}$, $Y^X$, $R^{13X}$ and $A^X$ are as defined above, respectively), are more preferable.

Still more preferably, in each of the groups of compounds (IA-A), (IA-B), (IA-C), and (IA-D), D is CH or N, $R^{1X}$ is preferably, for example, methyl, ethyl, propyl, cyclopropyl, cyclobutyl, cyclopentyl, cyclohexyl, methoxy, ethoxy, propoxy or the like, more preferably ethyl, propyl, cyclopropyl, ethoxy or the like, $R^{6X}$ is preferably, for example, a hydrogen atom, a fluorine atom, a chlorine atom, a bromine atom, methyl, ethyl, propyl, isopropyl or the like, more preferably a hydrogen atom, a chlorine atom, methyl or the like, still more preferably a chlorine atom, methyl or the like, $R^{7X}$ is preferably, for example, a hydrogen atom, a fluorine atom, a chlorine atom, a bromine atom, methyl, ethyl, propyl, isopropyl or the like, more preferably a hydrogen atom, methyl or the like, $Y^X$ is more preferably, for example, $CH_2CH_2$, $CH_2O$ or the like, $R^{13X}$ is preferably, for example, $C_{1-6}$ alkyl or the like, more preferably methyl, ethyl, propyl or the like, still more preferably methyl or the like, and $A^X$ is preferably, for example, the above-mentioned formula (b3).

The pharmaceutically acceptable salts of compound (I) and (IA) comprise, for example, pharmaceutically acceptable acid addition salts, metal salts, ammonium salts, organic amine addition salts, amino acid addition salts and the like. Examples of the pharmaceutically acceptable acid addition salts of compounds (I) and (IA) include inorganic acid salts such as hydrochloride, hydrobromide, nitrate, sulfate, phosphate and the like, organic acid salts such as acetate, oxalate, maleate, fumarate, citrate, benzoate, methanesulfonate etc., and the like. Examples of the pharmaceutically acceptable metal salts include alkali metal salts such as sodium salt, potassium salt and the like, alkaline earth metal salts such as magnesium salt, calcium salt and the like, aluminum salt, zinc salt and the like. Examples of the pharmaceutically acceptable ammonium salt include salts of ammonium, tetramethylammonium and the like. Examples of the pharmaceutically acceptable organic amine addition salt include addition salts such as morpholine, piperidine and the like. Examples of the pharmaceutically acceptable amino acid addition salt include addition salts such as lysine, glycine, phenylalanine, aspartic acid, glutamic acid and the like.

The production methods of compound (I) are explained in the following.

In the production methods shown below, when the defined groups change under the conditions of the production methods or are inappropriate for performing the production methods, the desired compound can be produced by performing the methods for the introduction and removal of the protecting groups conventionally performed in the synthetic organic chemistry (e.g., methods described in Protective Groups in Organic Synthesis, third edition, T. W. Greene, John Wiley & Sons Inc., 1999 etc.) or the like. If necessary, the order of the reaction steps such as substituent introduction or the like can also be changed.

Production Method 1

Of compound (I), a compound wherein A is the following formula (b1) or (b2)

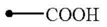
(b1)

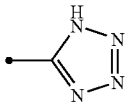
(b2)

can be produced by known methods (e.g., JP-B-2526005, JP-A-7-61983 and the like), or similar methods thereto.

Production Method 2

Of compound (I), compounds (Ia) to (Id) wherein each of $Z^1$-$Z^2$ is N—$CR^{16}R^{17}$ (wherein $R^{16}$ and $R^{17}$ are as defined above, respectively) and A is the following formula (b2), (b3), (b4) or (b5)

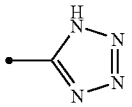
(b2)

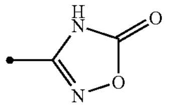
(b3)

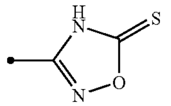
(b4)

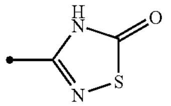
(b5)

can be produced according to the following steps.

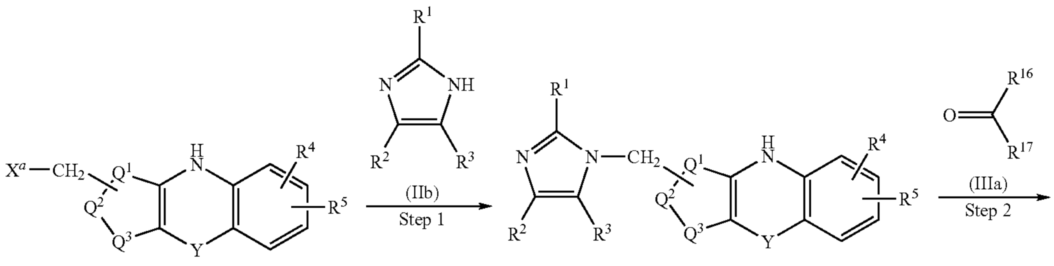

(IIa) (III)

-continued

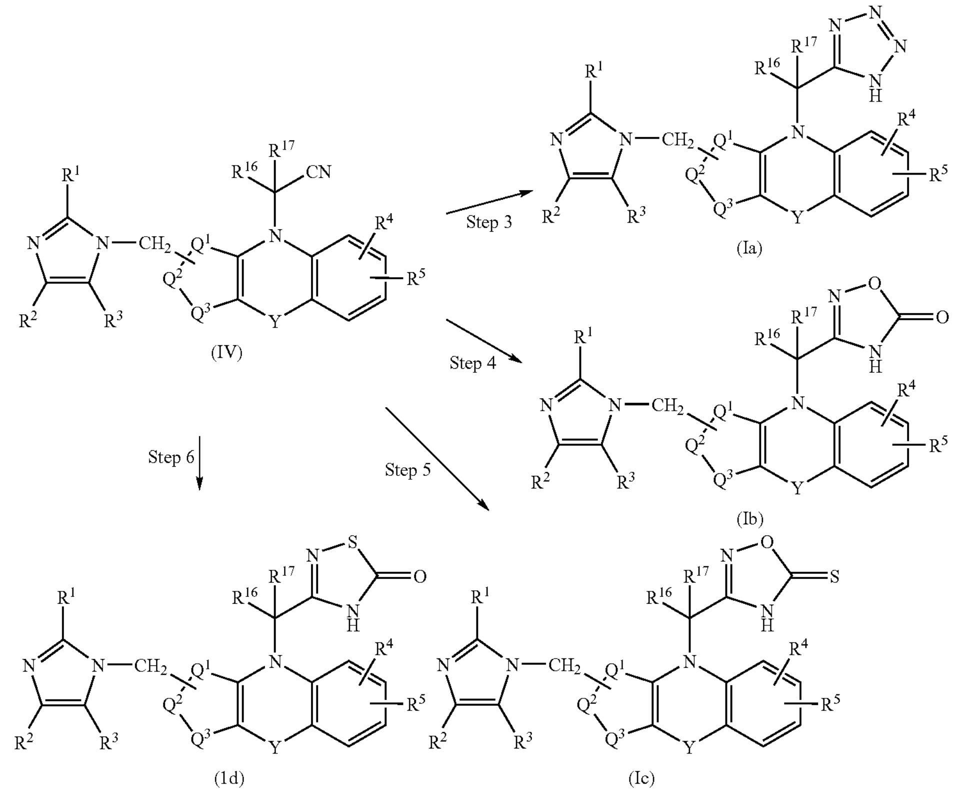

[wherein $R^1$, $R^2$, $R^3$, $R^4$, $R^5$, $R^{16}$, $R^{17}$, $Q^1$-$Q^2$-$Q^3$ and Y are as defined above, respectively, $X^a$ represents a leaving group such as a chlorine atom, a bromine atom, an iodine atom, trifluoromethanesulfonyloxy, methanesulfonyloxy, benzenesulfonyloxy, p-toluenesulfonyloxy or the like or a group represented by the following formula

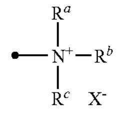

(wherein X represents a chlorine atom, a bromine atom, an iodine atom, trifluoromethanesulfonyloxy, methanesulfonyloxy, benzenesulfonyloxy, p-toluenesulfonyloxy or the like, $R^a$ represents $C_{1-10}$ alkyl, $C_{2-10}$ alkenyl, phenyl or benzyl, $R^b$ and $R^c$ are the same or different and each represents $C_{1-10}$ alkyl or $C_{3-8}$ cycloalkyl, or $R^b$ and $R^c$ form a nitrogen-containing heterocyclic group together with the adjacent nitrogen atom thereto)].

Step 1

Compound (III) can be obtained by reacting compound (IIa) with 1 equivalent amount to 5 equivalent amount of compound (IIb) in a solvent in the presence of, if necessary, 1 equivalent amount to large excess amount of a base for 5 min to 120 hr at a temperature between −20° C. and the boiling point of the solvent to be used.

Examples of the base include sodium carbonate, potassium carbonate, lithium carbonate, cesium carbonate, sodium hydrogen carbonate, potassium hydrogen carbonate, lithium hydrogen carbonate, sodium hydroxide, potassium hydroxide, lithium hydroxide, sodium methoxide, potassium ethoxide, potassium tert-butoxide, sodium hydride, potassium hydride, butyl lithium, lithium bistrimethylsilylamide, sodium bistrimethylsilylamide, triethylamine, diisopropylethylamine, tributylamine, dicyclohexylmethylamine and the like. Examples of the solvent include dimethylformamide (DMF), dimethylacetamide (DMA), N-methylpyrrolidone (NMP), dimethyl sulfoxide (DMSO), tetrahydrofuran (THF), acetonitrile, isopropyl alcohol and the like, and these can be used alone or in a mixture.

Here, compound (IIa) can be obtained by the methods described in JP-B-2526005, JP-A-7-61983 and the like, and compound (IIb) can be obtained according to known methods (e.g., U.S. Pat. No. 5,332,744, EP-B-400835, JP-A-5-783228 etc.) or similar methods thereto.

Step 2

Compound (IV) can be obtained by reacting compound (III) obtained in step 1 with 1 equivalent amount to large excess amount of compound (IIIa) and 1 equivalent amount to large excess amount of a cyanide salt in a solvent or without solvent in the presence of 1 equivalent amount to large excess amount of an acid for 5 min to 72 hr at a temperature between −20° C. and the boiling point of the solvent to be used.

Examples of the cyanide salt include sodium cyanide, potassium cyanide and the like. Examples of the acid include acetic acid, trifluoroacetic acid and the like. Examples of the solvent include dichloroethane, dioxane, THF, ethanol and the like, and these can be used alone or in a mixture.

Here, compound (IIIa) can be obtained as a commercially available product.

Step 3

Compound (Ia) can be obtained by reacting compound (IV) obtained in step 2 with 1 equivalent amount to 10 equivalent amount of sodium azide in a solvent in the presence of 1 equivalent amount to large excess amount of a weak acid for 5 min to 120 hr at a temperature between −20° C. and the boiling point of the solvent to be used.

Examples of the weak acid include ammonium chloride, triethylamine hydrochloride and the like. Examples of the solvent include DMF, DMA, NMP, DMSO and the like, and these can be used alone or in a mixture.

In addition, as another method, compound (Ia) can be also obtained by reacting compound (IV) with 1 equivalent amount to 10 equivalent amount of sodium azide in a solvent in the presence of 0.01 to 10 equivalent amount of an additive for 1 hr to 120 hr at a temperature between −10° C. and the boiling point of the solvent to be used.

Examples of the additive include tributyltin chloride, trimethyltin chloride, dibutyltin oxide and the like. Examples of the solvent include toluene, xylene and the like, and these can be used alone or in a mixture.

Step 4

Compound (Ib) can be produced using compound (IV) obtained in step 2 and according to the following steps.

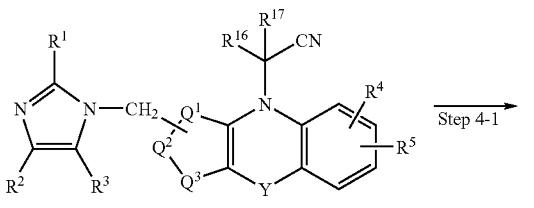

(IV)

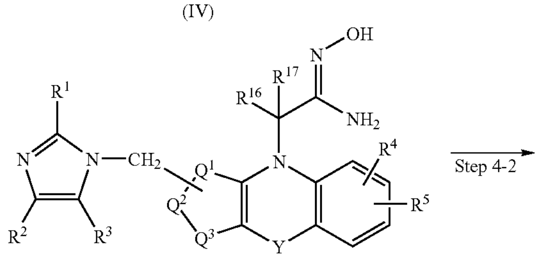

(Ib-1)

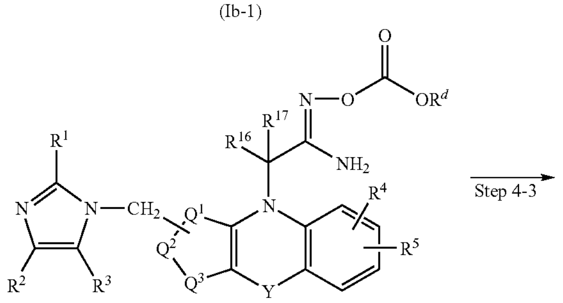

(Ib-2)

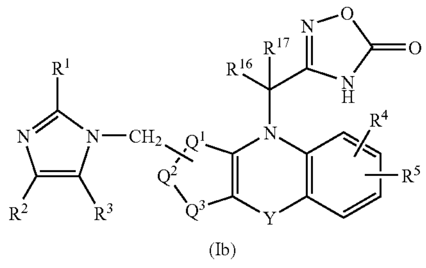

(Ib)

(wherein $R^1$, $R^2$, $R^3$, $R^4$, $R^5$, $R^{16}$, $R^{17}$, $Q^1$-$Q^2$-$Q^3$ and Y are as defined above, respectively, and $R^d$ represents methyl, ethyl, propyl, phenyl or the like).

Step 4-1

Compound (Ib-1) can be obtained by reacting compound (IV) with 1 equivalent amount to large excess amount of hydroxylamine in a solvent for 5 min to 120 hr at a temperature between −20° C. and the boiling point of the solvent to be used.

As hydroxylamine, for example, an inorganic acid salt such as hydroxylamine hydrochloride or the like can be used. In this case, it is preferred that an equivalent amount of a base such as sodium methoxide or the like coexist. Examples of the solvent include methanol, ethanol, DMF, DMA, DMSO and the like, and these can be used alone or in a mixture.

Step 4-2

Compound (Ib-2) can be obtained by reacting compound (Ib-1) obtained in the above-mentioned step 4-1 with 1 equivalent amount to large excess amount of chlorocarbonate ester in a solvent in the presence of 1 equivalent amount to large excess amount of a base for 5 min to 72 hr at a temperature between −20° C. and the boiling point of the solvent to be used.

Examples of chlorocarbonate ester include methyl chlorocarbonate, ethyl chlorocarbonate, propyl chlorocarbonate, phenyl chlorocarbonate and the like. Examples of the base include triethylamine, pyridine, 4-dimethylaminopyridine (DMAP), sodium hydroxide, sodium hydride, potassium tert-butoxide, sodium methoxide and the like. Examples of the solvent include THF, DMF, DMA, toluene, xylene and the like, and these can be used alone or in a mixture.

Step 4-3

Compound (Ib) can be obtained by reacting compound (Ib-2) obtained in the above-mentioned step 4-2 in a solvent in the presence of, if necessary, a catalytic amount to 10 equivalent amount of a base for 5 min to 72 hr at a temperature between −20° C. and the boiling point of the solvent to be used.

Examples of the base include sodium hydroxide, sodium hydride, potassium tert-butoxide, sodium methoxide and the like. Examples of the solvent include THF, DMF, DMA, toluene, xylene and the like, and these can be used alone or in a mixture.

The above-mentioned steps 4-1 to 4-3 can also be performed continuously by successively adding a reagent to the reaction mixture without isolating the resultant product.

Step 5

Compound (Ic) can be obtained by reacting compound (Ib-1) obtained from compound (IV) in the same manner as in the above-mentioned step 4-1, with 1 equivalent amount to large excess amount of N,N'-thiocarbonyldiimidazole in a solvent in the presence of 1 equivalent amount to large excess amount of a base for 5 min to 72 hr at a temperature between −20° C. and the boiling point of the solvent to be used.

Examples of the base include triethylamine, pyridine, DMAP, diazabicycloundecene (DBU) and the like. Examples of the solvent include THF, 1,4-dioxane, dichloromethane, chloroform, acetonitrile, acetone and the like, and these can be used alone or in a mixture.

Step 6

Compound (Id) can be obtained by reacting compound (Ib-1) obtained from compound (IV) in the same manner as in the above-mentioned step 4-1, with 1 equivalent amount to large excess amount of N,N'-thiocarbonyldiimidazole in a solvent in the presence of 1 equivalent amount to large excess amount of a Lewis acid for 5 min to 72 hr at a temperature between −20° C. and the boiling point of the solvent to be used.

Examples of Lewis acid include boron trifluoride diethyl ether complex, stannous chloride, zinc chloride, silica gel and the like. Examples of the solvent include THF, 1,4-dioxane, dichloromethane, chloroform, methanol, ethanol and the like, and these can be used alone or in a mixture.

Production Method 3

Compound (III) can also be produced according to the following steps.

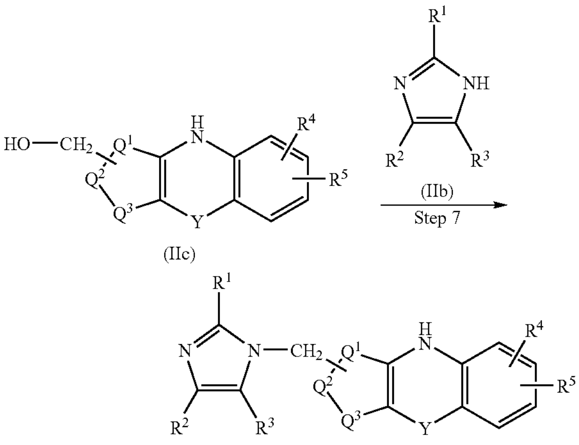

(IIc)

(III)

(wherein $R^1$, $R^2$, $R^3$, $R^4$, $R^5$, $Q^1$-$Q^2$-$Q^3$ and Y are as defined above, respectively).

Step 7

Compound (III) can be obtained by reacting compound (IIc) with 1 equivalent amount to 5 equivalent amount of compound (IIb) in a solvent in the presence of 1 equivalent amount to large excess amount of a condensation agent and, if necessary, 1 equivalent amount to large excess amount of a phosphine compound for 5 min to 72 hr at a temperature between −20° C. and the boiling point of the solvent to be used.

Examples of the condensation agent include diethyl azodicarboxylate, diisopropyl azodicarboxylate, di(tert-butyl) azodicarboxylate, (cyanomethylene)trimethylphosphorane, (cyanomethylene)tributylphosphorane and the like. Examples of the phosphine compound include triphenylphosphine, tributylphosphine, polymer supported triphenylphosphine and the like. Examples of the solvent include THF, DMF, dichloromethane, acetonitrile and the like, and these can be used alone or in a mixture.

As another method, compound (III) can also be obtained by reacting compound (IIc) in a solvent or without solvent in the presence of 1 equivalent amount to large excess amount of a halogenating agent for 5 min to 72 hr at a temperature between −20° C. and the boiling point of the solvent to be used, and successively in the same manner as in step 1 of production method 2.

Examples of the halogenating agent include thionyl chloride; phosphorus tribromide; a combination of triphenylphosphine, 2,6-lutidine and carbon tetrachloride; a combination of triphenylphosphine, 2,6-lutidine and carbon tetrabromide; a combination of methanesulfonyl chloride and lithium chloride, a combination of methanesulfonyl chloride and lithium bromide and the like. Examples of the solvent include THF, DMF, DMA, dichloromethane, dichloroethane, acetonitrile and the like, and these can be used alone or in a mixture.

Here, compound (IIc) can be obtained according to JP-B-2526005.

Production Method 4

Of compound (I), compound (Ie) wherein A is the following formula (b1), (b2), (b3), (b4) or (b5)

(b1)

(b2)

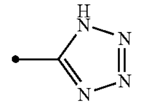

(b3)

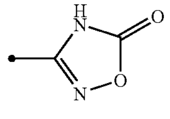

(b4)

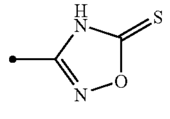

(b5)

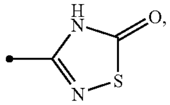

and $Z^1$-$Z^2$ is C═$CR^{13}$ (wherein $R^{13}$ is as defined above), can be produced according to the following steps.

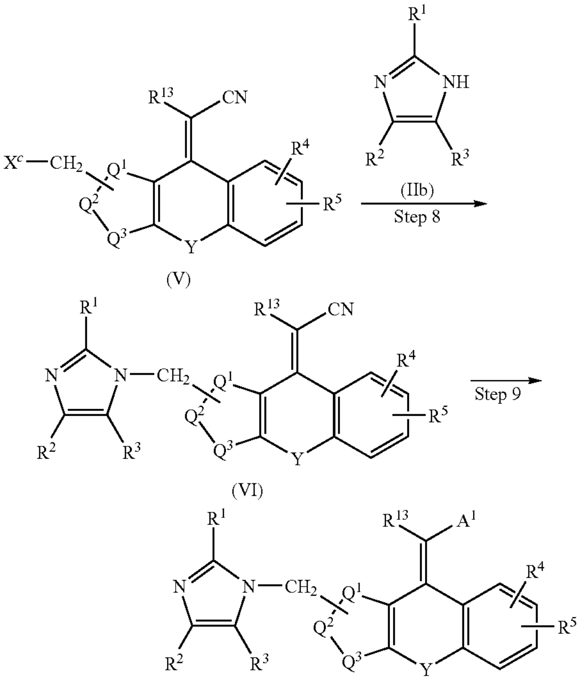

(V)

(VI)

(Ie)

(wherein $X^c$ is as $X^a$ defined above or hydroxy, $R^1$, $R^2$, $R^3$, $R^4$, $R^5$, $R^{13}$, $Q^1$-$Q^2$-$Q^3$ and Y are as defined above, respectively and $A^1$ represents a group represented by any of the above-mentioned formulas (b1) to (b5)).

Step 8

Compound (VI) can be obtained by using compound (V) and compound (IIb) and in the same manner as in the known methods described in production method 1, step 1 of production method 2 or production method 3.

Here, compound (V) can be obtained according the method described in JP-B-2526005 and the like.

Step 9

Compound (Ie) can be obtained by using compound (VI) obtained in step 8 and in the same manner as in the known method described in production method 1 or steps 3 to 6 of production method 2.

Production Method 5

Of compound (I), compound (If) wherein $Z^1$-$Z^2$ is CH—$CR^{14}R^{15}$ (wherein $R^{14}$ and $R^{15}$ are as defined above, respectively) can be obtained according to the following steps.

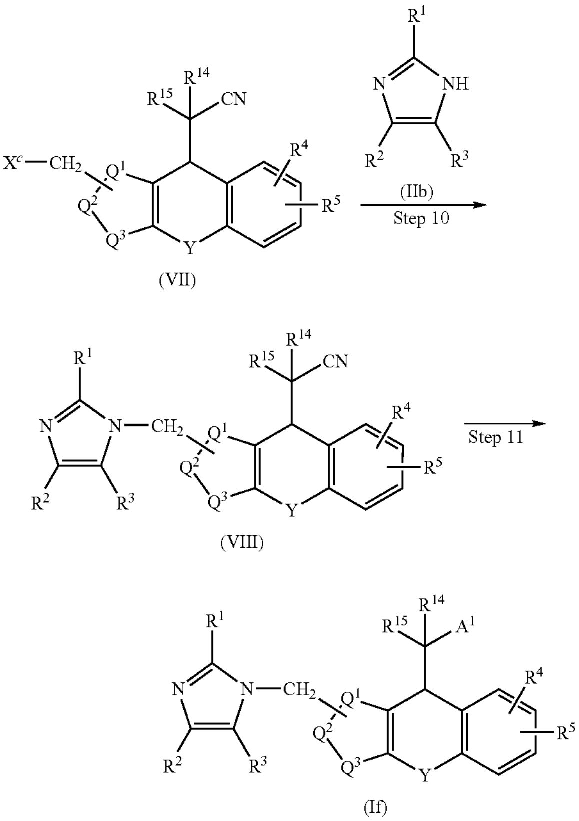

(wherein $X^c$, $R^1$, $R^2$, $R^3$, $R^4$, $R^5$, $R^{14}$, $R^{15}$, $Q^1$-$Q^2$-$Q^3$, Y and $A^1$ are as defined above, respectively).

Step 10

Compound (VIII) can be obtained by using compound (VII) and compound (IIb) and in the same manner as in the known methods described in production method 1, step 1 of production method 2 or production method 3.

Here, compound (VII) can be obtained according to the method described in JP-B-2526005 and the like.

Step 11

Compound (If) can be obtained by using compound (VIII) obtained in step 10 and in the same manner as in the known methods described in production method 1 or steps 3 to 6 of production method 2.

Production Method 6

Of compound (I), compound (Ih) wherein A is

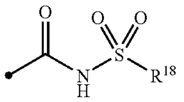

(wherein $R^{18}$ is as defined above), can be obtained according to the following step.

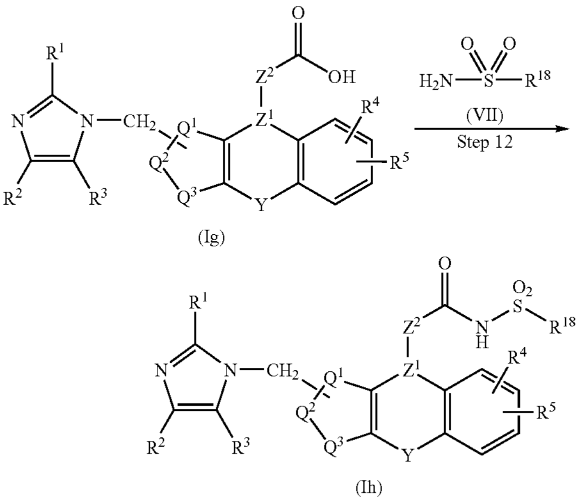

(wherein $R^1$, $R^2$, $R^3$, $R^4$, $R^5$, $R^{18}$, $Q^1$-$Q^2$-$Q^3$, $Z^1$-$Z^2$ and Y are as defined above, respectively).

Step 12

Compound (Ih) can be obtained by treating compound (Ig) obtained in production method 1 with 1 to 50 equivalent amount of a carboxylic acid activator, and then, by reacting the compound with 1 to 50 equivalent amount of compound (VII) in a solvent in the presence of 1 to 30 equivalent amount of a base for 5 min to 72 hr at a temperature between −20° C. and the boiling point of the solvent to be used.

Examples of the carboxylic acid activator include N,N'-carbonyldiimidazole (CDI), 1-(3-dimethylaminopropyl)-3-ethylcarbodiimide (EDCI) or hydrochloride thereof, dicyclohexylcarbodiimide (DCC) and the like. Examples of the solvent include dichloromethane, acetonitrile, toluene, ethyl acetate, THF, 1,4-dioxane, DMF, NMP and the like, and these can be used alone or in a mixture. Examples of the base include DBU, triethylamine, DMAP, N,N-dimethylaniline, pyridine, N-methylmorpholine and the like. In addition, compound (VII) can be obtained as a commercially available product.

The functional groups contained in $R^1$, $R^2$, $R^3$, $R^4$, $R^5$, $Z^1$, $Z^2$, A, and Y in compound (I) can also be converted by a known method (e.g., the method described in Comprehensive Organic Transformations 2nd edition, R. C. Larock, Vch Verlagsgesellschaft Mbh, 1999 and the like) or similar methods thereto.

The intermediates and the desired compounds in the above-mentioned respective production methods can be isolated and purified by applying separation purification methods usually used in the synthetic organic chemistry such as filtration, extraction, washing, drying, concentration, recrystallization, various chromatographies or the like. In addition, intermediates can also be subjected to a next reaction without particular purification.

Some of compounds (1) and (IA) contain a geometric isomer, a stereoisomer such as an optical isomer and the like, a tautomer and the like. The present invention comprises all possible isomers and mixtures thereof including these.

When a salt of compound (I) or (IA) is to be obtained, compound (I) or (IA) obtained in the form of a salt can be directly purified. When it is obtained in a free form, compound (I) or (IA) may be dissolved or suspended in a suitable solvent, and an acid or base is added thereto to form a salt, which may be isolated and purified.

While compounds (I) and (IA) and pharmaceutically acceptable salts thereof may exist in the form of adducts with water or various solvents, these adducts are also comprised in the present invention.

Specific examples of compound (I) obtained by the present invention are shown in Table 1 to Table 34. However, the compound of the present invention is not limited to them.

TABLE 1

(I)

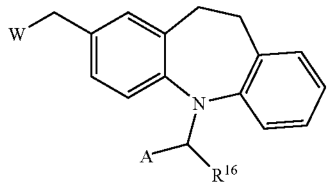

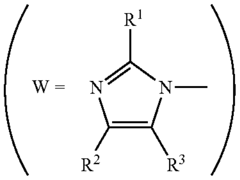

| Ex. No. | Compound No. | W | A | $R^{16}$ |
|---|---|---|---|---|
| 1 | 1 | 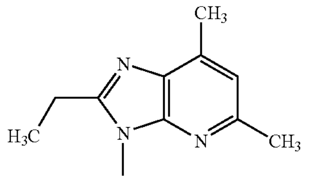 | 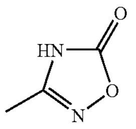 | H |
| 2 | 2 | 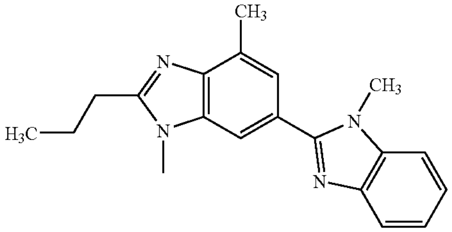 | 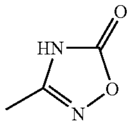 | H |
| 3 | 3 | 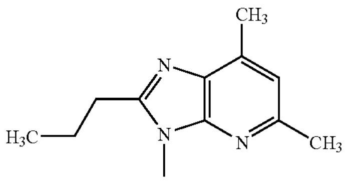 | 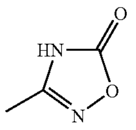 | H |
| 4 | 4 | 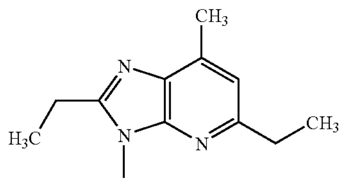 | 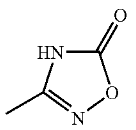 | H |

TABLE 1-continued
| | | | | |
|---|---|---|---|---|
| 5 | 5 | 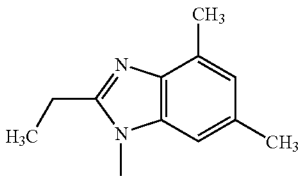 | 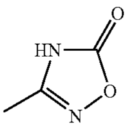 | H |
| 6 | 6 | 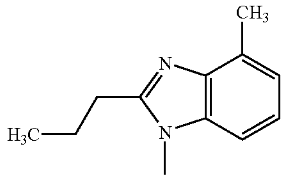 | 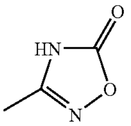 | H |
TABLE 2
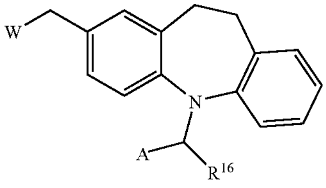
(I)
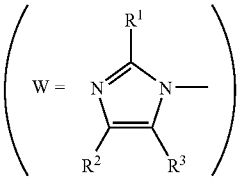
| Ex. No. | Compound No. | W | A | $R^{16}$ |
|---|---|---|---|---|
| 7 | 7 | 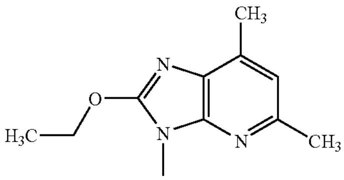 | 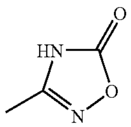 | H |
| 8 | 8 | 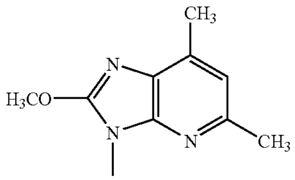 | 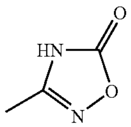 | H |
| 9 | 9 | 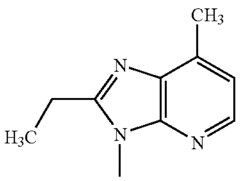 | 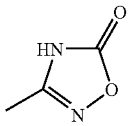 | H |

TABLE 2-continued
| | | | | |
|---|---|---|---|---|
| 10 | 10 | 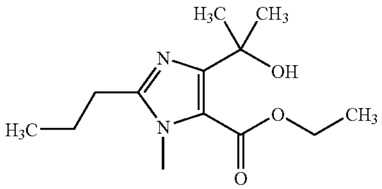 | 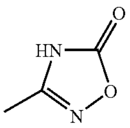 | H |
| 11 | 11 | 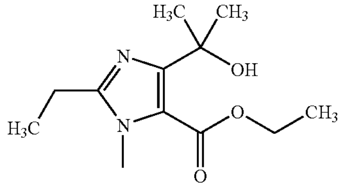 | 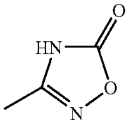 | H |
| 12 | 12 | 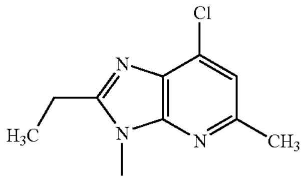 | 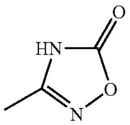 | H |
| 13 | 13 | 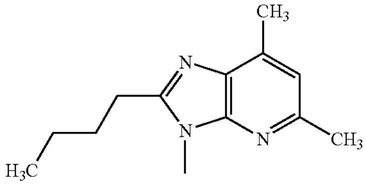 | 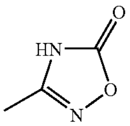 | H |
TABLE 3
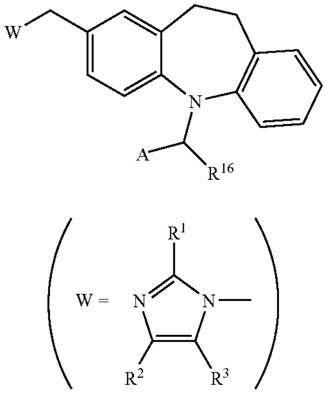
(I)
| Ex. No. | Compound No. | W | A | $R^{16}$ |
|---|---|---|---|---|
| 14 | 14 | 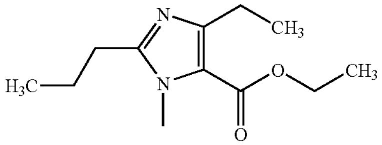 | 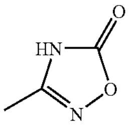 | H |

TABLE 3-continued
| | | | | |
|---|---|---|---|---|
| 15 | 15 | 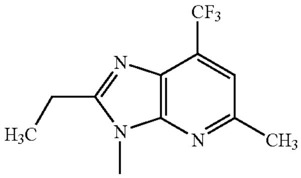 | 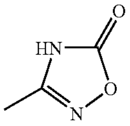 | H |
| 16 | 16 | 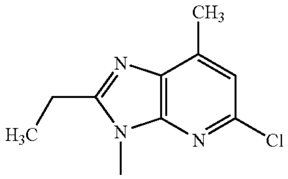 | 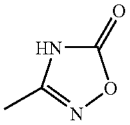 | H |
| 17 | 17 | 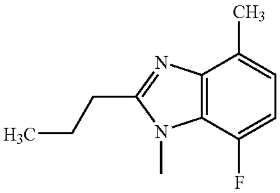 | 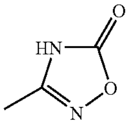 | H |
| 18 | 18 | 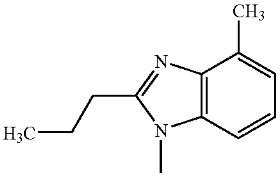 | 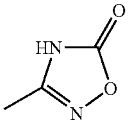 | $CH_3$ |
| 19 | 19 | 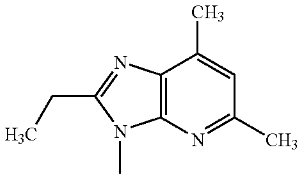 | 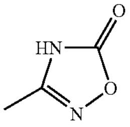 | $CH_3$ |
| 20 | 20 | 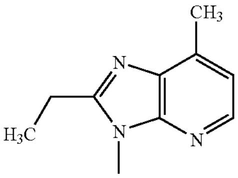 | 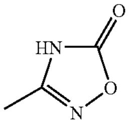 | $CH_3$ |

TABLE 4
(I)
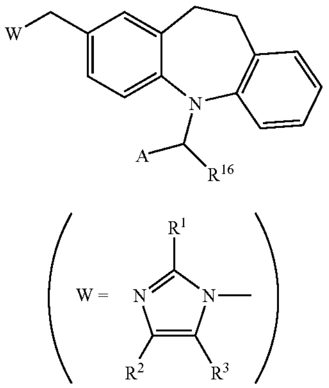
| Ex. No. | Compound No. | W | A | $R^{16}$ |
| --- | --- | --- | --- | --- |
| 21 | 21 | 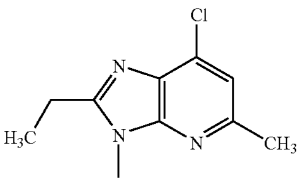 | 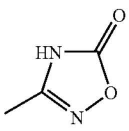 | $CH_3$ |
| 22 | 22 | 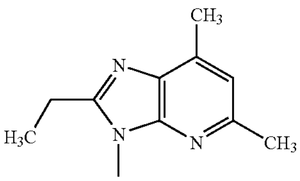 | 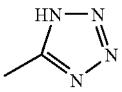 | $CH_3$ |
| 23 | 23 | 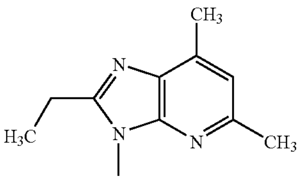 | 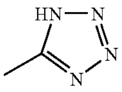 | $CH_2CH_3$ |
| 24 | 24 | 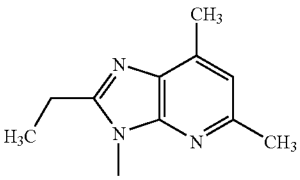 | 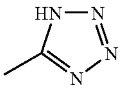 | $CH_2CH_2CH_3$ |
| 25 | 25 | 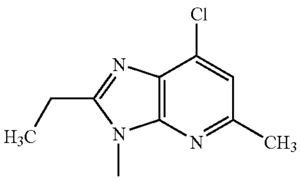 | 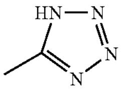 | $CH_3$ |
| 26 | 26 | 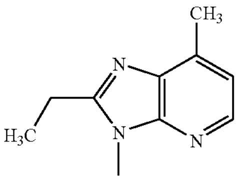 | 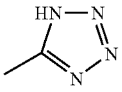 | $CH_3$ |

TABLE 4-continued
| | | | | |
|---|---|---|---|---|
| 27 | 27 | 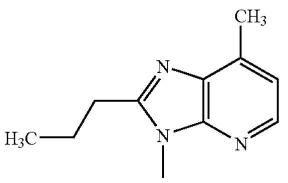 | 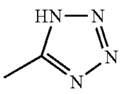 | $CH_3$ |
TABLE 5
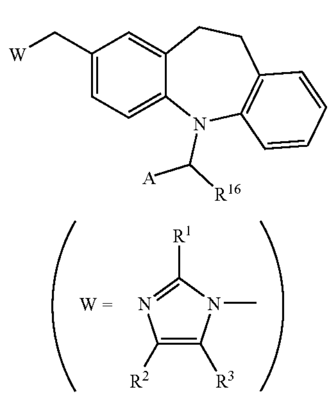
(I)
| Ex. No. | Compound No. | W | A | $R^{16}$ |
|---|---|---|---|---|
| 28 | 28 | 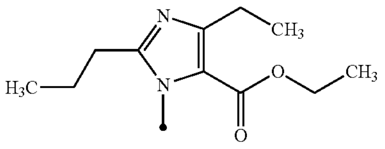 | 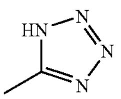 | $CH_3$ |
| 67 | 67 | 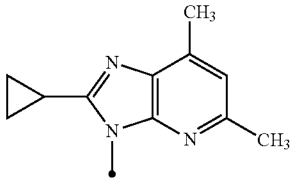 | 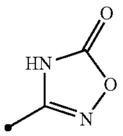 | H |
| 68 | 68 | 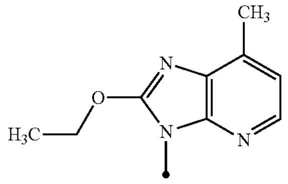 | 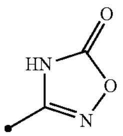 | H |
| 69 | 69 | 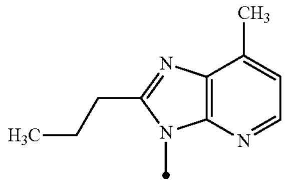 | 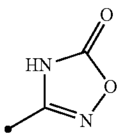 | $CH_3$ |

TABLE 5-continued
(I)
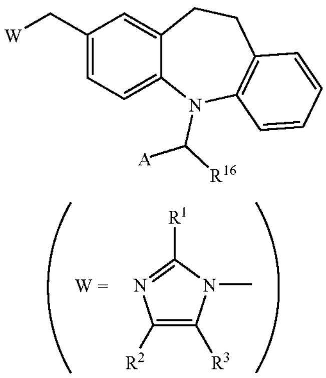
| Ex. No. | Compound No. | W | A | $R^{16}$ |
|---|---|---|---|---|
| 70 | 70 | 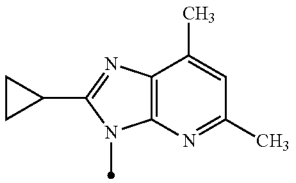 | 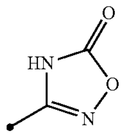 | $CH_3$ |
| 71 | 71 | 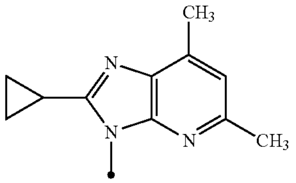 | 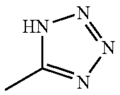 | $CH_3$ |
TABLE 6
(I)
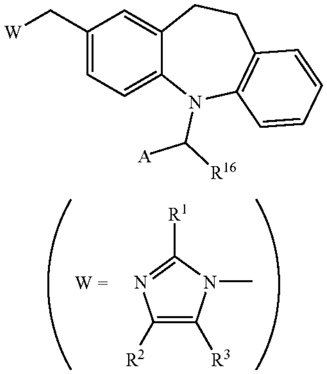
| Ex. No. | Compound No. | W | A | $R^{16}$ |
|---|---|---|---|---|
| 72 | 72 | 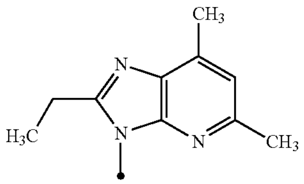 | 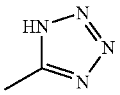 | (−) form $CH_3$ |

TABLE 6-continued
(I)
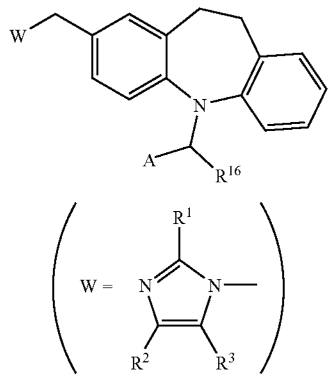
| Ex. No. | Compound No. | W | A | $R^{16}$ |
|---|---|---|---|---|
| 73 | 73 | 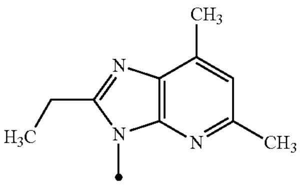 | 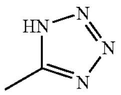 | (+) form $CH_3$ |
| 74 | 74 | 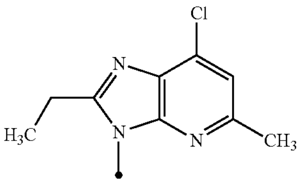 | 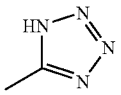 | (−) form $CH_3$ |
| 75 | 75 | 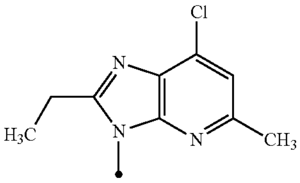 | 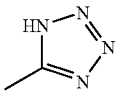 | (+) form $CH_3$ |
| 76 | 76 | 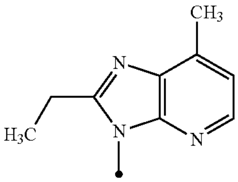 | 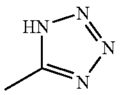 | (−) form $CH_3$ |
| 77 | 77 | 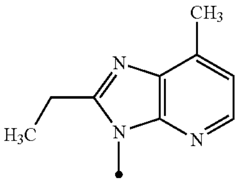 | 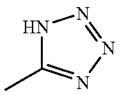 | (+) form $CH_3$ |

TABLE 7
(I)
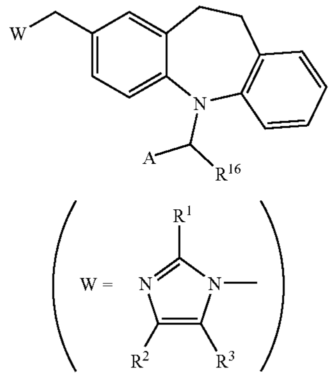
| Ex. No. | Compound No. | W | A | $R^{16}$ |
|---|---|---|---|---|
| 78 | 78 | 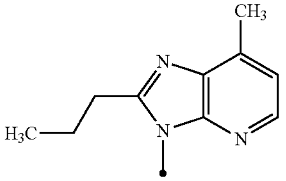 | 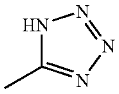 | (−) form $CH_3$ |
| 79 | 79 | 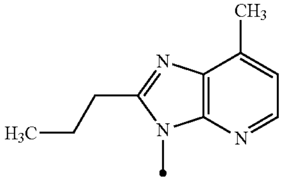 | 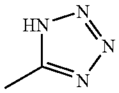 | (+) form $CH_3$ |
| 80 | 80 | 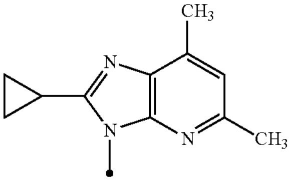 | 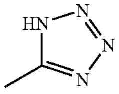 | (−) form $CH_3$ |
| 81 | 81 | 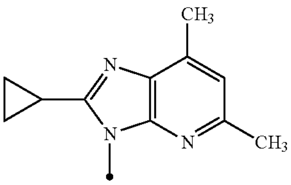 | 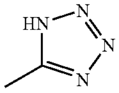 | (+) form $CH_3$ |

TABLE 8
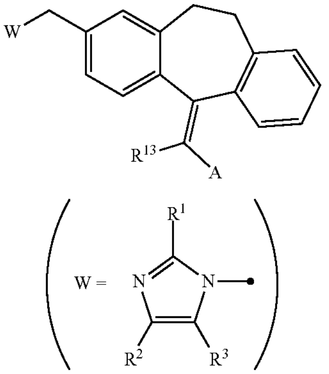
(I)
| Ex. No. | Compound No. | W | A | $R^{13}$ |
|---|---|---|---|---|
| 29 | 29 | 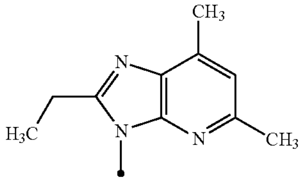 | 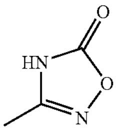 | H |
| 30 | 30 | 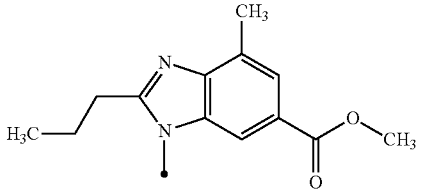 | 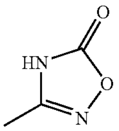 | H |
| 31 | 31 | 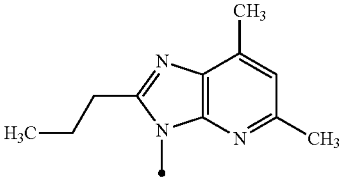 | 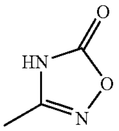 | H |
| 32 | 32 | 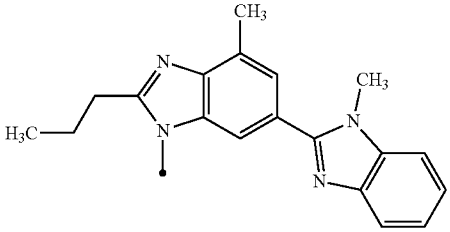 | 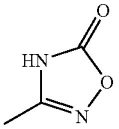 | H |
| 33 | 33 | 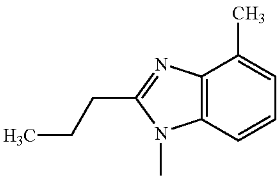 | 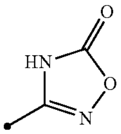 | H |

TABLE 8-continued
(I)
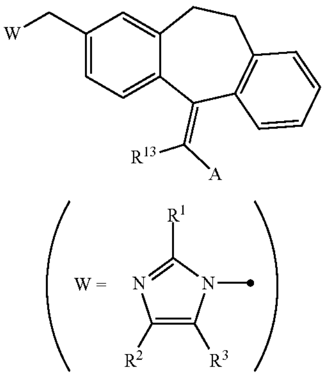
| Ex. No. | Compound No. | W | A | $R^{13}$ |
|---|---|---|---|---|
| 34 | 34 | 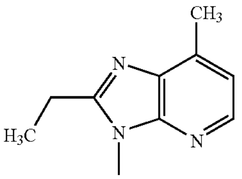 | 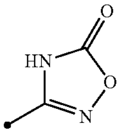 | H |
TABLE 9
(I)
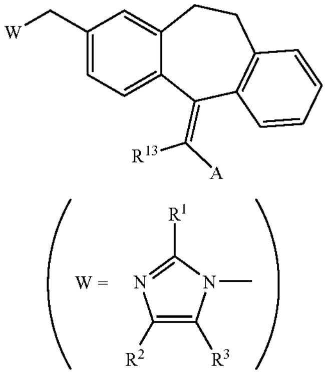
| Ex. No. | Compound No. | W | A | $R^{13}$ |
|---|---|---|---|---|
| 35 | 35 | 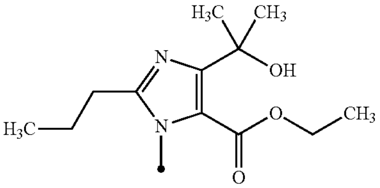 | 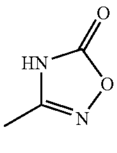 | H |
| 36 | 36 | 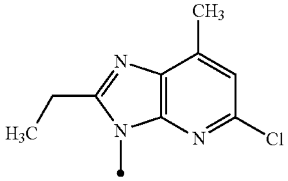 | 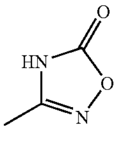 | H |

TABLE 9-continued
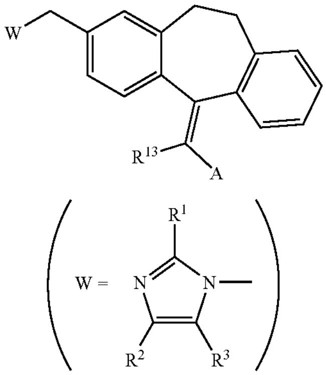
(I)
| Ex. No. | Compound No. | W | A | $R^{13}$ |
|---|---|---|---|---|
| 37 | 37 | 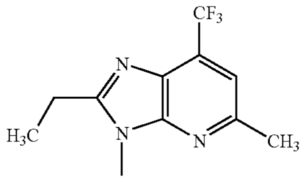 | 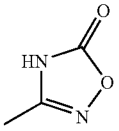 | H |
| 38 | 38 | 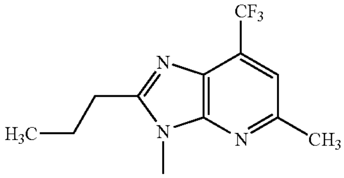 | 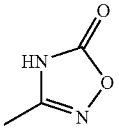 | H |
| 39 | 39 | 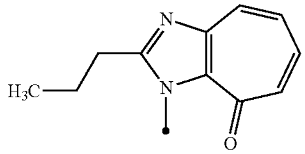 | 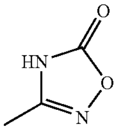 | H |
| 40 | 40 | 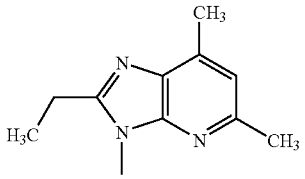 | 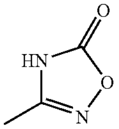 | $CH_3$ |
| 41 | 41 | 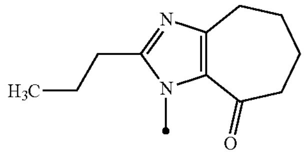 | 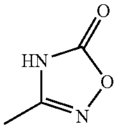 | H |

TABLE 10
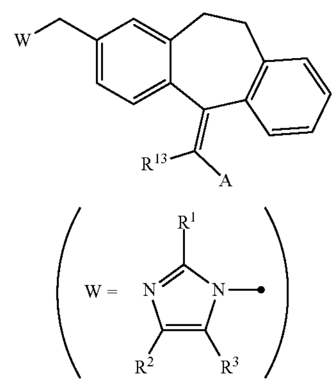
(I)
| Ex. No. | Compound No. | W | A | $R^{13}$ |
|---|---|---|---|---|
| 42 | 42 | 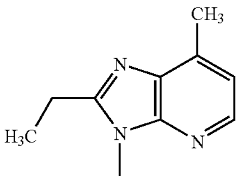 | 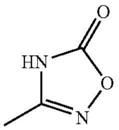 | $CH_3$ |
| 43 | 43 | 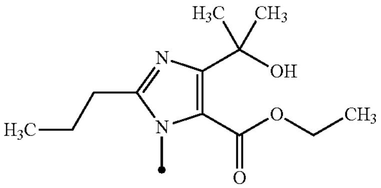 | 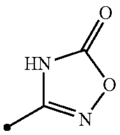 | $CH_3$ |
| 44 | 44 | 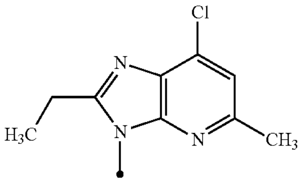 | 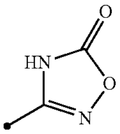 | $CH_3$ |
| 45 | 45 | 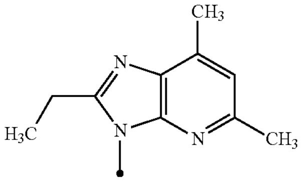 | 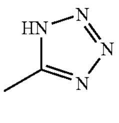 | $CH_3$ |
| 46 | 46 | 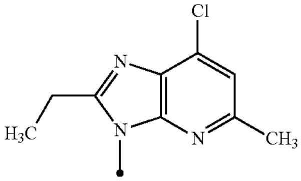 | 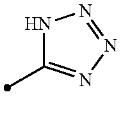 | $CH_3$ |
| 47 | 47 | 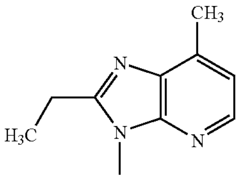 | 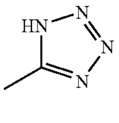 | $CH_3$ |

TABLE 11
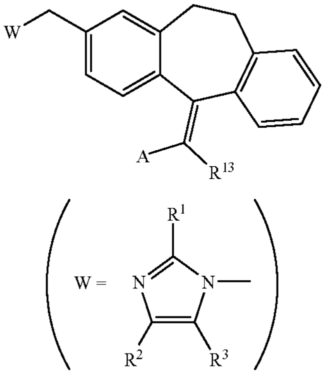
(I)
| Ex. No. | Compound No. | W | A | $R^{13}$ |
|---|---|---|---|---|
| 48 | 48 | 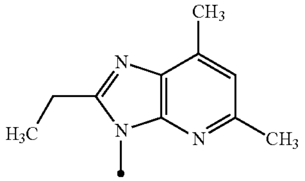 | 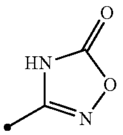 | H |
| 49 | 49 | 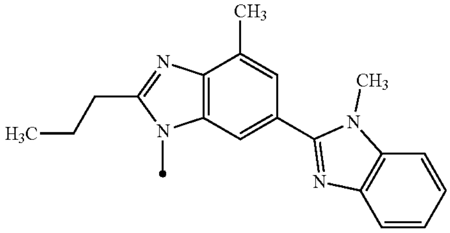 | 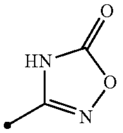 | H |
| 50 | 50 | 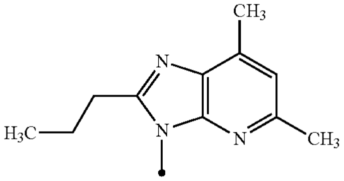 | 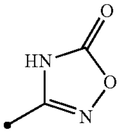 | H |
| 51 | 51 | 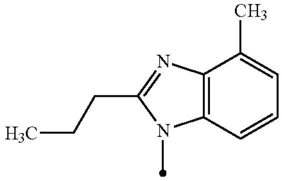 | 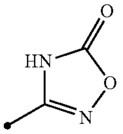 | H |
| 52 | 52 | 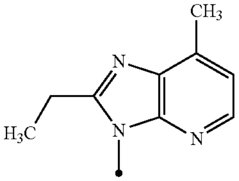 | 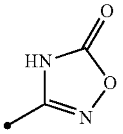 | H |

TABLE 11-continued
(I)
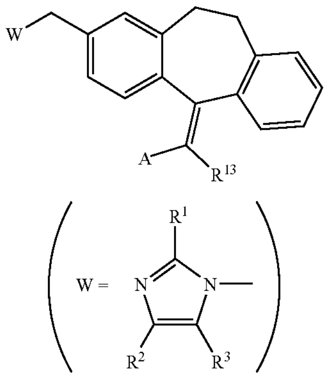
| Ex. No. | Compound No. | W | A | $R^{13}$ |
|---|---|---|---|---|
| 53 | 53 | 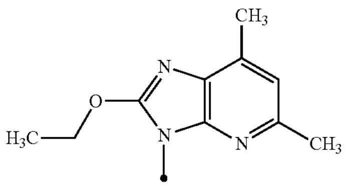 | 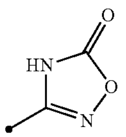 | H |
TABLE 12
(I)
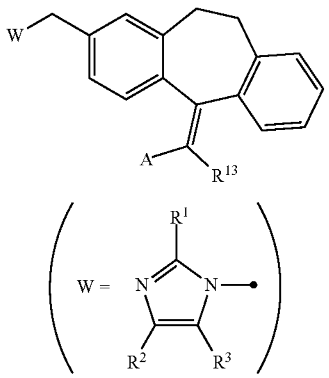
| Ex. No. | Compound No. | W | A | $R^{13}$ |
|---|---|---|---|---|
| 54 | 54 | 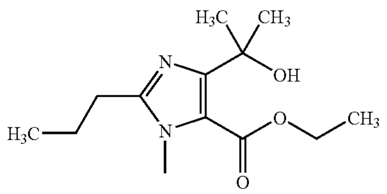 | 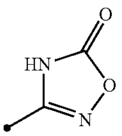 | H |
| 55 | 55 | 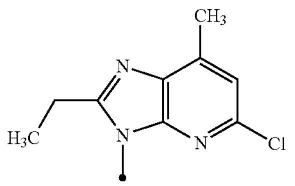 | 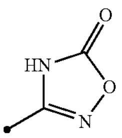 | H |

TABLE 12-continued
(I)
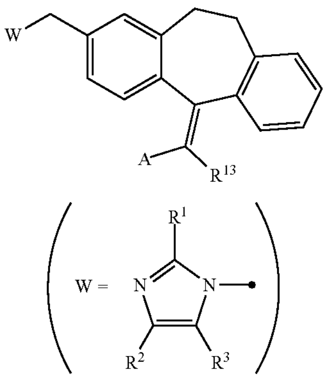
| Ex. No. | Compound No. | W | A | $R^{13}$ |
|---|---|---|---|---|
| 56 | 56 | 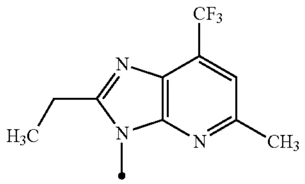 | 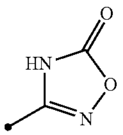 | H |
| 57 | 57 | 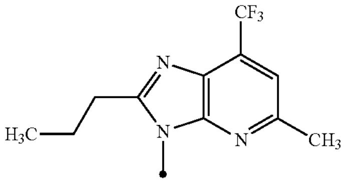 | 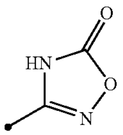 | H |
| 58 | 58 | 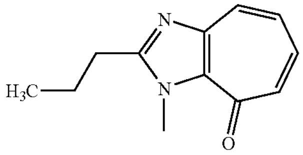 | 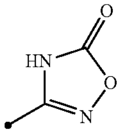 | H |
| 59 | 59 | 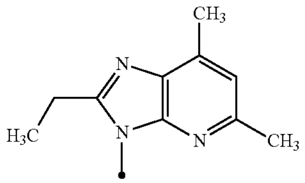 | 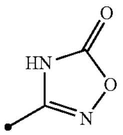 | $CH_3$ |
| 60 | 60 | 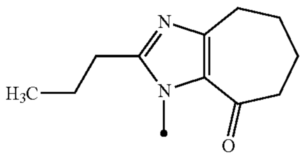 | 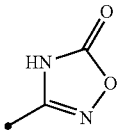 | H |

TABLE 13
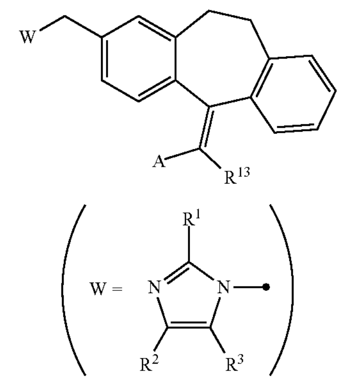
(I)
| Ex. No. | Compound No. | W | A | $R^{13}$ |
|---|---|---|---|---|
| 61 | 61 | 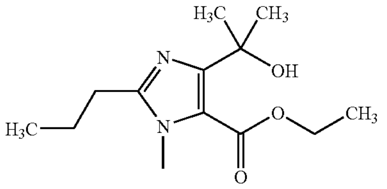 | 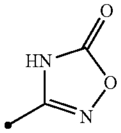 | $CH_3$ |
| 62 | 62 | 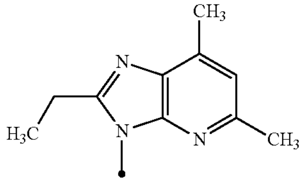 | 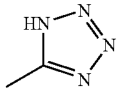 | $CH_3$ |
TABLE 14
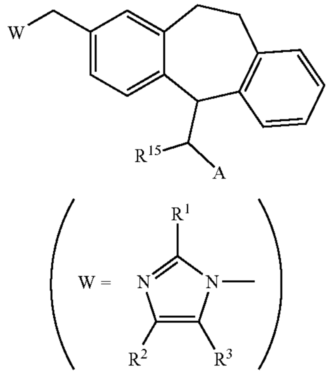
(I)
| Ex. No. | Compound No. | W | A | $R^{15}$ |
|---|---|---|---|---|
| 63 | 63 | 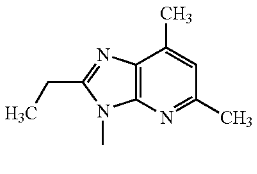 | 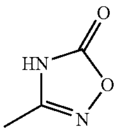 | H |
TABLE 14-continued
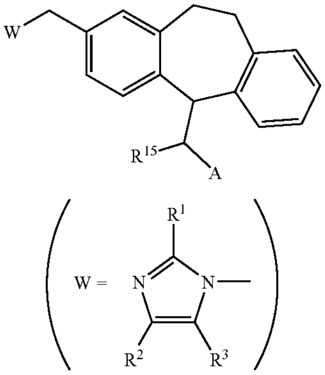
(I)
| Ex. No. | Compound No. | W | A | $R^{15}$ |
|---|---|---|---|---|
| 64 | 64 | 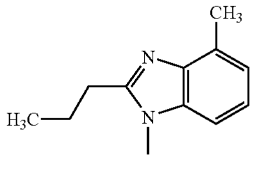 | 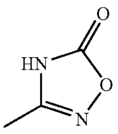 | H |

TABLE 14-continued
(I)
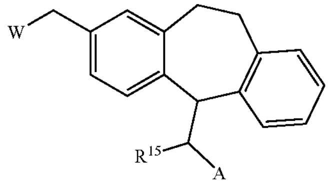
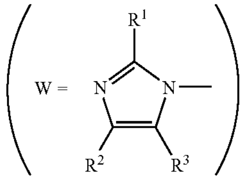
| Ex. No. | Compound No. | W | A | $R^{15}$ |
|---|---|---|---|---|
| 65 | 65 | 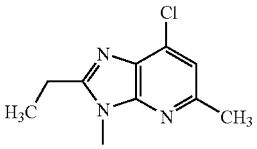 | 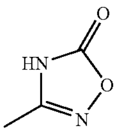 | H |
TABLE 14-continued
(I)
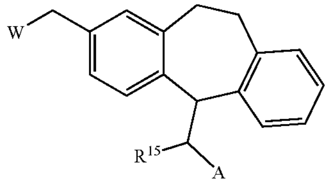
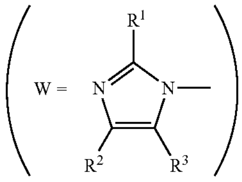
| Ex. No. | Compound No. | W | A | $R^{15}$ |
|---|---|---|---|---|
| 66 | 66 | 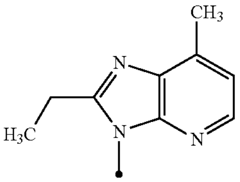 | 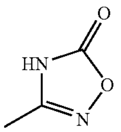 | H |
TABLE 15
(I)
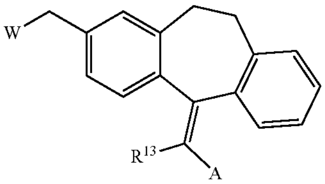
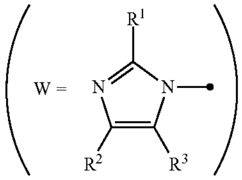
| Ex. No. | Compound No. | W | A | $R^{13}$ |
|---|---|---|---|---|
| 82 | 82 | 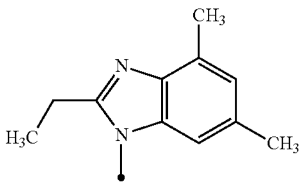 | 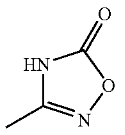 | $CH_3$ |
| 83 | 83 | 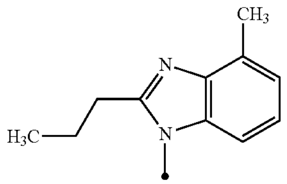 | 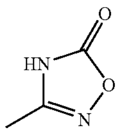 | $CH_3$ |

TABLE 15-continued
(I)
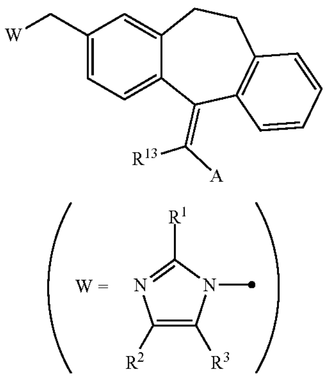
| Ex. No. | Compound No. | W | A | $R^{13}$ |
|---|---|---|---|---|
| 84 | 84 | 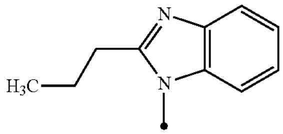 | 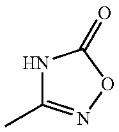 | $CH_3$ |
| 85 | 85 | 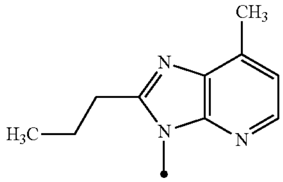 | 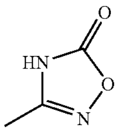 | $CH_3$ |
| 86 | 86 | 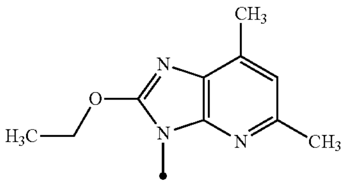 | 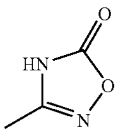 | $CH_3$ |
| 87 | 87 | 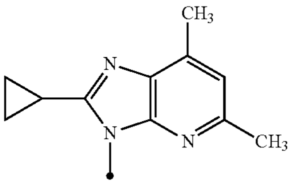 | 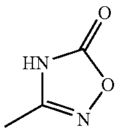 | $CH_3$ |

TABLE 16
(I)
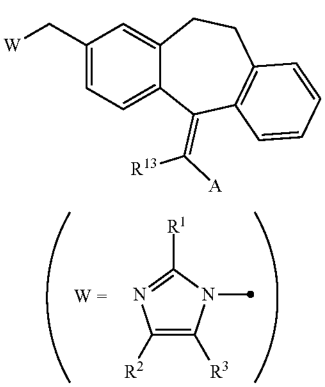
| Ex. No. | Compound No. | W | A | $R^{13}$ |
|---|---|---|---|---|
| 88 | 88 | 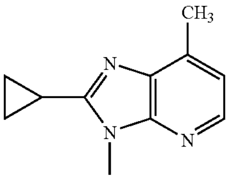 | 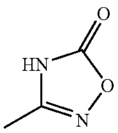 | $CH_3$ |
| 89 | 89 | 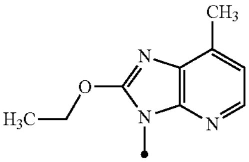 | 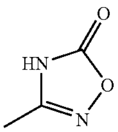 | $CH_3$ |
| 90 | 90 | 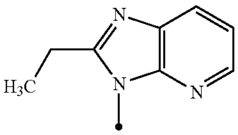 | 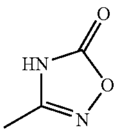 | $CH_3$ |
| 91 | 91 | 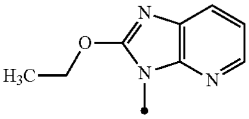 | 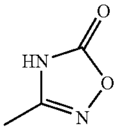 | $CH_3$ |
| 92 | 92 | 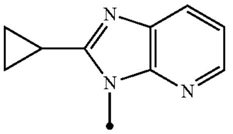 | 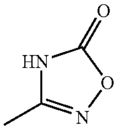 | $CH_3$ |
| 93 | 93 | 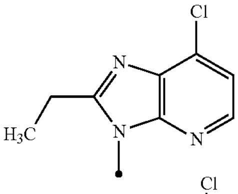 | 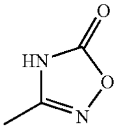 | $CH_3$ |
| 94 | 94 | 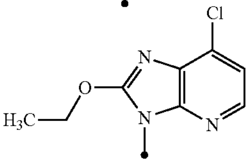 | 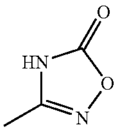 | $CH_3$ |
TABLE 17
(I)
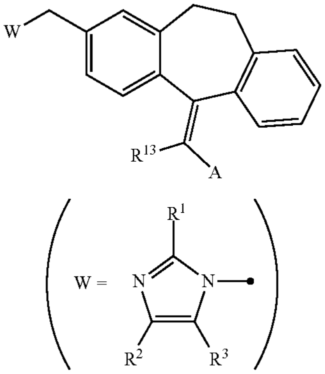
| Ex. No. | Compound No. | W | A | $R^{13}$ |
|---|---|---|---|---|
| 95 | 95 | 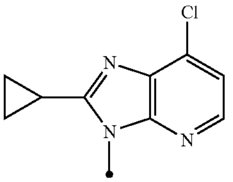 | 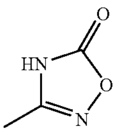 | $CH_3$ |
| 96 | 96 | 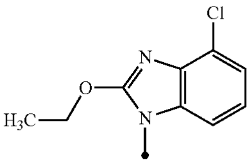 | 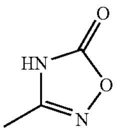 | $CH_3$ |
| 97 | 97 | 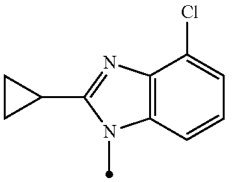 | 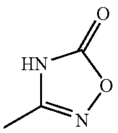 | $CH_3$ |
| 98 | 98 | 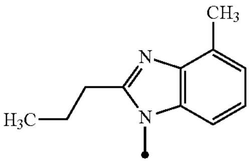 | 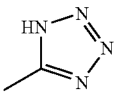 | $CH_3$ |
| 99 | 99 | 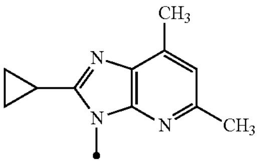 | 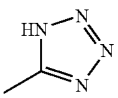 | $CH_3$ |
| 100 | 100 | 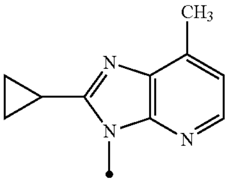 | 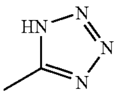 | $CH_3$ |

TABLE 18
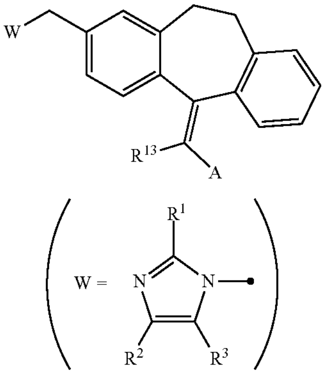
(I)
| Ex. No. | Compound No. | W | A | $R^{13}$ |
|---|---|---|---|---|
| 101 | 101 | 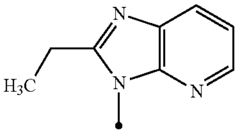 | 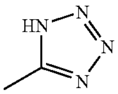 | $CH_3$ |
| 102 | 102 | 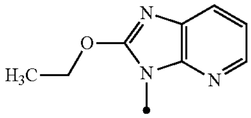 | 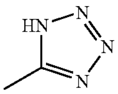 | $CH_3$ |
| 103 | 103 | 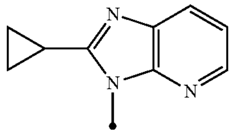 | 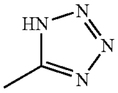 | $CH_3$ |
TABLE 19
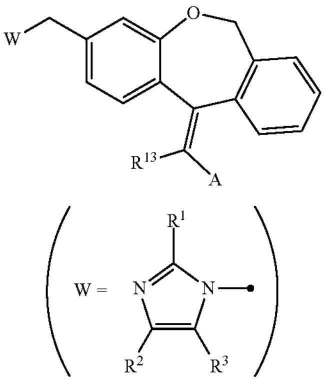
(I)
| Ex. No. | Compound No. | W | A | $R^{13}$ |
|---|---|---|---|---|
| 104 | 104 | 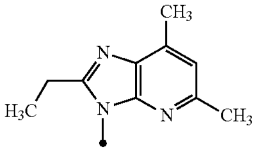 | 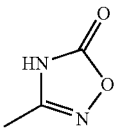 | H |
TABLE 19-continued
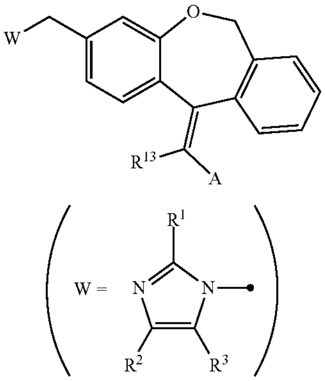
(I)
| Ex. No. | Compound No. | W | A | $R^{13}$ |
|---|---|---|---|---|
| 105 | 105 | 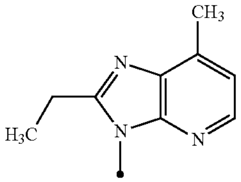 | 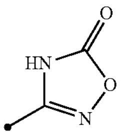 | H |
| 106 | 106 | 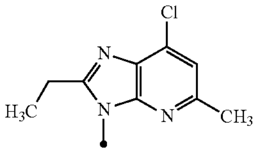 | 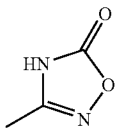 | H |
| 107 | 107 | 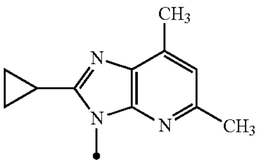 | 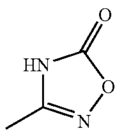 | H |
| 108 | 108 | 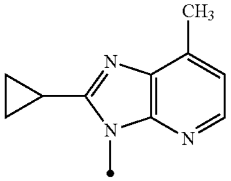 | 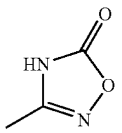 | H |
| 109 | 109 | 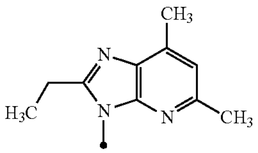 | 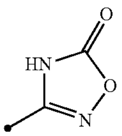 | $CH_3$ |

TABLE 20
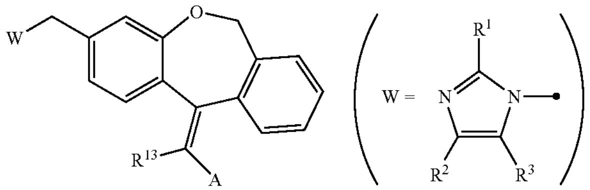
(I)
| Ex. No. | Compound No. | W | A | $R^{13}$ |
|---|---|---|---|---|
| 110 | 110 | 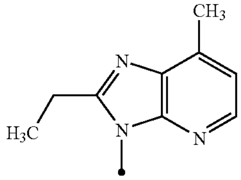 | 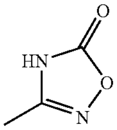 | $CH_3$ |
| 111 | 111 | 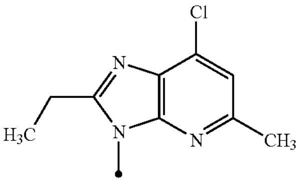 | 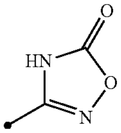 | $CH_3$ |
| 112 | 112 | 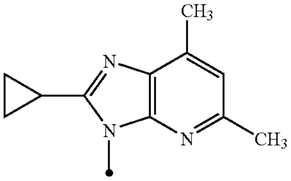 | 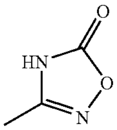 | $CH_3$ |
| 113 | 113 | 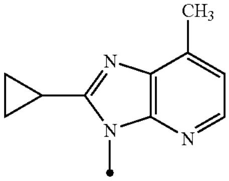 | 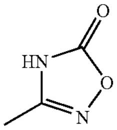 | $CH_3$ |
| 114 | 114 | 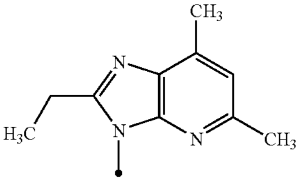 | 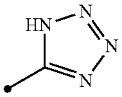 | $CH_3$ |
| 115 | 115 | 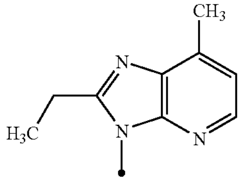 | 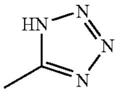 | $CH_3$ |

TABLE 21
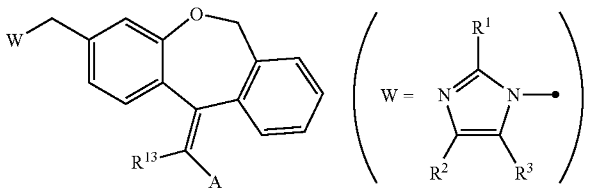
(I)
| Ex. No. | Compound No. | W | A | $R^{13}$ |
|---|---|---|---|---|
| 116 | 116 | 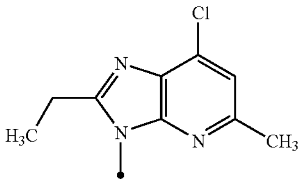 | 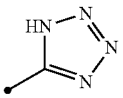 | $CH_3$ |
| 117 | 117 | 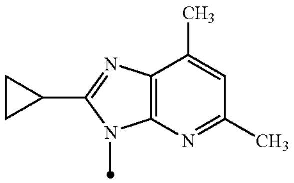 | 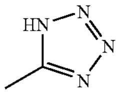 | $CH_3$ |
TABLE 22
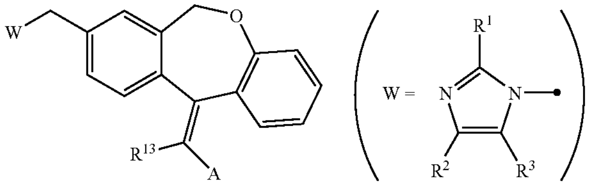
(I)
| Ex. No. | Compound No. | W | A | $R^{13}$ |
|---|---|---|---|---|
| 118 | 118 | 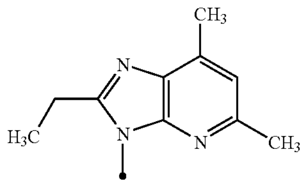 | 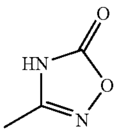 | H |
| 119 | 119 | 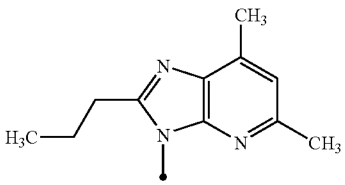 | 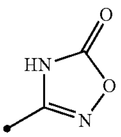 | H |
| 120 | 120 | 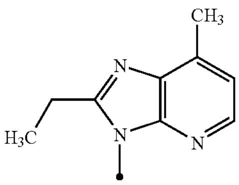 | 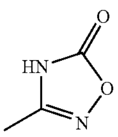 | H |

TABLE 22-continued
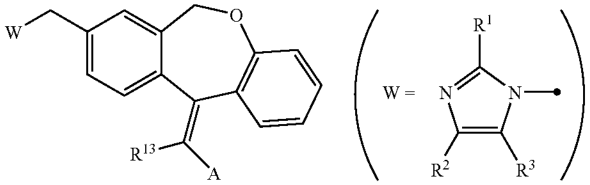
(I)
| Ex. No. | Compound No. | W | A | $R^{13}$ |
|---|---|---|---|---|
| 121 | 121 | 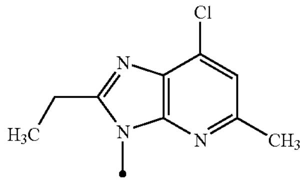 | 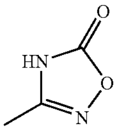 | H |
| 122 | 122 | 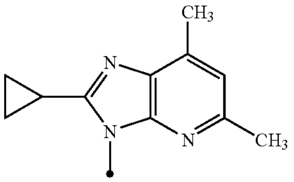 | 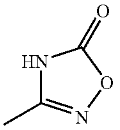 | H |
| 123 | 123 | 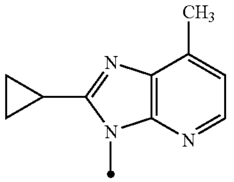 | 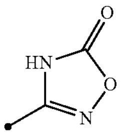 | H |
TABLE 23
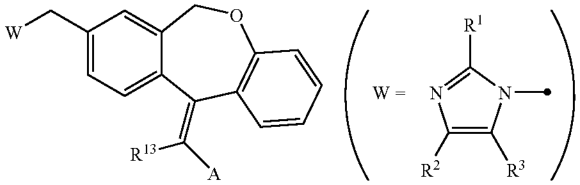
(I)
| Ex. No. | Compound No. | W | A | $R^{13}$ |
|---|---|---|---|---|
| 124 | 124 | 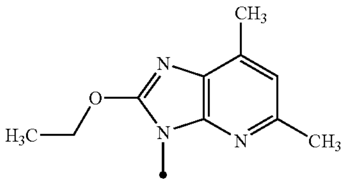 | 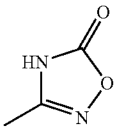 | H |
| 125 | 125 | 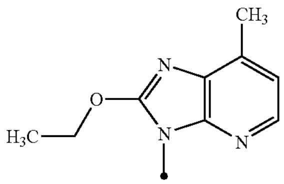 | 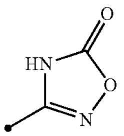 | H |

TABLE 23-continued
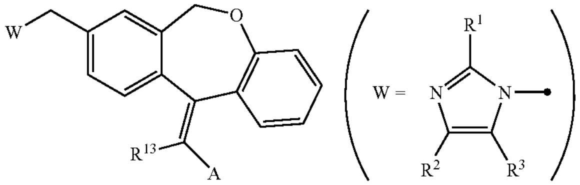
(I)
| Ex. No. | Compound No. | W | A | $R^{13}$ |
|---|---|---|---|---|
| 126 | 126 | 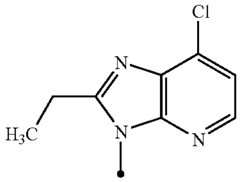 | 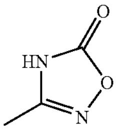 | H |
| 127 | 127 | 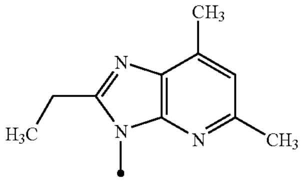 | 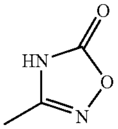 | $CH_3$ |
| 128 | 128 | 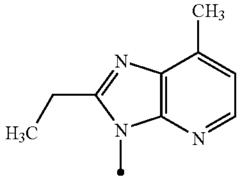 | 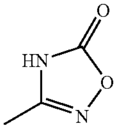 | $CH_3$ |
| 129 | 129 | 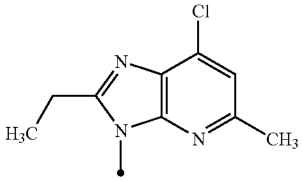 | 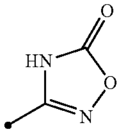 | $CH_3$ |
TABLE 24
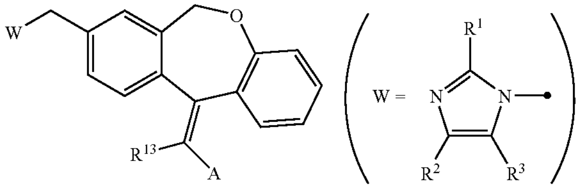
(I)
| Ex. No. | Compound No. | W | A | $R^{13}$ |
|---|---|---|---|---|
| 130 | 130 | 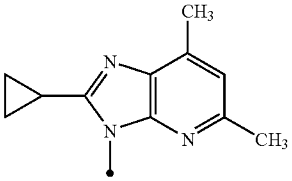 | 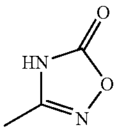 | $CH_3$ |

TABLE 24-continued
(I)
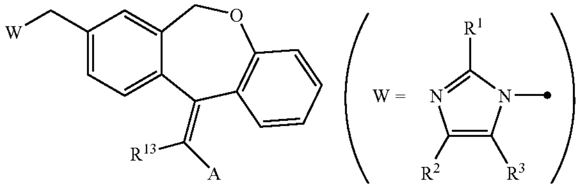
| Ex. No. | Compound No. | W | A | $R^{13}$ |
|---|---|---|---|---|
| 131 | 131 | 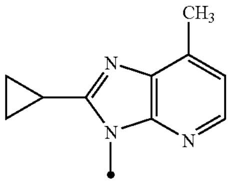 | 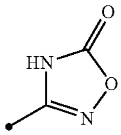 | $CH_3$ |
| 132 | 132 | 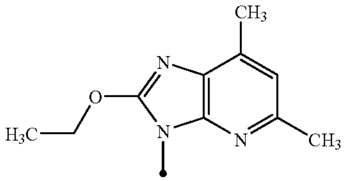 | 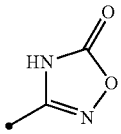 | $CH_3$ |
| 133 | 133 | 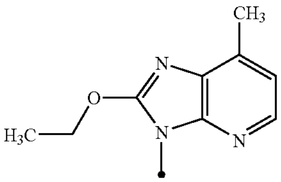 | 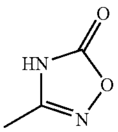 | $CH_3$ |
| 134 | 134 | 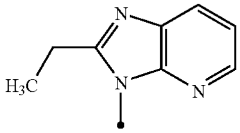 | 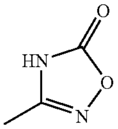 | $CH_3$ |
| 135 | 135 | 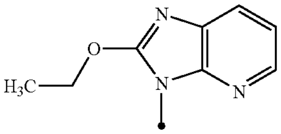 | 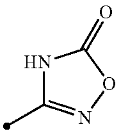 | $CH_3$ |
| 136 | 136 | 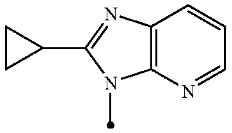 | 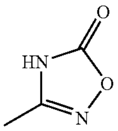 | $CH_3$ |

TABLE 25
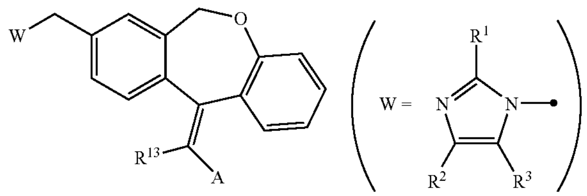
(I)
| Ex. No. | Compound No. | W | A | $R^{13}$ |
|---|---|---|---|---|
| 137 | 137 | 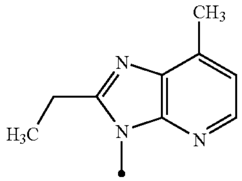 | 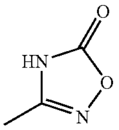 | $CH_3$ |
| 138 | 138 | 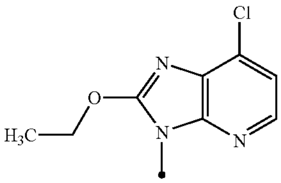 | 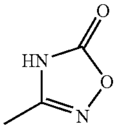 | $CH_3$ |
| 139 | 139 | 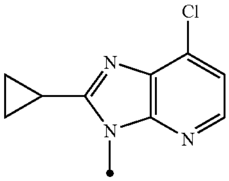 | 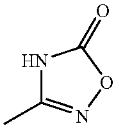 | $CH_3$ |
| 140 | 140 | 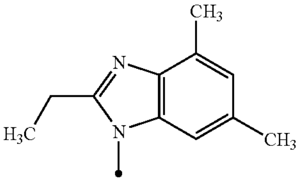 | 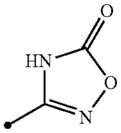 | $CH_3$ |
TABLE 26
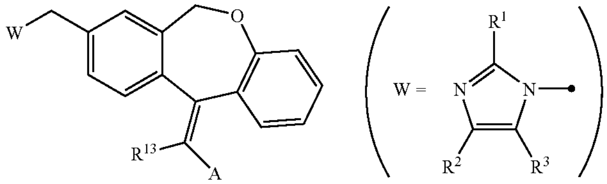
(I)
| Ex. No. | Compound No. | W | A | $R^{13}$ |
|---|---|---|---|---|
| 141 | 141 | 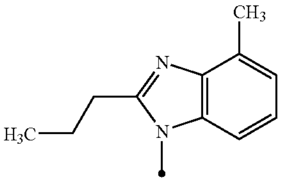 | 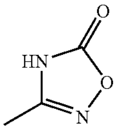 | $CH_3$ |

TABLE 26-continued
(I)
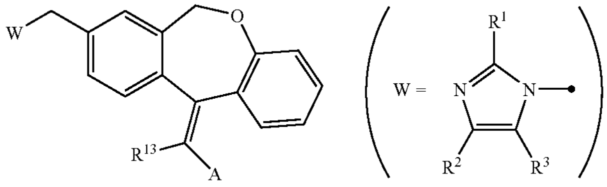
| Ex. No. | Compound No. | W | A | $R^{13}$ |
|---|---|---|---|---|
| 142 | 142 | 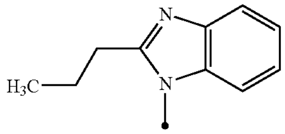 | 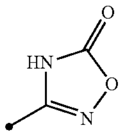 | $CH_3$ |
| 143 | 143 | 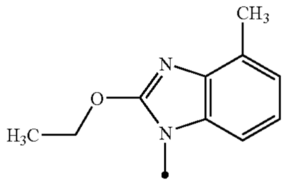 | 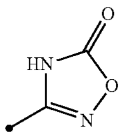 | $CH_3$ |
| 144 | 144 | 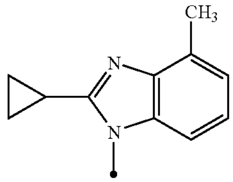 | 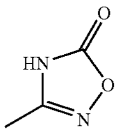 | $CH_3$ |
| 145 | 145 | 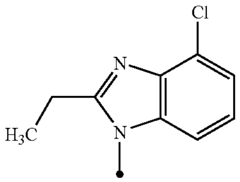 | 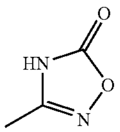 | $CH_3$ |
| 146 | 146 | 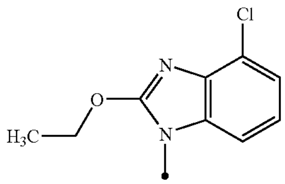 | 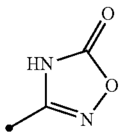 | $CH_3$ |

TABLE 27
(I)
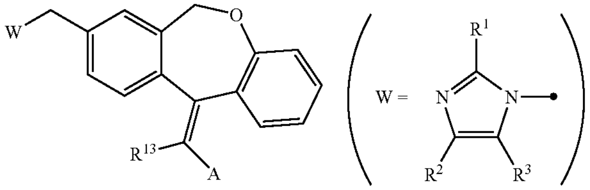
| Ex. No. | Compound No. | W | A | $R^{13}$ |
|---|---|---|---|---|
| 147 | 147 | 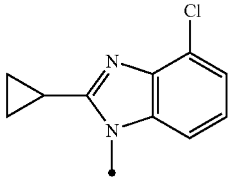 | 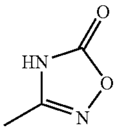 | $CH_3$ |
| 148 | 148 | 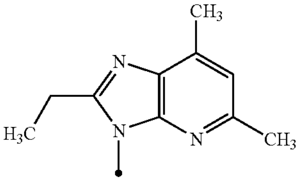 | 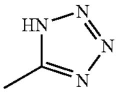 | $CH_3$ |
| 149 | 149 | 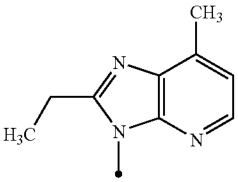 | 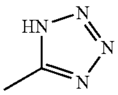 | $CH_3$ |
| 150 | 150 | 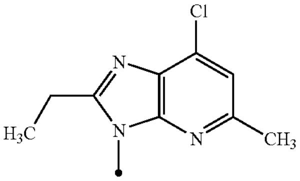 | 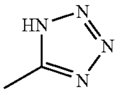 | $CH_3$ |
| 151 | 151 | 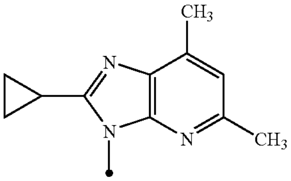 | 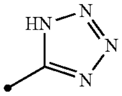 | $CH_3$ |
| 152 | 152 | 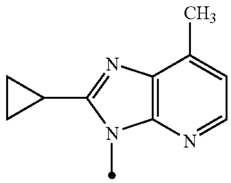 | 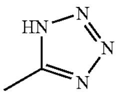 | $CH_3$ |

TABLE 28
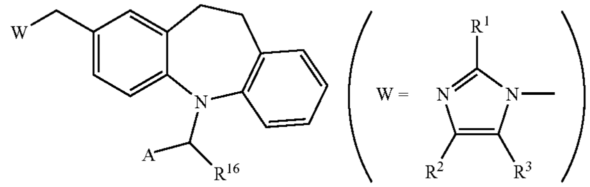
(I)
| Ref. No. | Compound No. | W | A | $R^{16}$ |
|---|---|---|---|---|
| 7 | S7 | 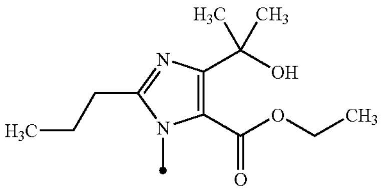 | 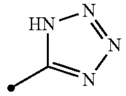 | H |
| 8 | S8 | 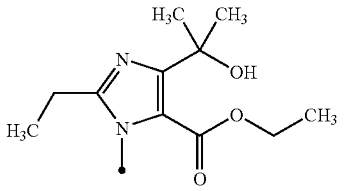 | 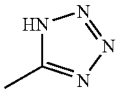 | H |
| 9 | S9 | 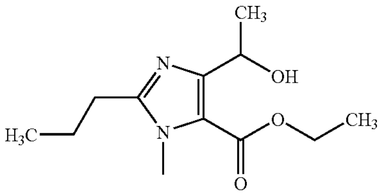 | 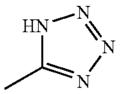 | H |
| 10 | S10 | 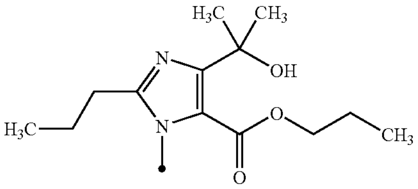 | 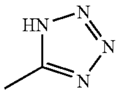 | H |
| 11 | S11 | 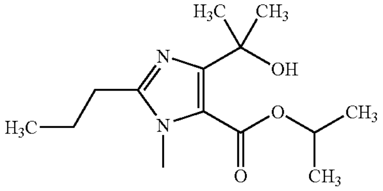 | 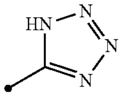 | H |
| 12 | S12 | 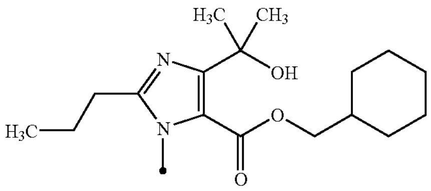 | 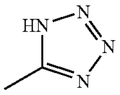 | H |

TABLE 29
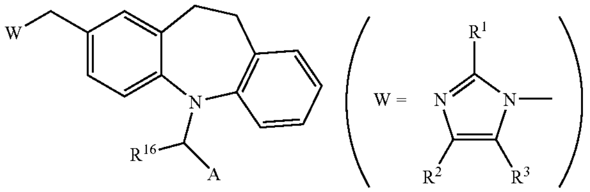
(I)
| Ref. No. | Compound No. | W | A | $R^{16}$ |
|---|---|---|---|---|
| 13 | S13 | 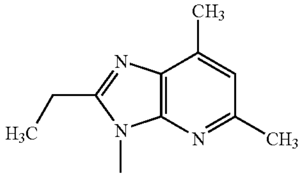 | 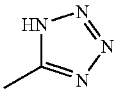 | H |
| 14 | S14 | 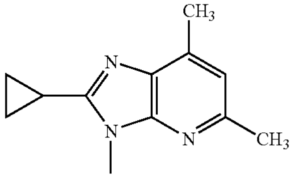 | 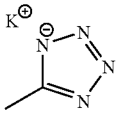 | H |
TABLE 30
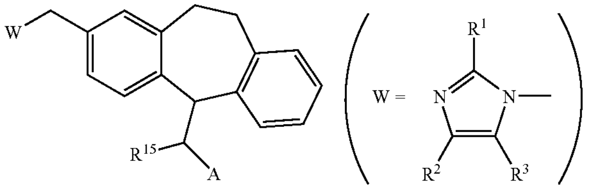
(I)
| Ref. No. | Compound No. | W | A | $R^{15}$ |
|---|---|---|---|---|
| 15 | S15 | 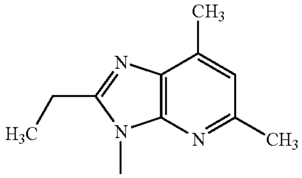 | 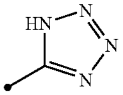 | H |

TABLE 31
(I)
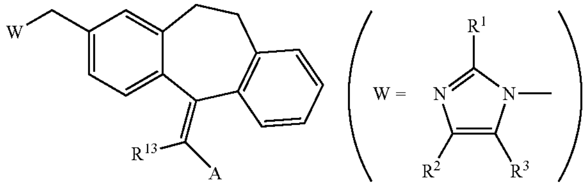
| Ref. No. | Compound No. | W | A | $R^{13}$ |
|---|---|---|---|---|
| 16 | S16 | 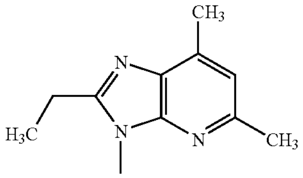 | 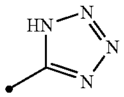 | H |
TABLE 32
(I)
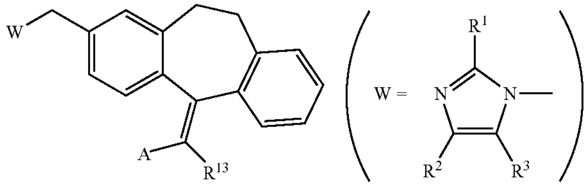
| Ref. No. | Compound No. | W | A | $R^{13}$ |
|---|---|---|---|---|
| 17 | S17 | 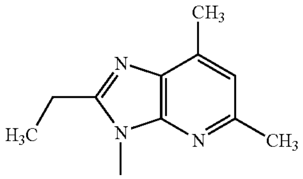 | 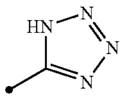 | H |
TABLE 33
(I)
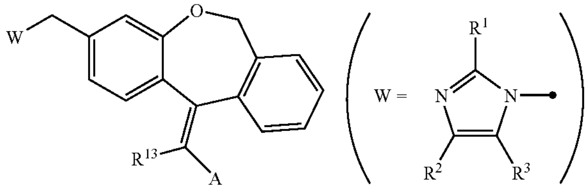
| Ref. No. | Compound No. | W | A | $R^{13}$ |
|---|---|---|---|---|
| 18 | S18 | 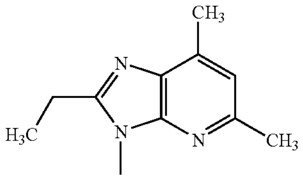 | 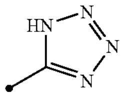 | H |

TABLE 34

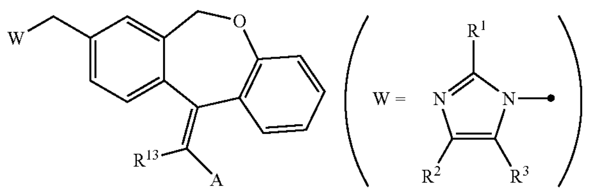

(I)

| Ref. No. | Compound No. | W | A | $R^{13}$ |
|---|---|---|---|---|
| 19 | S19 | 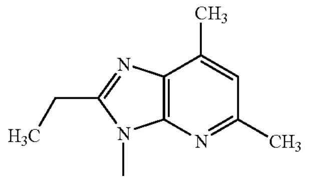 | 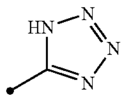 | H |

Next, the pharmacological action of the representative compound (I) is specifically explained by Test Examples.

Test Example 1

Examination of PPARγ Activation Action Based on Transactivation Assay of PPARγ by Transient Gene Transfer The agonist activity of compound (I) to PPARγ was determined by a transactivation assay method using a chimeric nuclear receptor of a DNA binding region of a yeast transcription factor GAL4 and a PPARγ ligand binding region. Specifically, the PPARγ agonist activity of compound (I) was evaluated by the following method based on the method of Lehmann et al. (J Biol. Chem., 1995, vol. 270, page 12953).

HEK293EBNA cells cultured in Dulbecco's Modified Eagle medium (Invitrogen) containing 10 v/v % fetal calf serum (Invitrogen) were used. 30 mL of the above-mentioned cells (density: $1\times10^5$ cells/mL) were inoculated in a 10 $cm^2$ culture dish (Iwaki Glass), and cultured overnight. Using SuperFect Transfection Reagent (QIAGEN), a plasmid expressing a GAL4-PPARγ chimeric nuclear receptor fusing 174-475 amino acids, which are human PPARγ ligand binding region, and 1-147 amino acids, which are GAL4 DNA binding region, and a reporter plasmid expressing a GAL4 responsive luciferase were transiently introduced into the cells at a proportion of 4:1. After 5 hr from gene introduction, the cells were detached from the culture dish, and the detached cells (density: $2\times10^4$ cells/mL) were inoculated by 100 μL in each well of a 96 well white plate (SUMITOMO BAKELITE), and cultured overnight. The medium was removed, compound (I) diluted in various concentrations with serum-free Dulbecco's Modified Eagle medium was added by 100 μL, and the mixture was reacted under a 5% carbon dioxide gas stream (5% $CO_2$) at 37° C. for 24 hr. On the other hand, as a positive control, 10 μmol/L of pioglitazone (100 μL) was added, and the mixture was reacted under a 5% carbon dioxide gas stream (5% $CO_2$) at 37° C. for 24 hr. As a substrate of luciferase, 100 μL of Steady-Glo (Promega) was added to each well and the mixture was thoroughly stirred. Immediately thereafter, the chemical luminescence due to luciferase was measured using TopCount NTX (Packard).

The agonist activity (activity rate (%)) of compound (I) to PPARγ was calculated according to the following formula, as a relative activity when the agonist activity on addition of pioglitazone (10 μmol/L) was 100%.

$$\text{activity rate (\%)} = \frac{\begin{pmatrix}\text{luminescence intensity with}\\ \text{addition of compound }(I)\end{pmatrix} - \begin{pmatrix}\text{luminescence intensity without}\\ \text{addition of compound }(I)\end{pmatrix}}{\begin{pmatrix}\text{luminescence intensity with}\\ \text{addition of pioglitazone 10 }\mu\text{mol/L}\end{pmatrix} - \begin{pmatrix}\text{luminescence intensity without}\\ \text{addition of compound }(I)\end{pmatrix}} \times 100$$

The activity rate at which compound (I) shows the maximum activity is referred as efficacy and the concentration showing 50% activity rate of the efficacy was calculated as $EC_{50}$ value. The results are shown in Table 35.

TABLE 35

| Compound No. | $EC_{50}$ value (nmol/L) | Compound No. | $EC_{50}$ value (nmol/L) |
|---|---|---|---|
| 6 | 97 | 18 | 48 |
| 22 | 1002 | 25 | 233 |
| 28 | 325 | 29 | 326 |
| 33 | 103 | 37 | 415 |
| 42 | 1018 | 44 | 784 |
| 45 | 1091 | 47 | 1935 |
| 51 | 94 | 57 | 440 |
| 62 | 251 | 64 | 73 |
| S13 | 4564 | S14 | 4130 |
| S15 | 1246 | S16 | 305 |
| S17 | 1290 | | |
| 70 | 53 | 71 | 235 |
| 83 | 342 | 86 | 323 |
| 91 | 1524 | 95 | 527 |
| 100 | 1021 | 106 | 310 |
| 112 | 1130 | 118 | 348 |
| 124 | 320 | 129 | 611 |
| 137 | 1837 | 138 | 550 |
| 146 | 336 | 147 | 226 |

From the above-mentioned results, compounds (I) and (IA) and pharmaceutically acceptable salts thereof of the present invention was confirmed to have a PPARγ agonist activity.

Accordingly, compounds (I) and (IA) and pharmaceutically acceptable salts thereof of the present invention are expected as agents for treating and/or preventing various diseases related to PPARγ, such as type 2 diabetes, impaired glucose tolerance, insulin resistance syndrome, hypertension, hyperlipidemia, metabolic syndrome, visceral obesity, obesity, hypertriglyceridemia, inflammatory dermatic diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis etc.), inflammatory neuropsychiatric diseases (e.g., multiple sclerosis etc.), neurodegenerative neuropsychiatric diseases (e.g., Alzheimer's disease, Parkinson's disease etc.) or the like. Specifically, they are expected as agents for treating and/or preventing type 2 diabetes, impaired glucose tolerance, insulin resistance syndrome, hypertension, hyperlipidemia, metabolic syndrome, visceral obesity, obesity, hypertriglyceridemia or the like.

Test Example 2

Human Angiotensin II Type 1 Receptor Binding Test

The membrane fraction (PerkinElmer) of CHO cells showing forced expression of human angiotensin II type 1 receptor was diluted 128-fold with assay buffer (50 mmol/L tris(hydroxymethyl)aminomethane, 5 mmol/L $MgCl_2$, 1 mmol/L ethylenediamine-N,N,N',N'-tetraacetic acid, and 0.1 w/v % bovine serum albumin (Seikagaku Corporation; pH 7.4)) and used for the following experiment. The prepared cellular membrane (150 μL, 2.1 μg protein), 200 pmol/L of $[^{125}I]$-angiotensin II (Amersham Bioscience) (10 μL), and compound (I) solution (10 μL) in various concentrations were added to a polypropylene tube (Assist Co., Ltd.). After reaction at 37° C. for 60 min, the reaction was stopped by suction filtration through a GF/C glass filter (Whatman) treated with 0.3 v/v % polyethylene imine, using a Cell Harvester M-48 (Brandel). Thereafter, the filter was washed 9 times with wash buffer (50 mmol/L tris(hydroxymethyl)aminomethane; pH 7.4, 500 μL). Then, the filter was placed in the polypropylene tube, and the radioactivity was measured using an automatic γ counter COBRA (Packard).

The binding inhibitory rate (%) of compound (I) against binding of $[^{125}I]$-angiotensin II and human angiotensin type 1 receptor was calculated according to the following formula.

$$\text{binding inhibitory rate (\%)} = \frac{\text{total binding amount} - \text{binding amount with addition of compound } (I)}{\text{total binding amount} - \text{nonspecific binding amount}} \times 100$$

The total binding amount refers to $[^{125}I]$-angiotensin II bound radiation amount in the absence of compound (I), the binding amount with the addition of compound (I) refers to $[^{125}I]$-angiotensin II bound radiation amount in the presence of compound (I), and the nonspecific binding amount refers to $[^{125}I]$-angiotensin II bound radiation amount when unlabeled angiotensin II (PEPTIDE INSTITUTE, INC.) 10 μmol/L was added instead of compound (I).

The concentration showing 50% inhibition of the binding was calculated as $IC_{50}$ value from respective binding inhibitory rates, and the binding inhibitory constant (Ki) was determined from the formula of Cheng-Prusoff (Biochem Pharmacol., 1973, vol. 22, p. 3099). Compounds 6, 22, 25, 29, 45, 42, 47, 44, 62, 64, S13, 83, 95, 137, 138, 139, 146, 147 and the like showed Ki values of 10 nmol/L or below.

From the foregoing, compounds (1) and (IA) were confirmed to strongly inhibit binding of angiotensin II with human angiotensin II type 1 receptor. That is, compounds (I) and (IA) and pharmaceutically acceptable salts thereof of the present invention have an angiotensin II type 1 receptor antagonistic action, and are expected as agents for treating and/or preventing cardiovascular diseases such as arteriosclerosis, hypertension, cardiac disease, cerebral apoplexy, renal diseases, etc. or the like.

Test Example 3

Blood Glucose- and Lipid-Lowering Action in Diabetes Mouse

Compound (I) was orally administered to db/db mouse (7-week-old, female), a model of spontaneous type 2 diabetes, at a dose of 30 mg/kg/day once a day for 6 days. A solvent (0.5% methylcellulose solution) was administered to the control group. After 7 days from the administration, glucose and triglyceride in plasma were measured. Statistically significant difference was examined using Student's t test, and risk rate $(P)<0.05$ was taken as significant.

As a result, compound (I) remarkably suppressed an increase of serum glucose and triglyceride, and compound (I) was confirmed to have a glucose- and lipid-lowering actions in the diabetes model in this Experiment.

Test Example 4

Ameliorating Action on Impaired Glucose Tolerance and Insulin Resistance in Type 2 Diabetic Rats A test compound was repeatedly administered orally to Zucker obese rat, a model of type 2 diabetes, once a day for 4 weeks at a dose of 3 mg/kg. A solvent (0.5% methylcellulose solution) was administered to the control group in a similar manner. After 4 weeks of administration, an oral glucose tolerance test was performed as shown below. In addition, plasma insulin level was measured under full feeding condition.

Oral glucose tolerance test: After rat was fasted overnight, a glucose solution was orally administered at a dose of 2 g/kg. Blood samples were collected from the rat tail vein at 30 min, 60 min and 120 min after administration of the glucose solution, and the blood glucose level was measured.

Some of the compound (I) of the present invention were evaluated as the above-mentioned test compounds. These compounds showed improving actions of impaired glucose tolerance and insulin resistance. It could also be confirmed that they improved obesity.

Test Example 5

Examination of Antihypertensive Action of Compound (I) by Tail Cuff Method 18- to 22-week-old spontaneously hypertensive rats (SHR) were used.

Before drug administration, the body weight, blood pressure and heart rate of each rat were measured, and the rats were grouped such that these values are almost the same between groups. A solvent (0.5% methylcellulose solution)

and a test compound were repeatedly administered orally once a day for 7 days. At about 4 to 9 hr after the final administration, systolic blood pressure and heart rate were non-invasively measured according to the following.

Measurement methods of blood pressure and heart rate

The rats were placed in a cylindrical restrainer, heated to 37° C., and blood pressure and heart rate were measured under resting state using a Tail Cuff Method. For the measurement, a non-invasive blood pressure measurement apparatus (PS-600, Riken Kaihatsu, Tokyo) was used. The blood pressure and heart rate of each rat was measured 5 times, and the average was taken as the value of each rat.

As the results of the above-mentioned test, compounds 26, 29, 42, 44, 47, S13, 95, 137, 139 and the like were confirmed to have antihypertensive action.

Test Example 6

Examination of Antihypertensive Action of Compound (I) by Telemetry Method

A telemetry transmitter was indwelled in the abdominal artery of spontaneously hypertensive rats (SHR), and the blood pressure and heart rate were monitored. The rats were acclimated and reared for 4 weeks or more, and only the rats with hypertension were used for the test. Before drug administration, the rats were grouped such that the blood pressure and heart rate of each rat would be of the same levels between the groups. A solvent (0.5% methylcellulose solution) and a test compound were repeatedly administered orally once a day for 4 days. The average systolic blood pressure for 24 hr, average diastolic blood pressure for 24 hr and average heart rate for 24 hr were calculated on each administration day.

As a result of the above-mentioned test, compounds 22, 25, 29, 42, 44, 45, 47, S13, S15, S16, 71, 86, 95, 100, 118, 124, 129, 137, 138, 146, 147 and the like were confirmed to have a antihypertensive action.

From the above-mentioned results, compounds (1) and (IA) and pharmaceutically acceptable salts thereof of the present invention were confirmed to have a PPARγ agonist activity. In addition, they were also confirmed to further have an angiotensin II receptor antagonistic action. Hence, compounds (I) and (IA) and pharmaceutically acceptable salts thereof of the present invention have been suggested to be useful as agents for treating and/or preventing not only diseases related to PPARγ but also diseases related to an angiotensin II receptor, and particularly useful as agents for treating and/or preventing diseases related to both PPARγ and angiotensin II receptor. That is, compounds (I) and (IA) or pharmaceutically acceptable salts thereof of the present invention are expected as agents for treating and/or preventing, for example, type 2 diabetes, impaired glucose tolerance, insulin resistance syndrome, hypertension, hyperlipidemia, metabolic syndrome, visceral obesity, obesity, hypertriglyceridemia, inflammatory dermatic diseases (e.g., psoriasis, atopic dermatitis, seborrheic dermatitis, solar dermatitis etc.), inflammatory diseases (e.g., rheumatoid arthritis, ulcerative colitis, Crohn's disease, endometritis etc.), proliferative diseases (e.g., atherosclerosis, angiostenosis, restenosis etc.), inflammatory neuropsychiatric diseases (e.g., multiple sclerosis etc.), neurodegenerative neuropsychiatric diseases (e.g., Alzheimer's disease, Parkinson's disease etc.), cardiovascular diseases such as arteriosclerosis, cardiac disease, cerebral apoplexy, renal diseases, etc. or the like; particularly, as agents for treating and/or preventing diseases such as type 2 diabetes, impaired glucose tolerance, insulin resistance syndrome, hypertension, hyperlipidemia, metabolic syndrome, visceral obesity, obesity, hypertriglyceridemia or the like.

It is known that about 60% of hypertension patients develops complications of impaired glucose tolerance or type 2 diabetes (insulin resistance). Accordingly, compound (I) or (IA) or a pharmaceutically acceptable salt thereof of the present invention is specifically expected as an agent for treating and/or preventing hypertension that concurrently developed impaired glucose tolerance or type 2 diabetes (insulin resistance), and as an agent for treating and/or preventing hypertension, which has a prophylactic effect on impaired glucose tolerance or type 2 diabetes (insulin resistance).

While compounds (I) or (IA) or pharmaceutically acceptable salts thereof can be administered alone as they are, generally, they are desirably provided as various pharmaceutical preparations. In addition, such pharmaceutical preparations are used for animals and humans.

The pharmaceutical preparation relating to the present invention can contain, as an active ingredient, compound (I) or (IA) or a pharmaceutically acceptable salt thereof alone or as a mixture with an active ingredient for any other treatment. Moreover, the pharmaceutical preparation can be produced by mixing the active ingredient with one or more kinds of pharmaceutically acceptable carriers (e.g., diluent, solvent, excipient or the like) according to any method well known in the technical field of galenical pharmacy.

As the administration route, a route most effective for the treatment is desirably employed, which may be an oral or parenteral route such as intravenous route or the like.

The dosage form may be, for example, tablet, injection or the like.

A form suitable for oral administration, such as tablet or the like, can be produced by using an excipient such as lactose or the like, a disintegrant such as starch or the like, a lubricant such as magnesium stearate or the like, a binder such as hydroxypropylcellulose or the like.

A form suitable for parenteral administration, such as injection or the like, can be produced by using a diluent such as a salt solution, a glucose solution or a mixture of salt solution and a glucose solution or the like, or a solvent or the like.

While the dose and administration frequency of compound (I) or (IA) or a pharmaceutically acceptable salt thereof varies depending on the mode of administration, age and body weight of patients, nature and severity of the symptom to be treated or the like, it is generally within the range of 0.01 to 1000 mg, preferably 0.05 to 100 mg, for oral administration to an adult, which is administered at once or in several portions a day. In the case of parenteral administration such as intravenous administration or the like, 0.001 to 1000 mg, preferably 0.01 to 100 mg, is administered to an adult at once or in several portions a day. However, these doses and administration frequencies vary depending on the aforementioned various conditions.

The PPARγ agonist of the present invention shows an excellent treatment and/or preventive effect on a disease related to PPARγ (e.g., type 2 diabetes, impaired glucose tolerance, insulin resistance syndrome, hypertension, hyperlipidemia, metabolic syndrome, visceral obesity, obesity, hyperglyceridemia etc.). As mentioned above, compound (I) or a pharmaceutically acceptable salt thereof can also be used in combination with one or more kinds of other pharmaceutical components.

Examples of other pharmaceutical components to be used in combination include pharmaceutical agents such as calcium channel blockers (e.g., verapamil, diltiazem, nifedipine, amlodipine, benidipine, nicardipine, nilvadipine, nisoldipine, nitrendipine, nimodipine, manidipine, bepridil, barnidipine, flunarizine, cilnidipine, lacidipine, efonidipine, felodipine, aranidipine and the like); ACE inhibitor (e.g., captopril, enalapril, alacepril, delapril, cilazapril, lisinopril, benazepril, imidapril, temocapril, quinapril, trandolapril, perindopril, fosinopril and the like); diuretic (e.g., amiloride, chlorothiazide, benzthiazide, ticrynafan, acetazolamide, aminophylline, cyclothiazide, trichloromethiazide, cyclopenthiazide, hydrochlorothiazide, methyclothiazide, benzylhydrochlorothiazide, penfluthiazide, ethiazide, hydroflumethiazide, polythiazide, clofenamide, chlortalidone, cyclothiazide, bendroflumethiazide, meticrane, tripamide, metolazone, indapamide, quinethazone, furosemide, bumetanide, mefruside, azosemide, ethacrynic acid, sodium ethacrynate, piretanide, spironolactone, eplerenone, potassium canrenoate, triamterene, carperitide and the like); β blockers (e.g., propranolol, pindolol, carteolol, atenolol, bopindolol, bisoprolol, celiprolol, tilisolol and the like); α blockers (e.g., prazosin, bunazosin, doxazosin, terazosin, urapidil and the like); αβ blockers (e.g., amosulalol, carvedilol, arotinolol and the like); sympathetic depressant drugs (e.g., guanabenz, clonidine, methyldopa and the like); sulfonylurea drugs (e.g., glibenclamide, gliclazide, tolbutamide, glimepiride and the like); fast-acting postprandial hypoglycemic drug (e.g., nateglinide, mitiglinide, repaglinide and the like); biguanide drugs (e.g., metformin, buformin and the like); insulin sensitizers (e.g., pioglitazone, rosiglitazone and the like); a glucosidase inhibitors (e.g., acarbose, voglibose, miglitol and the like); DPP-4 inhibitors (e.g., sitagliptin, vildagliptin and the like); glucagon-like peptide-1 or analogs thereof; insulin; statin drugs (e.g., pravastatin, simvastatin, atorvastatin, fluvastatin, cerivastatin, pitavastatin and the like); cholesterol absorption inhibitors (e.g., ezetimibe and the like); anion exchange resins (e.g., colestyramine, colestimide and the like); fibrate drugs (e.g., bezafibrate, fenofibrate, clinofibrate, clofibrate and the like); nicotinic acid drugs (e.g., tocopherol nicotinate, niceritrol, nicomol and the like); probucol; Eicosapentaenoic acid; polyenephosphatidylcholine; dextran sulfate sodium; elastase and the like.

When compound (I) or a pharmaceutically acceptable salt thereof and other pharmaceutical component are used in combination, compound (I) or a pharmaceutically acceptable salt thereof and other pharmaceutical component may be simultaneously administered or separately in a staggered manner. The dose thereof only need to follow clinically employed doses, which varies depending on the administration subject, administration route, disease, combination of pharmaceutical components or the like.

The present invention is explained in more detail in the following by Examples and Reference Examples, which are not to be construed as limitative.

The proton nuclear magnetic resonance spectrum ($^1$H NMR) used in the Examples and Reference Examples were measured at 270 MHz or 300 MHz, and exchanging protons may not be clearly observed depending on the compound and measurement conditions. The indication of the multiplicity of the signals is conventional, where br means an apparently broad signal.

Reference Example 1

2-ethyl-4,6-dimethylbenzimidazole

To a mixture of 2,4-dimethylaniline (0.918 mL, 7.42 mmol) and propionic anhydride (6.0 mL) fuming nitric acid (1.25 mL, 29.7 mmol) was added dropwise under ice-cooling over 20 min. Under ice-cooling, the mixture was stirred for 1 hr and added with water and ethyl acetate, followed by extraction. The organic layer was washed with saturated aqueous sodium hydrogen carbonate solution and brine, dried over anhydrous magnesium sulfate, and concentrated under reduced pressure. Ethyl acetate-hexane (1/1, 24 mL) was added to the residue, and the precipitated solid was collected by filtration. The obtained solid was dissolved in methanol (17 mL), and the mixture was stirred in the presence of 10% palladium carbon (448 mg) under a hydrogen atmosphere at room temperature for 1 hr. The mixture was filtrated, and the filtrate was concentrated under reduced pressure. The residue was dissolved in acetic acid (14 mL) and the mixture was stirred at 110° C. for 30 min. The mixture was concentrated under reduced pressure, diluted with chloroform, and washed with saturated aqueous sodium hydrogen carbonate solution and brine. The organic layer was dried over anhydrous magnesium sulfate, and concentrated under reduced pressure. Ethyl acetate-hexane (1/5, 30 mL) was added to the residue, and the precipitated solid was collected by filtration to give the title compound (585 mg, 45%).

$^1$H-NMR ($CDCl_3$, δ): 1.42 (t, J=7.7 Hz, 3H), 2.42 (s, 3H), 2.56 (br s, 3H), 2.95 (q, J=7.7 Hz, 2H), 6.86 (s, 1H), 7.04 (br s, 1H), 8.91 (s, 1H).

Reference Example 2

2-ethoxy-5,7-dimethyl-3H-imidazo[4,5-b]pyridine 2,3-Diamino-4,6-dimethylpyridine (U.S. Pat. No. 5,332,744; 2.70 g, 19.7 mmol) and tetraethoxymethane (16.5 mL, 78.7 mmol) were mixed, and the mixture was stirred at 155° C. for 2 hr. The mixture was cooled to room temperature, and diisopropyl ether (30 mL) was added. The precipitated solid was collected by filtration to give the title compound (2.42 g, 64%).

ESI-MS m/z: 192 $(M+H)^+$; $^1$H-NMR ($CDCl_3$, δ): 1.47 (t, J=7.1 Hz, 3H), 2.54 (s, 3H), 2.63 (s, 3H), 4.61 (q, J=7.1 Hz, 2H), 6.78 (br s, 1H), 13.42 (s, 1H).

Reference Example 3

2-ethyl-5-methyl-7-trifluoromethyl-3H-imidazo[4,5-b]pyridine

Ethyl propionimidate hydrochloride (1.37 g, 10.0 mmol), aminoacetonitrile hydrochloride (0.93 g, 10.0 mmol), 1,1,1-trifluoro-2,4-pentanedione (3.64 mL, 30.0 mmol) and diisopropylethylamine (5.23 mL, 30.0 mmol) were stirred in 1,2-dichloroethane (50 mL) under reflux for 4 hr. Ethyl acetate was added to the mixture, and the mixture was washed with water and brine, dried over anhydrous sodium sulfate, and concentrated under reduced pressure. The residue was purified by silica gel column chromatography (hexane/ethyl acetate=30/70) to give the title compound (1.07 g, 47%).

ESI-MS m/z: 230 $(M+H)^+$; $^1$H-NMR ($CDCl_3$, δ): 1.47 (t, J=7.6 Hz, 3H), 2.77 (s, 3H), 3.09 (q, J=7.6 Hz, 2H), 7.31 (s, 1H), 12.18 (br s, 1H).

Reference Example 4

4-fluoro-7-methyl-2-propylbenzimidazole

The title compound (0.70 g, 12%) was obtained in the same manner as in Reference Example 1, using 2-fluoro-5-methylaniline (3.75 g, 30.0 mmol) instead of 2,4-dimethylaniline and butyric anhydride (19 mL) instead of propionic anhydride.

ESI-MS m/z: 193 (M+H)$^+$; $^1$H-NMR ($CDCl_3$, δ): 1.03 (t, J=7.3 Hz, 3H), 1.83-1.95 (m, 2H), 2.48 (br s, 3H), 2.92 (t, J=7.7 Hz, 2H), 6.83 (dd, J=10.2, 8.0 Hz, 1H), 6.91 (dd, J=8.0, 5.0 Hz, 1H), 9.42 (br s, 1H).

Reference Example 5

5-methyl-2-propyl-7-trifluoromethyl-3H-imidazo[4,5-b]pyridine

The title compound (503 mg, 41%) was obtained in the same manner as in Reference Example 3, using ethyl butylimidate hydrochloride (758 mg, 5.0 mmol) instead of ethyl propionimidate hydrochloride.

$^1$H-NMR ($CDCl_3$, δ): 1.05 (t, J=7.4 Hz, 3H), 1.85-1.96 (m, 2H), 2.75 (s, 3H), 3.02 (t, J=7.8 Hz, 2H), 7.32 (br s, 1H), 11.52 (s, 1H).

Reference Example 6

(E)-2-(2-hydroxymethyl-10,11-dihydro-5H-dibenzo[a,d]cyclohepten-5-ylidene)propiononitrile and (Z)-2-(2-hydroxymethyl-10,11-dihydro-5H-dibenzo[a,d]cyclohepten-5-ylidene)propiononitrile

[step 1] 5-Oxo-10,11-dihydro-5H-dibenzo[a,d]cycloheptene-2-carboxylic acid (JP-B-2526005, 19.9 g, 79 mmol) and triethyl orthoformate (17.0 mL, 102 mmol) were dissolved in ethanol (130 mL), followed by adding concentrated sulfuric acid (1.68 mL, 32 mmol) and the mixture was stirred under reflux for 12 hr. The mixture was diluted with ethyl acetate, and the organic layer was washed with saturated aqueous sodium hydrogen carbonate solution, dried over anhydrous magnesium sulfate, and concentrated under reduced pressure. The residue was purified by silica gel column chromatography (hexane/ethyl acetate=90/10) to give ethyl 5-oxo-10,11-dihydro-5H-dibenzo[a,d]cycloheptene-2-carboxylate (20.8 g, 94%).

ESI-MS m/z: 281 (M+H)$^+$; $^1$H-NMR ($CDCl_3$, δ): 1.42 (t, J=7.2 Hz, 3H), 3.21-3.30 (m, 4H), 4.40 (q, J=7.2 Hz, 2H), 7.24 (d, J=7.5 Hz, 1H), 7.34 (td, J=7.5, 1.3 Hz, 1H), 7.46 (td, J=7.5, 1.5 Hz, 1H), 7.92-8.04 (m, 4H).

[step 2] To a solution of sodium hydride (60%, 0.856 g, 21.4 mmol) and diethyl 1-cyanoethylphosphonate (4.09 g, 21.4 mmol) in DMF (35 mL), a solution of ethyl 10,11-dihydro-5-oxo-5H-dibenzo[a,d]cycloheptene-2-carboxylate (3.0 g, 10.7 mmol) obtained in step 1 in DMF (10 mL) was added under ice-cooling, and the mixture was stirred at 80° C. for 3 hr. Water was added to the mixture, and the mixture was extracted with ethyl acetate. The organic layer was dried over anhydrous magnesium sulfate, and concentrated under reduced pressure to give a residue. The obtained residue was dissolved in THF (50 mL), followed by adding lithium borohydride (1.11 g, 50.9 mmol) and the mixture was stirred at 50° C. for 5 hr. The mixture was neutralized with 2 mol/L hydrochloric acid, and extracted with ethyl acetate. The organic layer was dried over anhydrous magnesium sulfate, and concentrated under reduced pressure. The residue was purified by silica gel column chromatography (chloroform/ethyl acetate=98/2) to give (E)-2-(2-hydroxymethyl-10,11-dihydro-5H-dibenzo[a,d]cyclohepten-5-ylidene)propiononitrile (0.730 g, 27%) and (Z)-2-(2-hydroxymethyl-10,11-dihydro-5H-dibenzo[a,d]cyclohepten-5-ylidene)propiononitrile (0.728 g, 27%), respectively.

E form; $^1$H-NMR ($CDCl_3$, δ): 2.04 (s, 3H), 2.82-2.95 (m, 2H), 3.27-3.40 (m, 2H), 4.67 (d, J=5.8 Hz, 2H), 7.08 (d, J=7.8 Hz, 1H), 7.13-7.29 (m, 5H), 7.41 (dd, J=7.1, 1.8 Hz, 1H).

Z form; $^1$H-NMR ($CDCl_3$, δ): 2.03 (s, 3H), 2.81-2.97 (m, 2H), 3.26-3.40 (m, 2H), 4.64 (d, J=5.6 Hz, 2H), 7.07 (d, J=7.1 Hz, 1H), 7.16-7.28 (m, 5H), 7.43 (d, J=7.8 Hz, 1H).

Reference Example 7

2-[5-ethoxycarbonyl-4-(1-hydroxy-1-methyl)ethyl-2-propylimidazol-1-yl]methyl-5-(1H-tetrazol-5-yl)methyl-10,11-dihydro-5H-dibenzo[b,f]azepine (Compound S7)

5-Cyanomethyl-2-[5-ethoxycarbonyl-4-(1-hydroxy-1-methyl)ethyl-2-propylimidazol-1-yl]methyl-10,11-dihydro-5H-dibenzo[b,f]azepine (2.21 g, 4.5 mmol) obtained in step 2 of Example 10, was dissolved in DMF (23 mL), and the solution was added with sodium azide (1.18 g, 18.2 mmol) and triethylamine hydrochloride (1.87 g, 13.6 mmol), followed by stirring at 90° C. for 20 hr. A 5% aqueous citric acid solution was added to the mixture, and the mixture was extracted with chloroform. The organic layer was washed with brine, dried over anhydrous magnesium sulfate, and concentrated under reduced pressure. The residue was purified by silica gel column chromatography (chloroform/methanol=25/1) to give the title compound (compound S7, 1.97 g, 81.9%).

ESI-MS m/z: 530 (M+H)$^+$; $^1$H-NMR (DMSO-$d_6$, δ): 0.85 (t, J=7.3 Hz, 3H), 1.02 (t, J=7.1 Hz, 3H), 1.45 (s, 6H), 1.55 (m, 2H), 2.57 (t, J=7.5 Hz, 2H), 3.11 (br s, 4H), 4.11 (q, J=7.2 Hz, 2H), 5.25 (s, 2H), 5.30 (s, 2H), 5.35 (s, 1H), 6.59-7.20 (m, 7H).

Reference Example 8

2-[5-ethoxycarbonyl-2-ethyl-4-(1-hydroxy-1-methyl)ethylimidazol-1-yl]methyl-5-(1H-tetrazol-5-yl)methyl-10,11-dihydro-5H-dibenzo[b,f]azepine (Compound S8)

The title compound (compound S8, 1.22 g, 79%) was obtained in the same manner as in Reference Example 7, using 5-cyanomethyl-2-[5-ethoxycarbonyl-2-ethyl-4-(1-hydroxy-1-methyl)ethylimidazol-1-yl]methyl-10,11-dihydro-5H-dibenzo[b,f]azepine (1.42 g, 3.00 mmol) obtained in step 2 of Example 11.

ESI-MS m/z: 516 (M+H)$^+$; $^1$H-NMR ($CDCl_3$, δ): 1.09 (t, J=6.4 Hz, 3H), 1.15 (t, J=6.8 Hz, 3H), 1.60 (s, 6H), 2.60 (q, J=7.5 Hz, 2H), 3.04-3.14 (m, 4H), 4.17 (q, J=7.1 Hz, 2H), 5.26 (s, 2H), 5.30 (s, 2H), 6.57-6.63 (m, 2H), 6.94-7.15 (m, 5H).

Reference Example 9

2-[5-ethoxycarbonyl-4-(1-hydroxy)ethyl-2-propylimidazol-1-yl]methyl-5-(1H-tetrazol-5-yl)methyl-10,11-dihydro-5H-dibenzo[b,f]azepine (Compound S9)

[step 1] 2-[5-Ethoxycarbonyl-4-(1-hydroxy)ethyl-2-propylimidazol-1-yl]methyl-10,11-dihydro-5H-dibenzo[b,f]azepine (1.20 g, 44.9%) was obtained in the same manner as in step 1 of Example 1, using 5-ethoxycarbonyl-4-(1-hydroxy)ethyl-2-propylimidazole (JP-A-5-783228; 1.40 g, 6.19 mmol) instead of 2-ethyl-5,7-dimethyl-3H-imidazo[4,5-b]pyridine and potassium tert-butoxide (763 mg, 6.81 mmol) instead of lithium hydroxide.

ESI-MS m/z: 434 (M+H)$^+$; $^1$H-NMR ($CDCl_3$, δ): 0.95 (t, J=7.3 Hz, 3H), 1.29 (t, J=7.1 Hz, 3H), 1.52 (d, J=6.4 Hz, 3H), 1.66-1.78 (m, 2H), 2.63 (t, J=7.8 Hz, 2H), 2.99-3.07 (m, 4H), 3.79 (d, J=7.9 Hz, 1H), 4.27 (q, J=7.2 Hz, 1H), 5.17-5.26 (m, 1H), 5.35 (d, J=16.0 Hz, 1H), 5.46 (d, J=16.0 Hz, 1H), 5.99 (s, 1H), 6.64-6.81 (m, 5H), 7.01-7.11 (m, 2H).

[step 2] 5-Cyanomethyl-2-[5-ethoxycarbonyl-4-(1-hydroxy)ethyl-2-propylimidazol-1-yl]methyl-10,11-dihydro-5H-dibenzo[b,f]azepine (742 mg, 72.6%) was obtained in the same manner as in step 2 of Example 1, using 2-[5-ethoxycarbonyl-4-(1-hydroxy)ethyl-2-propylimidazol-1-yl]methyl-10,11-dihydro-5H-dibenzo[b,f]azepine (938 mg, 2.16 mmol) obtained in step 1.

ESI-MS m/z: 473 $(M+H)^+$; $^1$H-NMR ($CDCl_3$, δ): 0.95 (t, J=7.3 Hz, 3H), 1.28 (t, J=7.2 Hz, 3H), 1.52 (d, J=6.6 Hz, 3H), 1.66-1.79 (m, 2H), 2.60 (t, J=7.7 Hz, 2H), 3.03-3.15 (m, 4H), 3.74 (d, J=7.9 Hz, 1H), 4.25 (q, J=7.3 Hz, 2H), 4.53 (s, 2H), 5.17-5.26 (m, 1H), 5.39 (d, J=16.3 Hz, 1H), 5.47 (d, J=16.3 Hz, 1H), 6.73-6.79 (m, 2H), 7.00-7.27 (m, 5H).

[step 3] The title compound (compound S9, 557 mg, 69.7%) was obtained in the same manner as in Reference Example 7, using 5-cyanomethyl-2-[5-ethoxycarbonyl-4-(1-hydroxy)ethyl-2-propylimidazol-1-yl]methyl-10,11-dihydro-5H-dibenzo[b,f]azepine (732 mg, 1.55 mmol) obtained in step 2.

ESI-MS m/z: 516 $(M+H)^+$; $^1$H-NMR ($CDCl_3$, δ): 0.81 (t, J=7.3 Hz, 3H), 1.22 (t, J=7.1 Hz, 3H), 1.47 (d, J=6.4 Hz, 3H), 1.58 (m, 2H), 2.56 (t, J=7.8 Hz, 2H), 3.02-3.11 (m, 4H), 4.15-4.27 (m, 2H), 5.24 (s, 2H), 5.25 (m, 1H), 5.29 (d, J=16.1 Hz, 1H), 5.44 (d, J=16.1 Hz, 1H), 6.62-6.66 (m, 2H), 6.92-7.11 (m, 5H).

Reference Example 10

2-[4-(1-hydroxy-1-methyl)ethyl-5-propoxycarbonyl-2-propylimidazol-1-yl]methyl-5-(1H-tetrazol-5-yl)methyl-10,11-dihydro-5H-dibenzo[b,f]azepine (Compound S10)

[step 1] Compound S7 (793 mg, 1.50 mmol) obtained in Reference Example 7 was dissolved in DMF (15 mL) and the solution was added with chlorotriphenylmethane (543 mg, 1.94 mmol) and triethylamine (313 μL, 2.25 mmol), followed by stirring at room temperature for 3.5 hr. Ethyl acetate was added to the mixture, and the organic layer was washed with 5% aqueous citric acid solution, saturated aqueous sodium hydrogen carbonate solution, and brine. The organic layer was dried over anhydrous magnesium sulfate, and concentrated under reduced pressure. The residue was purified by silica gel column chromatography (chloroform/methanol=99/1) to give 2-[5-ethoxycarbonyl-4-(1-hydroxy-1-methyl)ethyl-2-propylimidazol-1-yl]methyl-5-(2-trityl-2H-tetrazol-5-yl)methyl-10,11-dihydro-5H-dibenzo[b,f]azepine (981 mg, 85%).

ESI-MS m/z: 772 $(M+H)^+$; $^1$H-NMR ($CDCl_3$, δ): 0.91 (t, J=7.3 Hz, 3H), 1.12 (t, J=7.1 Hz, 3H), 1.61-1.73 (m, 2H), 1.63 (s, 6H), 2.56 (t, J=7.8 Hz, 2H), 3.03 (br s, 4H), 4.15 (q, J=7.1 Hz, 2H), 5.21 (s, 2H), 5.32 (s, 2H), 5.76 (s, 1H), 6.60-6.65 (m, 2H), 6.86-7.35 (m, 20H).

[step 2] 2-[5-Ethoxycarbonyl-4-(1-hydroxy-1-methyl)ethyl-2-propylimidazol-1-yl]methyl-5-(2-trityl-2H-tetrazol-5-yl)methyl-10,11-dihydro-5H-dibenzo[b,f]azepine (979 mg, 1.27 mmol) obtained in step 1 was dissolved in a mixed solvent of THF-methanol-water (12 mL-3 mL-3 mL), and the solution was added with lithium hydroxide monohydrate (266 mg, 6.34 mmol), followed by stirring at room temperature for 15 min. The mixture was concentrated under reduced pressure. Chloroform and brine were added to the residue, and the mixture was neutralized with 1 mol/L hydrochloric acid and extracted with chloroform. The organic layer was dried over anhydrous magnesium sulfate, and concentrated under reduced pressure to give 2-[5-carboxy-4-(1-hydroxy-1-methyl)ethyl-2-propylimidazol-1-yl]methyl-5-(2-trityl-2H-tetrazol-5-yl)methyl-10,11-dihydro-5H-dibenzo[b,f]azepine (1.15 g) quantitatively.

ESI-MS m/z: 744 $(M+H)^+$; $^1$H-NMR ($CDCl_3$, δ): 0.67 (t, J=6.9 Hz, 3H), 1.32-1.40 (m, 2H), 1.62 (s, 6H), 2.60-2.69 (m, 2H), 2.98 (br s, 4H), 5.14 (s, 2H), 5.62 (s, 2H), 6.70-6.74 (m, 2H), 6.85-7.32 (m, 20H).

[step 3] 2-[5-Carboxy-4-(1-hydroxy-1-methyl)ethyl-2-propylimidazol-1-yl]methyl-5-(2-trityl-2H-tetrazol-5-yl)methyl-10,11-dihydro-5H-dibenzo[b,f]azepine (200 mg, 0.269 mmol) obtained in step 2 was dissolved in DMF (1.3 mL), and the solution was added with potassium carbonate (93.0 mg, 0.673 mmol) and 1-bromopropane (48.8 μL, 0.537 mmol), followed by stirring at 50° C. for 2 hr. Ethyl acetate was added to the mixture. The organic layer was washed with water and brine, dried over anhydrous magnesium sulfate, and concentrated under reduced pressure. The residue was purified by silica gel column chromatography (hexane/ethyl acetate=70/30) to give 2-[4-(1-hydroxy-1-methyl)ethyl-5-propoxycarbonyl-2-propylimidazol-1-yl]methyl-5-(2-trityl-2H-tetrazol-5-yl)methyl-10,11-dihydro-5H-dibenzo[b,f]azepine (130 mg, 62%).

ESI-MS m/z: 786 $(M+H)^+$; $^1$H-NMR ($CDCl_3$, δ): 0.76 (t, J=7.4 Hz, 3H), 0.90 (t, J=7.4 Hz, 3H), 1.45-1.72 (m, 4H), 1.63 (s, 6H), 2.55 (t, J=7.8 Hz, 2H), 3.03 (br s, 4H), 4.06 (t, J=6.8 Hz, 2H), 5.21 (s, 2H), 5.32 (s, 2H), 5.78 (s, 1H), 6.61-6.64 (m, 2H), 6.87-7.35 (m, 20H).

[step 4] 2-[4-(1-Hydroxy-1-methyl)ethyl-5-propoxycarbonyl-2-propylimidazol-1-yl]methyl-5-(2-trityl-2H-tetrazol-5-yl)methyl-10,11-dihydro-5H-dibenzo[b,f]azepine (128 mg, 0.163 mmol) obtained in step 3 was suspended in a mixed solvent of acetic acid-acetone-water (1.6 mL-1.6 mL-1.6 mL), and the mixture was stirred at 50° C. for 2 hr. The mixture was concentrated under reduced pressure, and the residue was purified by silica gel column chromatography (chloroform/methanol=99/1) to give the title compound (compound S10, 64.5 mg, 73%).

ESI-MS m/z: 544 $(M+H)^+$; $^1$H-NMR ($CDCl_3$, δ): 0.75 (t, J=7.4 Hz, 3H), 0.84 (t, J=7.3 Hz, 3H), 1.43-1.64 (m, 4H), 1.60 (s, 6H), 2.54 (t, J=7.8 Hz, 2H), 3.00-3.13 (m, 4H), 4.07 (t, J=6.8 Hz, 2H), 5.24 (s, 2H), 5.31 (s, 2H), 6.56-6.61 (m, 2H), 6.92-7.13 (m, 5H).

Reference Example 11

2-[4-(1-hydroxy-1-methyl)ethyl-5-isopropoxycarbonyl-2-propylimidazol-1-yl]methyl-5-(1H-tetrazol-5-yl)methyl-10,11-dihydro-5H-dibenzo[b,f]azepine (Compound S11)

[step 1] 2-[4-(1-Hydroxy-1-methyl)ethyl-5-isopropoxycarbonyl-2-propylimidazol-1-yl]methyl-5-(2-trityl-2H-tetrazol-5-yl)methyl-10,11-dihydro-5H-dibenzo[b,f]azepine (140 mg, 66%) was obtained in the same manner as in step 3 of Reference Example 10, using 2-[5-carboxy-4-(1-hydroxy-1-methyl)ethyl-2-propylimidazol-1-yl]methyl-5-(2-trityl-2H-tetrazol-5-yl)methyl-10,11-dihydro-5H-dibenzo[b,f]azepine (200 mg, 0.269 mmol) obtained in step 2 of Reference Example 10 and 2-bromopropane (101 μL, 1.08 mmol) instead of 1-bromopropane.

ESI-MS m/z: 786 $(M+H)^+$; $^1$H-NMR ($CDCl_3$, δ): 0.90 (t, J=7.3 Hz, 3H), 1.08 (d, J=6.3 Hz, 6H), 1.58-1.71 (m, 2H), 1.63 (s, 6H), 2.54 (t, J=7.8 Hz, 2H), 3.04 (br s, 4H), 5.01-5.11 (m, 1H), 5.21 (s, 2H), 5.32 (s, 2H), 5.84 (s, 1H), 6.61-6.64 (m, 2H), 6.87-7.34 (m, 20H).

[step 2] The title compound (compound S11, 75.8 mg, 80%) was obtained in the same manner as in step 4 of Reference Example 10, using 2-[4-(1-hydroxy-1-methyl)ethyl-5-isopropoxycarbonyl-2-propylimidazol-1-yl]methyl-5-(2-trityl-2H-tetrazol-5-yl)methyl-10,11-dihydro-5H-dibenzo[b,f]azepine (137 mg, 0.174 mmol) obtained in step 1.

ESI-MS m/z: 544 $(M+H)^+$; $^1$H-NMR ($CDCl_3$, δ): 0.83 (t, J=7.3 Hz, 3H), 1.02 (d, J=6.2 Hz, 6H), 1.51-1.61 (m, 2H), 1.60 (s, 6H), 2.55 (t, J=7.8 Hz, 2H), 3.02-3.13 (m, 4H), 5.06 (q, J=6.2 Hz, 1H), 5.24 (s, 2H), 5.30 (s, 2H), 6.55-6.60 (m, 2H), 6.92-7.14 (m, 5H).

Reference Example 12

2-[5-cyclohexylmethoxycarbonyl-4-(1-hydroxy-1-methyl)ethyl2-propylimidazol-1-yl]methyl-5-(1H-tetrazol-5-yl)methyl-10,11-dihydro-5H-dibenzo[b,f]azepine (Compound S12)

[step 1] 2-[5-Cyclohexylmethoxycarbonyl-4-(1-hydroxy-1-methyl)ethyl-2-propylimidazol-1-yl]methyl-5-(2-trityl-2H-tetrazol-5-yl)methyl-10,11-dihydro-5H-dibenzo[b,f]azepine (159 mg, 62%) was obtained in the same manner as in step 3 of Reference Example 10, using 2-[5-carboxy-4-(1-hydroxy-1-methyl)ethyl-2-propylimidazol-1-yl]methyl-5-(2-trityl-2H-tetrazol-5-yl)methyl-10,11-dihydro-5H-dibenzo[b,f]azepine (228 mg, 0.306 mmol) obtained in step 2 of Example 10 and bromomethylcyclohexane (257 μL, 1.84 mmol) instead of 1-bromopropane.

ESI-MS m/z: 840 $(M+H)^+$; $^1$H-NMR ($CDCl_3$, δ): 0.68-1.08 (m, 5H), 0.90 (t, J=7.3 Hz, 3H), 1.35-1.65 (m, 8H), 1.60 (s, 6H), 2.54 (t, J=7.8 Hz, 2H), 3.03 (br s, 4H), 3.92 (d, J=6.1 Hz, 2H), 5.20 (s, 2H), 5.32 (s, 2H), 5.89 (br s, 1H), 6.57-6.61 (m, 2H), 6.87-7.11 (m, 10H), 7.20-7.34 (m, 10H).

[step 2] The title compound (compound S12, 75.4 mg, 68%) was obtained in the same manner as in step 4 of Reference Example 10, using 2-[5-cyclohexylmethoxycarbonyl-4-(1-hydroxy-1-methyl)ethyl-2-propylimidazol-1-yl]methyl-5-(2-trityl-2H-tetrazol-5-yl)methyl-10,11-dihydro-5H-dibenzo[b,f]azepine (156 mg, 0.186 mmol) obtained in step 1.

ESI-MS m/z: 598 $(M+H)^+$; $^1$H-NMR ($CDCl_3$, δ): 0.68-1.06 (m, 5H), 0.82 (t, J=7.3 Hz, 3H), 1.35-1.64 (m, 8H), 1.60 (s, 6H), 2.53 (t, J=7.8 Hz, 2H), 3.01-3.13 (m, 4H), 3.93 (d, J=6.1 Hz, 2H), 5.23 (s, 2H), 5.31 (s, 2H), 6.53-6.57 (m, 2H), 6.90-7.10 (m, 5H).

In the same manner as in JP-B-2526005, the compounds (S13-S19) of the following Reference Examples 13 to 19 were obtained.

Reference Example 13

2-(2-ethyl-5,7-dimethyl-3H-imidazo[4,5-b]pyridin-3-yl)methyl-5-(1H-tetrazol-5-yl)methyl-10,11-dihydro-5H-dibenzo[b,f]azepine (Compound S13)

Reference Example 14

2-(2-cyclopropyl-5,7-dimethyl-3H-imidazo[4,5-b]pyridin-3-yl)methyl-5-(1H-tetrazol-5-yl)methyl-10,11-dihydro-5H-dibenzo[b,f]azepine (Compound S14)

Reference Example 15

[2-(2-ethyl-5,7-dimethyl-3H-imidazo[4,5-b]pyridin-3-yl)methyl-10,11-dihydro-5H-dibenzo[a,d]cyclohepten-5-ylidene]acetonitrile (Compound S15)

Reference Example 16

(E)-2-(2-ethyl-5,7-dimethyl-3H-imidazo[4,5-b]pyridin-3-yl)methyl-5-(1H-tetrazol-5-yl)methylene-10,11-dihydro-5H-dibenzo[a,d]cycloheptene (Compound S16)

Reference Example 17

(Z)-2-(2-ethyl-5,7-dimethyl-3H-imidazo[4,5-b]pyridin-3-yl)methyl-5-(1H-tetrazol-5-yl)methylene-10,11-dihydro-5H-dibenzo[a,d]cycloheptene (Compound S17)

Reference Example 18

(E)-3-(2-ethyl-5,7-dimethyl-3H-imidazo[4,5-b]pyridin-3-yl)methyl-11-(1H-tetrazol-5-yl)methylene-6,11-dihydrodibenzo[b,e]oxepine (Compound S18)

Reference Example 19

(Z)-8-(2-ethyl-5,7-dimethyl-3H-imidazo[4,5-b]pyridin-3-yl)methyl-11-(1H-tetrazol-5-yl)methylene-6,11-dihydrodibenzo[b,e]oxepine (Compound S19)

Reference Example 20

2-ethoxy-7-methyl-3H-imidazo[4,5-b]pyridine 2,3-Diamino-4-methylpyridine (U.S. Pat. No. 5,332,744; 2.00 g, 16.2 mmol) and tetraethoxymethane (15.0 mL, 71.7 mmol) were mixed, and the mixture was stirred at 150° C. for 2 hr. The mixture was cooled to room temperature, diisopropyl ether (15 mL) was added thereto and the precipitated solid was collected by filtration to give the title compound (1.96 g, 68%).

ESI-MS m/z: 178 $(M+H)^+$; $^1$H-NMR ($CDCl_3$, δ): 1.49 (t, J=7.2 Hz, 3H), 2.57 (s, 3H), 4.63 (q, J=7.2 Hz, 2H), 6.93 (d, J=5.1 Hz, 1H), 8.03 (d, J=5.1 Hz, 1H).

Reference Example 21

2-ethoxy-3H-imidazo[4,5-b]pyridine 2,3-Diaminopyridine (7.84 g, 71.9 mmol) and tetraethoxymethane (35 mL, 167 mmol) were mixed, and the mixture was stirred at 130° C. for 2 hr. The mixture was cooled to room temperature, ethyl acetate (100 mL) was added thereto and the precipitated solid was collected by filtration to give the title compound (4.17 g, 36%).

ESI-MS m/z: 164 $(M+H)^+$; $^1$H-NMR ($CDCl_3$, δ): 1.52 (t, J=7.2 Hz, 3H), 4.65 (q, J=7.2 Hz, 2H), 7.13 (dd, J=7.9, 5.0 Hz, 1H), 7.80 (dd, J=7.9, 1.3 Hz, 1H), 8.18 (dd, J=5.0, 1.3 Hz, 1H).

Reference Example 22

7-chloro-2-ethyl-3H-imidazo[4,5-b]pyridine

2-Ethyl-3H-imidazo[4,5-b]pyridine (U.S. Pat. No. 5,332,744; 4.00 g, 27.2 mmol) was dissolved in chloroform (45 mL), and the solution was added with m-chloroperbenzoic acid (5.18 g, 29.9 mmol) followed by stirring at room temperature for 5 hr. The reaction mixture was concentrated, added with ethyl acetate and water, and partitioned between ethyl acetate and water. The aqueous layer was concentrated and the residue was dissolved in chloroform (8 mL). Phosphorus oxychloride (24 mL, 257 mmol) was added thereto and the mixture was stirred at room temperature for 2 hr. The reaction mixture was poured onto ice, neutralized with aqueous ammonia, and extracted with ethyl acetate. The organic layer was washed with brine, dried over anhydrous magnesium sulfate, and concentrated under reduced pressure. Ethyl acetate (30 mL) was added to the residue and the precipitated solid was collected by filtration to give the title compound (3.32 g, 67%).

ESI-MS m/z: 182 $(M+H)^+$; $^1$H-NMR ($CDCl_3$, δ): 1.55 (t, J=7.6 Hz, 3H), 3.13 (q, J=7.6 Hz, 2H), 7.29 (d, J=5.4 Hz, 1H), 8.21 (d, J=5.4 Hz, 1H).

Reference Example 23

7-chloro-2-ethoxy-3H-imidazo[4,5-b]pyridine

The title compound (0.34 g, 31%) was obtained in the same manner as in Reference Example 21, using 4-chloro-2,3-diaminopyridine (EP420237; 0.79 g, 5.5 mmol) instead of 2,3-diaminopyridine.

ESI-MS m/z: 198 $(M+H)^+$; $^1$H-NMR ($CDCl_3$, δ): 1.51 (t, J=7.1 Hz, 3H), 4.70 (q, J=7.1 Hz, 2H), 7.16 (d, J=5.3 Hz, 1H), 8.06 (d, J=5.3 Hz, 1H).

Reference Example 24

7-chloro-2-cyclopropyl-3H-imidazo[4,5-b]pyridine

The title compound (3.22 g, 55%) was obtained in the same manner as in Reference Example 22, using 2-cyclopropyl-3H-imidazo[4,5-b]pyridine (EP420237; 4.79 g, 30.1 mmol) instead of 2-ethyl-3H-imidazo[4,5-b]pyridine.

ESI-MS m/z: 194 $(M+H)^+$; $^1$H-NMR (DMSO-$d_6$, 6): 1.09-1.18 (m, 4H), 2.10-2.20 (m, 1H), 7.26 (d, J=5.4 Hz, 1H), 8.14 (d, J=5.4 Hz, 1H).

Reference Example 25

4-chloro-2-ethoxybenzimidazole

2-Chloro-6-nitroaniline (3.45 g, 20.0 mmol) and stannous chloride dihydrate (18.05 g, 80.0 mmol) were heated under reflux in ethanol (80 mL) for 3 hr. The reaction mixture was neutralized with aqueous sodium hydroxide solution, and the precipitate was filtered off. The filtrate was extracted with ethyl acetate, washed with brine, dried over anhydrous magnesium sulfate, and concentrated under reduced pressure. The residue was mixed with tetraethoxymethane (10 mL, 47.7 mmol) and the mixture was stirred at 130° C. for 12 hr. The reaction mixture was purified by silica gel column chromatography (hexane/ethyl acetate=50/50) to give the title compound (1.38 g, 35%).

ESI-MS m/z: 197 $(M+H)^+$; $^1$H-NMR ($CDCl_3$, b): 1.42-1.50 (m, 3H), 4.52-4.74 (m, 2H), 6.99-7.46 (m, 3H).

Reference Example 26

4-chloro-2-cyclopropylbenzimidazole

2-Chloro-6-nitroaniline (3.00 g, 17.4 mmol) and pyridine (7.0 mL, 86.9 mmol) were dissolved in DMA (17 mL), and the solution was added with cyclopropanecarbonylchloride (4.0 mL, 43.5), followed by stirring at 50° C. for 3 hr. Methanol (10 mL) and aqueous ammonia (9 mL) were added to the reaction mixture, and the mixture was stirred at room temperature for 30 min. Water (10 mL) was added, and the precipitated solid was collected by filtration. The solid was suspended in ethanol (38 mL) and water (38 mL) and the solution was added with ferrous sulfate 7 hydrate (13.86 g, 49.9 mmol) and aqueous ammonia (19 mL), followed by stirring at 50° C. for 4 hr. The reaction mixture was filtrated, and the filtrate was extracted with ethyl acetate, washed with brine, dried over anhydrous magnesium sulfate, and concentrated under reduced pressure. Acetic acid (8 mL) was added to the residue, and the mixture was stirred at 90° C. for 1 hr. The reaction mixture was concentrated under reduced pressure, and the residue was neutralized with aqueous sodium hydroxide solution, and the mixture was extracted with ethyl acetate. The organic layer was washed with brine, dried over anhydrous magnesium sulfate, and concentrated under reduced pressure. Ethyl acetate (5 mL) and diisopropyl ether (5 mL) were added to the residue and the precipitated solid was collected by filtration to give the title compound (1.20 g, 36%).

ESI-MS m/z: 193 $(M+H)^+$; $^1$H-NMR ($CDCl_3$, δ): 1.11-1.25 (m, 4H), 2.01-2.14 (m, 1H), 7.05-7.55 (m, 3H).

Reference Example 27

2-Ethoxy-4-methylbenzimidazole 2,3-Diaminotoluene (6.09 g, 49.8 mmol) and tetraethoxymethane (25 mL, 119 mmol) were mixed, and the mixture was stirred at 130° C. for 16 hr. The mixture was cooled to room temperature, diluted with ethyl acetate, washed with brine, dried over anhydrous magnesium sulfate, and concentrated under reduced pressure. The residue was purified by silica gel column chromatography (hexane/ethyl acetate=70/30) to give the title compound (6.89 g, 78%).

ESI-MS m/z: 177 $(M+H)^+$; $^1$H-NMR ($CDCl_3$, δ): 1.45 (t, J=7.1 Hz, 1.2H), 1.46 (t, J=7.1 Hz, 1.8H), 2.41 (s, 1.8H), 2.56 (s, 1.2H), 4.59 (q, J=7.1 Hz, 1.2H), 4.60 (q, J=7.1 Hz, 0.8H), 6.91-7.10 (m, 2.4H), 7.38 (d, J=7.9 Hz, 0.6H).

Reference Example 28

2-cyclopropyl-4-methylbenzimidazole

The title compound (6.91 g, 80%) was obtained in the same manner as in Reference Example 26, using 2-methyl-6-nitroaniline (7.61 g, 50.0 mmol).

ESI-MS m/z: 173 $(M+H)^+$; $^1$H-NMR ($CDCl_3$, δ): 1.08-1.23 (m, 4H), 2.11 (br s, 1H), 2.51-2.62 (br m, 3H), 7.00 (d, J=7.5 Hz, 1H), 7.11 (t, J=7.5 Hz, 1H), 7.18-7.52 (br m, 2H).

Reference Example 29

4-chloro-2-ethylbenzimidazole

[step 1] Propionic anhydride (40 mL) was cooled to 0° C., added with 2-chloroaniline (5.0 mL, 47.5 mmol) and the mixture was stirred for 15 min. While maintaining the inside temperature at 10° C. or below, fuming nitric acid (8.0 mL, 190 mmol) was added dropwise, and the mixture was stirred under ice-cooling for 15 min. Water (100 mL) was added to the reaction mixture, and the precipitated solid was collected by filtration. The solid was dried and recrystallized from ethyl acetate (50 mL) to give N-(2-chloro-6-nitrophenyl)propionamide (3.73 g, 34%).

$^1$H-NMR ($CDCl_3$, δ): 1.27 (t, J=7.6 Hz, 3H), 2.49 (q, J=7.6 Hz, 2H), 7.31 (t, J=8.3 Hz, 1H), 7.70 (dd, J=8.3, 1.3 Hz, 1H), 7.88 (dd, J=8.3, 1.3 Hz, 1H).

[step 2] The title compound (1.53 g, 52%) was obtained in the same manner as in Reference Example 26, using N-(2-chloro-6-nitrophenyl)propionamide (3.72 g, 16.3 mmol) obtained in step 1.

$^1$H-NMR ($CDCl_3$, δ): 1.45 (t, J=7.7 Hz, 3H), 2.99 (q, J=7.7 Hz, 2H), 7.12-7.59 (m, 3H).

Reference Example 30

(E)-2-(3-hydroxymethyl-6,11-dihydrodibenzo[b,e]oxepin-11-ylidene)propiononitrile

[step 1] Lithium diisopropylamide (2.0 mol/L heptane/THF/ethylbenzene solution, 100 mL, 200 mmol) was diluted with THF (40 mL), and a solution of propiononitrile (7.13 mL, 100 mmol) in THF (40 mL) was added dropwise at 0° C. over 15 min with stirring. After stirring at 0° C. for 30 min, a solution of diethyl chlorophosphate (14.4 mL, 100 mmol) in THF (40 mL) was added dropwise over 45 min. After stirring at room temperature for 2 hr, methyl 11-oxo-6,11-dihydrodibenzo[b,e]oxepine-3-carboxylate (JP-B-2526005, 10.7 g, 40 mmol) was added, and the mixture was stirred at room temperature for 1.5 hr. Ethyl acetate and water were added to the reaction mixture, and the mixture was extracted 3 times with ethyl acetate. The organic layer was washed with brine, dried over anhydrous magnesium sulfate, and concentrated under reduced pressure. The residue was purified by silica gel column chromatography (ethyl acetate:hexane=15:85) to give methyl (E)-11-(1-cyanoethylidene)-6,11-dihydrodibenzo[b,e]oxepine-3-carboxylate (6.40 g, 21.0 mmol, 52.6%) and methyl (Z)-11-(1-cyanoethylidene)-6,11-dihydrodibenzo[b,e]oxepine-3-carboxylate (4.47 g, 14.6 mmol, 36.7%).

E form; $^1$H-NMR (DNSO-$d_6$, δ): 2.20 (s, 3H), 3.83 (s, 3H), 5.04 (d, J=12.7 Hz, 1H), 5.57 (d, J=12.7 Hz, 1H), 7.34-7.62 (m, 7H).

Z form; $^1$H-NMR (DMSO-$d_6$, δ): 1.98 (s, 3H), 3.83 (s, 3H), 5.03 (d, J=12.7 Hz, 1H), 5.55 (d, J=12.7 Hz, 1H), 7.33-7.65 (m, 7H).

[step 2] Methyl (E)-11-(1-cyanoethylidene)-6,11-dihydrodibenzo[b,e]oxepine-3-carboxylate (6.40 g, 21.0 mmol) was suspended in THF (105 mL), and the solution was added with lithium borohydride (2.29 g, 105 mmol), followed by stirring at 50° C. for 6 hr. Ice was added to the reaction mixture, and the mixture was neutralized with 1 mol/L hydrochloric acid to pH 2, and extracted twice with ethyl acetate. The organic layer was washed with brine, dried over anhydrous magnesium sulfate, and concentrated under reduced pressure. The residue was purified by silica gel column chromatography (ethyl acetate:hexane=30:70) to give the title compound (4.89 g, 17.6 mmol, 84.1%).

$^1$H-NMR ($CDCl_3$, δ): 1.63 (t, J=5.9 Hz, 1H), 2.26 (s, 3H), 4.61 (d, J=5.9 Hz, 2H), 4.87 (d, J=12.5 Hz, 1H), 5.48 (d, J=12.5 Hz, 1H), 6.84-6.96 (m, 2H), 7.07 (d, J=7.9 Hz, 1H), 7.36-7.50 (m, 4H).

Reference Example 31

(Z)-2-(8-hydroxymethyl-6,11-dihydrodibenzo[b,e]oxepin-11-ylidene)propiononitrile The title compound (0.178 g, 17%) and an E isomer thereof (0.260 g, 25%) were obtained in the same manner as in Step 2 of Reference Example 6, using Methyl 11-oxo-6,11-dihydrodibenzo[b,e]oxepine-8-carboxylate (JP-B-2526005, 1.00 g, 3.73 mmol).

Z form; $^1$H-NMR ($CDCl_3$, δ): 2.03 (s, 3H), 4.72 (br s, 2H), 4.85 (d, J=12.6 Hz, 1H), 5.48 (d, J=12.6 Hz, 1H), 6.82 (dd, J=8.2, 1.1 Hz, 1H), 6.93-6.98 (m, 1H), 7.16 (d, J=7.9 Hz, 1H), 7.22-7.27 (m, 1H), 7.37 (dd, J=7.8, 1.7 Hz, 1H), 7.42 (br s, 1H), 7.51 (dd, J=7.9, 1.6 Hz, 1H).

E form; $^1$H-NMR ($CDCl_3$, δ): 2.23 (s, 3H), 4.61 (s, 2H), 4.82 (d, J=12.6 Hz, 1H), 5.45 (d, J=12.6 Hz, 1H), 6.83-6.92 (m, 2H), 7.05 (dd, J=7.8, 1.7 Hz, 1H), 7.18-7.24 (m, 1H), 7.30-7.34 (m, 2H), 7.42 (d, J=8.3 Hz, 1H).

Example 1

2-(2-ethyl-5,7-dimethyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 1)

[step 1] 2-Ethyl-5,7-dimethyl-3H-imidazo[4,5-b]pyridine (U.S. Pat. No. 5,332,744; 36.55 g, 209 mmol) was dissolved in DMF (365.5 mL), and the solution was added with lithium hydroxide (5.62 g, 235 mmol), followed by stirring at room temperature for 15 min. 1-(10,11-Dihydro-5H-dibenzo[b,f]azepin-2-ylmethyl)-1-methylpiperidinium iodide (JP-A-7-61983; 95.0 g, 219 mmol) and DMF (73.1 mL) were added thereto, and the mixture was stirred at 40° C. for 8 hr. After cooling to room temperature, water (175.4 mL) was added dropwise, and the mixture was stirred under ice-cooling for 2 hr. The precipitate was collected by filtration, and dissolved in chloroform (520 mL) with heating. Activated carbon (5.2 g) was added, and the mixture was stirred for 30 min with heating, and the hot solution was filtered. Ethyl acetate (1041 mL) was added to the filtrate, and the precipitate was collected by filtration to give 2-(2-ethyl-5,7-dimethyl-3H-imidazo[4,5-b]pyridin-3-yl)methyl-10,11-dihydro-5H-dibenzo[b,f]azepine (36.7 g, 46%).

ESI-MS m/z: 384 $(M+H)^+$; $^1$H-NMR ($CDCl_3$, δ): 1.30 (t, J=7.5 Hz, 3H), 2.60 (s, 3H), 2.63 (s, 3H), 2.78 (q, J=7.5 Hz, 2H), 2.90-3.10 (m, 4H), 5.34 (s, 2H), 6.15 (s, 1H), 6.26 (d, J=8.0 Hz, 1H), 6.65-6.85 (m, 4H), 6.89 (s, 1H), 6.95-7.10 (s, 2H).

[step 2] 2-(2-Ethyl-5,7-dimethyl-3H-imidazo[4,5-b]pyridin-3-yl)methyl-10,11-dihydro-5H-dibenzo[b,f]azepine (55.4 g, 145 mmol) obtained in step 1 was dissolved in acetic acid (500 mL) and the solution was added with potassium cyanide (11 g, 169 mmol) and paraformaldehyde (4.6 g, 152 mmol) at 10° C., followed by stirring at room temperature for 24 hr. The mixture was added to a mixed solution of 10 mol/L aqueous sodium hydroxide solution (900 mL), ice (1 L) and dichloromethane (1 L). The organic layer was washed with 0.1 mol/L aqueous sodium hydroxide solution and brine, dried over anhydrous magnesium sulfate, and concentrated under reduced pressure. The residue was purified by silica gel column chromatography (hexane/ethyl acetate/triethylamine=10/10/1) to give 5-cyanomethyl-2-(2-ethyl-5,7-dimethyl-3H-imidazo[4,5-b]pyridin-3-yl)methyl-10,11-dihydro-5H-dibenzo[b,f]azepine (39.0 g, 64%).

ESI-MS m/z: 422 $(M+H)^+$; $^1$H-NMR ($CDCl_3$, δ): 1.32 (t, J=7.6 Hz, 3H), 2.58 (s, 3H), 2.63 (s, 3H), 2.77 (q, J=7.6 Hz, 2H), 3.06 (br s, 4H), 4.51 (s, 2H), 5.37 (s, 2H), 6.89-7.04 (m, 6H), 7.10-7.26 (s, 4H).

[step 3] 5-Cyanomethyl-2-(2-ethyl-5,7-dimethyl-3H-imidazo[4,5-b]pyridin-3-yl)methyl-10,11-dihydro-5H-dibenzo[b,f]azepine (200 mg, 0.47 mmol) obtained in step 2 was dissolved in ethanol (4 mL), and the solution was added with hydroxylamine (50% aqueous solution, 0.15 mL, 2.37 mmol), followed by heating under reflux for 1 hr. The mixture was concentrated under reduced pressure. The obtained residue was dissolved in DMF (1 mL) and the solution was added with pyridine (46 μL, 0.57 mmol) and ethyl chlorocarbonate (54 μL, 0.57 mmol) at 0° C., followed by stirring at room temperature for 2 hr. Ethyl acetate and saturated aqueous sodium hydrogen carbonate solution were added thereto. The organic layer was washed with brine, dried over anhydrous magnesium sulfate, and concentrated under reduced pressure. The obtained residue was dissolved in toluene (10 mL), and the solution was added with potassium tert-butoxide (51 mg, 0.45 mmol), followed by stirring at room temperature for 15 min. Ethyl acetate was added to the mixture, and the organic layer was washed with 5% aqueous citric acid solution, dried over anhydrous magnesium sulfate, and concentrated under reduced pressure to give the title compound (compound 1, 190 mg, 83%).

ESI-MS m/z: 481 $[M+H]^+$; $^1$H-NMR (DMSO-$d_6$, δ): 1.19 (t, J=7.5 Hz, 3H), 2.65 (d, J=15.4 Hz, 3H), 2.75 (d, J=15.4 Hz, 3H), 3.05-3.12 (m, 4H), 3.37 (q, J=7.0 Hz, 2H), 4.84 (s, 2H), 5.34 (s, 2H), 6.93 (dd, J=8.4, 2.2 Hz, 1H), 6.93 (s, 1H), 6.95-6.97 (m, 2H), 7.10-7.18 (m, 4H), 12.32 (br s, 1H).

Example 2

2-[4-methyl-6-(1-methylbenzimidazol-2-yl)-2-propylbenzimidazol-1-yl]methyl-5-(5-oxo-4,5-dihydro-1,2,4-oxadiazol-3-yl)methyl-10,11-dihydro-5H-dibenzo[b,f]azepine (Compound 2)

[step 1] 2-[4-Methyl-6-(1-methylbenzimidazol-2-yl)-2-propylbenzimidazol-1-yl]methyl-10,11-dihydro-5H-dibenzo[b,f]azepine (1.67 g, 98%) was obtained in the same manner as in step 1 of Example 1, using 4-methyl-6-(1-methylbenzimidazol-2-yl)-2-propylbenzimidazole (EP502314; 1.0 g, 3.29 mmol) instead of 2-ethyl-5,7-dimethyl-3H-imidazo[4,5-b]pyridine.

ESI-MS m/z: 512 $(M+H)^+$; $^1$H-NMR ($CDCl_3$, δ): 1.04 (t, J=6.9 Hz, 3H), 1.78-1.92 (m, 2H), 2.76 (s, 3H), 2.88-3.03 (m, 6H), 3.79 (s, 3H), 5.28 (s, 2H), 6.02 (s, 1H), 6.62-6.79 (m, 5H), 7.00-7.08 (m, 2H), 7.26-7.37 (m, 3H), 7.41 (s, 1H), 7.47 (s, 1H), 7.78-7.81 (m, 1H).

[step 2] 5-Cyanomethyl-2-[4-methyl-6-(1-methylbenzimidazol-2-yl)-2-propylbenzimidazol-1-yl]methyl-10,11-dihydro-5H-dibenzo[b,f]azepine (1.43 g, 80%) was obtained in the same manner as in step 2 of Example 1, using 2-[4-methyl-6-(1-methylbenzimidazol-2-yl)-2-propylbenzimidazol-1-yl]methyl-10,11-dihydro-5H-dibenzo[b,f]azepine (1.67 g, 3.26 mmol) obtained in step 1.

ESI-MS m/z: 551 $(M+H)^+$; $^1$H-NMR ($CDCl_3$, δ): 1.04 (t, J=7.1 Hz, 3H), 1.80-1.92 (m, 2H), 2.76 (s, 3H), 2.89 (t, J=7.9 Hz, 2H), 3.01-3.10 (m, 4H), 3.72 (s, 3H), 4.51 (s, 2H), 5.32 (s, 2H), 6.82-6.89 (m, 2H), 7.00-7.35 (m, 8H), 7.39 (s, 1H), 7.42 (s, 1H), 7.77-7.80 (m, 1H).

[step 3] The title compound (compound 2, 69 mg, 32%) was obtained in the same manner as in step 3 of Example 1, using 5-cyanomethyl-2-[4-methyl-6-(1-methylbenzimidazol-2-yl)-2-propylbenzimidazol-1-yl]methyl-10,11-dihydro-5H-dibenzo[b,f]azepine (0.20 g, 0.36 mmol) obtained in step 2.

ESI-MS m/z: 610 $(M+H)^+$; $^1$H-NMR (DMSO-$d_6$, δ): 0.98 (t, J=7.8 Hz, 3H), 1.79 (q, J=7.1 Hz, 2H), 2.61 (s, 3H), 2.89 (t, J=7.9 Hz, 2H), 3.07 (br s, 4H), 3.74 (s, 3H), 4.44 (s, 2H), 5.44 (s, 2H), 6.83-6.93 (m, 2H), 6.99-7.11 (m, 5H), 7.19-7.29 (m, 2H), 7.45 (s, 1H), 7.54 (t, J=7.1 Hz, 1H), 7.64 (d, J=7.5 Hz, 1H), 7.67 (s, 1H), 12.54 (br s, 1H).

Example 3

2-(5,7-dimethyl-2-propyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 3)

[step 1] 2-(5,7-Dimethyl-2-propyl-3H-imidazo[4,5-b]pyridin-3-yl)methyl-10,11-dihydro-5H-dibenzo[b,f]azepine (2.74 g, 69%) was obtained in the same manner as in step 1 of Example 1, using 5,7-dimethyl-2-propyl-3H-imidazo[4,5-b]pyridine (U.S. Pat. No. 5,332,744; 1.89 g, 10.0 mmol) instead of 2-ethyl-5,7-dimethyl-3H-imidazo[4,5-b]pyridine.

ESI-MS m/z: 397 $(M+H)^+$; $^1$H-NMR ($CDCl_3$, δ): 0.96 (t, J=7.3 Hz, 3H), 1.66-1.79 (m, 2H), 2.60 (s, 3H), 2.62 (s, 3H), 2.75 (t, J=7.8 Hz, 2H), 2.97-3.03 (m, 4H), 5.35 (s, 2H), 5.99 (s, 1H), 6.60-6.84 (m, 5H), 6.88 (s, 1H), 7.00-7.09 (m, 2H).

[step 2] 5-Cyanomethyl-2-(5,7-dimethyl-2-propyl-3H-imidazo[4,5-b]pyridin-3-yl)methyl-10,11-dihydro-5H-dibenzo[b,f]azepine (2.01 g, 72%) was obtained in the same manner as in step 2 of Example 1, using 2-(5,7-dimethyl-2-propyl-3H-imidazo[4,5-b]pyridin-3-yl)methyl-10,11-dihydro-5H-dibenzo[b,f]azepine (2.54 g, 6.41 mmol) obtained in step 1.

ESI-MS m/z: 436 $(M+H)^+$; $^1$H-NMR ($CDCl_3$, δ): 0.97 (t, J=7.3 Hz, 3H), 1.68-1.82 (m, 2H), 2.58 (s, 3H), 2.62 (s, 3H), 2.73 (t, J=7.8 Hz, 2H), 3.01-3.12 (m, 4H), 4.51 (s, 2H), 5.37 (s, 2H), 6.88-7.24 (m, 8H).

[step 3] The title compound (compound 3, 173 mg, 70%) was obtained in the same manner as in step 3 of Example 1, using 5-cyanomethyl-2-(5,7-dimethyl-2-propyl-3H-imidazo[4,5-b]pyridin-3-yl)methyl-10,11-dihydro-5H-dibenzo[b,f]azepine (218 mg, 0.501 mmol) obtained in step 2.

ESI-MS m/z: 495 $(M+H)^+$; $^1$H-NMR (DMSO-$d_6$, δ): 0.86 (t, J=7.3 Hz, 3H), 1.57-1.71 (m, 2H), 2.49 (s, 6H), 2.70 (t, J=7.5 Hz, 2H), 3.09 (br s, 4H), 4.84 (s, 2H), 5.34 (s, 2H), 6.80-7.18 (m, 8H), 12.33 (br s, 1H).

Example 4

2-(2,5-diethyl-7-methyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 4)

[step 1] 2-(2,5-Diethyl-7-methyl-3H-imidazo[4,5-b]pyridin-3-yl)methyl-10,11-dihydro-5H-dibenzo[b,f]azepine (139 mg, 74%) was obtained in the same manner as in step 1 of Example 1, using 2,5-diethyl-7-methyl-3H-imidazo[4,5- b]pyridine (U.S. Pat. No. 5,332,744; 226 mg, 0.520 mmol) instead of 2-ethyl-5,7-dimethyl-3H-imidazo[4,5-b]pyridine.

ESI-MS m/z: 367 $(M+H)^+$; $^1$H-NMR ($CDCl_3$, δ): 1.31 (t, J=7.6 Hz, 3H), 1.34 (t, J=7.5 Hz, 3H), 2.64 (s, 3H), 2.78-2.90 (m, 4H), 2.96-3.04 (m, 4H), 5.35 (s, 2H), 5.99 (s, 1H), 6.61-7.08 (m, 8H).

[step 2] 5-Cyanomethyl-2-(2,5-diethyl-7-methyl-3H-imidazo[4,5-b]pyridin-3-yl)methyl-10,11-dihydro-5H-dibenzo[b,f]azepine (102 mg, 68%) was obtained in the same manner as in step 2 of Example 1, using 2-(2,5-diethyl-7-methyl-3H-imidazo[4,5-b]pyridin-3-yl)methyl-10,11-dihydro-5H-dibenzo[b,f]azepine (136 mg, 0.343 mmol) obtained in step 1.

ESI-MS m/z: 436 $(M+H)^+$; $^1$H-NMR ($CDCl_3$, δ): 1.32 (t, J=7.6 Hz, 3H), 1.33 (t, J=7.6 Hz, 3H), 2.63 (s, 3H), 2.79 (q, J=7.6 Hz, 2H), 2.85 (q, J=7.6 Hz, 2H), 3.03-3.11 (m, 4H), 4.51 (s, 2H), 5.37 (s, 2H), 6.89-7.26 (m, 8H).

[step 3] The title compound (compound 4, 28.2 mg, 46%) was obtained in the same manner as in step 3 of Example 1, using 5-cyanomethyl-2-(2,5-diethyl-7-methyl-3H-imidazo[4,5-b]pyridin-3-yl)methyl-10,11-dihydro-5H-dibenzo[b,f]azepine (54.0 mg, 0.124 mmol) obtained in step 2.

ESI-MS m/z: 495 $(M+H)^+$; $^1$H-NMR (DMSO-$d_6$, δ): 1.20 (t, J=7.5 Hz, 3H), 1.25 (t, J=7.5 Hz, 3H), 2.50 (s, 3H), 2.77 (q, J=7.5 Hz, 2H), 2.77 (q, J=7.5 Hz, 2H), 3.08 (br s, 4H), 4.84 (s, 2H), 5.33 (s, 2H), 6.89-6.97 (m, 3H), 7.02-7.18 (m, 5H), 12.31 (s, 1H).

Example 5

2-(2-ethyl-4,6-dimethylbenzimidazol-1-yl)methyl-5-(5-oxo-4,5-dihydro-1,2,4-oxadiazol-3-yl)methyl-10,11-dihydro-5H-dibenzo[b,f]azepine (Compound 5)

[step 1] 2-(2-Ethyl-4,6-dimethylbenzimidazol-1-yl)methyl-10,11-dihydro-5H-dibenzo[b,f]azepine (422 mg, 75%) was obtained in the same manner as in step 1 of Example 1, using 2-ethyl-4,6-dimethylbenzimidazole (256 mg, 1.47 mmol), obtained in Reference Example 1, instead of 2-ethyl-5,7-dimethyl-3H-imidazo[4,5-b]pyridine.

ESI-MS m/z: 382 $(M+H)^+$; $^1$H-NMR (DMSO-$d_6$, δ): 1.25 (t, J=7.4 Hz, 3H), 2.33 (s, 3H), 2.46 (s, 3H), 2.81 (q, J=7.4 Hz, 2H), 2.85-2.91 (m, 4H), 5.22 (s, 2H), 6.62-7.05 (m, 10H).

[step 2] 5-Cyanomethyl-2-(2-ethyl-4,6-dimethylbenzimidazol-1-yl)methyl-10,11-dihydro-5H-dibenzo[b,f]azepine (241 mg, 52%) was obtained in the same manner as in step 2 of Example 1, using 2-(2-ethyl-4,6-dimethylbenzimidazol-1-yl)methyl-10,11-dihydro-5H-dibenzo[b,f]azepine (422 mg, 1.11 mmol) obtained in step 1.

ESI-MS m/z: 421 $(M+H)^+$; $^1$H-NMR ($CDCl_3$, δ): 1.34 (t, J=7.6 Hz, 3H), 2.38 (s, 3H), 2.64 (s, 3H), 2.85 (q, J=7.6 Hz, 2H), 3.02-3.12 (m, 4H), 4.52 (s, 2H), 5.21 (s, 2H), 6.78-6.87 (m, 4H), 7.00-7.24 (m, 5H).

[step 3] The title compound (compound 5, 71.5 mg, 51%) was obtained in the same manner as in step 3 of Example 1, using 5-cyanomethyl-2-(2-ethyl-4,6-dimethylbenzimidazol-1-yl)methyl-10,11-dihydro-5H-dibenzo[b,f]azepine (122 mg, 0.290 mmol) obtained in step 2.

ESI-MS m/z: 480 $(M+H)^+$; $^1$H-NMR (DMSO-$d_6$, δ): 1.22 (t, J=7.5 Hz, 3H), 2.31 (s, 3H), 2.46 (s, 3H), 2.77 (q, J=7.4 Hz, 2H), 3.09 (br s, 4H), 4.83 (s, 2H), 5.28 (s, 2H), 6.74-7.18 (m, 9H), 12.34 (s, 1H).

Example 6

2-(4-methyl-2-propylbenzimidazol-1-yl)methyl-5-(5-oxo-4,5-dihydro-1,2,4-oxadiazol-3-yl)methyl-10,11-dihydro-5H-dibenzo[b,f]azepine (Compound 6)

[step 1] 2-(4-Methyl-2-propylbenzimidazol-1-yl)methyl-10,11-dihydro-5H-dibenzo[b,f]azepine (4.46 g, 71%) was obtained in the same manner as in step 1 of Example 1, using 4-methyl-2-propylbenzimidazole (EP400835; 3.00 g, 17.2 mmol) instead of 2-ethyl-5,7-dimethyl-3H-imidazo[4,5-b]pyridine.

ESI-MS m/z: 382 $(M+H)^+$; $^1$H-NMR ($CDCl_3$, δ): 1.00 (t, J=7.3 Hz, 3H), 1.73-1.86 (m, 2H), 2.69 (s, 3H), 2.86 (t, J=8.1 Hz, 2H), 2.97-3.04 (s, 4H), 5.22 (s, 2H), 6.02 (s, 1H), 6.61-6.64 (m, 1H), 6.70-6.80 (m, 4H), 7.01-7.12 (m, 5H).

[step 2] 5-Cyanomethyl-2-(4-methyl-2-propylbenzimidazol-1-yl)methyl-10,11-dihydro-5H-dibenzo[b,f]azepine (3.73 g, 76%) was obtained in the same manner as in step 2 of Example 1, using 2-(4-methyl-2-propylbenzimidazol-1-yl)methyl-10,11-dihydro-5H-dibenzo[b,f]azepine (4.46 g, 11.7 mmol) obtained in step 1.

ESI-MS m/z: 421 $(M+H)^+$; $^1$H-NMR ($CDCl_3$, δ): 1.00 (t, J=7.1 Hz, 3H), 1.74-1.87 (m, 2H), 2.69 (s, 3H), 2.84 (t, J=8.1 Hz, 2H), 3.00-3.11 (s, 4H), 4.51 (s, 2H), 5.24 (s, 2H), 6.79-6.80 (m, 1H), 6.87 (dd, J=8.4, 2.2 Hz, 1H), 6.98-7.24 (m, 8H).

[step 3] The title compound (compound 6, 0.20 g, 35%) was obtained in the same manner as in step 3 of Example 1, using 5-cyanomethyl-2-(4-methyl-2-propylbenzimidazol-1-yl)methyl-10,11-dihydro-5H-dibenzo[b,f]azepine (0.50 g, 1.19 mmol) obtained in step 2.

ESI-MS m/z: 480 $(M+H)^+$; $^1$H-NMR (DMSO-$d_6$, δ): 0.90 (t, J=7.4 Hz, 3H), 1.69 (q, J=7.3 Hz, 2H), 2.48 (s, 3H), 2.75 (t, J=7.6 Hz, 2H), 3.07 (br s, 4H), 4.82 (s, 2H), 5.32 (s, 2H), 6.75-6.79 (m, 1H), 6.90-7.02 (m, 4H), 7.07-7.20 (m, 5H), 12.35 (br s, 1H).

Example 7

2-(2-ethoxy-5,7-dimethyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 7)

[step 1] 2-(2-Ethoxy-5,7-dimethyl-3H-imidazo[4,5-b]pyridin-3-yl)methyl-10,11-dihydro-5H-dibenzo[b,f]azepine (324 mg, 33%) was obtained in the same manner as in step 1 of Example 1, using 2-ethoxy-5,7-dimethyl-3H-imidazo[4,5-b]pyridine (478 mg, 2.50 mmol), obtained in Reference Example 2, instead of 2-ethyl-5,7-dimethyl-3H-imidazo[4,5-b]pyridine.

ESI-MS m/z: 399 $(M+H)^+$; $^1$H-NMR ($CDCl_3$, δ): 1.44 (t, J=7.1 Hz, 3H), 2.49 (s, 3H), 2.56 (s, 3H), 3.02 (br s, 4H), 4.58 (q, J=7.0 Hz, 2H), 5.12 (s, 2H), 5.98 (s, 1H), 6.60-6.78 (m, 4H), 7.00-7.08 (m, 4H).

[step 2] 5-Cyanomethyl-2-(2-ethoxy-5,7-dimethyl-3H-imidazo[4,5-b]pyridin-3-yl)methyl-10,11-dihydro-5H-dibenzo[b,f]azepine (336 mg, 96%) was obtained in the same manner as in step 2 of Example 1, using 2-(2-ethoxy-5,7-dimethyl-3H-imidazo[4,5-b]pyridin-3-yl)methyl-10,11-dihydro-5H-dibenzo[b,f]azepine (320 mg, 0.803 mmol) obtained in step 1.

ESI-MS m/z: 438 $(M+H)^+$; $^1$H-NMR (DMSO-$d_6$, δ): 1.36 (t, J=7.1 Hz, 3H), 2.40 (s, 3H), 2.44 (s, 3H), 3.04 (br s, 4H), 4.53 (q, J=7.1 Hz, 2H), 4.89 (s, 2H), 5.09 (s, 2H), 6.84 (s, 1H), 6.98-7.19 (m, 7H).

[step 3] The title compound (compound 7, 119 mg, 66%) was obtained in the same manner as in step 3 of Example 1, using 5-cyanomethyl-2-(2-ethoxy-5,7-dimethyl-3H-imidazo[4,5-b]pyridin-3-yl)methyl-10,11-dihydro-5H-dibenzo[b,f]azepine (159 mg, 0.363 mmol) obtained in step 2.

ESI-MS m/z: 497 $(M+H)^+$; $^1$H-NMR (DMSO-$d_6$, δ): 1.34 (t, J=7.0 Hz, 3H), 2.39 (s, 3H), 2.43 (s, 3H), 3.10 (br s, 4H), 4.51 (q, J=7.1 Hz, 2H), 4.84 (s, 2H), 5.06 (s, 2H), 6.83 (s, 1H), 6.92-6.97 (m, 2H), 7.03-7.18 (m, 5H), 12.33 (s, 1H).

Example 8

2-(2-methoxy-5,7-dimethyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 8)

[step 1] 2-(2-Methoxy-5,7-dimethyl-3H-imidazo[4,5-b]pyridin-3-yl)methyl-10,11-dihydro-5H-dibenzo[b,f]azepine (285 mg, 30%) was obtained in the same manner as in step 1 of Example 1, using 2-methoxy-5,7-dimethyl-3H-imidazo[4,5-b]pyridine (WO2005/82905; 443 mg, 2.50 mmol) instead of 2-ethyl-5,7-dimethyl-3H-imidazo[4,5-b]pyridine.

ESI-MS m/z: 385 $(M+H)^+$; $^1$H-NMR ($CDCl_3$, δ): 2.51 (s, 3H), 2.56 (s, 3H), 3.01 (br s, 4H), 4.17 (s, 3H), 5.12 (s, 2H), 5.99 (s, 1H), 6.60-6.79 (m, 4H), 6.99-7.08 (m, 4H).

[step 2] 5-Cyanomethyl-2-(2-methoxy-5,7-dimethyl-3H-imidazo[4,5-b]pyridin-3-yl)methyl-10,11-dihydro-5H-dibenzo[b,f]azepine (210 mg, 68%) was obtained in the same manner as in step 2 of Example 1, using 2-(2-methoxy-5,7-dimethyl-3H-imidazo[4,5-b]pyridin-3-yl)methyl-10,11-dihydro-5H-dibenzo[b,f]azepine (281 mg, 0.731 mmol) obtained in step 1.

ESI-MS m/z: 424 $(M+H)^+$; $^1$H-NMR (DMSO-$d_6$, δ): 2.41 (s, 3H), 2.44 (s, 3H), 3.04 (br s, 4H), 4.10 (s, 3H), 4.89 (s, 2H), 5.10 (s, 2H), 6.86 (s, 1H), 6.97-7.06 (m, 3H), 7.12-7.20 (m, 4H).

[step 3] The title compound (compound 8, 69.0 mg, 60%) was obtained in the same manner as in step 3 of Example 1, using 5-cyanomethyl-2-(2-methoxy-5,7-dimethyl-3H-imidazo[4,5-b]pyridin-3-yl)methyl-10,11-dihydro-5H-dibenzo[b,f]azepine (101 mg, 0.238 mmol) obtained in step 2.

ESI-MS m/z: 483 $(M+H)^+$; $^1$H-NMR ($CDCl_3$, δ): 2.49 (s, 3H), 2.52 (s, 3H), 3.06 (br s, 4H), 4.13 (s, 3H), 4.72 (s, 2H), 5.11 (s, 2H), 6.77 (s, 1H), 6.87-7.11 (m, 7H).

Example 9

2-(2-ethyl-7-methyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 9)

[step 1] 2-(2-Ethyl-7-methyl-3H-imidazo[4,5-b]pyridin-3-yl)methyl-10,11-dihydro-5H-dibenzo[b,f]azepine (153 mg, 21%) was obtained in the same manner as in step 1 of Example 1, using 2-ethyl-7-methyl-3H-imidazo[4,5-b]pyridine (U.S. Pat. No. 5,332,744; 322 mg, 2.00 mmol) instead of 2-ethyl-5,7-dimethyl-3H-imidazo[4,5-b]pyridine.

ESI-MS m/z: 369 $(M+H)^+$; $^1$H-NMR (DMSO-$d_6$, δ): 1.25 (t, J=7.4 Hz, 3H), 2.55 (s, 3H), 2.85 (q, J=7.4 Hz, 2H), 2.89 (br s, 4H), 5.33 (s, 2H), 6.61-6.66 (m, 1H), 6.82-7.08 (m, 7H), 8.16 (d, J=4.8 Hz, 1H), 8.30 (s, 1H).

[step 2] 5-Cyanomethyl-2-(2-ethyl-7-methyl-3H-imidazo[4,5-b]pyridin-3-yl)methyl-10,11-dihydro-5H-dibenzo[b,f]azepine (156 mg, 94%) was obtained in the same manner as in step 2 of Example 1, using 2-(2-ethyl-7-methyl-3H-imidazo[4,5-b]pyridin-3-yl)methyl-10,11-dihydro-5H-dibenzo[b,f]azepine (150 mg, 0.407 mmol) obtained in step 1.

ESI-MS m/z: 408 $(M+H)^+$; $^1$H-NMR ($CDCl_3$, δ): 1.35 (t, J=7.5 Hz, 3H), 2.69 (s, 3H), 2.84 (q, J=7.5 Hz, 2H), 3.02-3.10 (m, 4H), 4.50 (s, 2H), 5.40 (s, 2H), 6.90-7.26 (m, 8H), 8.19 (d, J=5.0 Hz, 1H).

[step 3] The title compound (compound 9, 20.6 mg, 23%) was obtained in the same manner as in step 3 of Example 1, using 5-cyanomethyl-2-(2-ethyl-7-methyl-3H-imidazo[4,5-b]pyridin-3-yl)methyl-10,11-dihydro-5H-dibenzo[b,f]azepine (79.0 mg, 0.194 mmol) obtained in step 2.

ESI-MS m/z: 467 $(M+H)^+$; $^1$H-NMR ($CDCl_3$, δ): 1.23 (t, J=7.6 Hz, 3H), 2.58 (s, 3H), 2.79 (q, J=7.6 Hz, 2H), 2.87-2.99 (m, 4H), 4.74 (s, 2H), 5.35 (s, 2H), 6.50 (s, 1H), 6.77 (s, 1H), 6.84-7.16 (m, 7H), 8.13 (d, J=5.0 Hz, 1H).

Example 10

2-[5-ethoxycarbonyl-4-(1-hydroxy-1-methyl)ethyl-2-propylimidazol-1-yl]methyl-5-(5-oxo-4,5-dihydro-1,2,4-oxadiazol-3-yl)methyl-10,11-dihydro-5H-dibenzo[b,f]azepine (Compound 10)

[step 1] 2-[5-Ethoxycarbonyl-4-(1-hydroxy-1-methyl)ethyl-2-propylimidazol-1-yl]methyl-10,11-dihydro-5H-dibenzo[b,f]azepine (2.73 g, 45%) was obtained in the same manner as in step 1 of Example 1, using 5-ethoxycarbonyl-4-(1-hydroxy-1-methyl)ethyl-2-propylimidazole (JP-A-5-783228; 5.87 g, 13.5 mmol) instead of 2-ethyl-5,7-dimethyl-3H-imidazo[4,5-b]pyridine and potassium tert-butoxide (1.67 g, 14.9 mmol) instead of lithium hydroxide.

ESI-MS m/z: 448 $(M+H)^+$; $^1$H-NMR ($CDCl_3$, δ): 0.95 (t, J=7.3 Hz, 3H), 1.21 (t, J=7.1 Hz, 3H), 1.63-1.76 (m, 2H), 1.63 (s, 6H), 2.63 (t, J=7.8 Hz, 2H), 2.99-3.07 (m, 4H), 4.25 (q, J=7.1 Hz, 2H), 5.34 (s, 2H), 5.80 (s, 1H), 5.99 (s, 1H), 6.58-6.81 (m, 5H), 7.02-7.10 (m, 2H).

[step 2] 5-Cyanomethyl-2-[5-ethoxycarbonyl-4-(1-hydroxy-1-methyl)ethyl-2-propylimidazol-1-yl]methyl-10,11-dihydro-5H-dibenzo[b,f]azepine (2.21 g, 74%) was obtained in the same manner as in step 2 of Example 1, using 2-[5-ethoxycarbonyl-4-(1-hydroxy-1-methyl)ethyl-2-propylimidazol-1-yl]methyl-10,11-dihydro-5H-dibenzo[b,f]azepine (2.73 g, 6.1 mmol) obtained in step 1.

ESI-MS m/z: 487 $(M+H)^+$; $^1$H-NMR ($CDCl_3$, δ): 0.94 (t, J=7.3 Hz, 3H), 1.19 (t, J=7.1 Hz, 3H), 1.62-1.77 (m, 2H), 1.63 (s, 6H), 2.60 (t, J=7.8 Hz, 2H), 3.06-3.14 (m, 4H), 4.23 (q, J=7.1 Hz, 2H), 4.54 (s, 2H), 5.37 (s, 2H), 5.73 (s, 1H), 6.68-6.76 (m, 2H), 7.01-7.28 (m, 5H).

[step 3] The title compound (compound 10, 106 mg, 72%) was obtained in the same manner as in step 3 of Example 1, using 5-cyanomethyl-2-[5-ethoxycarbonyl-4-(1-hydroxy-1-methyl)ethyl-2-propylimidazol-1-yl]methyl-10,11-dihydro-5H-dibenzo[b,f]azepine (131 mg, 0.269 mmol) obtained in step 2.

ESI-MS m/z: 546 $(M+H)^+$; $^1$H-NMR ($CDCl_3$, δ): 0.92 (t, J=7.3 Hz, 3H), 1.13 (t, J=7.1 Hz, 3H), 1.61 (s, 6H), 1.68 (m, 2H), 2.58 (t, J=7.8 Hz, 2H), 3.13 (br s, 4H), 4.18 (q, J=7.2 Hz, 2H), 4.81 (s, 2H), 5.33 (s, 2H), 5.79 (br s, 1H), 6.66-6.70 (m, 2H), 7.20-6.97 (m, 5H).

Example 11

2-[5-ethoxycarbonyl-2-ethyl-4-(1-hydroxy-1-methyl)ethylimidazol-1-yl]methyl-5-(5-oxo-4,5-dihydro-1,2,4-oxadiazol-3-yl)methyl-10,11-dihydro-5H-dibenzo[b,f]azepine (Compound 11)

[step 1] 2-[5-Ethoxycarbonyl-2-ethyl-4-(1-hydroxy-1-methyl)ethylimidazol-1-yl]methyl-10,11-dihydro-5H-dibenzo[b,f]azepine (302 mg, 47%) was obtained in the same manner as in step 1 of Example 1, using 5-ethoxycarbonyl-2-ethyl-4-(1-hydroxy-1-methyl)ethylimidazole (JP-A-5-783228; 650 mg, 1.50 mmol) instead of 2-ethyl-5,7-dimethyl-3H-imidazo

[4,5-b]pyridine and potassium tert-butoxide (1.67 g, 14.9 mmol) instead of lithium hydroxide.

ESI-MS m/z: 434 $(M+H)^+$; $^1$H-NMR ($CDCl_3$, δ): 1.22 (t, J=7.1 Hz, 3H), 1.25 (t, J=7.5 Hz, 3H), 1.64 (s, 6H), 2.69 (q, J=7.5 Hz, 2H), 2.99-3.07 (m, 4H), 4.26 (q, J=7.1 Hz, 2H), 5.34 (s, 2H), 5.79 (s, 1H), 5.98 (s, 1H), 6.57-6.81 (m, 5H), 7.02-7.10 (m, 2H).

[step 2] 5-Cyanomethyl-2-[5-ethoxycarbonyl-2-ethyl-4-(1-hydroxy-1-methyl)ethylimidazol-1-yl]methyl-10,11-dihydro-5H-dibenzo[b,f]azepine (253 mg, 78%) was obtained in the same manner as in step 2 of Example 1, using 2-[5-ethoxycarbonyl-2-ethyl-4-(1-hydroxy-1-methyl)ethylimidazol-1-yl]methyl-10,11-dihydro-5H-dibenzo[b,f]azepine (299 mg, 0.690 mmol) obtained in step 1.

ESI-MS m/z: 473 $(M+H)^+$; $^1$H-NMR ($CDCl_3$, δ): 1.20 (t, J=7.2 Hz, 3H), 1.25 (t, J=7.6 Hz, 3H), 1.63 (s, 6H), 2.65 (q, J=7.6 Hz, 2H), 3.06-3.14 (m, 4H), 4.24 (q, J=7.2 Hz, 2H), 4.54 (s, 2H), 5.37 (s, 2H), 5.71 (s, 1H), 6.69-6.77 (m, 2H), 7.01-7.28 (m, 5H).

[step 3] The title compound (compound 11, 97.5 mg, 69%) was obtained in the same manner as in step 3 of Example 1, using 5-cyanomethyl-2-[5-ethoxycarbonyl-2-ethyl-4-(1-hydroxy-1-methyl)ethylimidazol-1-yl]methyl-10,11-dihydro-5H-dibenzo[b,f]azepine (126 mg, 0.267 mmol) obtained in step 2.

ESI-MS m/z: 532 $(M+H)^+$; $^1$H-NMR ($CDCl_3$, δ): 1.14 (t, J=7.1 Hz, 3H), 1.23 (t, J=7.6 Hz, 3H), 1.61 (s, 6H), 2.63 (q, J=7.5 Hz, 2H), 3.14 (br s, 4H), 4.20 (q, J=7.1 Hz, 2H), 4.82 (s, 2H), 5.34 (s, 2H), 5.77 (s, 1H), 6.68-6.71 (m, 2H), 6.98-7.19 (m, 5H).

Example 12

2-(7-chloro-2-ethyl-5-methyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 12)

[step 1] 2-(7-Chloro-2-ethyl-5-methyl-3H-imidazo[4,5-b]pyridin-3-yl)methyl-10,11-dihydro-5H-dibenzo[b,f]azepine (246 mg, 72%) was obtained in the same manner as in step 1 of Example 1, using 7-chloro-2-ethyl-5-methyl-3H-imidazo[4,5-b]pyridine (U.S. Pat. No. 5,332,744; 166 mg, 0.850 mmol) instead of 2-ethyl-5,7-dimethyl-3H-imidazo[4,5-b]pyridine.

ESI-MS m/z: 403 $(M+H)^+$; $^1$H-NMR (DMSO-$d_6$, δ): 1.25 (t, J=7.5 Hz, 3H), 2.57 (s, 3H), 2.83 (q, J=7.4 Hz, 2H), 2.89 (br s, 4H), 5.32 (s, 2H), 6.61-7.03 (m, 7H), 7.28 (s, 1H).

[step 2] 2-(7-Chloro-2-ethyl-5-methyl-3H-imidazo[4,5-b]pyridin-3-yl)methyl-5-cyanomethyl-10,11-dihydro-5H-dibenzo[b,f]azepine (208 mg, 78%) was obtained in the same manner as in step 2 of Example 1, using 2-(7-chloro-2-ethyl-5-methyl-3H-imidazo[4,5-b]pyridin-3-yl)methyl-10,11-dihydro-5H-dibenzo[b,f]azepine (242 mg, 0.601 mmol) obtained in step 1.

ESI-MS m/z: 442 $(M+H)^+$; $^1$H-NMR ($CDCl_3$, δ): 1.35 (t, J=7.5 Hz, 3H), 2.60 (s, 3H), 2.80 (q, J=7.5 Hz, 2H), 3.01-3.12 (m, 4H), 4.52 (s, 2H), 5.37 (s, 2H), 6.86-7.25 (m, 8H).

[step 3] The title compound (compound 12, 92.4 mg, 81%) was obtained in the same manner as in step 3 of Example 1, using 2-(7-chloro-2-ethyl-5-methyl-3H-imidazo[4,5-b]pyridin-3-yl)methyl-5-cyanomethyl-10,11-dihydro-5H-dibenzo[b,f]azepine (101 mg, 0229 mmol) obtained in step 2.

ESI-MS m/z: 501 $(M+H)^+$; $^1$H-NMR (DMSO-$d_6$, δ): 1.21 (t, J=7.4 Hz, 3H), 2.54 (s, 3H), 2.78 (q, J=7.5 Hz, 2H), 3.09 (br s, 4H), 4.84 (s, 2H), 5.37 (s, 2H), 6.84-6.98 (m, 3H), 7.09-7.18 (m, 4H), 7.27 (s, 1H), 12.33 (s, 1H).

Example 13

2-(2-butyl-5,7-dimethyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 13)

[step 1] 2-(2-Butyl-5,7-dimethyl-3H-imidazo[4,5-b]pyridin-3-yl)methyl-10,11-dihydro-5H-dibenzo[b,f]azepine (2.35 g, 57%) was obtained in the same manner as in step 1 of Example 1, using 2-butyl-5,7-dimethyl-3H-imidazo[4,5-b]pyridine (U.S. Pat. No. 5,332,744; 2.03 g, 10.0 mmol) instead of 2-ethyl-5,7-dimethyl-3H-imidazo[4,5-b]pyridine.

ESI-MS m/z: 411 $(M+H)^+$; $^1$H-NMR ($CDCl_3$, δ): 0.88 (t, J=7.3 Hz, 3H), 1.32-1.43 (m, 2H), 1.62-1.72 (m, 2H), 2.60 (s, 3H), 2.62 (s, 3H), 2.77 (t, J=8.0 Hz, 2H), 2.96-3.04 (m, 4H), 5.35 (s, 2H), 5.99 (s, 1H), 6.61-6.88 (m, 6H), 7.00-7.09 (m, 2H).

[step 2] 2-(2-Butyl-5,7-dimethyl-3H-imidazo[4,5-b]pyridin-3-yl)methyl-5-cyanomethyl-10,11-dihydro-5H-dibenzo[b,f]azepine (1.48 g, 63%) was obtained in the same manner as in step 2 of Example 1, using 2-(2-butyl-5,7-dimethyl-3H-imidazo[4,5-b]pyridin-3-yl)methyl-10,11-dihydro-5H-dibenzo[b,f]azepine (2.15 g, 5.24 mmol) obtained in step 1.

ESI-MS m/z: 450 $(M+H)^+$; $^1$H-NMR ($CDCl_3$, δ): 0.87 (t, J=7.3 Hz, 3H), 1.30-1.43 (m, 2H), 1.62-1.74 (m, 2H), 2.58 (s, 3H), 2.62 (s, 3H), 2.74 (t, J=8.0 Hz, 2H), 3.01-3.12 (m, 4H), 4.51 (s, 2H), 5.37 (s, 2H), 6.88-7.24 (m, 8H).

[step 3] The title compound (compound 13, 195 mg, 77%) was obtained in the same manner as in step 3 of Example 1, using 2-(2-butyl-5,7-dimethyl-3H-imidazo[4,5-b]pyridin-3-yl)methyl-5-cyanomethyl-10,11-dihydro-5H-dibenzo[b,f]azepine (225 mg, 0.500 mmol) obtained in step 2.

ESI-MS m/z: 509 $(M+H)^+$; $^1$H-NMR (DMSO-$d_6$, δ): 0.77 (t, J=7.3 Hz, 3H), 1.20-1.34 (m, 2H), 1.51-1.62 (m, 2H), 2.49 (s, 6H), 2.71 (t, J=7.7 Hz, 2H), 3.09 (br s, 4H), 4.84 (s, 2H), 5.34 (s, 2H), 6.80-7.19 (m, 8H), 12.34 (br s, 1H).

Example 14

2-(5-ethoxycarbonyl-4-ethyl-2-propylimidazol-1-yl)methyl-5-(5-oxo-4,5-dihydro-1,2,4-oxadiazol-3-yl)methyl-10,11-dihydro-5H-dibenzo[b,f]azepine (Compound 14)

[step 1] 2-(5-Ethoxycarbonyl-4-ethyl-2-propylimidazol-1-yl)methyl-10,11-dihydro-5H-dibenzo[b,f]azepine (372 mg, 26%) was obtained in the same manner as in step 1 of Example 1, using 5-ethoxycarbonyl-4-ethyl-2-propylimidazole (Bioorg. Med. Chem. Lett., 1994, vol. 4, p. 63; 1.50 g, 3.45 mmol) instead of 2-ethyl-5,7-dimethyl-3H-imidazo[4,5-b]pyridine and potassium tert-butoxide (1.67 g, 14.9 mmol) instead of lithium hydroxide.

ESI-MS m/z: 418 $(M+H)^+$; $^1$H-NMR ($CDCl_3$, δ): 0.94 (t, J=7.3 Hz, 3H), 1.25 (t, J=7.8 Hz, 3H), 1.30 (t, J=7.5 Hz, 3H), 1.63-1.76 (m, 2H), 2.62 (t, J=7.8 Hz, 2H), 2.90 (q, J=7.5 Hz, 2H), 2.98-3.06 (m, 4H), 4.25 (q, J=7.3 Hz, 2H), 5.41 (s, 2H), 5.97 (s, 1H), 6.65-6.79 (m, 5H), 7.01-7.10 (m, 2H).

[step 2] 5-Cyanomethyl-2-(5-ethoxycarbonyl-4-ethyl-2-propylimidazol-1-yl)methyl-10,11-dihydro-5H-dibenzo[b,f]azepine (356 mg, 88%) was obtained in the same manner as in step 2 of Example 1, using 2-(5-ethoxycarbonyl-4-ethyl-2-propylimidazol-1-yl)methyl-10,11-dihydro-5H-dibenzo[b,f]azepine (369 mg, 0.884 mmol) obtained in step 1.

ESI-MS m/z: 457 $(M+H)^+$; $^1H$-NMR ($CDCl_3$, δ): 0.94 (t, J=7.1 Hz, 3H), 1.22-1.32 (m, 6H), 1.65-1.75 (m, 2H), 2.59 (t, J=7.6 Hz, 2H), 2.90 (q, J=7.4 Hz, 2H), 3.05-3.13 (m, 4H), 4.23 (q, J=7.1 Hz, 2H), 4.52 (s, 2H), 5.43 (s, 2H), 6.74-6.78 (m, 2H), 6.99-7.28 (m, 5H).

[step 3] The title compound (compound 14, 163 mg, 60%) was obtained in the same manner as in step 3 of Example 1, using 5-cyanomethyl-2-(5-ethoxycarbonyl-4-ethyl-2-propylimidazol-1-yl)methyl-10,11-dihydro-5H-dibenzo[b,f]azepine (242 mg, 0.530 mmol) obtained in step 2.

ESI-MS m/z: 516 $(M+H)^+$; $^1H$-NMR ($CDCl_3$, δ): 0.90 (t, J=7.3 Hz, 3H), 1.28 (t, J=7.4 Hz, 3H), 1.29 (t, J=7.1 Hz, 3H), 1.68 (m, 2H), 2.76 (t, J=7.8 Hz, 2H), 2.97 (q, J=7.5 Hz, 2H), 3.14 (br s, 4H), 4.26 (q, J=7.2 Hz, 2H), 4.83 (s, 2H), 5.47 (s, 2H), 6.75 (m, 2H), 6.98-7.18 (m, 5H).

Example 15

2-(2-ethyl-5-methyl-7-trifluoromethyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 15)

[step 1] 2-(2-Ethyl-5-methyl-7-trifluoromethyl-3H-imidazo[4,5-b]pyridin-3-yl)methyl-10,11-dihydro-5H-dibenzo[b,f]azepine (153 mg, 50%) was obtained in the same manner as in step 1 of Example 1, using 2-ethyl-5-methyl-7-trifluoromethyl-3H-imidazo[4,5-b]pyridine (160 mg, 0.700 mmol), obtained in Reference Example 3, instead of 2-ethyl-5,7-dimethyl-3H-imidazo[4,5-b]pyridine.

ESI-MS m/z: 437 $(M+H)^+$; $^1H$-NMR (DMSO-$d_6$, δ): 1.24 (t, J=7.4 Hz, 3H), 2.67 (s, 3H), 2.89 (q, J=7.4 Hz, 2H), 2.90 (br s, 4H), 5.38 (s, 2H), 6.61-7.04 (m, 7H), 7.46 (s, 1H).

[step 2] 5-Cyanomethyl-2-(2-ethyl-5-methyl-7-trifluoromethyl-3H-imidazo[4,5-b]pyridin-3-yl)methyl-10,11-dihydro-5H-dibenzo[b,f]azepine (134 mg, 82%) was obtained in the same manner as in step 2 of Example 1, using 2-(2-ethyl-5-methyl-7-trifluoromethyl-3H-imidazo[4,5-b]pyridin-3-yl)methyl-10,11-dihydro-5H-dibenzo[b,f]azepine (150 mg, 0.344 mmol) obtained in step 1.

ESI-MS m/z: 476 $(M+H)^+$; $^1H$-NMR ($CDCl_3$, δ): 1.34 (t, J=7.6 Hz, 3H), 2.69 (s, 3H), 2.85 (q, J=7.5 Hz, 2H), 3.03-3.13 (m, 4H), 4.52 (s, 2H), 5.41 (s, 2H), 6.89-7.29 (m, 8H).

[step 3] The title compound (compound 15, 65.3 mg, 87%) was obtained in the same manner as in step 3 of Example 1, using 5-cyanomethyl-2-(2-ethyl-5-methyl-7-trifluoromethyl-3H-imidazo[4,5-b]pyridin-3-yl)methyl-10,11-dihydro-5H-dibenzo[b,f]azepine (66.6 mg, 0.140 mmol) obtained in step 2.

ESI-MS m/z: 535 $(M+H)^+$; $^1H$-NMR ($CDCl_3$, δ): 1.30 (t, J=7.5 Hz, 3H), 2.67 (s, 3H), 2.82 (q, J=7.5 Hz, 2H), 3.11 (br s, 4H), 4.80 (s, 2H), 5.38 (s, 2H), 6.89-7.18 (m, 7H), 7.27 (s, 1H).

Example 16

2-(5-chloro-2-ethyl-7-methyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 16)

[step 1] 2-(5-Chloro-2-ethyl-7-methyl-3H-imidazo[4,5-b]pyridin-3-yl)methyl-10,11-dihydro-5H-dibenzo[b,f]azepine (222 mg, 67%) was obtained in the same manner as in step 1 of Example 1, using 5-chloro-2-ethyl-7-methyl-3H-imidazo[4,5-b]pyridine (U.S. Pat. No. 5,332,744; 355 mg, 0.817 mmol) instead of 2-ethyl-5,7-dimethyl-3H-imidazo[4,5-b]pyridine.

ESI-MS m/z: 403 $(M+H)^+$; $^1H$-NMR (DMSO-$d_6$, δ): 1.24 (t, J=7.5 Hz, 3H), 2.56 (s, 3H), 2.83 (q, J=7.5 Hz, 2H), 2.90 (br s, 4H), 5.29 (s, 2H), 6.62-7.03 (m, 7H), 7.18 (s, 1H).

[step 2] 2-(5-Chloro-2-ethyl-7-methyl-3H-imidazo[4,5-b]pyridin-3-yl)methyl-5-cyanomethyl-10,11-dihydro-5H-dibenzo[b,f]azepine (164 mg, 75%) was obtained in the same manner as in step 2 of Example 1, using 2-(5-chloro-2-ethyl-7-methyl-3H-imidazo[4,5-b]pyridin-3-yl)methyl-10,11-dihydro-5H-dibenzo[b,f]azepine (199 mg, 0.494 mmol) obtained in step 1.

ESI-MS m/z: 442 $(M+H)^+$; $^1H$-NMR ($CDCl_3$, δ): 1.33 (t, J=7.5 Hz, 3H), 2.65 (s, 3H), 2.78 (q, J=7.5 Hz, 2H), 3.03-3.12 (m, 4H), 4.51 (s, 2H), 5.34 (s, 2H), 6.88-7.28 (m, 8H).

[step 3] The title compound (compound 16, 48.1 mg, 84%) was obtained in the same manner as in step 3 of Example 1, using 2-(5-chloro-2-ethyl-7-methyl-3H-imidazo[4,5-b]pyridin-3-yl)methyl-5-cyanomethyl-10,11-dihydro-5H-dibenzo[b,f]azepine (50.7 mg, 0.115 mmol) obtained in step 2.

ESI-MS m/z: 501 $(M+H)^+$; $^1H$-NMR ($CDCl_3$, δ): 1.27 (t, J=7.6 Hz, 3H), 2.61 (s, 3H), 2.76 (q, J=7.5 Hz, 2H), 3.08 (br s, 4H), 4.80 (s, 2H), 5.31 (s, 2H), 6.84-7.18 (m, 8H).

Example 17

2-(7-fluoro-4-methyl-2-propylbenzimidazol-1-yl)methyl-5-(5-oxo-4,5-dihydro-1,2,4-oxadiazol-3-yl)methyl-10,11-dihydro-5H-dibenzo[b,f]azepine (Compound 17)

[step 1] 2-(7-Fluoro-4-methyl-2-propylbenzimidazol-1-yl)methyl-10,11-dihydro-5H-dibenzo[b,f]azepine (370 mg, 92%) was obtained in the same manner as in step 1 of Example 1, using 4-fluoro-7-methyl-2-propylbenzimidazole (478 mg, 1.10 mmol), obtained in Reference Example 4, instead of 2-ethyl-5,7-dimethyl-3H-imidazo[4,5-b]pyridine.

ESI-MS m/z: 400 $(M+H)^+$; $^1H$-NMR (DMSO-$d_6$, δ): 0.96 (t, J=7.3 Hz, 3H), 1.72-1.75 (m, 2H), 2.47 (s, 3H), 2.84 (q, J=7.3 Hz, 2H), 2.89 (br s, 4H), 5.37 (s, 2H), 6.61-7.03 (m, 9H).

[step 2] 5-Cyanomethyl-2-(7-fluoro-4-methyl-2-propylbenzimidazol-1-yl)methyl-10,11-dihydro-5H-dibenzo[b,f]azepine (323 mg, 80%) was obtained in the same manner as in step 2 of Example 1, using 2-(7-fluoro-4-methyl-2-propylbenzimidazol-1-yl)methyl-10,11-dihydro-5H-dibenzo[b,f]azepine (367 mg, 0.919 mmol) obtained in step 1.

ESI-MS m/z: 439 $(M+H)^+$; $^1H$-NMR ($CDCl_3$, δ): 1.01 (t, J=7.3 Hz, 3H), 1.76-1.85 (m, 2H), 2.61 (s, 3H), 2.80 (t, J=7.8 Hz, 2H), 3.02-3.12 (m, 4H), 4.51 (s, 2H), 5.41 (s, 2H), 6.73-7.27 (m, 9H).

[step 3] The title compound (compound 17, 118 mg, 64%) was obtained in the same manner as in step 3 of Example 1, using 5-cyanomethyl-2-(7-fluoro-4-methyl-2-propylbenzimidazol-1-yl)methyl-10,11-dihydro-5H-dibenzo[b,f]azepine (162 mg, 0.369 mmol) obtained in step 2.

ESI-MS m/z: 498 $(M+H)^+$; $^1H$-NMR ($CDCl_3$, δ): 0.92 (t, J=7.3 Hz, 3H), 1.72 (m, 2H), 2.55 (s, 3H), 2.88 (t, J=7.9 Hz, 2H), 3.05 (br s, 4H), 4.78 (s, 2H), 5.39 (s, 2H), 6.77-7.15 (m, 9H).

Example 18

2-(4-methyl-2-propylbenzimidazol-1-yl)methyl-5-[1-(5-oxo-4,5-dihydro-1,2,4-oxadiazol-3-yl)ethyl]-10,11-dihydro-5H-dibenzo[b,f]azepine (Compound 18)

[step 1] 5-(1-Cyanoethyl)-2-(4-methyl-2-propylbenzimidazol-1-yl)methyl-10,11-dihydro-5H-dibenzo[b,f]azepine (527 mg, 87%) was obtained in the same manner as in step 2 of Example 1, using 2-(4-methyl-2-propylbenzimidazol-1-yl)methyl-10,11-dihydro-5H-dibenzo[b,f]azepine (531 mg, 1.39 mmol) obtained in step 1 of Example 6 and acetaldehyde (117 μL, 2.09 mmol) instead of paraformaldehyde.

ESI-MS m/z: 435 $(M+H)^+$; $^1$H-NMR ($CDCl_3$, δ): 1.00 (t, J=7.3 Hz, 3H), 1.48 (d, J=7.3 Hz, 3H), 1.75-1.85 (m, 2H), 2.68 (s, 3H), 2.84 (t, J=7.9 Hz, 2H), 2.89-3.10 (m, 4H), 4.65 (q, J=7.3 Hz, 1H), 5.24 (s, 2H), 6.75-7.58 (m, 10H).

[step 2] The title compound (compound 18, 55.5 mg, 19%) was 75 obtained in the same manner as in step 3 of Example 1, using 5-(1-cyanoethyl)-2-(4-methyl-2-propylbenzimidazol-1-yl)methyl-10,11-dihydro-5H-dibenzo[b,f]azepine (251 mg, 0.578 mmol) obtained in step 1.

ESI-MS m/z: 494 $(M+H)^+$; $^1$H-NMR ($CDCl_3$, δ): 0.95 (t, J=7.3 Hz, 3H), 1.48 (d, J=6.4 Hz, 3H), 1.75 (m, 2H), 2.64 (s, 3H), 2.79 (t, J=7.9 Hz, 2H), 2.88-3.16 (m, 4H), 5.20 (s, 2H), 5.21 (q, J=6.5 Hz, 1H), 6.74-6.79 (m, 2H), 6.96-7.12 (m, 8H).

Example 19

2-(2-ethyl-5,7-dimethyl-3H-imidazo[4,5-b]pyridin-3-yl)methyl-5-[1-(5-oxo-4,5-dihydro-1,2,4-oxadiazol-3-yl)ethyl]-10,11-dihydro-5H-dibenzo[b,f]azepine (Compound 19)

[step 1] 5-(1-Cyanoethyl)-2-(2-ethyl-5,7-dimethyl-3H-imidazo[4,5-b]pyridin-3-yl)methyl-10,11-dihydro-5H-dibenzo[b,f]azepine (595 mg, 99%) was obtained in the same manner as in step 2 of Example 1, using 2-(2-ethyl-5,7-dimethyl-3H-imidazo[4,5-b]pyridin-3-yl)methyl-10,11-dihydro-5H-dibenzo[b,f]azepine (532 mg, 1.39 mmol) obtained in step 1 of Example 1, acetaldehyde (156 μL, 2.78 mmol) instead of paraformaldehyde.

ESI-MS m/z: 436 $(M+H)^+$; $^1$H-NMR (DMSO-$d_6$, δ): 1.22 (t, J=7.5 Hz, 3H), 1.37 (d, J=6.9 Hz, 3H), 2.50 (s, 6H), 2.77 (q, J=7.5 Hz, 2H), 2.99 (br s, 4H), 5.08 (q, J=6.9 Hz, 1H), 5.36 (s, 2H), 6.92-7.42 (m, 8H).

[step 2] The title compound (compound 19, 114 mg, 30%) was obtained in the same manner as in step 3 of Example 1, using 5-(1-cyanoethyl)-2-(2-ethyl-5,7-dimethyl-3H-imidazo[4,5-b]pyridin-3-yl)methyl-10,11-dihydro-5H-dibenzo[b,f]azepine (337 mg, 0.774 mmol) obtained in step 1.

ESI-MS m/z: 495 $(M+H)^+$; $^1$H-NMR (DMSO-$d_6$, δ): 1.17 (t, J=7.4 Hz, 3H), 1.37 (d, J=6.4 Hz, 3H), 2.49 (s, 6H), 2.72 (q, J=7.4 Hz, 2H), 3.07 (br s, 4H), 5.29 (q, J=6.4 Hz, 1H), 5.32 (s, 2H), 6.77-7.22 (m, 8H), 12.38 (s, 1H).

Example 20

2-(2-ethyl-7-methyl-3H-imidazo[4,5-b]pyridin-3-yl)methyl-5-[1-(5-oxo-4,5-dihydro-1,2,4-oxadiazol-3-yl)ethyl]-10,11-dihydro-5H-dibenzo[b,f]azepine (Compound 20)

[step 1] 5-(1-Cyanoethyl)-2-(2-ethyl-7-methyl-3H-imidazo[4,5-b]pyridin-3-yl)methyl-10,11-dihydro-5H-dibenzo[b,f]azepine (593 mg, 88%) was obtained in the same manner as in step 2 of Example 1, using 2-(2-ethyl-7-methyl-3H-imidazo[4,5-b]pyridin-3-yl)methyl-10,11-dihydro-5H-dibenzo[b,f]azepine (586 mg, 1.6 mmol) obtained in step 1 of Example 9 and acetaldehyde (134 μL, 2.4 mmol) instead of paraformaldehyde.

ESI-MS m/z: 422 $(M+H)^+$; $^1$H-NMR ($CDCl_3$, δ): 1.34 (t, J=7.6 Hz, 3H), 1.47 (d, J=7.1 Hz, 3H), 2.68 (s, 3H), 2.83 (q, J=7.6 Hz, 2H), 2.85-3.14 (m, 4H), 4.64 (q, J=7.1 Hz, 1H), 5.40 (s, 2H), 6.87 (d, J=1.5 Hz, 1H), 6.96-7.12 (m, 4H), 7.16-7.22 (m, 1H), 7.48-7.56 (m, 2H), 8.20 (d, J=5.0 Hz, 1H).

[step 2] The title compound (compound 20, 98 mg, 46%) was obtained in the same manner as in step 3 of Example 1, using 5-(1-cyanoethyl)-2-(2-ethyl-7-methyl-3H-imidazo[4,5-b]pyridin-3-yl)methyl-10,11-dihydro-5H-dibenzo[b,f]azepine (186 mg, 0.44 mmol) obtained in step 1.

ESI-MS m/z: 481 $(M+H)^+$; $^1$H-NMR ($CDCl_3$, δ): 1.29 (t, J=7.5 Hz, 3H), 1.45 (d, J=6.4 Hz, 3H), 2.66 (s, 3H), 2.79 (q, J=7.5 Hz, 2H), 2.87-3.11 (m, 4H), 5.19 (q, J=6.4 Hz, 1H), 5.35 (s, 2H), 6.82-6.85 (m, 2H), 6.95-7.11 (m, 6H), 8.15 (d, J=4.9 Hz, 1H).

Example 21

2-(7-chloro-2-ethyl-5-methyl-3H-imidazo[4,5-b]pyridin-3-yl)methyl-5-[1-(5-oxo-4,5-dihydro-1,2,4-oxadiazol-3-yl)ethyl]-10,11-dihydro-5H-dibenzo[b,f]azepine (Compound 21)

[step 1] 2-(7-Chloro-2-ethyl-5-methyl-3H-imidazo[4,5-b]pyridin-3-yl)methyl-5-(1-cyanoethyl)-10,11-dihydro-5H-dibenzo[b,f]azepine (1.59 g, 82%) was obtained in the same manner as in step 2 of Example 1, using 2-(7-chloro-2-ethyl-5-methyl-3H-imidazo[4,5-b]pyridin-3-yl)methyl-10,11-dihydro-5H-dibenzo[b,f]azepine (1.71 g, 4.3 mmol) obtained in step 1 of Example 12 and acetaldehyde (358 μL, 6.4 mmol) instead of paraformaldehyde.

ESI-MS m/z: 456 $(M+H)^+$; $^1$H-NMR ($CDCl_3$, δ): 1.34 (t, J=7.5 Hz, 3H), 1.48 (d, J=7.3 Hz, 3H), 2.61 (s, 3H), 2.80 (q, J=7.5 Hz, 2H), 2.90-3.11 (m, 4H), 4.65 (q, J=7.3 Hz, 1H), 5.37 (s, 2H), 6.84 (d, J=2.0 Hz, 1H), 6.99-7.13 (m, 4H), 7.17-7.23 (m, 1H), 7.50-7.58 (m, 2H).

[step 2] The title compound (compound 21, 255 mg, 41%) was obtained in the same manner as in step 3 of Example 1, using 2-(7-chloro-2-ethyl-5-methyl-3H-imidazo[4,5-b]pyridin-3-yl)methyl-5-(1-cyanoethyl)-10,11-dihydro-5H-dibenzo[b,f]azepine (550 mg, 1.2 mmol) obtained in step 1.

ESI-MS m/z: 515 $(M+H)^+$; $^1$H-NMR ($CDCl_3$, δ): 1.27 (t, J=7.5 Hz, 3H), 1.47 (d, J=6.4 Hz, 3H), 2.59 (s, 3H), 2.74 (q, J=7.5 Hz, 2H), 2.95-3.17 (m, 4H), 5.21 (q, J=6.4 Hz, 1H), 5.26-5.38 (m, 2H), 6.83-6.87 (m, 2H), 6.95-7.09 (m, 6H).

Example 22

2-(2-ethyl-5,7-dimethyl-3H-imidazo[4,5-b]pyridin-3-yl)methyl-5-[1-(1H-tetrazol-5-yl)ethyl]-10,11-dihydro-5H-dibenzo[b,f]azepine (Compound 22)

5-(1-Cyanoethyl)-2-(2-ethyl-5,7-dimethyl-3H-imidazo[4,5-b]pyridin-3-yl)methyl-10,11-dihydro-5H-dibenzo[b,f]azepine (520 mg, 1.19 mmol) obtained in step 1 of Example 19 was dissolved in toluene (12 mL), and the solution was added with trimethylsilylazide (2.54 mL, 19.1 mmol) and dibutyltinoxide (177 mg, 0.71 mmol), followed by stirring at 70° C. for 2 days. The mixture was concentrated under reduced pressure, and the residue was purified by silica gel column chromatography (chloroform/methanol=25/1) to give the title compound (compound 22, 354 mg, 62%).

ESI-MS m/z: 479 $(M+H)^+$; $^1$H-NMR ($CDCl_3$, δ): 1.17 (t, J=7.5 Hz, 3H), 1.57 (d, J=6.6 Hz, 3H), 2.60 (s, 3H), 2.61 (s, 3H), 2.82 (q, J=7.5 Hz, 2H), 2.80-3.26 (m, 4H), 5.36 (s, 2H), 5.71 (q, J=6.6 Hz, 1H), 6.71-7.19 (m, 8H).

Example 23

2-(2-ethyl-5,7-dimethyl-3H-imidazo[4,5-b]pyridin-3-yl)methyl-5-[1-(1H-tetrazol-5-yl)propyl]-10,11-dihydro-5H-dibenzo[b,f]azepine (Compound 23)

[step 1] 5-(1-Cyanopropyl)-2-(2-ethyl-5,7-dimethyl-3H-imidazo[4,5-b]pyridin-3-yl)methyl-10,11-dihydro-5H-dibenzo[b,f]azepine (669 mg, 95%) was obtained in the same manner as in step 2 of Example 1, using 2-(2-ethyl-5,7-dimethyl-3H-imidazo[4,5-b]pyridin-3-yl)methyl-10,11-dihydro-5H-dibenzo[b,f]azepine (600 mg, 1.57 mmol) obtained in step 1 of Example 1, propionaldehyde (227 μL, 3.14 mmol) instead of paraformaldehyde.

ESI-MS m/z: 450 $(M+H)^+$; $^1$H-NMR ($CDCl_3$, δ): 1.01 (t, J=7.4 Hz, 3H), 1.31 (t, J=7.6 Hz, 3H), 1.79-1.89 (m, 2H), 2.59 (s, 3H), 2.63 (s, 3H), 2.77 (q, J=7.5 Hz, 2H), 2.92-3.10 (m, 4H), 4.36 (t, J=7.9 Hz, 1H), 5.37 (s, 2H), 6.61-7.26 (m, 6H), 7.49-7.58 (m, 2H).

[step 2] The title compound (compound 23, 265 mg, 36%) was obtained in the same manner as in Example 22, using 5-(1-cyanopropyl)-2-(2-ethyl-5,7-dimethyl-3H-imidazo[4,5-b]pyridin-3-yl)methyl-10,11-dihydro-5H-dibenzo[b,f]azepine (671 mg, 1.49 mmol) obtained in step 1.

ESI-MS m/z: 493 $(M+H)^+$; $^1$H-NMR ($CDCl_3$, δ): 0.75 (t, J=7.3 Hz, 3H), 1.12 (t, J=7.5 Hz, 3H), 1.91-2.17 (m, 2H), 2.46 (s, 3H), 2.56 (s, 3H), 2.66 (q, J=7.5 Hz, 2H), 2.77-3.05 (m, 4H), 5.29 (s, 2H), 5.49 (dd, J=8.5, 4.7 Hz, 1H), 6.67-6.73 (m, 2H), 6.87-7.03 (m, 5H), 7.14 (d, J=7.5 Hz, 1H).

Example 24

2-(2-ethyl-5,7-dimethyl-3H-imidazo[4,5-b]pyridin-3-yl)methyl-5-[1-(1H-tetrazol-5-yl)butyl]-10,11-dihydro-5H-dibenzo[b,f]azepine (Compound 24)

[step 1] 5-(1-Cyanobutyl)-2-(2-ethyl-5,7-dimethyl-3H-imidazo[4,5-b]pyridin-3-yl)methyl-10,11-dihydro-5H-dibenzo[b,f]azepine (697 mg, 96%) was obtained in the same manner as in step 2 of Example 1, using 2-(2-ethyl-5,7-dimethyl-3H-imidazo[4,5-b]pyridin-3-yl)methyl-10,11-dihydro-5H-dibenzo[b,f]azepine (600 mg, 1.57 mmol) obtained in step 1 of Example 1 and butylaldehyde (283 μL, 3.14 mmol) instead of paraformaldehyde.

ESI-MS m/z: 464 $(M+H)^+$; $^1$H-NMR ($CDCl_3$, δ): 0.87 (t, J=7.4 Hz, 3H), 1.31 (t, J=7.6 Hz, 3H), 1.40-1.51 (m, 2H), 1.74-1.83 (m, 2H), 2.59 (s, 3H), 2.63 (s, 3H), 2.77 (q, J=7.5 Hz, 2H), 2.95-3.08 (m, 4H), 4.44 (t, J=7.8 Hz, 1H), 5.37 (s, 2H), 6.61-7.26 (m, 6H), 7.51-7.60 (m, 2H).

[step 2] The title compound (compound 24, 101 mg, 13%) was obtained in the same manner as in Example 22, using 5-(1-cyanobutyl)-2-(2-ethyl-5,7-dimethyl-3H-imidazo[4,5-b]pyridin-3-yl)methyl-10,11-dihydro-5H-dibenzo[b,f]azepine (695 mg, 1.50 mmol) obtained in step 1.

ESI-MS m/z: 507 $(M+H)^+$; $^1$H-NMR ($CDCl_3$, δ): 0.76 (t, J=7.2 Hz, 3H), 0.97-1.29 (m, 2H), 1.15 (t, J=7.6 Hz, 3H), 1.91-2.12 (m, 2H), 2.62 (s, 3H), 2.65 (s, 3H), 2.82-2.94 (m, 2H), 2.90 (q, J=7.6 Hz, 2H), 3.09-3.38 (m, 2H), 5.38 (s, 2H), 5.62 (dd, J=9.2, 4.4 Hz, 1H), 6.73 (dd, J=8.2, 1.8 Hz, 1H), 6.84 (d, J=1.8 Hz, 1H), 6.92-7.08 (m, 5H), 7.19 (d, J=7.7 Hz, 1H).

Example 25

2-(7-chloro-2-ethyl-5-methyl-3H-imidazo[4,5-b]pyridin-3-yl)methyl-5-[1-(1H-tetrazol-5-yl)ethyl]-10,11-dihydro-5H-dibenzo[b,f]azepine (Compound 25)

The title compound (compound 25, 738 mg, 67%) was obtained in the same manner as in Example 22, using 2-(7-chloro-2-ethyl-5-methyl-3H-imidazo[4,5-b]pyridin-3-yl)methyl-5-(1-cyanoethyl)-10,11-dihydro-5H-dibenzo[b,f]azepine (1.00 g, 2.2 mmol) obtained in step 1 of Example 21.

ESI-MS m/z: 499 $(M+H)^+$; $^1$H-NMR ($CDCl_3$, δ): 1.13 (t, J=7.5 Hz, 3H), 1.58 (d, J=6.6 Hz, 3H), 2.59 (s, 3H), 2.60 (q, J=7.5 Hz, 2H), 2.80-3.07 (m, 4H), 5.22-5.35 (m, 2H), 5.71 (q, J=6.6 Hz, 1H), 6.70-6.75 (m, 2H), 6.89-7.04 (m, 4H), 7.10-7.13 (m, 2H).

Example 26

2-(2-ethyl-7-methyl-3H-imidazo[4,5-b]pyridin-3-yl)methyl-5-[1-(1H-tetrazol-5-yl)ethyl]-10,11-dihydro-5H-dibenzo[b,f]azepine (Compound 26)

The title compound (compound 26, 1.00 g, 73%) was obtained in the same manner as in Example 22, using 5-(1-cyanoethyl)-2-(2-ethyl-7-methyl-3H-imidazo[4,5-b]pyridin-3-yl)methyl-10,11-dihydro-5H-dibenzo[b,f]azepine (1.24 g, 3.0 mmol) obtained in step 1 of Example 20.

ESI-MS m/z: 465 $(M+H)^+$; $^1$H-NMR ($CDCl_3$, δ): 1.22 (t, J=7.5 Hz, 3H), 1.49 (d, J=6.8 Hz, 3H), 2.57 (s, 3H), 2.74 (q, J=7.5 Hz, 2H), 2.75-2.96 (m, 4H), 5.32 (s, 2H), 5.66 (q, J=6.8 Hz, 1H), 6.69-6.72 (m, 2H), 6.90-7.03 (m, 5H), 7.10 (d, J=7.9 Hz, 1H), 8.12 (d, J=4.9 Hz, 1H).

Example 27

2-(7-methyl-2-propyl-3H-imidazo[4,5-b]pyridin-3-yl)methyl-5-[1-(1H-tetrazol-5-yl)ethyl]-10,11-dihydro-5H-dibenzo[b,f]azepine (Compound 27)

[step 1] 2-(7-Methyl-2-propyl-3H-imidazo[4,5-b]pyridin-3-yl)methyl-10,11-dihydro-5H-dibenzo[b,f]azepine (1.10 g, 25%) was obtained in the same manner as in step 1 of Example 1, using 7-methyl-2-propyl-3H-imidazo[4,5-b]pyridine (U.S. Pat. No. 5,332,744; 2.0 g, 11.4 mmol) instead of 2-ethyl-5,7-dimethyl-3H-imidazo[4,5-b]pyridine.

ESI-MS m/z: 383 $(M+H)^+$; $^1$H-NMR ($CDCl_3$, δ): 0.99 (t, J=7.3 Hz, 3H), 1.70-1.83 (m, 2H), 2.68 (s, 3H), 2.78-2.83 (m, 2H), 2.96-3.03 (m, 4H), 5.37 (s, 2H), 6.01 (s, 1H), 6.61-6.84 (m, 5H), 7.01-7.08 (m, 3H), 8.21 (d, J=4.9 Hz, 1H).

[step 2] 5-(1-Cyanoethyl)-2-(7-methyl-2-propyl-3H-imidazo[4,5-b]pyridin-3-yl)methyl-10,11-dihydro-5H-dibenzo[b,f]azepine (1.31 g, quantitative) was obtained in the same manner as in step 2 of Example 1, using 2-(7-methyl-2-propyl-3H-imidazo[4,5-b]pyridin-3-yl)methyl-10,11-dihydro-5H-dibenzo[b,f]azepine (1.09 g, 2.9 mmol) obtained in step 1 and acetaldehyde (0.48 mL, 8.6 mmol) instead of paraformaldehyde.

ESI-MS m/z: 436 $(M+H)^+$; $^1$H-NMR ($CDCl_3$, δ): 0.98 (t, J=7.3 Hz, 3H), 1.47 (d, J=7.1 Hz, 3H), 1.71-1.84 (m, 2H), 2.68 (s, 3H), 2.76-2.81 (m, 2H), 2.85-3.12 (m, 4H), 4.65 (q, J=7.1 Hz, 1H), 5.40 (s, 2H), 6.87 (d, J=1.8 Hz, 1H), 6.96-7.22 (m, 5H), 7.49-7.57 (m, 2H), 8.19 (d, J=4.9 Hz, 1H).

[step 3] The title compound (compound 27, 956 mg, 70%) was obtained in the same manner as in Example 22, using 5-(1-cyanoethyl)-2-(7-methyl-2-propyl-3H-imidazo[4,5-b]pyridin-3-yl)methyl-10,11-dihydro-5H-dibenzo[b,f]azepine (1.31 g, 2.9 mmol) obtained in step 2.

ESIMS m/z: 479 $(M+H)^+$; $^1$H-NMR ($CDCl_3$, δ): 0.87 (t, J=7.3 Hz, 3H), 1.50 (d, J=6.6 Hz, 3H), 1.61-1.73 (m, 2H), 2.58 (s, 3H), 2.70 (t, J=7.8 Hz, 2H), 2.76-2.93 (m, 4H), 5.33 (s, 2H), 5.66 (q, J=6.6 Hz, 1H), 6.69-6.72 (m, 2H), 6.90-7.03 (m, 5H), 7.10 (d, J=7.3 Hz, 1H), 8.12 (d, J=4.9 Hz, 1H).

Example 28

2-(5-ethoxycarbonyl-4-ethyl-2-propyl-1H-imidazol-1-yl)methyl-5-[1-(1H-tetrazol-5-yl)ethyl]-10,11-dihydro-5H-dibenzo[b,f]azepine (Compound 28)

[step 1] 5-(1-Cyanoethyl)-2-(5-ethoxycarbonyl-4-ethyl-2-propyl-1H-imidazol-1-yl)methyl-10,11-dihydro-5H-dibenzo[b,f]azepine (481 mg, 94%) was obtained in the same manner as in step 2 of Example 1, using 2-(5-ethoxycarbonyl-4-ethyl-2-propyl-1H-imidazol-1-yl)methyl-10,11-dihydro-5H-dibenzo[b,f]azepine (452 mg, 1.1 mmol) obtained in step 1 of Example 14 and acetaldehyde (183 μL, 3.3 mmol) instead of paraformaldehyde.

ESI-MS m/z: 471 $(M+H)^+$; $^1$H-NMR ($CDCl_3$, δ): 0.93 (t, J=7.3 Hz, 3H), 1.22-1.32 (m, 6H), 1.49 (d, J=7.2 Hz, 3H), 1.63-1.76 (m, 2H), 2.58 (t, J=7.8 Hz, 2H), 2.86-3.10 (m, 4H), 2.90 (q, J=7.5 Hz, 2H), 4.23 (q, J=7.3 Hz, 2H), 4.66 (q, J=7.2 Hz, 1H), 5.43 (s, 2H), 6.72-6.80 (m, 2H), 7.01-7.23 (m, 3H), 7.48-7.58 (m, 2H).

[step 2] The title compound (compound S7, 200 mg, 38%) was obtained in the same manner as in Example 22, using 5-(1-cyanoethyl)-2-(5-ethoxycarbonyl-4-ethyl-2-propyl-1H-imidazol-1-yl)methyl-10,11-dihydro-5H-dibenzo[b,f]azepine (480 mg, 1.0 mmol) obtained in step 2.

ESI-MS m/z: 514 $(M+H)^+$; $^1$H-NMR ($CDCl_3$, δ): 0.81 (t, J=7.1 Hz, 3H), 1.26 (t, J=7.3 Hz, 3H), 1.30 (t, J=7.1 Hz, 3H), 1.53-1.62 (m, 2H), 1.61 (d, J=6.9 Hz, 3H), 2.68 (t, J=7.8 Hz, 2H), 2.94-3.33 (m, 4H), 2.97 (q, J=7.3 Hz, 2H), 4.28 (q, J=7.1 Hz, 2H), 5.45 (s, 2H), 5.72 (q, J=6.9 Hz, 1H), 6.54 (dd, J=8.3, 1.8 Hz, 1H), 6.73 (d, J=1.8 Hz, 1H), 6.95-7.00 (m, 1H), 7.05-7.10 (m, 3H), 7.24 (d, J=7.9 Hz, 1H).

Example 29

(E)-2-(2-ethyl-5,7-dimethyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 29)

[step 1] (E)-(2-Hydroxymethyl-10,11-dihydro-5H-dibenzo[a,d]cyclohepten-5-ylidene)acetonitrile (JP-B-2526005; 1.26 g, 4.8 mmol) was dissolved in THF (50 mL), and the solution was added with 2,6-lutidine (3.4 mL, 29.2 mmol), lithium bromide (2.54 g, 29.2 mmol) and methanesulfonic anhydride (2.02 g, 11.6 mmol), followed by stirring at room temperature for 24 hr. Ethyl acetate was added to the mixture, and the organic layer was washed with brine. The organic layer was dried over anhydrous magnesium sulfate, and concentrated under reduced pressure to give a residue.

2-Ethyl-5,7-dimethyl-3H-imidazo[4,5-b]pyridine (0.85 g, 4.8 mmol) was dissolved in DMF (15 mL), and the solution was added with potassium tert-butoxide (0.60 g, 5.3 mmol) at 0° C. followed by stirring for 10 min. Thereto was added a solution of the residue obtained above in DMF (8 mL), and the mixture was stirred at room temperature for 2 hr. Ethyl acetate was added to the mixture, the organic layer was washed with brine, dried over anhydrous magnesium sulfate, and concentrated under reduced pressure. The residue was purified by silica gel column chromatography (hexane/ethyl acetate=3/1-1/3) to give (E)-[2-(2-ethyl-5,7-dimethyl-3H-imidazo[4,5-b]pyridin-3-yl)methyl-10,11-dihydro-5H-dibenzo[a,d]cyclohepten-5-ylidene]acetonitrile (1.28 g, 63%).

ESI-MS m/z: 419 $(M+H)^+$; $^1$H-NMR ($CDCl_3$, δ): 1.32 (t, J=7.5 Hz, 3H), 2.57 (s, 3H), 2.63 (s, 3H), 2.75 (q, J=7.5 Hz, 2H), 3.06 (br s, 4H), 5.41 (s, 2H), 5.66 (s, 1H), 6.88-6.92 (m, 3H), 7.19-7.32 (m, 4H), 7.41-7.42 (m, 1H).

[step 2] The title compound (compound 29, 215 mg, 75%) was obtained in the same manner as in step 3 of Example 1, using (E)-[2-(2-ethyl-5,7-dimethyl-3H-imidazo[4,5-b]pyridin-3-yl)methyl-10,11-dihydro-5H-dibenzo[a,d]cyclohepten-5-ylidene]acetonitrile (250 mg, 0.60 mmol) obtained in step 1.

ESI-MS m/z: 478 $(M+H)^+$; $^1$H-NMR (DMSO-$d_6$, δ): 1.22 (t, J=7.6 Hz, 3H), 2.46 (s, 3H), 2.53 (s, 3H), 2.70-2.78 (m, 2H), 2.80-3.39 (m, 4H), 5.39 (s, 2H), 6.32 (s, 1H), 6.85 (dd, J=7.8, 1.4 Hz, 1H), 6.92 (s, 1H), 6.99-7.12 (m, 3H), 7.22-7.30 (m, 3H).

Example 30

(E)-2-(6-methoxycarbonyl-4-methyl-2-propylbenzimidazol-1-yl)methyl-5-(5-oxo-4,5-dihydro-1,2,4-oxadiazol-3-yl)methylene-10,11-dihydro-5H-dibenzo[a,d]cycloheptene (Compound 30)

[step 1] (E)-[2-(6-Methoxycarbonyl-4-methyl-2-propylbenzimidazol-1-yl)methyl-10,11-dihydro-5H-dibenzo[a,d]cyclohepten-5-ylidene]acetonitrile (1.78 g, 73%) was obtained in the same manner as in step 1 of Example 29, using 5-methoxycarbonyl-7-methyl-2-propylbenzimidazole (EP502314; 1.19 g, 5.13 mmol) instead of 2-ethyl-5,7-dimethyl-3H-imidazo[4,5-b]pyridine.

ESI-MS m/z; 476 $(M+H)^+$; $^1$H-NMR ($CDCl_3$, δ): 1.00 (t, J=7.3 Hz, 3H), 1.75-1.89 (m, 2H), 2.70 (s, 3H), 2.82 (t, J=7.8 Hz, 2H), 3.06 (br s, 4H), 3.88 (s, 3H), 5.33 (s, 2H), 5.67 (s, 1H), 6.68 (s, 1H), 6.81 (dd, J=8.1, 1.4 Hz, 1H), 7.20-7.34 (m, 4H), 7.43 (dd, J=7.4, 1.8 Hz, 1H), 7.74 (d, J=1.0 Hz, 1H), 7.77 (d, J=1.0 Hz, 1H).

[step 2] The title compound (compound 30, 0.27 g, 35%) was obtained in the same manner as in step 3 of Example 1, using (E)-[2-(6-methoxycarbonyl-4-methyl-2-propylbenzimidazol-1-yl)methyl-10,11-dihydro-5H-dibenzo[a,d]cyclohepten-5-ylidene]acetonitrile (0.68 g, 1.43 mmol) obtained in step 1.

ESI-MS m/z; 535 $(M+H)^+$; $^1$H-NMR (DMSO-$d_6$, δ): 0.93 (t, J=7.3 Hz, 3H), 1.68-1.81 (m, 2H), 2.55 (s, 3H), 2.81 (t, J=7.5 Hz, 2H), 2.83-3.25 (m, 4H), 3.79 (s, 3H), 5.53 (s, 2H), 6.33 (s, 1H), 6.77 (d, J=7.9 Hz, 1H), 6.94 (s, 1H), 7.05 (d, J=7.3 Hz, 1H), 7.09-7.14 (m, 1H), 7.23-7.25 (m, 2H), 7.30 (d, J=7.9 Hz, 1H), 7.62 (d, J=1.0 Hz, 1H), 7.84 (d, J=1.2 Hz, 1H).

Example 31

(E)-2-(5,7-dimethyl-2-propyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 31)

[step 1] (E)-2-(5,7-Dimethyl-2-propyl-3H-imidazo[4,5-b]pyridin-3-yl)methyl-10,11-dihydro-5H-dibenzo[a,d]cyclohepten-5-ylidene]acetonitrile (0.86 g, 65%) was obtained in the same manner as in step 1 of Example 29, using 5,7-dimethyl-2-propyl-3H-imidazo[4,5-b]pyridine (0.80 g, 3.07 mmol) instead of 2-ethyl-5,7-dimethyl-3H-imidazo[4,5-b]pyridine.

ESI-MS m/z: 433 $(M+H)^+$; $^1$H-NMR ($CDCl_3$, δ): 0.96 (t, J=7.4 Hz, 3H), 1.69-1.83 (m, 2H), 2.56 (s, 3H), 2.63 (s, 3H), 2.70 (t, J=8.1 Hz, 2H), 3.06 (br s, 4H), 5.41 (s, 2H), 5.66 (s, 1H), 6.87-6.94 (m, 3H), 7.19-7.35 (m, 4H), 7.43 (dd, J=7.4, 1.8 Hz, 1H).

[step 2] The title compound (compound 31, 0.31 g, 66%) was obtained in the same manner as in step 3 of Example 1, using (E)-2-(5,7-dimethyl-2-propyl-3H-imidazo[4,5-b]pyridin-3-yl)methyl-10,11-dihydro-5H-dibenzo[a,d]cyclohepten-5-ylidene]acetonitrile (0.42 g, 0.96 mmol) obtained in step 1.

ESI-MS m/z: 492 $(M+H)^+$; $^1$H-NMR (DMSO-$d_6$, δ): 0.90 (t, J=7.3 Hz, 3H), 1.61-1.76 (m, 2H), 2.47 (s, 3H), 2.51 (s, 3H), 2.72 (t, J=8.4 Hz, 2H), 2.90-3.19 (m, 4H), 5.42 (s, 2H), 6.35 (s, 1H), 6.85-6.88 (m, 1H), 6.93 (s, 1H), 7.00-7.01 (m, 1H), 7.06-7.08 (m, 1H), 7.11-7.17 (m, 1H), 7.26-7.32 (m, 3H).

Example 32

(E)-2-[4-methyl-6-(1-methylbenzimidazol-2-yl)-2-propylbenzimidazol-1-yl]methyl-5-(5-oxo-4,5-dihydro-1,2,4-oxadiazol-3-yl)methylene-10,11-dihydro-5H-dibenzo[a,d]cycloheptene (Compound 32)

[step 1] (E)-2-[4-Methyl-6-(1-methylbenzimidazol-2-yl)-2-propylbenzimidazol-1-yl]methyl-10,11-dihydro-5H-dibenzo[a,d]cyclohepten-5-ylidene]acetonitrile (1.13 g, 64%) was obtained in the same manner as in step 1 of Example 29, using 4-methyl-6-(1-methylbenzimidazol-2-yl)-2-propylbenzimidazole (0.99 g, 3.25 mmol) instead of 2-ethyl-5,7-dimethyl-3H-imidazo[4,5-b]pyridine.

ESI-MS m/z: 548 $(M+H)^+$; $^1$H-NMR ($CDCl_3$, δ): 1.03 (t, J=7.3 Hz, 3H), 1.78-1.92 (m, 2H), 2.76 (s, 3H), 2.84-2.91 (m, 2H), 3.05 (br s, 4H), 3.73 (s, 3H), 5.35 (s, 2H), 5.66 (s, 1H), 6.81-6.89 (m, 2H), 7.17-7.44 (m, 10H), 7.76-7.79 (m, 1H).

[step 2] The title compound (compound 32, 0.20 g, 88%) was obtained in the same manner as in step 3 of Example 1, using (E)-2-[4-methyl-6-(1-methylbenzimidazol-2-yl)-2-propylbenzimidazol-1-yl]methyl-10,11-dihydro-5H-dibenzo[a,d]cyclohepten-5-ylidene]acetonitrile (0.20 g, 0.37 mmol) obtained in step 1.

ESI-MS m/z: 607 $(M+H)^+$; $^1$H-NMR (DMSO-$d_6$, δ): 0.96 (t, J=7.5 Hz, 3H), 1.73-1.84 (m, 2H), 2.61 (s, 3H), 2.86 (t, J=7.5 Hz, 2H), 2.88-3.27 (m, 4H), 3.71 (s, 3H), 5.53 (s, 2H), 6.32 (s, 1H), 6.88 (d, J=8.1 Hz, 1H), 7.05 (d, J=7.9 Hz, 2H), 7.10-7.32 (m, 6H), 7.45 (s, 1H), 7.53 (d, J=7.1 Hz, 1H), 7.61 (d, J=7.5 Hz, 2H).

Example 33

(E)-2-(4-methyl-2-propylbenzimidazol-1-yl)methyl-5-(5-oxo-4,5-dihydro-1,2,4-oxadiazol-3-yl)methylene-10,11-dihydro-5H-dibenzo[a,d]cycloheptene (Compound 33)

[step 1] (E)-2-(4-Methyl-2-propylbenzimidazol-1-yl)methyl-10,11-dihydro-5H-dibenzo[a,d]cyclohepten-5-ylidene] acetonitrile (0.94 g, 57%) was obtained in the same manner as in step 1 of Example 29, using 4-methyl-2-propylbenzimidazole (1.04 g, 4.00 mmol) instead of 2-ethyl-5,7-dimethyl-3H-imidazo[4,5-b]pyridine.

ESI-MS m/z: 418 $(M+H)^+$; $^1$H-NMR ($CDCl_3$, δ): 1.00 (t, J=7.5 Hz, 3H), 1.73-1.86 (m, 2H), 2.69 (s, 3H), 2.82 (t, J=8.2 Hz, 2H), 3.06 (br s, 4H), 5.28 (s, 2H), 5.67 (s, 1H), 6.80 (s, 1H), 6.85 (dd, J=7.9, 1.7 Hz, 1H), 6.95 (dd, J=6.6, 2.0 Hz, 1H), 7.03-7.10 (m, 2H), 7.18-7.35 (m, 4H), 7.43 (dd, J=7.3, 1.7 Hz, 1H).

[step 2] The title compound (compound 33, 0.20 g, 45%) was obtained in the same manner as in step 3 of Example 1, using (E)-2-(4-methyl-2-propylbenzimidazol-1-yl)methyl-10,11-dihydro-5H-dibenzo[a,d]cyclohepten-5-ylidene]acetonitrile (0.40 g, 0.96 mmol) obtained in step 1.

ESI-MS m/z: 477 $(M+H)^+$; $^1$H-NMR (DMSO-$d_6$, δ): 0.94 (t, J=7.3 Hz, 3H), 1.69-1.80 (m, 2H), 2.52 (s, 3H), 2.79 (t, J=7.6 Hz, 2H), 2.82-3.30 (m, 4H), 5.42 (s, 2H), 6.33 (s, 1H), 6.82 (d, J=7.9 Hz, 1H), 6.94-7.19 (m, 6H), 7.25-7.32 (m, 3H).

Example 34

(E)-2-(2-ethyl-7-methyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 34)

[step 1] (E)-[2-(2-Ethyl-7-methyl-3H-imidazo[4,5-b]pyridin-3-yl)methyl-10,11-dihydro-5H-dibenzo[a,d]cyclohepten-5-ylidene]acetonitrile (470 mg, 27%) was obtained in the same manner as in step 1 of Example 29, using 2-ethyl-7-methyl-3H-imidazo[4,5-b]pyridine (684 mg, 4.3 mmol) instead of 2-ethyl-5,7-dimethyl-3H-imidazo[4,5-b]pyridine.

ESI-MS m/z: 405 $(M+H)^+$; $^1$H-NMR ($CDCl_3$, δ): 1.35 (t, J=7.6 Hz, 3H), 2.69 (s, 3H), 2.82 (q, J=7.6 Hz, 2H), 3.06 (br s, 4H), 5.43 (s, 2H), 5.66 (s, 1H), 6.89 (s, 1H), 6.93 (d, J=8.1 Hz, 1H), 7.03 (d, J=4.9 Hz, 1H), 7.20 (d, J=7.7 Hz, 2H), 7.28-7.35 (m, 2H), 7.42 (dd, J=7.4, 1.6 Hz, 1H), 8.18 (d, J=4.9 Hz, 1H).

[step 2] The title compound (compound 34, 102 mg, 44%) was obtained in the same manner as in step 3 of Example 1, using (E)-[2-(2-ethyl-7-methyl-3H-imidazo[4,5-b]pyridin-3-yl)methyl-10,11-dihydro-5H-dibenzo[a,d]cyclohepten-5-ylidene]acetonitrile (200 mg, 0.49 mmol) obtained in step 1.

ESI-MS m/z: 464 $(M+H)^+$; $^1$H-NMR (DMSO-$d_6$, δ): 1.24 (t, J=7.4 Hz, 3H), 2.54 (s, 3H), 2.80 (q, J=7.4 Hz, 2H), 2.85-3.28 (m, 4H), 5.43 (s, 2H), 6.32 (s, 1H), 6.91 (d, J=8.4 Hz, 1H), 7.02-7.14 (m, 4H), 7.23-7.30 (m, 3H), 8.11 (d, J=5.0 Hz, 1H).

Example 35

(E)-2-[5-ethoxycarbonyl-4-(1-hydroxy-1-methyl)ethyl-2-propylimidazol-1-yl]methyl-5-(5-oxo-4,5-dihydro-1,2,4-oxadiazol-3-yl)methylene-10,11-dihydro-5H-dibenzo[a,d]cycloheptene (Compound 35)

[step 1] (E)-(2-[5-Ethoxycarbonyl-4-(1-hydroxy-1-methyl)ethyl-2-propylimidazol-1-yl]methyl-10,11-dihydro-5H-dibenzo[a,d]cyclohepten-5-ylidene)acetonitrile (379 mg, 82%) was obtained in the same manner as in step 1 of Example 29, using 5-ethoxycarbonyl-4-(1-hydroxy-1-methyl)ethyl-2-propylimidazole (253 mg, 1.05 mmol) instead of 2-ethyl-5,7-dimethyl-3H-imidazo[4,5-b]pyridine.

ESI-MS m/z: 484 $(M+H)^+$; $^1$H-NMR ($CDCl_3$, δ): 0.94 (t, J=7.3 Hz, 3H), 1.18 (t, J=7.2 Hz, 3H), 1.63 (s, 6H), 1.77-1.66 (m, 2H), 2.57 (t, J=7.8 Hz, 2H), 3.24-3.00 (m, 4H), 4.21 (q, J=7.2 Hz, 2H), 5.41 (s, 2H), 5.67 (s, 1H), 5.69 (s, 1H), 6.68 (s, 1H), 6.73 (d, J=7.9 Hz, 1H), 7.37-7.19 (m, 4H), 7.44 (dd, J=7.3, 1.7 Hz, 1H).

[step 2] The title compound (compound 35, 80 mg, 49%) was obtained in the same manner as in step 3 of Example 1, using (E)-{2-[5-ethoxycarbonyl-4-(1-hydroxy-1-methyl)ethyl-2-propylimidazol-1-yl]methyl-10,11-dihydro-5H-dibenzo[a,d]cyclohepten-5-ylidene}acetonitrile (144 mg, 0.3 mmol) obtained in step 1.

ESI-MS m/z: 543 $(M+H)^+$; $^1$H-NMR ($CDCl_3$, δ): 0.94 (t, J=7.3 Hz, 3H), 1.18 (t, J=7.1 Hz, 3H), 1.63 (s, 6H), 1.77-1.66 (m, 2H), 2.58 (t, J=7.8 Hz, 2H), 3.00-2.81 (m, 2H), 3.43-3.19

(m, 2H), 4.22 (q, J=7.1 Hz, 2H), 5.40 (s, 2H), 5.66 (s, 1H), 6.50 (s, 1H), 6.62 (s, 1H), 6.79 (d, J=8.2 Hz, 1H), 7.46-7.17 (m, 5H).

Example 36

(E)-2-(5-chloro-2-ethyl-7-methyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 36)

[step 1] (E)-(2-Hydroxymethyl-10,11-dihydro-5H-dibenzo[a,d]cyclohepten-5-ylidene)acetonitrile (120 mg, 0.46 mmol) and 5-chloro-2-ethyl-7-methyl-3H-imidazo[4,5-b]pyridine (117 mg, 0.60 mmol) were dissolved in THF (6.6 mL) and the solution was added with polymer supported triphenylphosphine (469 mg, 0.92 mmol) and di-t-butyl azodicarboxylate (211 mg, 0.92 mmol) at 0° C., followed by stirring at room temperature for 2 hr. The mixture was filtrated, and the filtrate was concentrated under reduced pressure. The residue was purified by silica gel column chromatography (hexane/ethyl acetate=3/1) to give (E)-[2-(5-chloro-2-ethyl-7-methyl-3H-imidazo[4,5-b]pyridin-3-yl)methyl-10,11-dihydro-5H-dibenzo[a,d]cyclohepten-5-ylidene]acetonitrile (90 mg, 45%).

ESI-MS m/z: 439 $(M+H)^+$; $^1H$-NMR ($CDCl_3$, δ): 1.33 (t, J=7.6 Hz, 3H), 2.65 (s, 3H), 2.76 (q, J=7.5 Hz, 2H), 3.02-3.12 (m, 4H), 5.38 (s, 2H), 5.67 (s, 1H), 6.88 (s, 1H), 6.93 (dd, J=8.0, 1.7 Hz, 1H), 7.06 (d, J=0.7 Hz, 1H), 7.18-7.35 (m, 4H), 7.43 (dd, J=7.3, 1.5 Hz, 1H).

[step 2] The title compound (compound 36, 54 mg, 52%) was obtained in the same manner as in step 3 of Example 1, using (E)-[2-(5-chloro-2-ethyl-7-methyl-3H-imidazo[4,5-b]pyridin-3-yl)methyl-10,11-dihydro-5H-dibenzo[a,d]cyclohepten-5-ylidene]acetonitrile (90 mg, 0.21 mmol) obtained in step 1.

ESI-MS m/z: 498 $(M+H)^+$; $^1H$-NMR ($CDCl_3$, δ): 1.34 (t, J=7.5 Hz, 3H), 2.65 (d, J=0.7 Hz, 3H), 2.73-2.96 (m, 2H), 2.77 (q, J=7.5 Hz, 2H), 3.22-3.39 (m, 2H), 5.37 (s, 2H), 6.48 (s, 1H), 6.84 (s, 1H), 6.96 (d, J=8.1 Hz, 1H), 7.06 (d, J=0.7 Hz, 1H), 7.16 (dd, J=7.5, 0.9 Hz, 1H), 7.26-7.44 (m, 4H).

Example 37

(E)-2-(2-ethyl-5-methyl-7-trifluoromethyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 37)

[step 1] (E)-[2-(2-Ethyl-5-methyl-7-trifluoromethyl-3H-imidazo[4,5-b]pyridin-3-yl)methyl-10,11-dihydro-5H-dibenzo[a,d]cyclohepten-5-ylidene]acetonitrile (221 mg, 87%) was obtained in the same manner as in step 1 of Example 36, using 2-ethyl-5-methyl-7-trifluoromethyl-3H-imidazo[4,5-b]pyridine (160 mg, 0.7 mmol) instead of 5-chloro-2-ethyl-7-methyl-3H-imidazo[4,5-b]pyridine.

ESI-MS m/z: 473 $(M+H)^+$; $^1H$-NMR ($CDCl_3$, δ): 1.34 (t, J=7.5 Hz, 3H), 2.67 (s, 3H), 2.83 (q, J=7.5 Hz, 2H), 3.00-3.13 (m, 4H), 5.45 (s, 2H), 5.67 (s, 1H), 6.89 (s, 1H), 6.95 (dd, J=7.9, 1.6 Hz, 1H), 7.19-7.36 (m, 5H), 7.43 (dd, J=7.2, 1.6 Hz, 1H).

[step 2] The title compound (compound 37, 184 mg, 76%) was obtained in the same manner as in step 3 of Example 1, using (E)-[2-(2-ethyl-5-methyl-7-trifluoromethyl-3H-imidazo[4,5-b]pyridin-3-yl)methyl-10,11-dihydro-5H-dibenzo[a,d]cyclohepten-5-ylidene]acetonitrile (221 mg, 0.47 mmol) obtained in step 1.

ESI-MS m/z: 532 $(M+H)^+$; $^1H$-NMR ($CDCl_3$, δ): 1.34 (t, J=7.5 Hz, 3H), 2.67 (s, 3H), 2.80-2.98 (m, 2H), 2.83 (q, J=7.6 Hz, 2H), 3.22-3.39 (m, 2H), 5.45 (s, 2H), 6.49 (s, 1H), 6.85 (s, 1H), 6.99 (d, J=7.9 Hz, 1H), 7.17 (dd, J=7.4, 1.0 Hz, 1H), 7.26-7.44 (m, 5H).

Example 38

(E)-2-(5-methyl-2-propyl-7-trifluoromethyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 38)

[step 1] (E)-[2-(5-Methyl-2-propyl-7-trifluoromethyl-3H-imidazo[4,5-b]pyridin-3-yl)methyl-10,11-dihydro-5H-dibenzo[a,d]cyclohepten-5-ylidene]acetonitrile was obtained as a crude product in the same manner as in step 1 of Example 36, using 5-methyl-2-propyl-7-trifluoromethyl-3H-imidazo[4,5-b]pyridine (169 mg, 0.7 mmol), obtained in Reference Example 5, instead of 5-chloro-2-ethyl-7-methyl-3H-imidazo[4,5-b]pyridine.

[step 2] The title compound (compound 38, 170 mg, 58%) was obtained in the same manner as in step 3 of Example 1, using (E)-[2-(5-methyl-2-propyl-7-trifluoromethyl-3H-imidazo[4,5-b]pyridin-3-yl)methyl-10,11-dihydro-5H-dibenzo[a,d]cyclohepten-5-ylidene]acetonitrile obtained in step 1.

ESI-MS m/z: 546 $(M+H)^+$; $^1H$-NMR ($CDCl_3$, δ): 0.97 (t, J=7.3 Hz, 3H), 1.73-1.85 (m, 2H), 2.67 (s, 3H), 2.78 (t, J=7.9 Hz, 2H), 2.78-2.96 (m, 2H), 3.23-3.40 (m, 2H), 5.45 (s, 2H), 6.50 (s, 1H), 6.84 (s, 1H), 6.99 (d, J=7.9 Hz, 1H), 7.17 (dd, J=7.4, 1.2 Hz, 1H), 7.26-7.44 (m, 5H).

Example 39

(E)-2-(8-oxo-2-propyl-8H-cycloheptaimidazol-1-yl)methyl-5-(5-oxo-4,5-dihydro-1,2,4-oxadiazol-3-yl)methylene-10,11-dihydro-5H-dibenzo[a,d]cycloheptene (Compound 39)

[step 1] (E)-[2-(8-Oxo-2-propyl-8H-cycloheptaimidazol-1-yl)methyl-10,11-dihydro-5H-dibenzo[a,d]cyclohepten-5-ylidene]acetonitrile (146 mg, 63%) was obtained in the same manner as in step 1 of Example 36, using (E)-(2-hydroxymethyl-10,11-dihydro-5H-dibenzo[a,d]cyclohepten-5-ylidene)acetonitrile (140 mg, 0.54 mmol) and 8-oxo-2-propylcycloheptaimidazole (BioMed. Chem. Lett., 1993. vol. 3, p. 1559; 150 mg, 0.8 mmol) instead of 5-chloro-2-ethyl-7-methyl-3H-imidazo[4,5-b]pyridine.

ESI-MS m/z: 432 $(M+H)^+$; $^1H$-NMR ($CDCl_3$, δ): 1.00 (t, J=7.3 Hz, 3H), 1.76-1.90 (m, 2H), 2.73 (t, J=7.7 Hz, 2H), 2.98-3.10 (m, 4H), 5.66 (s, 1H), 5.95 (s, 2H), 6.79 (s, 1H), 6.80 (d, J=7.7 Hz, 1H), 6.95 (ddd, J=11.0, 8.3, 1.0 Hz, 1H), 7.07 (dt, J=12.5, 0.9 Hz, 1H), 7.14-7.34 (m, 5H), 7.41 (dd, J=7.3, 1.5 Hz, 1H), 7.72 (dt, J=10.9, 1.0 Hz, 1H).

[step 2] The title compound (compound 39, 115 mg, 70%) was obtained in the same manner as in step 3 of Example 1, using (E)-[2-(8-oxo-2-propyl-8H-cycloheptaimidazol-1-yl)methyl-10,11-dihydro-5H-dibenzo[a,d]cyclohepten-5-ylidene]acetonitrile (146 mg, 0.34 mmol) obtained in step 1.

ESI-MS m/z: 491 $(M+H)^+$; $^1H$-NMR ($CDCl_3$, δ): 1.00 (t, J=7.3 Hz, 3H), 1.77-1.90 (m, 2H), 2.74 (t, J=7.7 Hz, 2H), 2.79-2.97 (m, 2H), 3.22-3.38 (m, 2H), 5.94 (s, 2H), 6.48 (s, 1H), 6.75 (s, 1H), 6.82 (d, J=8.1 Hz, 1H), 6.94 (ddd, J=11.0, 8.2, 0.9 Hz, 1H), 7.05-7.43 (m, 7H), 7.72 (dt, J=10.9, 1.0 Hz, 1H).

Example 40

(E)-2-(2-ethyl-5,7-dimethyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 40)

[step 1] (E)-2-[2-(2-Ethyl-5,7-dimethyl-3H-imidazo[4,5-b]pyridin-3-yl)methyl-10,11-dihydro-5H-dibenzo[a,d]cyclohepten-5-ylidene]propiononitrile (399 mg, 69%) was obtained in the same manner as in step 1 of Example 36, using (E)-2-(2-hydroxymethyl-10,11-dihydro-5H-dibenzo[a,d]cyclohepten-5-ylidene)propiononitrile (367 mg, 1.3 mmol) obtained in Reference Example 6 and 2-ethyl-5,7-dimethyl-3H-imidazo[4,5-b]pyridine (366 mg, 2.1 mmol) instead of 5-chloro-2-ethyl-7-methyl-3H-imidazo[4,5-b]pyridine.

ESI-MS m/z: 433 $(M+H)^+$; $^1$H-NMR ($CDCl_3$, δ): 1.31 (t, J=7.6 Hz, 3H), 1.99 (s, 3H), 2.58 (s, 3H), 2.63 (s, 3H), 2.73-2.88 (m, 2H), 2.76 (q, J=7.6 Hz, 2H), 3.18-3.34 (m, 2H), 5.41 (s, 2H), 6.90-7.01 (m, 4H), 7.13 (dd, J=7.1, 1.6 Hz, 1H), 7.18-7.28 (m, 2H), 7.39 (dd, J=7.1, 1.6 Hz, 1H).

[step 2] The title compound (compound 40, 166 mg, 76%) was obtained in the same manner as in step 3 of Example 1, using (E)-2-[2-(2-ethyl-5,7-dimethyl-3H-imidazo[4,5-b]pyridin-3-yl)methyl-10,11-dihydro-5H-dibenzo[a,d]cyclohepten-5-ylidene]propiononitrile (192 mg, 0.44 mmol) obtained in step 1.

ESI-MS m/z: 492 $(M+H)^+$; $^1$H-NMR ($CDCl_3$, δ): 1.31 (t, J=7.5 Hz, 3H), 2.09 (s, 3H), 2.57 (s, 3H), 2.62 (s, 3H), 2.72-2.87 (m, 4H), 3.21-3.37 (m, 2H), 5.40 (s, 2H), 6.91-6.94 (m, 3H), 7.06-7.11 (m, 2H), 7.19-7.35 (m, 3H).

Example 41

(E)-2-(8-oxo-2-propyl-4,5,6,7-tetrahydro-8H-cycloheptaimidazol-1-yl)methyl-5-(5-oxo-4,5-dihydro-1,2,4-oxadiazol-3-yl)methylene-10,11-dihydro-5H-dibenzo[a,d]cycloheptene (Compound 41)

Compound 39 (50 mg, 0.1 mmol) obtained in Example 39 was dissolved in THF (1 mL), and platinum (IV) oxide (23 mg, 0.1 mmol) was added under nitrogen atmosphere. Under hydrogen atmosphere, the mixture was stirred at room temperature for 7 hr. The mixture was filtrated, and the filtrate was concentrated under reduced pressure. The obtained residue was purified by preparative thin layer chromatography (hexane/ethyl acetate=1/4) to give the title compound (compound 41, 12 mg, 24%).

ESI-MS m/z: 495 $(M+H)^+$; $^1$H-NMR ($CDCl_3$, δ): 0.95 (t, J=7.3 Hz, 3H), 1.66-1.79 (m, 2H), 1.83-1.97 (m, 4H), 2.54-2.65 (m, 4H), 2.81-3.03 (m, 2H), 3.01 (t, J=6.1 Hz, 2H), 3.24-3.39 (m, 2H), 5.48 (s, 2H), 6.49 (s, 1H), 6.71 (s, 1H), 6.78 (d, J=8.1 Hz, 1H), 7.16 (dd, J=7.3, 0.9 Hz, 1H), 7.26-7.43 (m, 4H).

Example 42

(E)-2-(2-ethyl-7-methyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 42)

[step 1] (E)-2-[2-(2-Ethyl-7-methyl-3H-imidazo[4,5-b]pyridin-3-yl)methyl-10,11-dihydro-5H-dibenzo[a,d]cyclohepten-5-ylidene]propiononitrile (153 mg, 50%) was obtained in the same manner as in step 1 of Example 29, using (E)-2-(2-hydroxymethyl-10,11-dihydro-5H-dibenzo[a,d]cyclohepten-5-ylidene)propiononitrile (200 mg, 0.73 mmol) and 2-ethyl-7-methyl-3H-imidazo[4,5-b]pyridine (152 mg, 0.94 mmol) instead of 2-ethyl-5,7-dimethyl-3H-imidazo[4,5-b]pyridine.

ESI-MS m/z: 419 $(M+H)^+$; $^1$H-NMR ($CDCl_3$, δ): 1.34 (t, J=7.5 Hz, 3H), 1.98 (s, 3H), 2.69 (s, 3H), 2.71-2.88 (m, 2H), 2.82 (q, J=7.6 Hz, 2H), 3.18-3.34 (m, 2H), 5.44 (s, 2H), 6.91-7.04 (m, 4H), 7.12 (dd, J=7.1, 1.4 Hz, 1H), 7.18-7.28 (m, 2H), 7.38 (dd, J=7.3, 1.6 Hz, 1H), 8.19 (d, J=4.9 Hz, 1H).

[step 2] The title compound (compound 42, 111 mg, 64%) was obtained in the same manner as in step 3 of Example 1, using ((E)-2-[2-(2-ethyl-7-methyl-3H-imidazo[4,5-b]pyridin-3-yl)methyl-10,11-dihydro-5H-dibenzo[a,d]cyclohepten-5-ylidene]propiononitrile (153 mg, 0.37 mmol) obtained in step 1.

ESI-MS m/z: 478 $(M+H)^+$; $^1$H-NMR ($CDCl_3$, δ): 1.35 (t, J=7.5 Hz, 3H), 2.09 (s, 3H), 2.69 (s, 3H), 2.73-2.87 (m, 2H), 2.83 (q, J=7.5 Hz, 2H), 3.22-3.36 (m, 2H), 5.43 (s, 2H), 6.92 (s, 1H), 6.94 (d, J=7.5 Hz, 1H), 7.02-7.11 (m, 4H), 7.19-7.35 (m, 2H), 8.19 (d, J=4.9 Hz, 1H).

Example 43

(E)-2-[5-ethoxycarbonyl-4-(1-hydroxy-1-methyl)ethyl-2-propylimidazol-1-yl]methyl-5-[1-(5-oxo-4,5-dihydro-1,2,4-oxadiazol-3-yl)ethylidene]-10,11-dihydro-5H-dibenzo[a,d]cycloheptene (Compound 43)

[step 1] (E)-2-{2-[5-Ethoxycarbonyl-4-(1-hydroxy-1-methyl)ethyl-2-propylimidazol-1-yl]methyl-10,11-dihydro-5H-dibenzo[a,d]cyclohepten-5-ylidene}propiononitrile (311 mg, 86%) was obtained in the same manner as in step 1 of Example 29, using (E)-2-(2-hydroxymethyl-10,11-dihydro-5H-dibenzo[a,d]cyclohepten-5-ylidene)propiononitrile (200 mg, 0.73 mmol) and 5-ethoxycarbonyl-4-(1-hydroxy-1-methyl)ethyl-2-propylimidazole (192 mg, 0.8 mmol) instead of 2-ethyl-5,7-dimethyl-3H-imidazo[4,5-b]pyridine.

ESI-MS m/z: 498 $(M+H)^+$; $^1$H-NMR ($CDCl_3$, δ): 0.93 (t, J=7.3 Hz, 3H), 1.14 (t, J=7.1 Hz, 3H), 1.63 (s, 6H), 1.65-1.75 (m, 2H), 2.01 (s, 3H), 2.59 (t, J=7.8 Hz, 2H), 2.75-2.92 (m, 2H), 3.22-3.38 (m, 2H), 4.21 (q, J=7.1 Hz, 2H), 5.41 (s, 2H), 5.71 (s, 1H), 6.73 (d, J=8.1 Hz, 1H), 6.77 (s, 1H), 7.03 (d, J=7.9 Hz, 1H), 7.15 (dd, J=7.1, 1.5 Hz, 1H), 7.20-7.30 (m, 2H), 7.41 (dd, J=7.1, 1.6 Hz, 1H).

[step 2] The title compound (compound 43, 195 mg, 56%) was obtained in the same manner as in step 3 of Example 1, using (E)-2-[2-(5-ethoxycarbonyl-4-(1-hydroxy-1-methyl)ethyl-2-propylimidazol-1-yl)methyl-10,11-dihydro-5H-dibenzo[a,d]cyclohepten-5-ylidene]propiononitrile (311 mg, 0.63 mmol) obtained in step 1.

ESI-MS m/z: 557 $(M+H)^+$; $^1$H-NMR ($CDCl_3$, δ): 0.93 (t, J=7.3 Hz, 3H), 1.11 (t, J=7.2 Hz, 3H), 1.63 (s, 6H), 1.66-1.76 (m, 2H), 2.11 (s, 3H), 2.59 (t, J=7.7 Hz, 2H), 2.76-2.90 (m, 2H), 3.26-3.42 (m, 2H), 4.21 (q, J=7.1 Hz, 2H), 5.39 (s, 2H), 5.70 (s, 1H), 6.70-6.84 (m, 2H), 7.09-7.13 (m, 2H), 7.17-7.37 (m, 3H).

Example 44

(E)-2-(7-chloro-2-ethyl-5-methyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 44)

[step 1] (E)-2-[2-(7-Chloro-2-ethyl-5-methyl-3H-imidazo[4,5-b]pyridin-3-yl)methyl-10,11-dihydro-5H-dibenzo[a,d]

cyclohepten-5-ylidene]propiononitrile (674 mg, 74%) was obtained in the same manner as in step 1 of Example 40, using 7-chloro-2-ethyl-5-methyl-3H-imidazo[4,5-b]pyridine (586 mg, 3.0 mmol) instead of 2-ethyl-5,7-dimethyl-3H-imidazo [4,5-b]pyridine.

ESI-MS m/z: 453 $(M+H)^+$; $^1$H-NMR ($CDCl_3$, δ): 1.34 (t, J=7.5 Hz, 3H), 1.99 (s, 3H), 2.60 (s, 3H), 2.72-2.89 (m, 2H), 2.78 (q, J=7.6 Hz, 2H), 3.19-3.35 (m, 2H), 5.41 (s, 2H), 6.92 (d, J=7.5 Hz, 1H), 6.94 (s, 1H), 7.01 (d, J=8.6 Hz, 1H), 7.12-7.28 (m, 4H), 7.39 (dd, J=7.0, 1.8 Hz, 1H).

[step 2] The title compound (compound 44, 324 mg, 85%) was obtained in the same manner as in step 3 of Example 1, using (E)-2-[2-(7-chloro-2-ethyl-5-methyl-3H-imidazo[4,5-b]pyridin-3-yl)methyl-10,11-dihydro-5H-dibenzo[a,d]cyclohepten-5-ylidene]propiononitrile (337 mg, 0.74 mmol) obtained in step 1.

ESI-MS m/z: 512 $(M+H)^+$; $^1$H-NMR ($CDCl_3$, δ): 1.34 (t, J=7.5 Hz, 3H), 2.10 (s, 3H), 2.60 (s, 3H), 2.74-2.88 (m, 2H), 2.79 (q, J=7.6 Hz, 2H), 3.22-3.39 (m, 2H), 5.40 (s, 2H), 6.90 (s, 1H), 6.95 (d, J=7.9 Hz, 1H), 7.08-7.12 (m, 3H), 7.20-7.36 (m, 3H).

Example 45

(E)-2-(2-ethyl-5,7-dimethyl-3H-imidazo[4,5-b]pyridin-3-yl)methyl-5-[1-(1H-tetrazol-5-yl)ethylidene]-10,11-dihydro-5H-dibenzo[a,d]cycloheptene (Compound 45)

The title compound (compound 45, 190 mg, 90%) was obtained in the same manner as in Example 22, using (E)-2-[2-(2-ethyl-5,7-dimethyl-3H-imidazo[4,5-b]pyridin-3-yl) methyl-10,11-dihydro-5H-dibenzo[a,d]cyclohepten-5-ylidene]propiononitrile (193 mg, 0.45 mmol) obtained in step 1 of Example 40.

ESI-MS m/z: 476 $(M+H)^+$; $^1$H-NMR ($CDCl_3$, δ): 1.28 (t, J=7.5 Hz, 3H), 2.31 (s, 3H), 2.53 (s, 3H), 2.58 (s, 3H), 2.66-2.78 (m, 4H), 3.09-3.25 (m, 2H), 5.41 (s, 2H), 6.88-6.91 (m, 2H), 6.99-7.02 (m, 2H), 7.13-7.32 (m, 4H).

Example 46

(E)-2-(7-chloro-2-ethyl-5-methyl-3H-imidazo[4,5-b]pyridin-3-yl)methyl-5-[1-(1H-tetrazol-5-yl)ethylidene]-10,11-dihydro-5H-dibenzo[a,d]cycloheptene (Compound 46)

The title compound (compound 46, 313 mg, 85%) was obtained in the same manner as in Example 22, using (E)-2-[2-(7-chloro-2-ethyl-5-methyl-3H-imidazo[4,5-b]pyridin-3-yl)methyl-10,11-dihydro-5H-dibenzo[a,d]cyclohepten-5-ylidene]propiononitrile (337 mg, 0.74 mmol) obtained in step 1 of Example 44.

ESI-MS m/z: 496 $(M+H)^+$; $^1$H-NMR ($CDCl_3$, δ): 1.32 (t, J=7.5 Hz, 3H), 2.34 (s, 3H), 2.60 (s, 3H), 2.74-2.83 (m, 2H), 2.78 (q, J=7.6 Hz, 2H), 3.23-3.32 (m, 2H), 5.41 (s, 2H), 6.89 (s, 1H), 6.97-7.03 (m, 2H), 7.12 (s, 1H), 7.16-7.22 (m, 2H), 7.29-7.36 (m, 2H).

Example 47

(E)-2-(2-ethyl-7-methyl-3H-imidazo[4,5-b]pyridin-3-yl)methyl-5-[1-(1H-tetrazol-5-yl)ethylidene]-10,11-dihydro-5H-dibenzo[a,d]cycloheptene (Compound 47)

The title compound (compound 47, 261 mg, 82%) was obtained in the same manner as in Example 22, using (E)-2-[2-(2-ethyl-7-methyl-3H-imidazo[4,5-b]pyridin-3-yl)methyl-10,11-dihydro-5H-dibenzo[a,d]cyclohepten-5-ylidene] propiononitrile (288 mg, 0.69 mmol) obtained in step 1 of Example 42.

ESI-MS m/z: 462 $(M+H)^+$; $^1$H-NMR ($CDCl_3$, δ): 1.34 (t, J=7.5 Hz, 3H), 2.32 (s, 3H), 2.65 (s, 3H), 2.68-2.87 (m, 2H), 2.83 (q, J=7.5 Hz, 2H), 3.21-3.29 (m, 2H), 5.44 (s, 2H), 6.91 (s, 1H), 6.96-7.04 (m, 3H), 7.16-7.22 (m, 2H), 7.29-7.36 (m, 2H), 8.19 (d, J=4.9 Hz, 1H).

Example 48

(Z)-2-(2-ethyl-5,7-dimethyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d] cycloheptene (Compound 48)

[step 1] (Z)-[2-(2-Ethyl-5,7-dimethyl-3H-imidazo[4,5-b] pyridin-3-yl)methyl-10,11-dihydro-5H-dibenzo[a,d]cyclohepten-5-ylidene]acetonitrile (1.66 g, 67%) was obtained in the same manner as in step 1 of Example 29, using (Z)-(2-hydroxymethyl-10,11-dihydro-5H-dibenzo[a,d]cyclohepten-5-ylidene)acetonitrile (JP-B-2526005; 1.54 g, 5.91 mmol) instead of (E)-(2-hydroxymethyl-10,11-dihydro-5H-dibenzo[a,d]cyclohepten-5-ylidene)acetonitrile.

ESI-MS m/z: 419 $(M+H)^+$; $^1$H-NMR ($CDCl_3$, δ): 1.31 (t, J=7.6 Hz, 3H), 2.58 (s, 3H), 2.64 (s, 3H), 2.77 (q, J=7.3 Hz, 2H), 2.99-3.13 (m, 4H), 5.45 (s, 2H), 5.68 (s, 1H), 6.90-6.92 (m, 2H), 7.05 (dd, J=7.6, 1.6 Hz, 1H), 7.12 (d, J=7.1 Hz, 1H), 7.20-7.31 (m, 3H), 7.40 (d, J=7.8 Hz, 1H).

[step 2] The title compound (compound 48, 0.16 g, 47%) was obtained in the same manner as in step 3 of Example 1, using (Z)-[2-(2-ethyl-5,7-dimethyl-3H-imidazo[4,5-b]pyridin-3-yl)methyl-10,11-dihydro-5H-dibenzo[a,d]cyclohepten-5-ylidene]acetonitrile (0.30 g, 0.72 mmol) obtained in step 1.

ESI-MS m/z: 478 $(M+H)^+$; $^1$H-NMR (DMSO-$d_6$, 6): 1.20 (t, J=7.4 Hz, 3H), 2.49 (s, 3H), 2.50 (s, 3H), 2.70-2.77 (m, 2H), 2.78-3.38 (m, 4H), 5.43 (s, 2H), 6.34 (s, 1H), 6.83 (dd, J=8.0, 1.4 Hz, 1H), 6.94 (s, 1H), 7.06 (d, J=8.0 Hz, 2H), 7.17-7.32 (m, 4H).

Example 49

(Z)-2-[4-methyl-6-(1-methylbenzimidazol-2-yl)-2-propylbenzimidazol-1-yl]methyl-5-(5-oxo-4,5-dihydro-1,2,4-oxadiazol-3-yl)methylene-10,11-dihydro-5H-dibenzo[a,d]cycloheptene (Compound 49)

[step 1] (Z)-2-[4-Methyl-6-(1-methylbenzimidazol-2-yl)-2-propylbenzimidazol-1-yl]methyl-10,11-dihydro-5H-dibenzo[a,d]cyclohepten-5-ylidene]acetonitrile (1.30 g, 73%) was obtained in the same manner as in step 1 of Example 32, using (Z)-(2-hydroxymethyl-10,11-dihydro-5H-dibenzo[a,d]cyclohepten-5-ylidene)acetonitrile (0.85 g, 3.25 mmol) instead of (E)-(2-hydroxymethyl-10,11-dihydro-5H-dibenzo[a,d]cyclohepten-5-ylidene)acetonitrile.

ESI-MS m/z; 548 $(M+H)^+$; $^1$H-NMR ($CDCl_3$, δ): 1.05 (t, J=7.4 Hz, 3H), 1.80-1.93 (m, 2H), 2.77 (s, 3H), 2.87-2.95 (m, 2H), 2.98-3.13 (m, 4H), 3.68 (s, 3H), 5.39 (s, 2H), 5.69 (s, 1H), 6.88 (s, 1H), 7.00 (d, J=8.4 Hz, 1H), 7.11 (d, J=7.6 Hz, 1H), 7.17-7.33 (m, 6H), 7.36-7.45 (m, 3H), 7.75-7.79 (m, 1H).

[step 2] The title compound (compound 49, 0.26 g, 58%) was obtained in the same manner as in step 3 of Example 1, using (Z)-2-[4-methyl-6-(1-methylbenzimidazol-2-yl)-2- propylbenzimidazol-1-yl]methyl-10,11-dihydro-5H-dibenzo[a,d]cyclohepten-5-ylidene]acetonitrile (0.40 g, 0.73 mmol) obtained in step 1.

ESI-MS m/z: 607 $(M+H)^+$; $^1$H-NMR (DMSO-$d_6$, δ): 0.95 (t, J=7.3 Hz, 3H), 1.70-1.82 (m, 2H), 2.61 (s, 3H), 2.78-3.25 (m, 4H), 2.86 (t, J=7.5 Hz, 2H), 3.71 (s, 3H), 5.55 (s, 2H), 6.33 (s, 1H), 6.90 (d, J=7.8 Hz, 1H), 7.07-7.34 (m, 8H), 7.46 (s, 1H), 7.52 (d, J=6.6 Hz, 1H), 7.63 (dd, J=7.0, 1.6 Hz, 1H), 7.71 (s, 1H).

Example 50

(Z)-2-(5,7-dimethyl-2-propyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 50)

[step 1] (Z)-2-(5,7-Dimethyl-2-propyl-3H-imidazo[4,5-b]pyridin-3-yl)methyl-10,11-dihydro-5H-dibenzo[a,d]cyclohepten-5-ylidene]acetonitrile (0.64 g, 49%) was obtained in the same manner as in step 1 of Example 31, using (Z)-(2-hydroxymethyl-10,11-dihydro-5H-dibenzo[a,d]cyclohepten-5-ylidene)acetonitrile (0.80 g, 3.07 mmol) instead of (E)-(2-hydroxymethyl-10,11-dihydro-5H-dibenzo[a,d]cyclohepten-5-ylidene)acetonitrile.

ESI-MS m/z; 433 $(M+H)^+$; $^1$H-NMR ($CDCl_3$, δ): 0.96 (t, J=7.5 Hz, 3H), 1.69-1.82 (m, 2H), 2.58 (s, 3H), 2.64 (s, 3H), 2.72 (t, J=7.9 Hz, 2H), 3.00-3.11 (m, 4H), 5.45 (s, 2H), 5.69 (s, 1H), 6.89-6.91 (m, 2H), 7.04 (dd, J=7.7, 1.5 Hz, 1H), 7.12 (d, J=7.3 Hz, 1H), 7.18-7.31 (m, 3H), 7.40 (d, J=7.9 Hz, 1H).

[step 2] The title compound (compound 50, 0.20 g, 60%) was obtained in the same manner as in step 3 of Example 1, using (Z)-2-(5,7-dimethyl-2-propyl-3H-imidazo[4,5-b]pyridin-3-yl)methyl-10,11-dihydro-5H-dibenzo[a,d]cyclohepten-5-ylidene]acetonitrile (0.30 g, 0.69 mmol) obtained in step 1.

ESI-MS m/z: 492 $(M+H)^+$; $^1$H-NMR (DMSO-$d_6$, δ): 0.86 (t, J=7.3 Hz, 3H), 1.58-1.71 (m, 2H), 2.48 (s, 3H), 2.49 (s, 3H), 2.68 (t, J=7.3 Hz, 2H), 2.80-3.20 (m, 4H), 5.42 (s, 2H), 6.33 (s, 1H), 6.81 (d, J=7.9 Hz, 1H), 6.92 (s, 1H), 7.03-7.34 (m, 6H).

Example 51

(Z)-2-(4-methyl-2-propylbenzimidazol-1-yl)methyl-5-(5-oxo-4,5-dihydro-1,2,4-oxadiazol-3-yl)methylene-10,11-dihydro-5H-dibenzo[a,d]cycloheptene (Compound 51)

[step 1] (Z)-2-(4-Methyl-2-propylbenzimidazol-1-yl)methyl-10,11-dihydro-5H-dibenzo[a,d]cyclohepten-5-ylidene]acetonitrile (1.20 g, 72%) was obtained in the same manner as in step 1 of Example 33, using (Z)-(2-hydroxymethyl-10,11-dihydro-5H-dibenzo[a,d]cyclohepten-5-ylidene)acetonitrile (1.04 g, 4.00 mmol) instead of (E)-(2-hydroxymethyl-10,11-dihydro-5H-dibenzo[a,d]cyclohepten-5-ylidene)acetonitrile.

ESI-MS m/z: 418 $(M+H)^+$; $^1$H-NMR ($CDCl_3$, δ): 1.00 (t, J=7.6 Hz, 3H), 1.73-1.87 (m, 2H), 2.69 (s, 3H), 2.84 (t, J=8.2 Hz, 2H), 2.96-3.11 (m, 4H), 5.32 (s, 2H), 5.69 (s, 1H), 6.81 (s, 1H), 6.98-7.13 (m, 5H), 7.20-7.32 (m, 3H), 7.42 (d, J=7.9 Hz, 1H).

[step 2] The title compound (compound 51, 0.36 g, 70%) was obtained in the same manner as in step 3 of Example 1, using (Z)-2-(4-methyl-2-propylbenzimidazol-1-yl)methyl-10,11-dihydro-5H-dibenzo[a,d]cyclohepten-5-ylidene]acetonitrile (0.45 g, 1.08 mmol) obtained in step 1.

ESI-MS m/z: 477 $(M+H)^+$; $^1$H-NMR (DMSO-$d_6$, δ): 0.92 (t, J=7.3 Hz, 3H), 1.65-1.77 (m, 2H), 2.52 (s, 3H), 2.78 (t, J=7.6 Hz, 2H), 2.79-3.25 (m, 4H), 5.43 (s, 2H), 6.34 (s, 1H), 6.83 (dd, J=7.9, 1.6 Hz, 1H), 6.95 (d, J=7.1 Hz, 1H), 7.00-7.08 (m, 3H), 7.16-7.34 (m, 5H).

Example 52

(Z)-2-(2-ethyl-7-methyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 52)

[step 1] (Z)-2-(2-Ethyl-7-methyl-3H-imidazo[4,5-b]pyridin-3-yl)methyl-10,11-dihydro-5H-dibenzo[a,d]cyclohepten-5-ylidene]acetonitrile (0.67 g, 44%) was obtained in the same manner as in step 1 of Example 34, using (Z)-(2-hydroxymethyl-10,11-dihydro-5H-dibenzo[a,d]cyclohepten-5-ylidene)acetonitrile (0.97 g, 3.71 mmol) instead of (E)-(2-hydroxymethyl-10,11-dihydro-5H-dibenzo[a,d]cyclohepten-5-ylidene)acetonitrile.

ESI-MS m/z: 405 $(M+H)^+$; $^1$H-NMR ($CDCl_3$, δ): 1.35 (t, J=7.4 Hz, 3H), 2.70 (s, 3H), 2.84 (q, J=7.4 Hz, 2H), 2.98-3.12 (m, 4H), 5.47 (s, 2H), 5.68 (s, 1H), 6.94-6.95 (m, 1H), 7.02-7.07 (m, 2H), 7.11 (d, J=8.1 Hz, 1H), 7.16-7.31 (m, 3H), 7.39 (d, J=8.1 Hz, 1H), 8.19 (d, J=5.0 Hz, 1H).

[step 2] The title compound (compound 52, 0.11 g, 64%) was obtained in the same manner as in step 3 of Example 1, using (Z)-2-(2-ethyl-7-methyl-3H-imidazo[4,5-b]pyridin-3-yl)methyl-10,11-dihydro-5H-dibenzo[a,d]cyclohepten-5-ylidene]acetonitrile (0.15 g, 0.37 mmol) obtained in step 1.

ESI-MS m/z: 464 $(M+H)^+$; $^1$H-NMR (DMSO-$d_6$, δ): 1.21 (t, J=7.5 Hz, 3H), 2.54 (s, 3H), 2.79 (q, J=7.5 Hz, 2H), 2.81-3.26 (m, 4H), 5.45 (s, 2H), 6.32 (s, 1H), 6.87 (dd, J=7.8, 1.7 Hz, 1H), 7.02-7.07 (m, 3H), 7.12-7.33 (m, 4H), 8.13 (d, J=4.8 Hz, 1H).

Example 53

(Z)-2-(2-ethoxy-5,7-dimethyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 53)

[step 1] (Z)-2-(2-Ethoxy-5,7-dimethyl-3H-imidazo[4,5-b]pyridin-3-yl)methyl-10,11-dihydro-5H-dibenzo[a,d]cyclohepten-5-ylidene]acetonitrile (1.11 g, 44%) was obtained in the same manner as in step 1 of Example 29, using (Z)-(2-hydroxymethyl-10,11-dihydro-5H-dibenzo[a,d]cyclohepten-5-ylidene)acetonitrile (1.50 g, 5.74 mmol) instead of (E)-(2-hydroxymethyl-10,11-dihydro-5H-dibenzo[a,d]cyclohepten-5-ylidene)acetonitrile and 2-ethoxy-5,7-dimethyl-3H-imidazo[4,5-b]pyridine (1.10 g, 5.74 mmol) instead of 2-ethyl-5,7-dimethyl-3H-imidazo[4,5-b]pyridine.

ESI-MS m/z: 435 $(M+H)^+$; $^1$H-NMR ($CDCl_3$, δ): 1.42 (t, J=7.0 Hz, 3H), 2.50 (s, 3H), 2.54 (s, 3H), 3.02-3.13 (m, 4H), 4.58 (q, J=7.1 Hz, 2H), 5.22 (s, 2H), 5.68 (s, 1H), 6.79 (s, 1H), 7.11-7.30 (m, 6H), 7.39 (d, J=7.9 Hz, 1H).

[step 2] The title compound (compound 53, 0.19 g, 56%) was obtained in the same manner as in step 3 of Example 1, using (Z)-2-(2-ethoxy-5,7-dimethyl-3H-imidazo[4,5-b]pyridin-3-yl)methyl-10,11-dihydro-5H-dibenzo[a,d]cyclohepten-5-ylidene]acetonitrile (0.30 g, 0.69 mmol) obtained in step 1.

ESI-MS m/z: 494 $(M+H)^+$; $^1$H-NMR (DMSO-$d_6$, δ): 1.32 (t, J=7.1 Hz, 3H), 2.39 (s, 3H), 2.42 (s, 3H), 2.86-3.24 (m,

4H), 4.51 (q, J=7.1 Hz, 2H), 5.14 (s, 2H), 6.32 (s, 1H), 6.83 (s, 1H), 6.92 (dd, J=8.0, 1.6 Hz, 1H), 7.05 (d, J=7.7 Hz, 1H), 7.13-7.32 (m, 5H).

Example 54

(Z)-2-(5-ethoxycarbonyl-4-(1-hydroxy-1-methyl)ethyl-2-propylimidazol-1-yl)methyl-5-(5-oxo-4,5-dihydro-1,2,4-oxadiazol-3-yl)methylene-10,11-dihydro-5H-dibenzo[a,d]cycloheptene (Compound 54)

[step 1] (Z)-[2-(5-Ethoxycarbonyl-4-(1-hydroxy-1-methyl)ethyl-2-propylimidazol-1-yl)methyl-10,11-dihydro-5H-dibenzo[a,d]cyclohepten-5-ylidene]acetonitrile (362 mg, 78%) was obtained in the same manner as in step 1 of Example 35, using (Z)-[2-hydroxymethyl-10,11-dihydro-5H-dibenzo[a,d]cyclohepten-5-ylidene]acetonitrile (250 mg, 0.96 mmol) instead of (E)-(2-hydroxymethyl-10,11-dihydro-5H-dibenzo[a,d]cyclohepten-5-ylidene)acetonitrile.

ESI-MS m/z: 484 $(M+H)^+$; $^1$H-NMR ($CDCl_3$, δ): 0.95 (t, J=7.3 Hz, 3H), 1.14 (t, J=7.1 Hz, 3H), 1.64 (s, 6H), 1.65-1.78 (m, 2H), 2.61 (t, J=7.8 Hz, 2H), 3.00-3.19 (m, 4H), 4.20 (q, J=7.2 Hz, 2H), 5.44 (s, 2H), 5.70 (s, 1H), 5.79 (s, 1H), 6.72 (s, 1H), 6.88 (dd, J=7.8, 1.4 Hz, 1H), 7.13-7.33 (m, 4H), 7.43 (d, J=7.9 Hz, 1H).

[step 2] The title compound (compound 54, 88 mg, 53%) was obtained in the same manner as in step 3 of Example 1, using (Z)-[2-(5-ethoxycarbonyl-4-(1-hydroxy-1-methyl)ethyl-2-propylimidazol-1-yl)methyl-10,11-dihydro-5H-dibenzo[a,d]cyclohepten-5-ylidene]acetonitrile (146 mg, 0.3 mmol) obtained in step 1.

ESI-MS m/z: 543 $(M+H)^+$; $^1$H-NMR ($CDCl_3$, δ): 0.97 (t, J=7.4 Hz, 3H), 1.19 (t, J=7.1 Hz, 3H), 1.64 (s, 6H), 1.68-1.78 (m, 2H), 2.65 (t, J=7.7 Hz, 2H), 2.75-3.01 (m, 2H), 3.27-3.43 (m, 2H), 4.23 (q, J=7.0 Hz, 2H), 5.47 (d, J=4.4 Hz, 2H), 5.60 (s, 1H), 6.53 (s, 1H), 6.87 (s, 1H), 6.90 (d, J=7.7 Hz, 1H), 7.10-7.31 (m, 4H), 7.37 (dd, J=7.4, 1.7 Hz, 1H).

Example 55

(Z)-2-(5-chloro-2-ethyl-7-methyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 55)

[step 1] (Z)-[2-(5-Chloro-2-ethyl-7-methyl-3H-imidazo[4,5-b]pyridin-3-yl)methyl-10,11-dihydro-5H-dibenzo[a,d]cyclohepten-5-ylidene]acetonitrile (147 mg, 73%) was obtained in the same manner as in step 1 of Example 36, using (Z)-(2-hydroxymethyl-10,11-dihydro-5H-dibenzo[a,d]cyclohepten-5-ylidene)acetonitrile (120 mg, 0.46 mmol) instead of (E)-(2-hydroxymethyl-10,11-dihydro-5H-dibenzo[a,d]cyclohepten-5-ylidene)acetonitrile.

ESI-MS m/z: 439 $(M+H)^+$; $^1$H-NMR ($CDCl_3$, δ): 1.33 (t, J=7.5 Hz, 3H), 2.66 (s, 3H), 2.79 (q, J=7.5 Hz, 2H), 2.98-3.14 (m, 4H), 5.42 (s, 2H), 5.69 (s, 1H), 6.94 (s, 1H), 7.02-7.07 (m, 2H), 7.13 (d, J=7.5 Hz, 1H), 7.20-7.32 (m, 3H), 7.41 (d, J=7.7 Hz, 1H).

[step 2] The title compound (compound 55, 99 mg, 59%) was obtained in the same manner as in step 3 of Example 1, using (Z)-[2-(5-chloro-2-ethyl-7-methyl-3H-imidazo[4,5-b]pyridin-3-yl)methyl-10,11-dihydro-5H-dibenzo[a,d]cyclohepten-5-ylidene]acetonitrile (147 mg, 0.33 mmol) obtained in step 1.

ESI-MS m/z: 498 $(M+H)^+$; $^1$H-NMR ($CDCl_3$, δ): 1.37 (t, J=7.5 Hz, 3H), 2.66 (d, J=0.5 Hz, 3H), 2.75-3.00 (m, 2H), 2.84 (q, J=7.5 Hz, 2H), 3.25-3.40 (m, 2H), 5.45 (s, 2H), 6.51 (s, 1H), 7.05-7.17 (m, 5H), 7.20-7.30 (m, 2H), 7.36 (dd, J=7.3, 1.6 Hz, 1H).

Example 56

(Z)-2-(2-ethyl-5-methyl-7-trifluoromethyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 56)

[step 1] (Z)-[2-(2-Ethyl-5-methyl-7-trifluoromethyl-3H-imidazo[4,5-b]pyridin-3-yl)methyl-10,11-dihydro-5H-dibenzo[a,d]cyclohepten-5-ylidene]acetonitrile (214 mg, 85%) was obtained in the same manner as in Step 1 of Example 37, using (Z)-(2-hydroxymethyl-10,11-dihydro-5H-dibenzo[a,d]cyclohepten-5-ylidene)acetonitrile (140 mg, 0.54 mmol) instead of (E)-(2-hydroxymethyl-10,11-dihydro-5H-dibenzo[a,d]cyclohepten-5-ylidene)acetonitrile.

ESI-MS m/z: 473 $(M+H)^+$; $^1$H-NMR ($CDCl_3$, δ): 1.34 (t, J=7.6 Hz, 3H), 2.69 (s, 3H), 2.85 (q, J=7.5 Hz, 2H), 2.98-3.15 (m, 4H), 5.50 (s, 2H), 5.70 (s, 1H), 6.93 (s, 1H), 7.05-7.14 (m, 2H), 7.18-7.32 (m, 4H), 7.42 (d, J=7.9 Hz, 1H).

[step 2] The title compound (compound 56, 192 mg, 77%) was obtained in the same manner as in step 3 of Example 1, using (Z)-[2-(2-ethyl-5-methyl-7-trifluoromethyl-3H-imidazo[4,5-b]pyridin-3-yl)methyl-10,11-dihydro-5H-dibenzo[a,d]cyclohepten-5-ylidene]acetonitrile (214 mg, 0.45 mmol) obtained in step 1.

ESI-MS m/z: 532 $(M+H)^+$; $^1$H-NMR ($CDCl_3$, δ): 1.37 (t, J=7.6 Hz, 3H), 2.68 (s, 3H), 2.73-2.98 (m, 2H), 2.89 (q, J=7.6 Hz, 2H), 3.25-3.40 (m, 2H), 5.53 (s, 2H), 6.52 (s, 1H), 7.05-7.17 (m, 4H), 7.20-7.31 (m, 3H), 7.36 (dd, J=7.3, 1.6 Hz, 1H).

Example 57

(Z)-2-(5-methyl-2-propyl-7-trifluoromethyl-3H-imidazo[4,5-b]pyridin-3-yl)methyl-5-(5-oxo-4,5-dihydro-1,2,4-oxadiazol-3-yl)methylene-10,11-dihydro-5H-dibenzo[a,d]cycloheptene (Compound 57)

[step 1] (Z)-[2-(5-Methyl-2-propyl-7-trifluoromethyl-3H-imidazo[4,5-b]pyridin-3-yl)methyl-10,11-dihydro-5H-dibenzo[a,d]cyclohepten-5-ylidene]acetonitrile was obtained as a crude product in the same manner as in step 1 of Example 38, using (Z)-(2-hydroxymethyl-10,11-dihydro-5H-dibenzo[a,d]cyclohepten-5-ylidene)acetonitrile (140 mg, 0.54 mmol) instead of (E)-(2-hydroxymethyl-10,11-dihydro-5H-dibenzo[a,d]cyclohepten-5-ylidene)acetonitrile.

[step 2] The title compound (compound 57, 165 mg, 57%) was obtained in the same manner as in step 3 of Example 1, using (Z)-[2-(5-methyl-2-propyl-7-trifluoromethyl-3H-imidazo[4,5-b]pyridin-3-yl)methyl-10,11-dihydro-5H-dibenzo[a,d]cyclohepten-5-ylidene]acetonitrile obtained in step 1.

ESI-MS m/z: 546 $(M+H)^+$; $^1$H-NMR ($CDCl_3$, δ): 0.99 (t, J=7.3 Hz, 3H), 1.76-1.86 (m, 2H), 2.68 (s, 3H), 2.76-2.99 (m, 2H), 2.84 (t, J=7.8 Hz, 2H), 3.28-3.40 (m, 2H), 5.53 (s, 2H), 6.52 (s, 1H), 7.04-7.17 (m, 4H), 7.21-7.30 (m, 3H), 7.37 (dd, J=7.2, 1.7 Hz, 1H).

Example 58

(Z)-2-(8-oxo-2-propyl-8H-cycloheptaimidazol-1-yl)methyl-5-(5-oxo-4,5-dihydro-1,2,4-oxadiazol-3-yl)methylene-10,11-dihydro-5H-dibenzo[a,d]cycloheptene (Compound 58)

[step 1] (Z)-[2-(8-Oxo-2-propyl-8H-cycloheptaimidazol-1-yl)methyl-10,11-dihydro-5H-dibenzo[a,d]cyclohepten-5- ylidene]acetonitrile (206 mg, 89%) was obtained in the same manner as in step 1 of Example 39, using (Z)-(2-hydroxymethyl-10,11-dihydro-5H-dibenzo[a,d]cyclohepten-5-ylidene)acetonitrile (140 mg, 0.54 mmol) instead of (E)-(2-hydroxymethyl-10,11-dihydro-5H-dibenzo[a,d]cyclohepten-5-ylidene)acetonitrile.

ESI-MS m/z: 432 $(M+H)^+$; $^1$H-NMR ($CDCl_3$, δ): 1.00 (t, J=7.4 Hz, 3H), 1.77-1.89 (m, 2H), 2.76 (t, J=7.7 Hz, 2H), 2.99-3.15 (m, 4H), 5.67 (s, 1H), 6.01 (s, 2H), 6.89-6.99 (m, 3H), 7.07-7.31 (m, 6H), 7.40 (d, J=8.4 Hz, 1H), 7.73 (d, J=11.0 Hz, 1H).

[step 2] The title compound (compound 58, 108 mg, 46%) was obtained in the same manner as in step 3 of Example 1, using (Z)-[2-(8-oxo-2-propyl-8H-cycloheptaimidazol-1-yl)methyl-10,11-dihydro-5H-dibenzo[a,d]cyclohepten-5-ylidene]acetonitrile (206 mg, 0.48 mmol) obtained in step 1.

ESI-MS m/z: 491 $(M+H)^+$; $^1$H-NMR ($CDCl_3$, δ): 1.02 (t, J=7.3 Hz, 3H), 1.80-1.93 (m, 2H), 2.80 (t, J=7.7 Hz, 2H), 2.84-2.99 (m, 2H), 3.28-3.40 (m, 2H), 5.93 (s, 2H), 6.50 (s, 1H), 6.86 (d, J=7.9 Hz, 1H), 6.95-7.13 (m, 5H), 7.20-7.29 (m, 3H), 7.36 (dd, J=7.3, 1.8 Hz, 1H), 7.76 (d, J=11.0 Hz, 1H).

Example 59

(Z)-2-(2-ethyl-5,7-dimethyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 59)

[step 1] (Z)-2-[2-(2-Ethyl-5,7-dimethyl-3H-imidazo[4,5-b]pyridin-3-yl)methyl-10,11-dihydro-5H-dibenzo[a,d]cyclohepten-5-ylidene]propiononitrile (376 mg, 68%) was obtained in the same manner as in step 1 of Example 36, using (Z)-2-(2-hydroxymethyl-10,11-dihydro-5H-dibenzo[a,d]cyclohepten-5-ylidene)propiononitrile (350 mg, 1.3 mmol) obtained in Reference Example 6 and 2-ethyl-5,7-dimethyl-3H-imidazo[4,5-b]pyridine (349 mg, 2.0 mmol) instead of 5-chloro-2-ethyl-7-methyl-3H-imidazo[4,5-b]pyridine.

ESI-MS m/z: 433 $(M+H)^+$; $^1$H-NMR ($CDCl_3$, δ): 1.31 (t, J=7.4 Hz, 3H), 2.00 (s, 3H), 2.56 (s, 3H), 2.63 (s, 3H), 2.73-2.84 (m, 2H), 2.75 (q, J=7.4 Hz, 2H), 3.20-3.30 (m, 2H), 5.40 (s, 2H), 6.83 (s, 1H), 6.88 (s, 1H), 6.97 (dd, J=8.0, 1.6 Hz, 1H), 7.04 (dd, J=8.0, 1.6 Hz, 1H), 7.15-7.25 (m, 3H), 7.36 (d, J=7.9 Hz, 1H).

[step 2] The title compound (compound 59, 126 mg, 56%) was obtained in the same manner as in step 3 of Example 1, using (Z)-2-[2-(2-ethyl-5,7-dimethyl-3H-imidazo[4,5-b]pyridin-3-yl)methyl-10,11-dihydro-5H-dibenzo[a,d]cyclohepten-5-ylidene]propiononitrile (197 mg, 0.46 mmol) obtained in step 1.

ESI-MS m/z: 492 $(M+H)^+$; $^1$H-NMR ($CDCl_3$, δ): 1.33 (t, J=7.5 Hz, 3H), 2.11 (s, 3H), 2.55 (s, 3H), 2.63 (s, 3H), 2.75-2.83 (m, 4H), 3.26-3.33 (m, 2H), 5.42 (s, 2H), 6.89 (s, 1H), 6.91-6.94 (m, 2H), 7.05-7.24 (m, 5H).

Example 60

(Z)-2-(8-oxo-2-propyl-4,5,6,7-tetrahydro-8H-cycloheptaimidazol-1-yl)methyl-5-(5-oxo-4,5-dihydro-1,2,4-oxadiazol-3-yl)methylene-10,11-dihydro-5H-dibenzo[a,d]cycloheptene (Compound 60)

The title compound (compound 60, 5 mg, 4%) was obtained in the same manner as in Example 41, using compound 58 (131 mg, 0.27 mmol) obtained in Example 58.

ESI-MS m/z: 495 $(M+H)^+$; $^1$H-NMR ($CDCl_3$, δ): 0.98 (t, J=7.4 Hz, 3H), 1.68-1.79 (m, 2H), 1.82-1.98 (m, 4H), 2.54-2.67 (m, 4H), 2.80-3.04 (m, 2H), 3.02 (t, J=6.2 Hz, 2H), 3.22-3.40 (m, 2H), 5.50 (s, 2H), 6.50 (s, 1H), 6.71-6.85 (m, 2H), 6.96 (s, 1H), 7.06-7.45 (m, 4H).

Example 61

(Z)-2-(5-ethoxycarbonyl-4-(1-hydroxy-1-methyl)ethyl-2-propylimidazol-1-yl)methyl-5-[1-(5-oxo-4,5-dihydro-1,2,4-oxadiazol-3-yl)ethylidene]-10,11-dihydro-5H-dibenzo[a,d]cycloheptene (Compound 61)

[step 1] (Z)-2-[2-(5-Ethoxycarbonyl-4-(1-hydroxy-1-methyl)ethyl-2-propylimidazol-1-yl)methyl-10,11-dihydro-5H-dibenzo[a,d]cyclohepten-5-ylidene]propiononitrile (282 mg, 78%) was obtained in the same manner as in step 1 of Example 43, using (Z)-2-(2-hydroxymethyl-10,11-dihydro-5H-dibenzo[a,d]cyclohepten-5-ylidene)propiononitrile (200 mg, 0.73 mmol) instead of (E)-2-(2-hydroxymethyl-10,11-dihydro-5H-dibenzo[a,d]cyclohepten-5-ylidene)propiononitrile.

ESI-MS m/z: 498 $(M+H)^+$; $^1$H-NMR ($CDCl_3$, δ): 0.93 (t, J=7.3 Hz, 3H), 1.12 (t, J=7.1 Hz, 3H), 1.63 (s, 6H), 1.65-1.75 (m, 2H), 2.02 (s, 3H), 2.59 (t, J=7.8 Hz, 2H), 2.75-2.89 (m, 2H), 3.21-3.33 (m, 2H), 4.19 (q, J=7.1 Hz, 2H), 5.39 (s, 2H), 5.79 (s, 1H), 6.62 (s, 1H), 6.82 (dd, J=7.9, 1.6 Hz, 1H), 7.06 (dd, J=8.0, 1.4 Hz, 1H), 7.17-7.31 (m, 3H), 7.39 (d, J=7.9 Hz, 1H).

[step 2] The title compound (compound 61, 67 mg, 21%) was obtained in the same manner as in step 3 of Example 1, using (Z)-2-[2-(5-ethoxycarbonyl-4-(1-hydroxy-1-methyl)ethyl-2-propyl-1H-imidazol-1-yl)methyl-10,11-dihydro-5H-dibenzo[a,d]cyclohepten-5-ylidene]propiononitrile (282 mg, 0.57 mmol) obtained in step 1.

ESI-MS m/z: 557 $(M+H)^+$; $^1$H-NMR ($CDCl_3$, δ): 0.95 (t, J=7.3 Hz, 3H), 1.12 (t, J=7.2 Hz, 3H), 1.62 (s, 6H), 1.78-1.65 (m, 2H), 2.12 (s, 3H), 2.61 (t, J=7.8 Hz, 2H), 2.90-2.76 (m, 2H), 3.39-3.27 (m, 2H), 4.20 (q, J=7.2 Hz, 2H), 5.41 (s, 2H), 5.66 (s, 1H), 6.74 (s, 1H), 6.81 (dd, J=7.8, 1.8 Hz, 1H), 7.27-7.05 (m, 5H).

Example 62

(Z)-2-(2-ethyl-5,7-dimethyl-3H-imidazo[4,5-b]pyridin-3-yl)methyl-5-[1-(1H-tetrazol-5-yl)ethylidene]-10,11-dihydro-5H-dibenzo[a,d]cycloheptene (Compound 62)

The title compound (compound 62, 171 mg, 74%) was obtained in the same manner as in Example 22, using (Z)-2-[2-(2-ethyl-5,7-dimethyl-3H-imidazo[4,5-b]pyridin-3-yl)methyl-10,11-dihydro-5H-dibenzo[a,d]cyclohepten-5-ylidene]propiononitrile (212 mg, 0.49 mmol) obtained in step 1 of Example 59.

ESI-MS m/z: 476 $(M+H)^+$; $^1$H-NMR ($CDCl_3$, δ): 1.31 (t, J=7.6 Hz, 3H), 2.33 (s, 3H), 2.54 (s, 3H), 2.61 (s, 3H), 2.68-2.82 (m, 4H), 3.15-3.35 (m, 2H), 5.38 (s, 2H), 6.83-6.94 (m, 4H), 7.13-7.24 (m, 4H).

Example 63

2-(2-ethyl-5,7-dimethyl-3H-imidazo[4,5-b]pyridin-3-yl)methyl-5-(5-oxo-4,5-dihydro-1,2,4-oxadiazol-3-yl)methyl-10,11-dihydro-5H-dibenzo[a,d]cycloheptene (Compound 63)

[step 1] 5-Cyanomethyl-2-(2-ethyl-5,7-dimethyl-3H-imidazo[4,5-b]pyridin-3-yl)methyl-10,11-dihydro-5H-dibenzo

[a,d]cycloheptene (252 mg, 47%) was obtained in the same manner as in step 1 of Example 36, using 5-cyanomethyl-2-hydroxymethyl-10,11-dihydro-5H-dibenzo[a,d]cycloheptene (JP-B-2526005; 335 mg, 1.3 mmol) and 2-ethyl-5,7-dimethyl-3H-imidazo[4,5-b]pyridine (403 mg, 3.8 mmol) instead of 5-chloro-2-ethyl-7-methyl-3H-imidazo[4,5-b]pyridine.

ESI-MS m/z: 421 $(M+H)^+$; $^1$H-NMR ($CDCl_3$, δ): 1.30 (t, J=7.6 Hz, 3H), 2.58 (s, 3H), 2.63 (s, 3H), 2.75 (q, J=7.6 Hz, 2H), 2.90-3.05 (m, 4H), 3.14-3.26 (m, 2H), 4.38 (t, J=8.1 Hz, 1H), 5.40 (s, 2H), 6.87-6.94 (m, 3H), 7.10-7.23 (m, 5H).

[step 2] The title compound (compound 63, 224 mg, 78%) was obtained in the same manner as in step 3 of Example 1, using 5-cyanomethyl-2-(2-ethyl-5,7-dimethyl-3H-imidazo[4,5-b]pyridin-3-yl)methyl-10,11-dihydro-5H-dibenzo[a,d]cycloheptene (252 mg, 0.60 mmol) obtained in step 1.

ESI-MS m/z: 480 $(M+H)^+$; $^1$H-NMR ($CDCl_3$, δ): 1.27 (t, J=7.5 Hz, 3H), 2.55 (s, 3H), 2.58 (s, 3H), 2.73 (q, J=7.5 Hz, 2H), 2.79-2.91 (m, 2H), 3.02-3.24 (m, 4H), 4.28 (br s, 1H), 5.35 (s, 2H), 6.75 (d, J=7.8 Hz, 1H), 6.79 (s, 1H), 6.88 (d, J=7.8 Hz, 1H), 6.90 (s, 1H), 7.00-7.17 (m, 4H).

Example 64

2-(4-methyl-2-propylbenzimidazol-1-yl)methyl-5-(5-oxo-4,5-dihydro-1,2,4-oxadiazol-3-yl)methyl-10,11-dihydro-5H-dibenzo[a,d]cycloheptene (Compound 64)

[step 1] 5-Cyanomethyl-2-(4-methyl-2-propylbenzimidazol-1-yl)methyl-10,11-dihydro-5H-dibenzo[a,d]cycloheptene (508 mg, 78%) was obtained in the same manner as in step 1 of Example 29, using 5-cyanomethyl-2-hydroxymethyl-10,11-dihydro-5H-dibenzo[a,d]cycloheptene (408 mg, 1.55 mmol) and 4-methyl-2-propylbenzimidazole (297 mg, 1.70 mmol) instead of 2-ethyl-5,7-dimethyl-3H-imidazo[4,5-b]pyridine.

ESI-MS m/z: 420 $(M+H)^+$; $^1$H-NMR ($CDCl_3$, δ): 0.99 (t, J=7.3 Hz, 3H), 1.73-1.85 (m, 2H), 2.69 (s, 3H), 2.80-2.86 (m, 2H), 2.88-3.29 (m, 4H), 3.04 (d, J=8.2 Hz, 2H), 4.39 (t, J=8.2 Hz, 1H), 5.27 (s, 2H), 6.78 (s, 1H), 6.88 (d, J=7.7 Hz, 1H), 6.98-7.24 (m, 8H).

[step 2] The title compound (compound 64, 363 mg, 63%) was obtained in the same manner as in step 3 of Example 1, using 5-cyanomethyl-2-(4-methyl-2-propylbenzimidazol-1-yl)methyl-10,11-dihydro-5H-dibenzo[a,d]cycloheptene (508 mg, 1.2 mmol) obtained in step 1.

ESI-MS m/z: 479 $(M+H)^+$; $^1$H-NMR ($CDCl_3$, δ): 0.95 (t, J=7.3 Hz, 3H), 1.67-1.78 (m, 2H), 2.59 (s, 3H), 2.67-2.86 (m, 2H), 2.77 (t, J=7.8 Hz, 2H), 2.94-3.17 (m, 2H), 3.19-3.34 (m, 2H), 4.40 (br s, 1H), 5.24 (s, 2H), 6.70 (s, 1H), 6.76 (d, J=7.9 Hz, 1H), 6.97 (d, J=7.9 Hz, 1H), 7.03-7.17 (m, 7H).

Example 65

2-(7-chloro-2-ethyl-5-methyl-3H-imidazo[4,5-b]pyridin-3-yl)methyl-5-(5-oxo-4,5-dihydro-1,2,4-oxadiazol-3-yl)methyl-10,11-dihydro-5H-dibenzo[a,d]cycloheptene (Compound 65)

[step 1] 5-Cyanomethyl-2-(7-chloro-2-ethyl-5-methyl-3H-imidazo[4,5-b]pyridin-3-yl)methyl-10,11-dihydro-5H-dibenzo[a,d]cycloheptene (362 mg, 70%) was obtained in the same manner as in step 1 of Example 36, using 5-cyanomethyl-2-hydroxymethyl-10,11-dihydro-5H-dibenzo[a,d]cycloheptene (310 mg, 1.2 mmol) and 7-chloro-2-ethyl-5-methyl-3H-imidazo[4,5-b]pyridine (345 mg, 1.8 mmol) instead of 5-chloro-2-ethyl-7-methyl-3H-imidazo[4,5-b]pyridine.

ESI-MS m/z: 441 $(M+H)^+$; $^1$H-NMR ($CDCl_3$, δ): 1.33 (t, J=7.5 Hz, 3H), 2.60 (s, 3H), 2.78 (q, J=7.5 Hz, 2H), 2.90-3.05 (m, 2H), 3.04 (d, J=8.2 Hz, 2H), 3.14-3.28 (m, 2H), 4.39 (t, J=8.2 Hz, 1H), 5.40 (s, 2H), 6.85 (s, 1H), 6.94 (dd, J=7.9, 1.6 Hz, 1H), 7.11-7.15 (m, 2H), 7.17-7.23 (m, 4H).

[step 2] The title compound (compound 65, 338 mg, 82%) was obtained in the same manner as in step 3 of Example 1, using 5-cyanomethyl-2-(7-chloro-2-ethyl-5-methyl-3H-imidazo[4,5-b]pyridin-3-yl)methyl-10,11-dihydro-5H-dibenzo[a,d]cycloheptene (362 mg, 0.82 mmol) obtained in step 1.

ESI-MS m/z: 500 $(M+H)^+$; $^1$H-NMR ($CDCl_3$, δ): 1.27 (t, J=7.5 Hz, 3H), 2.60 (s, 3H), 2.74 (q, J=7.5 Hz, 2H), 2.82-2.95 (m, 2H), 3.06-3.33 (m, 4H), 4.39 (br s, 1H), 5.37 (s, 2H), 6.80-6.83 (m, 2H), 6.98 (d, J=8.3 Hz, 1H), 7.04-7.16 (m, 5H).

Example 66

2-(2-ethyl-7-methyl-3H-imidazo[4,5-b]pyridin-3-yl)methyl-5-(5-oxo-4,5-dihydro-1,2,4-oxadiazol-3-yl)methyl-10,11-dihydro-5H-dibenzo[a,d]cycloheptene (Compound 66)

[step 1] 5-Cyanomethyl-2-(2-ethyl-7-methyl-3H-imidazo[4,5-b]pyridin-3-yl)methyl-10,11-dihydro-5H-dibenzo[a,d]cycloheptene (171 mg, 35%) was obtained in the same manner as in step 1 of Example 29, using 5-cyanomethyl-2-hydroxymethyl-10,11-dihydro-5H-dibenzo[a,d]cycloheptene (362 mg, 1.4 mmol) and 2-ethyl-7-methyl-3H-imidazo[4,5-b]pyridine (214 mg, 1.3 mmol) instead of 2-ethyl-5,7-dimethyl-3H-imidazo[4,5-b]pyridine.

ESI-MS m/z: 407 $(M+H)^+$; $^1$H-NMR ($CDCl_3$, δ): 1.33 (t, J=7.6 Hz, 3H), 2.69 (s, 3H), 2.82 (q, J=7.6 Hz, 2H), 2.90-3.04 (m, 2H), 3.03 (d, J=8.1 Hz, 2H), 3.13-3.26 (m, 2H), 4.38 (t, J=8.1 Hz, 1H), 5.43 (s, 2H), 6.89 (s, 1H), 6.94 (dd, J=7.8, 1.7 Hz, 1H), 7.03 (dd, J=4.9, 0.7 Hz, 1H), 7.11-7.24 (m, 5H), 8.19 (d, J=4.9 Hz, 1H).

[step 2] The title compound (compound 66, 178 mg, 91%) was obtained in the same manner as in step 3 of Example 1, using 5-cyanomethyl-2-(2-ethyl-7-methyl-3H-imidazo[4,5-b]pyridin-3-yl)methyl-10,11-dihydro-5H-dibenzo[a,d]cycloheptene (171 mg, 0.42 mmol) obtained in step 1.

ESI-MS m/z: 466 $(M+H)^+$; $^1$H-NMR ($CDCl_3$, δ): 1.33 (t, J=7.5 Hz, 3H), 2.67 (s, 3H), 2.74-3.17 (m, 6H), 2.82 (q, J=7.5 Hz, 2H), 4.23 (br s, 1H), 5.38 (s, 2H), 6.72 (d, J=8.1 Hz, 1H), 6.81-6.85 (m, 2H), 6.97 (d, J=7.3 Hz, 1H), 7.03-7.18 (m, 4H), 8.10 (d, J=4.9 Hz, 1H).

Example 67

2-(2-cyclopropyl-5,7-dimethyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 67)

[step 1] 2-(2-Cyclopropyl-5,7-dimethyl-3H-imidazo[4,5-b]pyridin-3-yl)methyl-10,11-dihydro-5H-dibenzo[b,f]azepine (2.19 g, 52%) was obtained in the same manner as in step 1 of Example 1, using 2-cyclopropyl-5,7-dimethyl-3H-imidazo[4,5-b]pyridine (EP420237; 2.0 g, 10.7 mmol) instead of 2-ethyl-5,7-dimethyl-3H-imidazo[4,5-b]pyridine.

ESI-MS m/z: 395 $(M+H)^+$; $^1$H-NMR ($CDCl_3$, δ): 0.94-1.01 (m, 2H), 1.12-1.18 (m, 2H), 1.90 (tt, J=8.3, 5.0 Hz, 1H), 2.58 (s, 3H), 2.59 (s, 3H), 2.96-3.06 (m, 4H), 5.44 (s, 2H), 6.00 (s, 1H), 6.60-6.65 (m, 1H), 6.68-6.78 (m, 2H), 6.85-6.91 (m, 3H), 7.00-7.09 (m, 2H).

[step 2] 5-Cyanomethyl-2-(2-cyclopropyl-5,7-dimethyl-3H-imidazo[4,5-b]pyridin-3-yl)methyl-10,11-dihydro-5H-dibenzo[b,f]azepine (580 mg, 98%) was obtained in the same manner as in step 2 of Example 1, using 2-(2-cyclopropyl-5,7-dimethyl-3H-imidazo[4,5-b]pyridin-3-yl)methyl-10,11-dihydro-5H-dibenzo[b,f]azepine (540 mg, 1.37 mmol) obtained in step 1.

ESI-MS m/z: 434 $(M+H)^+$; $^1$H-NMR ($CDCl_3$, δ): 0.95-1.01 (m, 2H), 1.13-1.18 (m, 2H), 1.81-1.89 (m, 1H), 2.57 (s, 6H), 3.04-3.10 (m, 4H), 4.52 (s, 2H), 5.47 (s, 2H), 6.85 (s, 1H), 6.96-7.04 (m, 3H), 7.11 (dd, J=7.5, 1.5 Hz, 1H), 7.16-7.24 (m, 3H).

[step 3] The title compound (compound 67, 137 mg, 82%) was obtained in the same manner as in step 3 of Example 1, using 5-cyanomethyl-2-(2-cyclopropyl-5,7-dimethyl-3H-imidazo[4,5-b]pyridin-3-yl)methyl-10,11-dihydro-5H-dibenzo[b,f]azepine (146 mg, 0.34 mmol) obtained in step 2.

ESI-MS m/z: 493 $(M+H)^+$; $^1$H-NMR ($CDCl_3$, δ): 0.92-0.98 (m, 2H), 1.09-1.14 (m, 2H), 1.77-1.86 (m, 1H), 2.52 (s, 6H), 2.97-3.07 (m, 4H), 4.71 (s, 2H), 5.44 (s, 2H), 6.84 (s, 1H), 6.87-7.01 (m, 5H), 7.07-7.16 (m, 2H).

Example 68

2-(2-ethoxy-7-methyl-3H-imidazo[4,5-b]pyridin-3-yl)methyl-5-(5-oxo-4,5-dihydro-1,2,4-oxadiazol-3-yl)methyl-10,11-dihydro-5H-dibenzo[b,f]azepine (Compound 68)

[step 1] 2-(2-Ethoxy-7-methyl-3H-imidazo[4,5-b]pyridin-3-yl)methyl-10,11-dihydro-5H-dibenzo[b,f]azepine (300 mg, 6.9%) was obtained in the same manner as in step 1 of Example 1, using 2-ethoxy-7-methyl-3H-imidazo[4,5-b]pyridine (4.90 g, 11.3 mmol), obtained in Reference Example 20, instead of 2-ethyl-5,7-dimethyl-3H-imidazo[4,5-b]pyridine.

ESI-MS m/z: 385 $(M+H)^+$; $^1$H-NMR (DMSO-$d_6$, δ): 1.41 (t, J=7.0 Hz, 3H), 2.45 (s, 3H), 2.90 (m, 4H), 4.58 (q, J=7.0 Hz, 2H), 5.05 (s, 2H), 6.64 (td, J=7.2, 1.3 Hz, 1H), 6.86-7.04 (m, 7H), 7.99 (d, J=5.0 Hz, 1H), 8.29 (s, 1H).

[step 2] 5-Cyanomethyl-2-(2-ethoxy-7-methyl-3H-imidazo[4,5-b]pyridin-3-yl)methyl-10,11-dihydro-5H-dibenzo[b,f]azepine (261 mg, 80%) was obtained in the same manner as in step 2 of Example 1, using 2-(2-ethoxy-7-methyl-3H-imidazo[4,5-b]pyridin-3-yl)methyl-10,11-dihydro-5H-dibenzo[b,f]azepine (297 mg, 0.772 mmol) obtained in step 1.

ESI-MS m/z: 424 $(M+H)^+$; $^1$H-NMR ($CDCl_3$, δ): 1.46 (t, J=7.1 Hz, 3H), 2.54 (s, 3H), 3.05-3.11 (m, 4H), 4.50 (s, 2H), 4.62 (q, J=7.1 Hz, 2H), 5.16 (s, 2H), 6.89-7.23 (m, 8H), 8.03 (d, J=5.1 Hz, 1H).

[step 3] The title compound (compound 68, 135 mg, 89%) was obtained in the same manner as in step 3 of Example 1, using 5-cyanomethyl-2-(2-ethoxy-7-methyl-3H-imidazo[4,5-b]pyridin-3-yl)methyl-10,11-dihydro-5H-dibenzo[b,f]azepine (133 mg, 0.314 mmol) obtained in step 2.

ESI-MS m/z: 483 $(M+H)^+$; $^1$H-NMR ($CDCl_3$, δ): 1.43 (t, J=7.1 Hz, 3H), 2.51 (s, 3H), 3.02 (br s, 4H), 4.59 (q, J=7.1 Hz, 2H), 4.71 (s, 2H), 5.11 (s, 2H), 6.85-7.13 (m, 8H), 7.95 (d, J=5.1 Hz, 1H).

Example 69

2-(7-methyl-2-propyl-3H-imidazo[4,5-b]pyridin-3-yl)methyl-5-[1-(5-oxo-4,5-dihydro-1,2,4-oxadiazol-3-yl)ethyl]-10,11-dihydro-5H-dibenzo[b,f]azepine (Compound 69)

The title compound (compound 69, 109 mg, 47%) was obtained in the same manner as in step 3 of Example 1, using 5-(1-cyanoethyl)-2-(7-methyl-2-propyl-3H-imidazo[4,5-b]pyridin-3-yl)methyl-10,11-dihydro-5H-dibenzo[b,f]azepine (204 mg, 0.47 mmol) obtained in step 2 of Example 27.

ESIMS m/z: 495 $(M+H)^+$; $^1$H-NMR ($CDCl_3$, δ): 0.97 (t, J=7.3 Hz, 3H), 1.49 (d, J=6.5 Hz, 3H), 1.70-1.84 (m, 2H), 2.69 (s, 3H), 2.79 (t, J=7.8 Hz, 2H), 2.94-3.18 (m, 4H), 5.23 (q, J=6.5 Hz, 1H), 5.39 (s, 2H), 6.86-6.89 (m, 2H), 6.99-7.15 (m, 6H), 8.19 (d, J=5.0 Hz, 1H).

Example 70

2-(2-cyclopropyl-5,7-dimethyl-3H-imidazo[4,5-b]pyridin-3-yl)methyl-5-[1-(5-oxo-4,5-dihydro-1,2,4-oxadiazol-3-yl)ethyl]-10,11-dihydro-5H-dibenzo[b,f]azepine (Compound 70)

[step 1] 5-(1-Cyanoethyl)-2-(2-cyclopropyl-5,7-dimethyl-3H-imidazo[4,5-b]pyridin-3-yl)methyl-10,11-dihydro-5H-dibenzo[b,f]azepine (1.95 g, quantitative) was obtained in the same manner as in step 2 of Example 1, using 2-(2-cyclopropyl-5,7-dimethyl-3H-imidazo[4,5-b]pyridin-3-yl)methyl-10,11-dihydro-5H-dibenzo[b,f]azepine (1.66 g, 4.20 mmol) obtained in step 1 of Example 67 and acetaldehyde (707 μL, 12.6 mmol) instead of paraformaldehyde.

ESI-MS m/z: 448 $(M+H)^+$; $^1$H-NMR ($CDCl_3$, δ): 0.94-1.02 (m, 2H), 1.12-1.18 (m, 2H), 1.47 (d, J=7.1 Hz, 3H), 1.80-1.89 (m, 1H), 2.57 (s, 6H), 2.98-3.02 (br m, 4H), 4.65 (q, J=7.1 Hz, 1H), 5.47 (s, 2H), 6.85-7.22 (m, 6H), 7.51-7.54 (m, 2H).

[step 2] The title compound (compound 70, 242 mg, 47%) was obtained in the same manner as in step 3 of Example 1, using 5-(1-cyanoethyl)-2-(2-cyclopropyl-5,7-dimethyl-3H-imidazo[4,5-b]pyridin-3-yl)methyl-10,11-dihydro-5H-dibenzo[b,f]azepine (453 mg, 1.01 mmol) obtained in step 1.

ESI-MS m/z: 507 $(M+H)^+$; $^1$H-NMR ($CDCl_3$, δ): 0.90-0.96 (m, 2H), 1.08-1.13 (m, 2H), 1.48 (d, J=6.6 Hz, 3H), 1.75-1.85 (m, 1H), 2.52 (s, 3H), 2.55 (s, 3H), 2.90-3.13 (m, 4H), 5.21 (q, J=6.6 Hz, 1H), 5.42 (s, 2H), 6.83 (s, 1H), 6.91-7.10 (m, 7H).

Example 71

2-(2-cyclopropyl-5,7-dimethyl-3H-imidazo[4,5-b]pyridin-3-yl)methyl-5-[1-(1H-tetrazol-5-yl)ethyl]-10,11-dihydro-5H-dibenzo[b,f]azepine (Compound 71)

The title compound (compound 71, 736 mg, 45%) was obtained in the same manner as in Example 22, using 5-(1-cyanoethyl)-2-(2-cyclopropyl-5,7-dimethyl-3H-imidazo[4,5-b]pyridin-3-yl)methyl-10,11-dihydro-5H-dibenzo[b,f]azepine (1.50 g, 3.23 mmol) obtained in step 1 of Example 70.

ESI-MS m/z: 491 $(M+H)^+$; $^1$H-NMR ($CDCl_3$, δ): 0.82-0.87 (m, 2H), 1.00-1.04 (m, 2H), 1.52 (d, J=6.6 Hz, 3H), 1.70-1.79 (m, 1H), 2.28 (s, 3H), 2.47-2.87 (m, 4H), 2.55 (s, 3H), 5.42 (s, 2H), 5.71 (q, J=6.6 Hz, 1H), 6.77 (s, 1H), 6.84 (s, 1H), 6.86-6.89 (m, 3H), 6.93-7.10 (m, 3H).

Example 72

(−)-2-(2-ethyl-5,7-dimethyl-3H-imidazo[4,5-b]pyridin-3-yl)methyl-5-[1-(1H-tetrazol-5-yl)ethyl]-10,11-dihydro-5H-dibenzo[b,f]azepine (Compound 72)

The title compound (compound 72, $[a]_D$, $CHCl_3$: −37°) was obtained by separating compound 22 with CHIRALPAK AD (ethanol/hexane/trifluoroacetic acid=20/80/0.1) manufactured by Daicel Chemical Industries, Ltd.

Example 73

(+)-2-(2-ethyl-5,7-dimethyl-3H-imidazo[4,5-b]pyridin-3-yl)methyl-5-[1-(1H-tetrazol-5-yl)ethyl]-10,11-dihydro-5H-dibenzo[b,f]azepine (Compound 73)

The title compound (compound 73, $[a]_D$, $CHCl_3$: +42°) was obtained by separating compound 22 in the same manner as in Example 72.

Example 74

(−)-2-(7-chloro-2-ethyl-5-methyl-3H-imidazo[4,5-b]pyridin-3-yl)methyl-5-[1-(1H-tetrazol-5-yl)ethyl]-10,11-dihydro-5H-dibenzo[b,f]azepine (Compound 74)

The title compound (compound 74, $[a]_D$, $CHCl_3$: −34°) was obtained by separating compound 25 in the same manner as in Example 72.

Example 75

(+)-2-(7-chloro-2-ethyl-5-methyl-3H-imidazo[4,5-b]pyridin-3-yl)methyl-5-[1-(1H-tetrazol-5-yl)ethyl]-10,11-dihydro-5H-dibenzo[b,f]azepine (Compound 75)

The title compound (compound 75, $[a]_D$, $CHCl_3$: +35°) was obtained by separating compound 25 in the same manner as in Example 72.

Example 76

(−)-2-(2-ethyl-7-methyl-3H-imidazo[4,5-b]pyridin-3-yl)methyl-5-[1-(1H-tetrazol-5-yl)ethyl]-10,11-dihydro-5H-dibenzo[b,f]azepine (Compound 76)

The title compound (compound 76, $[a]_D$, $CHCl_3$: −30°) was obtained by separating compound 26 in the same manner as in Example 72.

Example 77

(+)-2-(2-ethyl-7-methyl-3H-imidazo[4,5-b]pyridin-3-yl)methyl-5-[1-(1H-tetrazol-5-yl)ethyl]-10,11-dihydro-5H-dibenzo[b,f]azepine (Compound 77)

The title compound (compound 77, $[a]_D$, $CHCl_3$: +30°) was obtained by separating compound 26 in the same manner as in Example 72.

Example 78

(−)-2-(7-methyl-2-propyl-3H-imidazo[4,5-b]pyridin-3-yl)methyl-5-[1-(1H-tetrazol-5-yl)ethyl]-10,11-dihydro-5H-dibenzo[b,f]azepine (Compound 78)

The title compound (compound 78, $[a]_D$, $CHCl_3$: −25°) was obtained by separating compound 27 in the same manner as in Example 72.

Example 79

(+)-2-(7-methyl-2-propyl-3H-imidazo[4,5-b]pyridin-3-yl)methyl-5-[1-(1H-tetrazol-5-yl)ethyl]-10,11-dihydro-5H-dibenzo[b,f]azepine (Compound 79)

The title compound (compound 79, $[a]_D$, $CHCl_3$: +26°) was obtained by separating compound 27 in the same manner as in Example 72.

Example 80

(−)-2-(2-cyclopropyl-5,7-dimethyl-3H-imidazo[4,5-b]pyridin-3-yl)methyl-5-[1-(1H-tetrazol-5-yl)ethyl]-10,11-dihydro-5H-dibenzo[b,f]azepine (Compound 80)

The title compound (compound 80, $[a]_D$, $CHCl_3$: −46°) was obtained by separating compound 71 in the same manner as in Example 72.

Example 81

(+)-2-(2-cyclopropyl-5,7-dimethyl-3H-imidazo[4,5-b]pyridin-3-yl)methyl-5-[1-(1H-tetrazol-5-yl)ethyl]-10,11-dihydro-5H-dibenzo[b,f]azepine (Compound 81)

The title compound (compound 81, $[a]_D$, $CHCl_3$: +40°) was obtained by separating compound 71 in the same manner as in Example 72.

Example 82

(E)-2-(2-ethyl-4,6-dimethylbenzimidazol-1-yl)methyl-5-[1-(5-oxo-4,5-dihydro-1,2,4-oxadiazol-3-yl)ethylidene]-10,11-dihydro-5H-dibenzo[a,d]cycloheptene (Compound 82)

[step 1] (E)-2-[2-(2-Ethyl-4,6-dimethylbenzimidazol-1-yl)methyl-10,11-dihydro-5H-dibenzo[a,d]cyclohepten-5-ylidene]propiononitrile (208 mg, 68%) was obtained in the same manner as in step 1 of Example 43, using 2-ethyl-4,6-dimethylbenzimidazole (123 mg, 0.71 mmol) instead of 5-ethoxycarbonyl-4-(1-hydroxy-1-methyl)ethyl-2-propylimidazole.

ESI-MS m/z: 432 $(M+H)^+$; $^1H$-NMR ($CDCl_3$, δ): 1.33 (t, J=7.6 Hz, 3H), 2.00 (s, 3H), 2.38 (s, 3H), 2.65 (s, 3H), 2.71-2.88 (m, 2H), 2.84 (q, J=7.6 Hz, 2H), 3.19-3.35 (m, 2H), 5.24 (s, 2H), 6.79 (s, 1H), 6.81-6.88 (m, 3H), 7.01 (d, J=7.9 Hz, 1H), 7.14 (dd, J=7.0, 2.0 Hz, 1H), 7.21-7.27 (m, 2H), 7.40 (dd, J=7.1, 1.8 Hz, 1H).

[step 2] The title compound (compound 82, 94 mg, 40%) was obtained in the same manner as in step 3 of Example 1, using (E)-2-[2-(2-ethyl-4,6-dimethylbenzimidazol-1-yl)methyl-10,11-dihydro-5H-dibenzo[a,d]cyclohepten-5-ylidene]propiononitrile (206 mg, 0.48 mmol) obtained in step 1.

ESI-MS m/z: 491 $(M+H)^+$; $^1H$-NMR (DMSO-$d_6$, δ): 1.23 (t, J=7.5 Hz, 3H), 1.92 (s, 3H), 2.30 (s, 3H), 2.46 (s, 3H), 2.75 (m, 2H), 2.76 (q, J=7.5 Hz, 2H), 3.30 (m, 2H), 5.37 (s, 2H), 6.70-7.19 (m, 9H).

Example 83

(E)-2-(4-methyl-2-propylbenzimidazol-1-yl)methyl-5-[1-(5-oxo-4,5-dihydro-1,2,4-oxadiazol-3-yl)ethylidene]-10,11-dihydro-5H-dibenzo[a,d]cycloheptene (Compound 83)

[step 1] (E)-2-[2-(4-Methyl-2-propylbenzimidazol-1-yl)methyl-10,11-dihydro-5H-dibenzo[a,d]cyclohepten-5-ylidene]propiononitrile (179 mg, 58%) was obtained in the same manner as in step 1 of Example 43, using 4-methyl-2-propylbenzimidazole (123 mg, 0.71 mmol) instead of 5-ethoxycarbonyl-4-(1-hydroxy-1-methyl)ethyl-2-propylimidazole.

ESI-MS m/z: 432 $(M+H)^+$; $^1$H-NMR ($CDCl_3$, δ): 0.99 (t, J=7.4 Hz, 3H), 1.73-1.86 (m, 2H), 1.99 (s, 3H), 2.69 (s, 3H), 2.71-2.88 (m, 4H), 3.18-3.35 (m, 2H), 5.28 (s, 2H), 6.84 (d, J=7.8 Hz, 1H), 6.88 (s, 1H), 6.97-7.29 (m, 7H), 7.40 (dd, J=7.3, 1.8 Hz, 1H).

[step 2] The title compound (compound 83, 65 mg, 41%) was obtained in the same manner as in step 3 of Example 1, using (E)-2-[2-(4-methyl-2-propylbenzimidazol-1-yl)methyl-10,11-dihydro-5H-dibenzo[a,d]cyclohepten-5-ylidene]propiononitrile (139 mg, 0.32 mmol) obtained in step 1.

ESI-MS m/z: 491 $(M+H)^+$; $^1$H-NMR (DMSO-$d_6$, δ): 0.90 (t, J=7.4 Hz, 3H), 1.70 (m, 2H), 1.92 (s, 3H), 2.50 (s, 3H), 2.70 (m, 2H), 2.78 (t, J=7.6 Hz, 2H), 3.28 (m, 2H), 5.42 (s, 2H), 6.76-7.25 (m, 10H).

Example 84

(E)-2-(2-propylbenzimidazol-1-yl)methyl-5-[1-(5-oxo-4,5-dihydro-1,2,4-oxadiazol-3-yl)ethylidene]-10,11-dihydro-5H-dibenzo[a,d]cycloheptene (Compound 84)

[step 1] (E)-2-[2-(2-Propylbenzimidazol-1-yl)methyl-10,11-dihydro-5H-dibenzo[a,d]cyclohepten-5-ylidene]propiononitrile (260 mg, 88%) was obtained in the same manner as in step 1 of Example 43, using 2-propylbenzimidazole (114 mg, 0.71 mmol) instead of 5-ethoxycarbonyl-4-(1-hydroxy-1-methyl)ethyl-2-propylimidazole.

ESI-MS m/z: 418 $(M+H)^+$; $^1$H-NMR ($CDCl_3$, δ): 1.00 (t, J=7.2 Hz, 3H), 1.80-1.94 (m, 2H), 2.00 (s, 3H), 2.67-2.89 (m, 4H), 3.19-3.36 (m, 2H), 5.30 (s, 2H), 6.82-6.88 (m, 2H), 7.02 (d, J=7.6 Hz, 1H), 7.12-7.29 (m, 6H), 7.40 (dd, J=7.1, 1.8 Hz, 1H), 7.77 (d, J=7.6 Hz, 1H).

[step 2] The title compound (compound 84, 93 mg, 32%) was obtained in the same manner as in step 3 of Example 1, using (E)-2-[2-(2-propylbenzimidazol-1-yl)methyl-10,11-dihydro-5H-dibenzo[a,d]cyclohepten-5-ylidene]propiononitrile (257 mg, 0.62 mmol) obtained in step 1.

ESI-MS m/z: 477 $(M+H)^+$; $^1$H-NMR (DMSO-$d_6$, δ): 0.90 (t, J=7.4 Hz, 3H), 1.72 (m, 2H), 1.92 (s, 3H), 2.74 (m, 2H), 2.78 (t, J=7.4 Hz, 2H), 3.30 (m, 2H), 5.44 (s, 2H), 6.75-7.65 (m, 11H).

Example 85

(E)-2-(7-methyl-2-propyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 85)

[step 1] (E)-2-[2-(7-Methyl-2-propyl-3H-imidazo[4,5-b]pyridin-3-yl)methyl-10,11-dihydro-5H-dibenzo[a,d]cyclohepten-5-ylidene]propiononitrile (198 mg, 36%) was obtained in the same manner as in step 1 of Example 40, using 7-methyl-2-propyl-3H-imidazo[4,5-b]pyridine (223 mg, 1.27 mmol) instead of 2-ethyl-5,7-dimethyl-3H-imidazo[4,5-b]pyridine.

ESI-MS m/z: 433 $(M+H)^+$; $^1$H-NMR ($CDCl_3$, δ): 0.97 (t, J=7.3 Hz, 3H), 1.73-1.78 (m, 2H), 1.98 (s, 3H), 2.68 (s, 3H), 2.71-2.88 (m, 4H), 3.18-3.34 (m, 2H), 5.44 (s, 2H), 6.91-7.04 (m, 4H), 7.12 (dd, J=7.1, 1.5 Hz, 1H), 7.18-7.25 (m, 2H), 7.39 (dd, J=7.2, 1.7 Hz, 1H), 8.19 (d, J=4.9 Hz, 1H).

[step 2] The title compound (compound 85, 147 mg, 66%) was obtained in the same manner as in step 3 of Example 1, using (E)-2-[2-(7-methyl-2-propyl-3H-imidazo[4,5-b]pyridin-3-yl)methyl-10,11-dihydro-5H-dibenzo[a,d]cyclohepten-5-ylidene]propiononitrile (196 mg, 0.45 mmol) obtained in step 1.

ESI-MS m/z: 492 $(M+H)^+$; $^1$H-NMR ($CDCl_3$, δ): 0.96 (t, J=7.5 Hz, 3H), 1.73-1.79 (m, 2H), 2.08 (s, 3H), 2.67 (s, 3H), 2.73-2.86 (m, 2H), 2.77 (t, J=7.5 Hz, 2H), 3.20-3.37 (m, 2H), 5.43 (s, 2H), 6.92-6.95 (m, 2H), 7.01-7.10 (m, 3H), 7.15-7.35 (m, 3H), 8.18 (d, J=5.0 Hz, 1H).

Example 86

(E)-2-(2-ethoxy-5,7-dimethyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 86)

[step 1] (E)-2-[2-(2-Ethoxy-5,7-dimethyl-3H-imidazo[4,5-b]pyridin-3-yl)methyl-10,11-dihydro-5H-dibenzo[a,d]cyclohepten-5-ylidene]propiononitrile (268 mg, 47%) was obtained in the same manner as in step 1 of Example 40, using 2-ethoxy-5,7-dimethyl-3H-imidazo[4,5-b]pyridine (243 mg, 1.27 mmol) instead of 2-ethyl-5,7-dimethyl-3H-imidazo[4,5-b]pyridine.

ESI-MS m/z: 449 $(M+H)^+$; $^1$H-NMR ($CDCl_3$, δ): 1.41 (t, J=7.1 Hz, 3H), 2.00 (s, 3H), 2.49 (s, 3H), 2.53 (s, 3H), 2.79-2.89 (m, 2H), 3.21-3.34 (m, 2H), 4.57 (q, J=7.1 Hz, 2H), 5.17 (s, 2H), 6.78 (s, 1H), 6.99 (d, J=7.9 Hz, 1H), 7.11-7.39 (m, 6H).

[step 2] The title compound (compound 86, 53 mg, 18%) was obtained in the same manner as in step 3 of Example 1, using (E)-2-[2-(2-ethoxy-5,7-dimethyl-3H-imidazo[4,5-b]pyridin-3-yl)methyl-10,11-dihydro-5H-dibenzo[a,d]cyclohepten-5-ylidene]propiononitrile (262 mg, 0.58 mmol) obtained in step 1.

ESI-MS m/z: 508 $(M+H)^+$; $^1$H-NMR ($CDCl_3$, δ): 1.41 (t, J=7.1 Hz, 3H), 2.10 (s, 3H), 2.49 (s, 3H), 2.53 (s, 3H), 2.76-2.88 (m, 2H), 3.23-3.38 (m, 2H), 4.57 (q, J=7.1 Hz, 2H), 5.17 (s, 2H), 6.78 (s, 1H), 7.05-7.33 (m, 7H).

Example 87

(E)-2-(2-cyclopropyl-5,7-dimethyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 87)

[step 1] (E)-2-[2-(2-Cyclopropyl-5,7-dimethyl-3H-imidazo[4,5-b]pyridin-3-yl)methyl-10,11-dihydro-5H-dibenzo[a,d]cyclohepten-5-ylidene]propiononitrile (401 mg, 48%) was obtained in the same manner as in step 1 of Example 40, using 2-cyclopropyl-5,7-dimethyl-3H-imidazo[4,5-b]pyridine (354 mg, 1.89 mmol) instead of 2-ethyl-5,7-dimethyl-3H-imidazo[4,5-b]pyridine.

ESI-MS m/z: 445 $(M+H)^+$; $^1$H-NMR ($CDCl_3$, δ): 0.93-0.99 (m, 2H), 1.12-1.17 (m, 2H), 1.77-1.86 (m, 1H), 1.99 (s,

3H), 2.56 (s, 3H), 2.58 (d, J=0.5 Hz, 3H), 2.72-2.86 (m, 2H), 3.19-3.35 (m, 2H), 5.51 (d, J=1.8 Hz, 2H), 6.86 (s, 1H), 7.00-7.02 (m, 3H), 7.13 (dd, J=7.0, 1.5 Hz, 1H), 7.19-7.28 (m, 2H), 7.39 (dd, J=7.2, 1.7 Hz, 1H).

[step 2] The title compound (compound 87, 152 mg, 70%) was obtained in the same manner as in step 3 of Example 1, using (E)-2-[2-(2-cyclopropyl-5,7-dimethyl-3H-imidazo[4,5-b]pyridin-3-yl)methyl-10,11-dihydro-5H-dibenzo[a,d]cyclohepten-5-ylidene]propiononitrile (190 mg, 0.43 mmol) obtained in step 1.

ESI-MS m/z: 504 $(M+H)^+$; $^1$H-NMR ($CDCl_3$, δ): 0.93-1.00 (m, 2H), 1.12-1.17 (m, 2H), 1.77-1.87 (m, 1H), 2.10 (s, 3H), 2.56 (s, 3H), 2.57 (s, 3H), 2.73-2.88 (m, 2H), 3.22-3.39 (m, 2H), 5.50 (s, 2H), 6.86 (s, 1H), 6.98-7.11 (m, 4H), 7.19-7.36 (m, 3H).

Example 88

(E)-2-(2-cyclopropyl-7-methyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 88)

[step 1] (E)-2-[2-(2-Cyclopropyl-7-methyl-3H-imidazo[4,5-b]pyridin-3-yl)methyl-10,11-dihydro-5H-dibenzo[a,d]cyclohepten-5-ylidene]propiononitrile (148 mg, 36%) was obtained in the same manner as in step 1 of Example 40, using 2-cyclopropyl-7-methyl-3H-imidazo[4,5-b]pyridine (EP420237; 164 mg, 0.94 mmol) instead of 2-ethyl-5,7-dimethyl-3H-imidazo[4,5-b]pyridine.

ESI-MS m/z: 431 $(M+H)^+$; $^1$H-NMR ($CDCl_3$, δ): 0.98-1.05 (m, 2H), 1.18-1.23 (m, 2H), 1.84-1.92 (m, 1H), 1.99 (s, 3H), 2.63 (s, 3H), 2.72-2.88 (m, 2H), 3.19-3.34 (m, 2H), 5.54 (s, 2H), 6.98-7.03 (m, 4H), 7.12 (dd, J=7.0, 1.5 Hz, 1H), 7.17-7.28 (m, 2H), 7.39 (dd, J=7.2, 1.9 Hz, 1H), 8.16 (d, J=4.9 Hz, 1H).

[step 2] The title compound (compound 88, 120 mg, 71%) was obtained in the same manner as in step 3 of Example 1, using (E)-2-[2-(2-cyclopropyl-7-methyl-3H-imidazo[4,5-b]pyridin-3-yl)methyl-10,11-dihydro-5H-dibenzo[a,d]cyclohepten-5-ylidene]propiononitrile (148 mg, 0.34 mmol) obtained in step 1.

ESI-MS m/z: 490 $(M+H)^+$; $^1$H-NMR ($CDCl_3$, δ): 0.98-1.05 (m, 2H), 1.18-1.23 (m, 2H), 1.84-1.94 (m, 1H), 2.09 (s, 3H), 2.62 (d, J=0.5 Hz, 3H), 2.72-2.87 (m, 2H), 3.21-3.37 (m, 2H), 5.53 (s, 2H), 6.97-7.10 (m, 5H), 7.18-7.35 (m, 3H), 8.15 (d, J=4.8 Hz, 1H).

Example 89

(E)-2-(2-ethoxy-7-methyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 89)

[step 1] (E)-2-[2-(2-Ethoxy-7-methyl-3H-imidazo[4,5-b]pyridin-3-yl)methyl-10,11-dihydro-5H-dibenzo[a,d]cyclohepten-5-ylidene]propiononitrile (109 mg, 11%) was obtained in the same manner as in step 1 of Example 40, using 2-ethoxy-7-methyl-3H-imidazo[4,5-b]pyridine (420 mg, 2.37 mmol) instead of 2-ethyl-5,7-dimethyl-3H-imidazo[4,5-b]pyridine.

ESI-MS m/z: 435 $(M+H)^+$; $^1$H-NMR ($CDCl_3$, δ): 1.44 (t, J=7.2 Hz, 3H), 1.99 (s, 3H), 2.55 (s, 3H), 2.75-2.88 (m, 2H), 3.20-3.35 (m, 2H), 4.62 (q, J=7.2 Hz, 2H), 5.20 (s, 2H), 6.92 (d, J=5.6 Hz, 1H), 6.99 (d, J=7.9 Hz, 1H), 7.11-7.24 (m, 5H), 7.37 (dd, J=7.3, 1.7 Hz, 1H), 8.03 (d, J=5.0 Hz, 1H).

[step 2] The title compound (compound 89, 85 mg, 72%) was obtained in the same manner as in step 3 of Example 1, using (E)-2-[2-(2-ethoxy-7-methyl-3H-imidazo[4,5-b]pyridin-3-yl)methyl-10,11-dihydro-5H-dibenzo[a,d]cyclohepten-5-ylidene]propiononitrile (104 mg, 0.24 mmol) obtained in step 1.

ESI-MS m/z: 494 $(M+H)^+$; $^1$H-NMR ($CDCl_3$, δ): 1.45 (t, J=7.1 Hz, 3H), 2.09 (s, 3H), 2.55 (s, 3H), 2.75-2.88 (m, 2H), 3.22-3.39 (m, 2H), 4.62 (q, J=7.1 Hz, 2H), 5.20 (s, 2H), 6.88-6.93 (m, 2H), 7.06-7.33 (m, 6H), 8.02 (d, J=5.1 Hz, 1H).

Example 90

(E)-2-(2-ethyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 90)

[step 1] (E)-2-[2-(2-Ethyl-3H-imidazo[4,5-b]pyridin-3-yl)methyl-10,11-dihydro-5H-dibenzo[a,d]cyclohepten-5-ylidene]propiononitrile (655 mg, 51%) was obtained in the same manner as in step 1 of Example 40, using 2-ethyl-3H-imidazo[4,5-b]pyridine (U.S. Pat. No. 5,332,744; 470 mg, 3.20 mmol) instead of 2-ethyl-5,7-dimethyl-3H-imidazo[4,5-b]pyridine.

ESI-MS m/z: 405 $(M+H)^+$; $^1$H-NMR ($CDCl_3$, δ): 1.40 (t, J=7.3 Hz, 3H), 1.99 (s, 3H), 2.72-2.88 (m, 4H), 3.19-3.33 (m, 2H), 5.45 (s, 2H), 6.92-7.02 (m, 3H), 7.13 (dd, J=7.3, 1.5 Hz, 1H), 7.20-7.27 (m, 3H), 7.39 (dd, J=7.3, 1.8 Hz, 1H), 8.03 (dd, J=8.1, 1.5 Hz, 1H), 8.34 (dd, J=5.1, 1.5 Hz, 1H).

[step 2] The title compound (compound 90, 433 mg, 85%) was obtained in the same manner as in step 3 of Example 1, using (E)-2-[2-(2-ethyl-3H-imidazo[4,5-b]pyridin-3-yl)methyl-10,11-dihydro-5H-dibenzo[a,d]cyclohepten-5-ylidene]propiononitrile (446 mg, 1.10 mmol) obtained in step 1.

ESI-MS m/z: 464 $(M+H)^+$; $^1$H-NMR ($CDCl_3$, δ): 1.40 (t, J=7.4 Hz, 3H), 2.09 (s, 3H), 2.72-2.87 (m, 2H), 2.82 (q, J=7.4 Hz, 2H), 3.21-3.38 (m, 2H), 5.44 (s, 2H), 6.94-6.98 (m, 2H), 7.09 (d, J=8.6 Hz, 2H), 7.17-7.34 (m, 4H), 8.02 (dd, J=7.9, 1.3 Hz, 1H), 8.33 (dd, J=4.8, 1.3 Hz, 1H).

Example 91

(E)-2-(2-ethoxy-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 91)

[step 1] (E)-2-[2-(2-Ethoxy-3H-imidazo[4,5-b]pyridin-3-yl)methyl-10,11-dihydro-5H-dibenzo[a,d]cyclohepten-5-ylidene]propiononitrile (471 mg, 28%) was obtained in the same manner as in step 1 of Example 40, using 2-ethoxy-3H-imidazo[4,5-b]pyridine (652 mg, 4.00 mmol) obtained in Reference Example 21 instead of 2-ethyl-5,7-dimethyl-3H-imidazo[4,5-b]pyridine.

ESI-MS m/z: 421 $(M+H)^+$; $^1$H-NMR ($CDCl_3$, δ): 1.47 (t, J=7.1 Hz, 3H), 2.00 (s, 3H), 2.76-2.89 (m, 2H), 3.22-3.35 (m, 2H), 4.62 (q, J=7.1 Hz, 2H), 5.22 (s, 2H), 7.01 (d, J=7.7 Hz, 1H), 7.09-7.26 (m, 6H), 7.38 (dd, J=7.3, 1.8 Hz, 1H), 7.75 (dd, J=7.9, 1.5 Hz, 1H), 8.17 (dd, J=5.1, 1.5 Hz, 1H).

[step 2] The title compound (compound 91, 330 mg, 78%) was obtained in the same manner as in step 3 of Example 1, using (E)-2-[2-(2-ethoxy-3H-imidazo[4,5-b]pyridin-3-yl)methyl-10,11-dihydro-5H-dibenzo[a,d]cyclohepten-5-ylidene]propiononitrile (370 mg, 0.88 mmol) obtained in step 1.

ESI-MS m/z: 480 $(M+H)^+$; $^1$H-NMR ($CDCl_3$, δ): 1.47 (t, J=7.1 Hz, 3H), 2.10 (s, 3H), 2.77-2.89 (m, 2H), 3.25-3.39 (m, 2H), 4.62 (q, J=7.1 Hz, 2H), 5.22 (s, 2H), 7.07-7.34 (m, 8H), 7.74 (dd, J=7.9, 1.3 Hz, 1H), 8.16 (dd, J=5.0, 1.3 Hz, 1H).

Example 92

(E)-2-(2-cyclopropyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 92)

[step 1] (E)-2-[2-(2-Cyclopropyl-3H-imidazo[4,5-b]pyridin-3-yl)methyl-10,11-dihydro-5H-dibenzo[a,d]cyclohepten-5-ylidene]propiononitrile (517 mg, 39%) was obtained in the same manner as in step 1 of Example 40, using 2-cyclopropyl-3H-imidazo[4,5-b]pyridine (EP420237; 509 mg, 3.20 mmol) instead of 2-ethyl-5,7-dimethyl-3H-imidazo[4,5-b]pyridine.

ESI-MS m/z: 417 $(M+H)^+$; $^1$H-NMR ($CDCl_3$, δ): 1.02-1.09 (m, 2H), 1.22-1.27 (m, 2H), 1.88-1.94 (m, 1H), 2.00 (s, 3H), 2.74-2.90 (m, 2H), 3.20-3.33 (m, 2H), 5.57 (s, 2H), 7.02-7.06 (m, 3H), 7.12-7.29 (m, 4H), 7.39 (dd, J=7.3, 1.7 Hz, 1H), 7.93 (dd, J=7.9, 1.5 Hz, 1H), 8.30 (dd, J=5.0, 1.5 Hz, 1H).

[step 2] The title compound (compound 92, 237 mg, 60%) was obtained in the same manner as in step 3 of Example 1, using (E)-2-[2-(2-cyclopropyl-3H-imidazo[4,5-b]pyridin-3-yl)methyl-10,11-dihydro-5H-dibenzo[a,d]cyclohepten-5-ylidene]propiononitrile (345 mg, 0.83 mmol) obtained in step 1.

ESI-MS m/z: 476 $(M+H)^+$; $^1$H-NMR ($CDCl_3$, δ): 1.03-1.10 (m, 2H), 1.21-1.29 (m, 2H), 1.88-1.98 (m, 1H), 2.10 (s, 3H), 2.75-2.88 (m, 2H), 3.23-3.39 (m, 2H), 5.56 (s, 2H), 7.02-7.12 (m, 4H), 7.16-7.35 (m, 4H), 7.92 (dd, J=8.1, 1.5 Hz, 1H), 8.29 (dd, J=4.8, 1.5 Hz, 1H).

Example 93

(E)-2-(7-chloro-2-ethyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 93)

[step 1] (E)-2-[2-(7-Chloro-2-ethyl-3H-imidazo[4,5-b]pyridin-3-yl)methyl-10,11-dihydro-5H-dibenzo[a,d]cyclohepten-5-ylidene]propiononitrile (280 mg, 45%) was obtained in the same manner as in step 1 of Example 40, using 7-chloro-2-ethyl-3H-imidazo[4,5-b]pyridine (257 mg, 1.42 mmol), obtained in Reference Example 22, instead of 2-ethyl-5,7-dimethyl-3H-imidazo[4,5-b]pyridine.

ESI-MS m/z: 439 $(M+H)^+$; $^1$H-NMR ($CDCl_3$, δ): 1.37 (t, J=7.5 Hz, 3H), 1.98 (s, 3H), 2.71-2.88 (m, 2H), 2.85 (q, J=7.5 Hz, 2H), 3.19-3.35 (m, 2H), 5.44 (s, 2H), 6.92-7.03 (m, 3H), 7.13 (dd, J=6.8, 2.1 Hz, 1H), 7.17-7.29 (m, 3H), 7.39 (dd, J=7.3, 1.7 Hz, 1H), 8.21 (d, J=5.3 Hz, 1H).

[step 2] The title compound (compound 93, 229 mg, 72%) was obtained in the same manner as in step 3 of Example 1, using (E)-2-[2-(7-chloro-2-ethyl-3H-imidazo[4,5-b]pyridin-3-yl)methyl-10,11-dihydro-5H-dibenzo[a,d]cyclohepten-5-ylidene]propiononitrile (280 mg, 0.64 mmol) obtained in step 1.

ESI-MS m/z: 498 $(M+H)^+$; $^1$H-NMR ($CDCl_3$, δ): 1.37 (t, J=7.5 Hz, 3H), 2.09 (s, 3H), 2.72-2.89 (m, 2H), 2.85 (q, J=7.5 Hz, 2H), 3.22-3.38 (m, 2H), 5.44 (s, 2H), 6.92 (s, 1H), 6.95 (dd, J=7.9, 1.6 Hz, 1H), 7.07-7.11 (m, 2H), 7.17-7.34 (m, 4H), 8.21 (d, J=5.3 Hz, 1H).

Example 94

(E)-2-(7-chloro-2-ethoxy-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 94)

[step 1] (E)-2-[2-(7-Chloro-2-ethoxy-3H-imidazo[4,5-b]pyridin-3-yl)methyl-10,11-dihydro-5H-dibenzo[a,d]cyclohepten-5-ylidene]propiononitrile (187 mg, 41%) was obtained in the same manner as in step 1 of Example 40, using 7-chloro-2-ethoxy-3H-imidazo[4,5-b]pyridine (200 mg, 1.01 mmol), obtained in Reference Example 23, instead of 2-ethyl-5,7-dimethyl-3H-imidazo[4,5-b]pyridine.

ESI-MS m/z: 455 $(M+H)^+$; $^1$H-NMR ($CDCl_3$, δ): 1.46 (t, J=7.0 Hz, 3H), 2.00 (s, 3H), 2.79-2.86 (m, 2H), 3.24-3.32 (m, 2H), 4.69 (q, J=7.0 Hz, 2H), 5.21 (s, 2H), 7.01 (d, J=7.6 Hz, 1H), 7.11-7.28 (m, 6H), 7.38 (dd, J=7.1, 1.8 Hz, 1H), 8.04 (d, J=5.6 Hz, 1H).

[step 2] The title compound (compound 94, 154 mg, 73%) was obtained in the same manner as in step 3 of Example 1, using (E)-2-[2-(7-chloro-2-ethoxy-3H-imidazo[4,5-b]pyridin-3-yl)methyl-10,11-dihydro-5H-dibenzo[a,d]cyclohepten-5-ylidene]propiononitrile (186 mg, 0.41 mmol) obtained in step 1.

ESI-MS m/z: 514 $(M+H)^+$; $^1$H-NMR ($CDCl_3$, δ): 1.47 (t, J=7.1 Hz, 3H), 2.08 (s, 3H), 2.77-2.90 (m, 2H), 3.26-3.43 (m, 2H), 4.68 (q, J=7.1 Hz, 2H), 5.21 (s, 2H), 7.06-7.30 (m, 8H), 8.05 (d, J=5.5 Hz, 1H).

Example 95

(E)-2-(7-chloro-2-cyclopropyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene (Compound 95)

[step 1] (E)-2-[2-(7-Chloro-2-cyclopropyl-3H-imidazo[4,5-b]pyridin-3-yl)methyl-10,11-dihydro-5H-dibenzo[a,d]cyclohepten-5-ylidene]propiononitrile (352 mg, 36%) was obtained in the same manner as in step 1 of Example 40, using 7-chloro-2-cyclopropyl-3H-imidazo[4,5-b]pyridine (422 mg, 2.18 mmol), obtained in Reference Example 24, instead of 2-ethyl-5,7-dimethyl-3H-imidazo[4,5-b]pyridine.

ESI-MS m/z: 451 $(M+H)^+$; $^1$H-NMR ($CDCl_3$, δ): 1.03-1.10 (m, 2H), 1.26-1.34 (m, 2H), 1.86-1.95 (m, 1H), 1.99 (s, 3H), 2.72-2.90 (m, 2H), 3.20-3.36 (m, 2H), 5.55 (s, 2H), 7.02-7.05 (m, 3H), 7.13 (dd, J=7.0, 1.7 Hz, 1H), 7.18-7.28 (m, 3H), 7.39 (dd, J=7.2, 1.8 Hz, 1H), 8.17 (d, J=5.3 Hz, 1H).

[step 2] The title compound (compound 95, 283 mg, 83%) was obtained in the same manner as in step 3 of Example 1, using (E)-2-[2-(7-chloro-2-cyclopropyl-3H-imidazo[4,5-b]pyridin-3-yl)methyl-10,11-dihydro-5H-dibenzo[a,d]cyclohepten-5-ylidene]propiononitrile (300 mg, 0.67 mmol) obtained in step 1.

ESI-MS m/z: 510 $(M+H)^+$; $^1$H-NMR ($CDCl_3$, δ): 1.03-1.10 (m, 2H), 1.28-1.34 (m, 2H), 1.87-1.97 (m, 1H), 2.10 (s, 3H), 2.74-2.89 (m, 2H), 3.22-3.40 (m, 2H), 5.54 (s, 2H), 6.87-7.13 (m, 4H), 7.18-7.35 (m, 4H), 8.17 (d, J=5.3 Hz, 1H).

Example 96

(E)-2-(4-chloro-2-ethoxybenzimidazol-1-yl)methyl-5-[1-(5-oxo-4,5-dihydro-1,2,4-oxadiazol-3-yl)ethylidene]-10,11-dihydro-5H-dibenzo[a,d]cycloheptene (Compound 96)

[step 1] (E)-2-[2-(4-Chloro-2-ethoxybenzimidazol-1-yl)methyl-10,11-dihydro-5H-dibenzo[a,d]cyclohepten-5- ylidene]propiononitrile (370 mg, 41%) was obtained in the same manner as in step 1 of Example 43, using 4-chloro-2-ethoxybenzimidazole (393 mg, 2.00 mmol), obtained in Reference Example 25, instead of 5-ethoxycarbonyl-4-(1-hydroxy-1-methyl)ethyl-2-propylimidazole.

ESI-MS m/z: 454 $(M+H)^+$; $^1H$-NMR ($CDCl_3$, δ): 1.46 (t, J=7.1 Hz, 3H), 2.00 (s, 3H), 2.74-2.89 (m, 2H), 3.20-3.33 (m, 2H), 4.71 (q, J=7.1 Hz, 2H), 5.11 (s, 2H), 6.92-7.02 (m, 5H), 7.11-7.26 (m, 4H), 7.39 (dd, J=7.1, 1.8 Hz, 1H).

[step 2] The title compound (compound 96, 228 mg, 54%) was obtained in the same manner as in step 3 of Example 1, using (E)-2-[2-(4-chloro-2-ethoxybenzimidazol-1-yl)methyl-10,11-dihydro-5H-dibenzo[a,d]cyclohepten-5-ylidene] propiononitrile (368 mg, 0.82 mmol) obtained in step 1.

ESI-MS m/z: 513 $(M+H)^+$; $^1H$-NMR (DMSO-$d_6$, δ): 1.38 (t, J=7.1 Hz, 3H), 1.92 (s, 3H), 2.74 (m, 2H), 3.30 (m, 2H), 4.59 (q, J=7.1 Hz, 2H), 5.20 (s, 2H), 6.89-7.39 (m, 10H).

Example 97

(E)-2-(4-chloro-2-cyclopropylbenzimidazol-1-yl) methyl-5-[1-(5-oxo-4,5-dihydro-1,2,4-oxadiazol-3-yl)ethylidene]-10,11-dihydro-5H-dibenzo[a,d]cycloheptene (Compound 97)

[step 1] (E)-2-[2-(4-Chloro-2-cyclopropylbenzimidazol-1-yl)methyl-10,11-dihydro-5H-dibenzo[a,d]cyclohepten-5-ylidene]propiononitrile (687 mg, 76%) was obtained in the same manner as in step 1 of Example 43, using 4-chloro-2-cyclopropylbenzimidazole (385 mg, 2.00 mmol) obtained in Reference Example 26 instead of 5-ethoxycarbonyl-4-(1-hydroxy-1-methyl)ethyl-2-propylimidazole.

ESI-MS m/z: 450 $(M+H)^+$; $^1H$-NMR ($CDCl_3$, δ): 0.96-1.36 (m, 4H), 1.82-1.94 (m, 1H), 2.00 (s, 3H), 2.70-2.92 (m, 2H), 3.18-3.39 (m, 2H), 5.41 (s, 2H), 6.91-7.42 (m, 10H).

[step 2] The title compound (compound 97, 125 mg, 19%) was obtained in the same manner as in step 3 of Example 1, using (E)-2-[2-(4-chloro-2-cyclopropylbenzimidazol-1-yl) methyl-10,11-dihydro-5H-dibenzo[a,d]cyclohepten-5-ylidene]propiononitrile (584 mg, 1.30 mmol) obtained in step 1.

ESI-MS m/z: 509 $(M+H)^+$; $^1H$-NMR (DMSO-$d_6$, δ): 0.98-1.12 (m, 4H), 1.92 (s, 3H), 2.25 (m, 1H), 2.77 (m, 2H), 3.30 (m, 2H), 5.59 (s, 2H), 6.90-7.20 (m, 9H), 7.44 (d, J=8.1 Hz, 1H).

Example 98

(E)-2-(4-methyl-2-propylbenzimidazol-1-yl)methyl-5-[1-(1H-tetrazol-5-yl)ethylidene]-10,11-dihydro-5H-dibenzo[a,d]cycloheptene (Compound 98)

The title compound (compound 98, 63 mg, 52%) was obtained in the same manner as in Example 22, using (E)-2-[2-(4-methyl-2-propylbenzimidazol-1-yl)methyl-10,11-dihydro-5H-dibenzo[a,d]cyclohepten-5-ylidene]propiononitrile (110 mg, 0.26 mmol) obtained in step 1 of Example 83.

ESI-MS m/z: 475 $(M+H)^+$; $^1H$-NMR (DMSO-$d_6$, δ): 0.91 (t, J=7.4 Hz, 3H), 1.71 (m, 2H), 2.01 (s, 3H), 2.50 (s, 3H), 2.75 (m, 2H), 2.79 (t, J=7.6 Hz, 2H), 3.38 (m, 2H), 5.43 (s, 2H), 6.57 (d, J=7.2 Hz, 1H), 6.77-7.28 (m, 9H).

Example 99

(E)-2-(2-cyclopropyl-5,7-dimethyl-3H-imidazo[4,5-b]pyridin-3-yl)methyl-5-[1-(1H-tetrazol-5-yl)ethylidene]-10,11-dihydro-5H-dibenzo[a,d]cycloheptene (Compound 99)

The title compound (compound 99, 156 mg, 67%) was obtained in the same manner as in Example 22, using (E)-2-[2-(2-cyclopropyl-5,7-dimethyl-3H-imidazo[4,5-b]pyridin-3-yl)methyl-10,11-dihydro-5H-dibenzo[a,d]cyclohepten-5-ylidene]propiononitrile (211 mg, 0.47 mmol) obtained in step 1 of Example 87.

ESI-MS m/z: 488 $(M+H)^+$; $^1H$-NMR ($CDCl_3$, δ): 0.90-0.98 (m, 2H), 1.04-1.11 (m, 2H), 1.76-1.86 (m, 1H), 2.27 (s, 3H), 2.39 (s, 3H), 2.51-2.67 (m, 2H), 2.58 (s, 3H), 2.89-2.99 (m, 1H), 3.08-3.18 (m, 1H), 5.47 (d, J=16.3 Hz, 1H), 5.56 (d, J=16.2 Hz, 1H), 6.86 (s, 1H), 6.90-6.98 (m, 2H), 7.07-7.13 (m, 3H), 7.18-7.23 (m, 2H).

Example 100

(E)-2-(2-cyclopropyl-7-methyl-3H-imidazo[4,5-b]pyridin-3-yl)methyl-5-[1-(1H-tetrazol-5-yl)ethylidene]-10,11-dihydro-5H-dibenzo[a,d]cycloheptene (Compound 100)

The title compound (compound 100, 38 mg, 26%) was obtained in the same manner as in Example 22, using (E)-2-[2-(2-cyclopropyl-7-methyl-3H-imidazo[4,5-b]pyridin-3-yl)methyl-10,11-dihydro-5H-dibenzo[a,d]cyclohepten-5-ylidene]propiononitrile (131 mg, 0.30 mmol) obtained in step 1 of Example 88.

ESI-MS m/z: 474 $(M+H)^+$; $^1H$-NMR ($CDCl_3$, δ): 0.99-1.06 (m, 2H), 1.16-1.21 (m, 2H), 1.86-1.95 (m, 1H), 2.32 (s, 3H), 2.58 (s, 3H), 2.71-2.80 (m, 2H), 3.16-3.28 (m, 2H), 5.54 (s, 2H), 6.91-7.08 (m, 4H), 7.16-7.34 (m, 4H), 8.15 (d, J=4.9 Hz, 1H).

Example 101

(E)-2-(2-ethyl-3H-imidazo[4,5-b]pyridin-3-yl)methyl-5-[1-(1H-tetrazol-5-yl)ethylidene]-10,11-dihydro-5H-dibenzo[a,d]cycloheptene (Compound 101)

The title compound (compound 101, 183 mg, 82%) was obtained in the same manner as in Example 22, using (E)-2-[2-(2-ethyl-3H-imidazo[4,5-b]pyridin-3-yl)methyl-10,11-dihydro-5H-dibenzo[a,d]cyclohepten-5-ylidene]propiononitrile (202 mg, 0.50 mmol) obtained in step 1 of Example 90.

ESI-MS m/z: 448 $(M+H)^+$; $^1H$-NMR ($CDCl_3$, δ): 1.38 (t, J=7.5 Hz, 3H), 2.32 (s, 3H), 2.68-2.82 (m, 2H), 2.82 (q, J=7.5 Hz, 2H), 3.16-3.29 (m, 2H), 5.45 (s, 2H), 6.92 (s, 1H), 6.98-7.02 (m, 2H), 7.14-7.34 (m, 5H), 7.96 (dd, J=7.9, 1.5 Hz, 1H), 8.33 (dd, J=4.8, 1.5 Hz, 1H).

Example 102

(E)-2-(2-ethoxy-3H-imidazo[4,5-b]pyridin-3-yl) methyl-5-[1-(1H-tetrazol-5-yl)ethylidene]-10,11-dihydro-5H-dibenzo[a,d]cycloheptene (Compound 102)

The title compound (compound 102, 66 mg, 60%) was obtained in the same manner as in Example 22, using (E)-2-[2-(2-ethoxy-3H-imidazo[4,5-b]pyridin-3-yl)methyl-10,11-dihydro-5H-dibenzo[a,d]cyclohepten-5-ylidene]propiononitrile (100 mg, 0.24 mmol) obtained in step 1 of Example 91.

ESI-MS m/z: 464 $(M+H)^+$; $^1H$-NMR ($CDCl_3$, δ): 1.47 (t, J=7.0 Hz, 3H), 2.36 (s, 3H), 2.76-2.91 (m, 2H), 3.25-3.38 (m, 2H), 4.62 (q, J=7.0 Hz, 2H), 5.23 (s, 2H), 7.02 (d, J=7.6 Hz, 1H), 7.09-7.34 (m, 7H), 7.74 (dd, J=7.4, 1.0 Hz, 1H), 8.16 (dd, J=5.0, 1.0 Hz, 1H).

Example 103

(E)-2-(2-cyclopropyl-3H-imidazo[4,5-b]pyridin-3-yl)methyl-5-[1-(1H-tetrazol-5-yl)ethylidene]-10,11-dihydro-5H-dibenzo[a,d]cycloheptene (Compound 103)

The title compound (compound 103, 148 mg, 83%) was obtained in the same manner as in Example 22, using (E)-2-[2-(2-cyclopropyl-3H-imidazo[4,5-b]pyridin-3-yl)methyl-10,11-dihydro-5H-dibenzo[a,d]cyclohepten-5-ylidene]propiononitrile (161 mg, 0.39 mmol) obtained in step 1 of Example 92.

ESI-MS m/z: 460 $(M+H)^+$; $^1$H-NMR ($CDCl_3$, δ): 1.02-1.09 (m, 2H), 1.19-1.24 (m, 2H), 1.88-1.97 (m, 1H), 2.31 (s, 3H), 2.68-2.79 (m, 2H), 3.13-3.29 (m, 2H), 5.57 (s, 2H), 6.98-7.01 (m, 2H), 7.07-7.32 (m, 6H), 7.86 (dd, J=8.1, 1.5 Hz, 1H), 8.29 (dd, J=4.8, 1.5 Hz, 1H).

Example 104

(E)-3-(2-ethyl-5,7-dimethyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 104)

[step 1] (E)-(3-Hydroxymethyl-6,11-dihydrodibenzo[b,e]oxepin-11-ylidene)acetonitrile (JP-B-2526005; 250 mg, 0.950 mmol) and 2-ethyl-5,7-dimethyl-3H-imidazo[4,5-b]pyridine (250 mg, 1.42 mmol) were dissolved in THF (9.5 mL), and the solution was added with polymer supported triphenylphosphine (633 mg, 1.90 mmol) and di-t-butyl azodicarboxylate (437 mg, 1.90 mmol) at 0° C., followed by stirring at room temperature for 3 hr. The mixture was filtrated and the filtrate was concentrated under reduced pressure. The residue was purified by silica gel column chromatography (hexane/ethyl acetate=1/1) to give (E)-[3-(2-ethyl-5,7-dimethyl-3H-imidazo[4,5-b]pyridin-3-yl)methyl-6,11-dihydrodibenzo[b,e]oxepin-11-ylidene]acetonitrile (158 mg, 26%).

ESI-MS m/z: 421 $(M+H)^+$; $^1$H-NMR (DMSO-$d_6$, δ): 1.22 (t, J=7.4 Hz, 3H), 2.47 (s, 3H), 2.50 (s, 3H), 2.74 (q, J=7.4 Hz, 2H), 5.14 (s, 2H), 5.39 (s, 2H), 6.33 (s, 1H), 6.52 (d, J=1.8 Hz, 1H), 6.72 (dd, J=8.2, 1.8 Hz, 1H), 6.94 (s, 1H), 7.42 (d, J=8.2 Hz, 1H), 7.47-7.54 (m, 4H).

[step 2] The title compound (compound 104, 94.3 mg, 53%) was obtained in the same manner as in step 3 of Example 1, using (E)-[3-(2-ethyl-5,7-dimethyl-3H-imidazo[4,5-b]pyridin-3-yl)methyl-6,11-dihydrodibenzo[b,e]oxepin-11-ylidene]acetonitrile (156 mg, 0.371 mmol) obtained in step 1.

ESI-MS m/z: 480 $(M+H)^+$; $^1$H-NMR ($CDCl_3$, δ): 1.32 (t, J=7.6 Hz, 3H), 2.56 (s, 3H), 2.61 (s, 3H), 2.75 (q, J=7.6 Hz, 2H), 4.86 (br s, 1H), 5.37 (s, 2H), 5.44 (br s, 1H), 6.54 (d, J=1.7 Hz, 1H), 6.58 (s, 1H), 6.74 (dd, J=8.1, 1.7 Hz, 1H), 6.88 (s, 1H), 7.24-7.31 (m, 2H), 7.44-7.52 (m, 3H).

Example 105

(E)-3-(2-ethyl-7-methyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 105)

[step 1] (E)-[3-(2-Ethyl-7-methyl-3H-imidazo[4,5-b]pyridin-3-yl)methyl-6,11-dihydrodibenzo[b,e]oxepin-11-ylidene]acetonitrile (151 mg, 22%) was obtained in the same manner as in step 1 of Example 104, using 2-ethyl-7-methyl-3H-imidazo[4,5-b]pyridine (276 mg, 1.71 mmol) instead of 2-ethyl-5,7-dimethyl-3H-imidazo[4,5-b]pyridine.

ESI-MS m/z: 407 $(M+H)^+$; $^1$H-NMR (DMSO-$d_3$, δ): 1.25 (t, J=7.5 Hz, 3H), 2.56 (s, 3H), 2.80 (q, J=7.5 Hz, 2H), 5.14 (s, 2H), 5.43 (s, 2H), 6.32 (s, 1H), 6.57 (d, J=1.6 Hz, 1H), 6.75 (dd, J=8.2, 1.6 Hz, 1H), 7.07 (d, J=4.9 Hz, 1H), 7.41 (d, J=8.2 Hz, 1H), 7.47-7.54 (m, 4H), 8.12 (d, J=4.9 Hz, 1H).

[step 2] The title compound (compound 105, 64.9 mg, 38%) was obtained in the same manner as in step 3 of Example 1, using (E)-[3-(2-ethyl-7-methyl-3H-imidazo[4,5-b]pyridin-3-yl)methyl-6,11-dihydrodibenzo[b,e]oxepin-11-ylidene]acetonitrile (149 mg, 0.367 mmol) obtained in step 1.

ESI-MS m/z: 466 $(M+H)^+$; $^1$H-NMR (DMSO-$d_6$, δ): 1.25 (t, J=7.5 Hz, 3H), 2.56 (s, 3H), 2.80 (q, J=7.5 Hz, 2H), 5.16 (br s, 2H), 5.42 (s, 2H), 6.54 (d, J=1.8 Hz, 1H), 6.55 (s, 1H), 6.75 (dd, J=8.1, 1.8 Hz, 1H), 7.07 (dd, J=4.9, 0.7 Hz, 1H), 7.21 (dd, J=7.3, 1.2 Hz, 1H), 7.31-7.50 (m, 4H), 8.12 (d, J=4.8 Hz, 1H), 11.99 (s, 1H).

Example 106

(E)-3-(7-chloro-2-ethyl-5-methyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 106)

[step 1] (E)-[3-(7-Chloro-2-ethyl-5-methyl-3H-imidazo[4,5-b]pyridin-3-yl)methyl-6,11-dihydrodibenzo[b,e]oxepin-11-ylidene]acetonitrile (199 mg, 44%) was obtained in the same manner as in step 1 of Example 104, using 7-chloro-2-ethyl-5-methyl-3H-imidazo[4,5-b]pyridine (201 mg, 1.03 mmol) instead of 2-ethyl-5,7-dimethyl-3H-imidazo[4,5-b]pyridine.

ESI-MS m/z: 441 $(M+H)^+$; $^1$H-NMR (DMSO-$d_6$, δ): 1.24 (t, J=7.5 Hz, 3H), 2.53 (s, 3H), 2.78 (q, J=7.5 Hz, 2H), 5.15 (s, 2H), 5.43 (s, 2H), 6.33 (s, 1H), 6.57 (d, J=1.7 Hz, 1H), 6.74 (dd, J=8.1, 1.7 Hz, 1H), 7.29 (s, 1H), 7.42 (d, J=8.1 Hz, 1H), 7.48-7.55 (m, 4H).

[step 2] The title compound (compound 106, 130 mg, 58%) was obtained in the same manner as in step 3 of Example 1, using (E)-[3-(7-chloro-2-ethyl-5-methyl-3H-imidazo[4,5-b]pyridin-3-yl)methyl-6,11-dihydrodibenzo[b,e]oxepin-11-ylidene]acetonitrile (196 mg, 0.445 mmol) obtained in step 1.

ESI-MS m/z: 500 $(M+H)^+$; $^1$H-NMR (DMSO-$d_6$, δ): 1.24 (t, J=7.4 Hz, 3H), 2.53 (s, 3H), 2.79 (q, J=7.5 Hz, 2H), 5.17 (br s, 2H), 5.42 (s, 2H), 6.53 (d, J=1.7 Hz, 1H), 6.56 (s, 1H), 6.73 (dd, J=8.1, 1.7 Hz, 1H), 7.20-7.51 (m, 6H).

Example 107

(E)-3-(2-cyclopropyl-5,7-dimethyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 107)

[step 1] (E)-[3-(2-Cyclopropyl-5,7-dimethyl-3H-imidazo[4,5-b]pyridin-3-yl)methyl-6,11-dihydrodibenzo[b,e]oxepin-11-ylidene]acetonitrile (147 mg, 27%) was obtained in the same manner as in step 1 of Example 104, using 2-cyclopropyl-5,7-dimethyl-3H-imidazo[4,5-b]pyridine (235 mg, 1.25 mmol) instead of 2-ethyl-5,7-dimethyl-3H-imidazo[4,5-b]pyridine.

ESI-MS m/z: 433 $(M+H)^+$; $^1$H-NMR (DMSO-$d_6$, δ): 0.96-1.01 (m, 4H), 2.07-2.15 (m, 1H), 2.44 (s, 3H), 2.46 (s, 3H), 5.15 (s, 2H), 5.50 (s, 2H), 6.33 (s, 1H), 6.61 (d, J=1.7 Hz, 1H), 6.79 (dd, J=8.2, 1.7 Hz, 1H), 6.90 (s, 1H), 7.42 (d, J=8.2 Hz, 1H), 7.47-7.55 (m, 4H).

[step 2] The title compound (compound 107, 97.7 mg, 59%) was obtained in the same manner as in step 3 of Example 1, using (E)-[3-(2-cyclopropyl-5,7-dimethyl-3H-imidazo[4,5-b]pyridin-3-yl)methyl-6,11-dihydrodibenzo[b,e]oxepin-11-ylidene]acetonitrile (145 mg, 0.335 mmol) obtained in step 1.

ESI-MS m/z: 492 $(M+H)^+$; $^1$H-NMR (DMSO-$d_6$, δ): 0.96-1.02 (m, 4H), 2.07-2.15 (m, 1H), 2.44 (s, 3H), 2.46 (s, 3H), 5.17 (br s, 2H), 5.49 (s, 2H), 6.56 (s, 1H), 6.57 (d, J=1.8 Hz, 1H), 6.79 (dd, J=8.1, 1.8 Hz, 1H), 6.90 (s, 1H), 7.19-7.51 (m, 5H).

Example 108

(E)-3-(2-cyclopropyl-7-methyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 108)

[step 1] (E)-[3-(2-Cyclopropyl-7-methyl-3H-imidazo[4,5-b]pyridin-3-yl)methyl-6,11-dihydrodibenzo[b,e]oxepin-11-ylidene]acetonitrile (62.5 mg, 15%) was obtained in the same manner as in step 1 of Example 104, using 2-cyclopropyl-7-methyl-3H-imidazo[4,5-b]pyridine (177 mg, 1.02 mmol) instead of 2-ethyl-5,7-dimethyl-3H-imidazo[4,5-b]pyridine.

ESI-MS m/z: 419 $(M+H)^+$; $^1$H-NMR (DMSO-$d_6$, δ): 1.01-1.11 (m, 4H), 2.18-2.24 (m, 1H), 2.49 (s, 3H), 5.15 (s, 2H), 5.54 (s, 2H), 6.33 (s, 1H), 6.67 (d, J=1.7 Hz, 1H), 6.83 (dd, J=8.2, 1.7 Hz, 1H), 7.04 (d, J=4.8 Hz, 1H), 7.42 (d, J=8.2 Hz, 1H), 7.47-7.54 (m, 4H), 8.08 (d, J=4.8 Hz, 1H).

[step 2] The title compound (compound 108, 26.8 mg, 39%) was obtained in the same manner as in step 3 of Example 1, using (E)-[3-(2-cyclopropyl-7-methyl-3H-imidazo[4,5-b]pyridin-3-yl)methyl-6,11-dihydrodibenzo[b,e]oxepin-11-ylidene]acetonitrile (60.3 mg, 0.144 mmol) obtained in step 1.

ESI-MS m/z: 478 $(M+H)^+$; $^1$H-NMR (DMSO-$d_6$, δ): 1.01-1.06 (m, 4H), 2.18-2.24 (m, 1H), 2.49 (s, 3H), 5.16 (br s, 2H), 5.53 (s, 2H), 6.56 (s, 1H), 6.63 (d, J=1.8 Hz, 1H), 6.83 (dd, J=8.1, 1.8 Hz, 1H), 7.03 (dd, J=4.9, 0.7 Hz, 1H), 7.21 (dd, J=7.4, 1.3 Hz, 1H), 7.31-7.50 (m, 4H), 8.09 (d, J=4.9 Hz, 1H).

Example 109

(E)-3-(2-ethyl-5,7-dimethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 109)

[step 1] (E)-2-[3-(2-Ethyl-5,7-dimethyl-3H-imidazo[4,5-b]pyridin-3-yl)methyl-6,11-dihydrodibenzo[b,e]oxepin-11-ylidene]propiononitrile (168 mg, 27%) was obtained in the same manner as in step 1 of Example 104, using (E)-2-(3-hydroxymethyl-6,11-dihydrodibenzo[b,e]oxepin-11-ylidene)propiononitrile (264 mg, 0.952 mmol) obtained in Reference Example 30 and 2-ethyl-5,7-dimethyl-3H-imidazo[4,5-b]pyridine (250 mg, 1.43 mmol).

ESI-MS m/z: 435 $(M+H)^+$; $^1$H-NMR ($CDCl_3$, δ): 1.31 (t, J=7.5 Hz, 3H), 2.22 (s, 3H), 2.56 (s, 3H), 2.62 (s, 3H), 2.74 (q, J=7.5 Hz, 2H), 4.81 (d, J=12.6 Hz, 1H), 5.35 (s, 2H), 5.44 (d, J=12.6 Hz, 1H), 6.58 (d, J=1.6 Hz, 1H), 6.64 (dd, J=8.1, 1.6 Hz, 1H), 6.88 (s, 1H), 6.98 (d, J=8.1 Hz, 1H), 7.32-7.45 (m, 4H).

[step 2] The title compound (compound 109, 90.5 mg, 48%) was obtained in the same manner as in step 3 of Example 1, using (E)-2-[3-(2-ethyl-5,7-dimethyl-3H-imidazo[4,5-b]pyridin-3-yl)methyl-6,11-dihydrodibenzo[b,e]oxepin-11-ylidene]propiononitrile (165 mg, 0.380 mmol) obtained in step 1.

ESI-MS m/z: 494 $(M+H)^+$; $^1$H-NMR ($CDCl_3$, δ): 1.22 (t, J=7.5 Hz, 3H), 2.15 (s, 3H), 2.48 (s, 3H), 2.50 (s, 3H), 2.73 (q, J=7.5 Hz, 2H), 4.90 (d, J=12.5 Hz, 1H), 5.37 (s, 2H), 5.49 (d, J=12.5 Hz, 1H), 6.49 (d, J=1.7 Hz, 1H), 6.65 (dd, J=7.9, 1.7 Hz, 1H), 6.94 (s, 1H), 7.03-7.06 (m, 1H), 7.16 (d, J=7.9 Hz, 1H), 7.24-7.35 (m, 2H), 7.42-7.45 (m, 1H).

Example 110

(E)-3-(2-ethyl-7-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 110)

[step 1] (E)-2-[3-(2-Ethyl-7-methyl-3H-imidazo[4,5-b]pyridin-3-yl)methyl-6,11-dihydrodibenzo[b,e]oxepin-11-ylidene]propiononitrile (173 mg, 24%) was obtained in the same manner as in step 1 of Example 109, using 2-ethyl-7-methyl-3H-imidazo[4,5-b]pyridine (279 mg, 1.73 mmol) instead of 2-ethyl-5,7-dimethyl-3H-imidazo[4,5-b]pyridine.

ESI-MS m/z: 421 $(M+H)^+$; $^1$H-NMR (DMSO-$d_6$, δ): 1.24 (t, J=7.5 Hz, 3H), 2.14 (s, 3H), 2.55 (s, 3H), 2.80 (q, J=7.5 Hz, 2H), 4.92 (d, J=12.7 Hz, 1H), 5.41 (s, 2H), 5.43 (d, J=12.7 Hz, 1H), 6.55 (d, J=1.7 Hz, 1H), 6.70 (dd, J=8.0, 1.7 Hz, 1H), 7.07 (d, J=4.9 Hz, 1H), 7.18 (d, J=8.0 Hz, 1H), 7.40-7.52 (m, 4H), 8.12 (d, J=4.9 Hz, 1H).

[step 2] The title compound (compound 110, 126 mg, 64%) was obtained in the same manner as in step 3 of Example 1, using (E)-2-[3-(2-ethyl-7-methyl-3H-imidazo[4,5-b]pyridin-3-yl)methyl-6,11-dihydrodibenzo[b,e]oxepin-11-ylidene]propiononitrile (172 mg, 0.409 mmol) obtained in step 1.

ESI-MS m/z: 480 $(M+H)^+$; $^1$H-NMR (DMSO-$d_6$, δ): 1.24 (t, J=7.5 Hz, 3H), 2.14 (s, 3H), 2.55 (s, 3H), 2.80 (q, J=7.5 Hz, 2H), 4.90 (d, J=12.4 Hz, 1H), 5.40 (s, 2H), 5.49 (d, J=12.4 Hz, 1H), 6.55 (d, J=1.6 Hz, 1H), 6.68 (dd, J=8.1, 1.6 Hz, 1H), 7.02-7.45 (m, 6H), 8.12 (d, J=4.9 Hz, 1H).

Example 111

(E)-3-(7-chloro-2-ethyl-5-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 111)

[step 1] (E)-2-[3-(7-Chloro-2-ethyl-5-methyl-3H-imidazo[4,5-b]pyridin-3-yl)methyl-6,11-dihydrodibenzo[b,e]oxepin-11-ylidene]propiononitrile (519 mg, 64%) was obtained in the same manner as in step 1 of Example 109, using 7-chloro-2-ethyl-5-methyl-3H-imidazo[4,5-b]pyridine (350 mg, 1.79 mmol) instead of 2-ethyl-5,7-dimethyl-3H-imidazo[4,5-b]pyridine.

ESI-MS m/z: 455 $(M+H)^+$; $^1$H-NMR (DMSO-$d_6$, δ): 1.23 (t, J=7.4 Hz, 3H), 2.15 (s, 3H), 2.52 (s, 3H), 2.78 (q, J=7.4 Hz, 2H), 4.93 (d, J=12.7 Hz, 1H), 5.41 (s, 2H), 5.44 (d, J=12.7 Hz, 1H), 6.55 (d, J=1.6 Hz, 1H), 6.68 (dd, J=8.1, 1.6 Hz, 1H), 7.19 (d, J=8.1 Hz, 1H), 7.28 (s, 1H), 7.41-7.52 (m, 4H).

[step 2] The title compound (compound 111, 296 mg, 66%) was obtained in the same manner as in step 3 of Example 1, using (E)-2-[3-(7-chloro-2-ethyl-5-methyl-3H-imidazo[4,5- b]pyridin-3-yl)methyl-6,11-dihydrodibenzo[b,e]oxepin-11-ylidene]propiononitrile (397 mg, 0.873 mmol) obtained in step 1.

ESI-MS m/z: 514 $(M+H)^+$; $^1$H-NMR (DMSO-$d_6$, δ): 1.23 (t, J=7.4 Hz, 3H), 2.15 (s, 3H), 2.53 (s, 3H), 2.78 (q, J=7.4 Hz, 2H), 4.91 (d, J=12.6 Hz, 1H), 5.41 (s, 2H), 5.50 (d, J=12.6 Hz, 1H), 6.55 (d, J=1.7 Hz, 1H), 6.67 (dd, J=8.1, 1.7 Hz, 1H), 7.03-7.07 (m, 1H), 7.17 (d, J=8.1 Hz, 1H), 7.25-7.35 (m, 3H), 7.43-7.46 (m, 1H).

Example 112

(E)-3-(2-cyclopropyl-5,7-dimethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 112)

[step 1] (E)-2-[3-(2-Cyclopropyl-5,7-dimethyl-3H-imidazo[4,5-b]pyridin-3-yl)methyl-6,11-dihydrodibenzo[b,e]oxepin-11-ylidene]propiononitrile (353 mg, 33%) was obtained in the same manner as in step 1 of Example 109, using 2-cyclopropyl-5,7-dimethyl-3H-imidazo[4,5-b]pyridine (446 mg, 2.38 mmol) instead of 2-ethyl-5,7-dimethyl-3H-imidazo[4,5-b]pyridine.

ESI-MS m/z: 447 $(M+H)^+$; $^1$H-NMR (DMSO-$d_6$, δ): 0.94-1.01 (m, 4H), 2.15 (s, 3H), 2.16-2.24 (m, 1H), 2.44 (s, 3H), 2.46 (s, 3H), 4.93 (d, J=12.7 Hz, 1H), 5.43 (d, J=12.7 Hz, 1H), 5.49 (s, 2H), 6.59 (d, J=1.8 Hz, 1H), 6.74 (dd, J=8.1, 1.8 Hz, 1H), 6.90 (s, 1H), 7.19 (d, J=8.1 Hz, 1H), 7.40-7.52 (m, 4H).

[step 2] The title compound (compound 112, 197 mg, 50%) was obtained in the same manner as in step 3 of Example 1, using (E)-2-[3-(2-cyclopropyl-5,7-dimethyl-3H-imidazo[4,5-b]pyridin-3-yl)methyl-6,11-dihydrodibenzo[b,e]oxepin-11-ylidene]propiononitrile (351 mg, 0.786 mmol) obtained in step 1.

ESI-MS m/z: 506 $(M+H)^+$; $^1$H-NMR (DMSO-$d_6$, δ): 1.01-1.05 (m, 4H), 2.15 (s, 3H), 2.16-2.24 (m, 1H), 2.44 (s, 3H), 2.46 (s, 3H), 4.91 (d, J=12.5 Hz, 1H), 5.49 (d, J=12.5 Hz, 1H), 5.51 (s, 2H), 6.63 (d, J=1.8 Hz, 1H), 6.76 (dd, J=8.1, 1.8 Hz, 1H), 7.02-7.06 (m, 2H), 7.17 (d, J=8.1 Hz, 1H), 7.24-7.35 (m, 2H), 7.42-7.45 (m, 1H), 8.08 (d, J=4.9 Hz, 1H).

Example 113

(E)-3-(2-cyclopropyl-7-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 113)

[step 1] (E)-2-[3-(2-Cyclopropyl-7-methyl-3H-imidazo[4,5-b]pyridin-3-yl)methyl-6,11-dihydrodibenzo[b,e]oxepin-11-ylidene]propiononitrile (109 mg, 15%) was obtained in the same manner as in step 1 of Example 109, using 2-cyclopropyl-7-methyl-3H-imidazo[4,5-b]pyridine (300 mg, 1.73 mmol) instead of 2-ethyl-5,7-dimethyl-3H-imidazo[4,5-b]pyridine.

ESI-MS m/z: 433 $(M+H)^+$; $^1$H-NMR (DMSO-$d_6$, δ): 0.99-1.05 (m, 4H), 2.15 (s, 3H), 2.15-2.19 (m, 1H), 2.49 (s, 3H), 4.92 (d, J=12.8 Hz, 1H), 5.43 (d, J=12.8 Hz, 1H), 5.52 (s, 2H), 6.64 (d, J=1.7 Hz, 1H), 6.77 (dd, J=8.1, 1.7 Hz, 1H), 7.03 (d, J=4.9 Hz, 1H), 7.18 (d, J=8.1 Hz, 1H), 7.40-7.50 (m, 4H), 8.08 (d, J=4.9 Hz, 1H).

[step 2] The title compound (compound 113, 78.2 mg, 64%) was obtained in the same manner as in step 3 of Example 1, using (E)-2-[3-(2-cyclopropyl-7-methyl-3H-imidazo[4,5-b]pyridin-3-yl)methyl-6,11-dihydrodibenzo[b,e]oxepin-11-ylidene]propiononitrile (107 mg, 0.247 mmol) obtained in step 1.

ESI-MS m/z: 492 $(M+H)^+$; $^1$H-NMR (DMSO-$d_6$, δ): 1.01-1.05 (m, 4H), 2.15 (s, 3H), 2.17-2.22 (m, 1H), 2.49 (s, 3H), 4.91 (d, J=12.5 Hz, 1H), 5.49 (d, J=12.5 Hz, 2H), 5.51 (s, 1H), 6.63 (d, J=1.8 Hz, 1H), 6.76 (dd, J=8.1, 1.8 Hz, 1H), 7.02-7.06 (m, 2H), 7.17 (d, J=8.1 Hz, 1H), 7.24-7.45 (m, 3H), 8.08 (d, J=4.9 Hz, 1H).

Example 114

(E)-3-(2-ethyl-5,7-dimethyl-3H-imidazo[4,5-b]pyridin-3-yl)methyl-11-[1-(1H-tetrazol-5-yl)ethylidene]-6,11-dihydrodibenzo[b,e]oxepine (Compound 114)

The title compound (compound 114, 40.2 mg, 44%) was obtained in the same manner as in Example 22, using (E)-2-[3-(2-ethyl-5,7-dimethyl-3H-imidazo[4,5-b]pyridin-3-yl)methyl-6,11-dihydrodibenzo[b,e]oxepin-11-ylidene]propiononitrile (82.2 mg, 0.189 mmol) obtained in step 1 of Example 109.

ESI-MS m/z: 478 $(M+H)^+$; $^1$H-NMR (DMSO-$d_6$, δ): 1.22 (t, J=7.5 Hz, 3H), 2.23 (s, 3H), 2.50 (s, 3H), 2.51 (s, 3H), 2.75 (q, J=7.5 Hz, 2H), 4.93 (d, J=12.3 Hz, 1H), 5.38 (s, 2H), 5.59 (d, J=12.3 Hz, 1H), 6.50 (d, J=1.6 Hz, 1H), 6.63-6.70 (m, 2H), 6.94 (s, 1H), 7.08 (td, J=7.5, 1.2 Hz, 1H), 7.20-7.27 (m, 2H), 7.41 (d, J=6.7 Hz, 1H).

Example 115

(E)-3-(2-ethyl-7-methyl-3H-imidazo[4,5-b]pyridin-3-yl)methyl-11-[1-(1H-tetrazol-5-yl)ethylidene]-6,11-dihydrodibenzo[b,e]oxepine (Compound 115)

The title compound (compound 115, 152 mg, 42%) was obtained in the same manner as in Example 22, using (E)-2-[3-(2-ethyl-7-methyl-3H-imidazo[4,5-b]pyridin-3-yl)methyl-6,11-dihydrodibenzo[b,e]oxepin-11-ylidene]propiononitrile (330 mg, 0.785 mmol) obtained in step 1 of Example 110.

ESI-MS m/z: 464 $(M+H)^+$; $^1$H-NMR (DMSO-$d_6$, δ): 1.25 (t, J=7.5 Hz, 3H), 2.23 (s, 3H), 2.56 (s, 3H), 2.81 (q, J=7.5 Hz, 2H), 4.93 (d, J=12.5 Hz, 1H), 5.41 (s, 2H), 5.59 (d, J=12.5 Hz, 1H), 6.56 (d, J=1.5 Hz, 1H), 6.67-6.71 (m, 2H), 7.07-7.10 (m, 2H), 7.19-7.27 (m, 2H), 7.41 (d, J=6.6 Hz, 1H), 8.13 (d, J=4.9 Hz, 1H).

Example 116

(E)-3-(7-chloro-2-ethyl-5-methyl-3H-imidazo[4,5-b]pyridin-3-yl)methyl-11-[1-(1H-tetrazol-5-yl)ethylidene]-6,11-dihydrodibenzo[b,e]oxepine (Compound 116)

The title compound (compound 116, 33.4 mg, 25%) was obtained in the same manner as in Example 22, using (E)-2-[3-(7-chloro-2-ethyl-5-methyl-3H-imidazo[4,5-b]pyridin-3-yl)methyl-6,11-dihydrodibenzo[b,e]oxepin-11-ylidene]propiononitrile (120 mg, 0.264 mmol) obtained in step 1 of Example 111.

ESI-MS m/z: 498 $(M+H)^+$; $^1$H-NMR (DMSO-$d_6$, δ): 1.24 (t, J=7.5 Hz, 3H), 2.24 (s, 3H), 2.54 (s, 3H), 2.79 (q, J=7.5 Hz, 2H), 4.94 (d, J=12.5 Hz, 1H), 5.41 (s, 2H), 5.60 (d, J=12.5 Hz, 1H), 6.55 (d, J=1.6 Hz, 1H), 6.66-6.70 (m, 2H), 7.09 (td, J=7.5, 1.2 Hz, 1H), 7.20-7.29 (m, 3H), 7.42 (d, J=6.6 Hz, 1H).

Example 117

(E)-3-(2-cyclopropyl-5,7-dimethyl-3H-imidazo[4,5-b]pyridin-3-yl)methyl-11-[1-(1H-tetrazol-5-yl)ethylidene]-6,11-dihydrodibenzo[b,e]oxepine (Compound 117)

The title compound (compound 117, 163 mg, 51%) was obtained in the same manner as in Example 22, using (E)-2-[3-(2-cyclopropyl-5,7-dimethyl-3H-imidazo[4,5-b]pyridin-3-yl)methyl-6,11-dihydrodibenzo[b,e]oxepin-11-ylidene]propiononitrile (292 mg, 0.654 mmol) obtained in step 1 of Example 112.

ESI-MS m/z: 490 $(M+H)^+$; $^1$H-NMR (DMSO-$d_6$, δ): 0.97-1.01 (m, 4H), 2.07-2.14 (m, 1H), 2.24 (s, 3H), 2.44 (s, 3H), 2.47 (s, 3H), 4.94 (d, J=12.3 Hz, 1H), 5.49 (s, 2H), 5.60 (d, J=12.3 Hz, 1H), 6.58 (d, J=1.6 Hz, 1H), 6.68-6.75 (m, 2H), 6.91 (s, 1H), 7.05-7.28 (m, 3H), 7.42 (d, J=6.6 Hz, 1H).

Example 118

(Z)-8-(2-ethyl-5,7-dimethyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 118)

[step 1] (Z)-[8-(2-Ethyl-5,7-dimethyl-3H-imidazo[4,5-b]pyridin-3-yl)methyl-6,11-dihydrodibenzo[b,e]oxepin-11-ylidene]acetonitrile (70 mg, 16%) was obtained in the same manner as in step 1 of Example 104, using (Z)-(8-hydroxymethyl-6,11-dihydrodibenzo[b,e]oxepin-11-ylidene)acetonitrile (JP-B-2526005; 270 mg, 1.00 mmol) and 2-ethyl-5,7-dimethyl-3H-imidazo[4,5-b]pyridine (270 mg, 1.50 mmol).

ESI-MS m/z: 421 $(M+H)^+$; $^1$H-NMR ($CDCl_3$, δ): 1.33 (t, J=7.5 Hz, 3H), 2.57 (s, 3H), 2.64 (s, 3H), 2.76 (q, J=7.5 Hz, 2H), 5.07 (s, 2H), 5.45 (s, 1H), 5.46 (s, 2H), 6.87-6.91 (m, 2H), 6.99-7.13 (m, 3H), 7.20-7.33 (m, 2H), 7.69 (dd, J=7.8, 1.6 Hz, 1H).

[step 2] The title compound (compound 118, 45 mg, 56%) was obtained in the same manner as in step 3 of Example 1, using (Z)-[8-(2-ethyl-5,7-dimethyl-3H-imidazo[4,5-b]pyridin-3-yl)methyl-6,11-dihydrodibenzo[b,e]oxepin-11-ylidene]acetonitrile (70 mg, 0.17 mmol) obtained in step 1.

ESI-MS m/z: 480 $(M+H)^+$; $^1$H-NMR ($CDCl_3$, δ): 1.30 (t, J=7.5 Hz, 3H), 2.57 (s, 3H), 2.61 (s, 3H), 2.74 (q, J=7.5 Hz, 2H), 5.07 (br s, 2H), 5.45 (s, 2H), 6.27 (s, 1H), 6.87-6.97 (m, 3H), 7.02 (s, 1H), 7.09-7.15 (m, 2H), 7.30 (d, J=7.8 Hz, 2H).

Example 119

(Z)-8-(5,7-dimethyl-2-propyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 119)

[step 1] (Z)-[8-(5,7-Dimethyl-2-propyl-3H-imidazo[4,5-b]pyridin-3-yl)methyl-6,11-dihydrodibenzo[b,e]oxepin-11-ylidene]acetonitrile (270 mg, 42%) was obtained in the same manner as in step 1 of Example 118, using 5,7-dimethyl-2-propyl-3H-imidazo[4,5-b]pyridine (281 mg, 1.49 mmol) instead of 2-ethyl-5,7-dimethyl-3H-imidazo[4,5-b]pyridine.

ESI-MS m/z: 435 $(M+H)^+$; $^1$H-NMR ($CDCl_3$, δ): 0.97 (t, J=7.3 Hz, 3H), 1.70-1.84 (m, 2H), 2.57 (s, 3H), 2.63 (s, 3H), 2.72 (t, J=7.8 Hz, 2H), 5.08 (s, 2H), 5.46 (s, 1H), 5.47 (s, 2H), 6.88-6.92 (m, 2H), 6.99-7.13 (m, 3H), 7.22 (d, J=7.8 Hz, 1H), 7.28-7.34 (m, 1H), 7.70 (dd, J=7.9, 1.7 Hz, 1H).

[step 2] The title compound (compound 119, 163 mg, 72%) was obtained in the same manner as in step 3 of Example 1, using (Z)-[8-(5,7-dimethyl-2-propyl-3H-imidazo[4,5-b]pyridin-3-yl)methyl-6,11-dihydrodibenzo[b,e]oxepin-11-ylidene]acetonitrile (200 mg, 0.46 mmol) obtained in step 1.

ESI-MS m/z: 494 $(M+H)^+$; $^1$H-NMR ($CDCl_3$, δ): 0.96 (t, J=7.3 Hz, 3H), 1.69-1.83 (m, 2H), 2.57 (s, 3H), 2.62 (s, 3H), 2.71 (t, J=7.8 Hz, 2H), 5.12 (br s, 2H), 5.46 (s, 2H), 6.31 (s, 1H), 6.90 (s, 1H), 6.94-7.03 (m, 3H), 7.09-7.17 (m, 2H), 7.30-7.37 (m, 2H).

Example 120

(Z)-8-(2-ethyl-7-methyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 120)

[step 1] (Z)-[8-(2-Ethyl-7-methyl-3H-imidazo[4,5-b]pyridin-3-yl)methyl-6,11-dihydrodibenzo[b,e]oxepin-11-ylidene]acetonitrile (135 mg, 28%) was obtained in the same manner as in step 1 of Example 118, using 2-ethyl-7-methyl-3H-imidazo[4,5-b]pyridine (189 mg, 1.17 mmol) instead of 2-ethyl-5,7-dimethyl-3H-imidazo[4,5-b]pyridine.

ESI-MS m/z: 407 $(M+H)^+$; $^1$H-NMR ($CDCl_3$, δ): 1.36 (t, J=7.5 Hz, 3H), 2.69 (s, 3H), 2.83 (q, J=7.5 Hz, 2H), 5.07 (s, 2H), 5.45 (s, 1H), 5.49 (s, 2H), 6.89 (dd, J=8.2, 1.1 Hz, 1H), 6.99-7.14 (m, 4H), 7.22 (d, J=7.9 Hz, 1H), 7.31 (ddd, J=8.6, 6.8, 1.5 Hz, 1H), 7.69 (dd, J=7.9, 1.5 Hz, 1H), 8.19 (d, J=4.9 Hz, 1H).

[step 2] The title compound (compound 120, 119 mg, 77%) was obtained in the same manner as in step 3 of Example 1, using (Z)-[8-(2-ethyl-7-methyl-3H-imidazo[4,5-b]pyridin-3-yl)methyl-6,11-dihydrodibenzo[b,e]oxepin-11-ylidene]acetonitrile (135 mg, 0.33 mmol) obtained in step 1.

ESI-MS m/z: 466 $(M+H)^+$; $^1$H-NMR ($CDCl_3$, δ): 1.35 (t, J=7.5 Hz, 3H), 2.68 (s, 3H), 2.82 (q, J=7.5 Hz, 2H), 5.04 (br s, 2H), 5.47 (s, 2H), 6.24 (s, 1H), 6.89-7.16 (m, 6H), 7.26-7.33 (m, 2H), 8.11 (d, J=5.0 Hz, 1H).

Example 121

(Z)-8-(7-chloro-2-ethyl-5-methyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 121)

[step 1] (Z)-[8-(7-Chloro-2-ethyl-5-methyl-3H-imidazo[4,5-b]pyridin-3-yl)methyl-6,11-dihydrodibenzo[b,e]oxepin-11-ylidene]acetonitrile (94 mg, 43%) was obtained in the same manner as in step 1 of Example 118, using 7-chloro-2-ethyl-5-methyl-3H-imidazo[4,5-b]pyridine (97 mg, 0.49 mmol) instead of 2-ethyl-5,7-dimethyl-3H-imidazo[4,5-b]pyridine.

ESI-MS m/z: 441 $(M+H)^+$; $^1$H-NMR ($CDCl_3$, δ): 1.36 (t, J=7.5 Hz, 3H), 2.60 (s, 3H), 2.79 (q, J=7.5 Hz, 2H), 5.09 (s, 2H), 5.47 (br s, 3H), 6.90 (dd, J=8.2, 1.1 Hz, 1H), 7.00-7.14 (m, 4H), 7.24 (d, J=7.9 Hz, 1H), 7.32 (ddd, J=8.4, 7.0, 1.6 Hz, 1H), 7.70 (dd, J=7.9, 1.6 Hz, 1H).

[step 2] The title compound (compound 121, 96 mg, 90%) was obtained in the same manner as in step 3 of Example 1, using (Z)-[8-(7-chloro-2-ethyl-5-methyl-3H-imidazo[4,5-b]pyridin-3-yl)methyl-6,11-dihydrodibenzo[b,e]oxepin-11-ylidene]acetonitrile (94 mg, 0.21 mmol) obtained in step 1.

ESI-MS m/z: 500 $(M+H)^+$; $^1$H-NMR ($CDCl_3$, δ): 1.34 (t, J=7.5 Hz, 3H), 2.60 (s, 3H), 2.77 (q, J=7.5 Hz, 2H), 5.14 (br s, 2H), 5.46 (s, 2H), 6.31 (s, 1H), 6.91-7.03 (m, 3H), 7.09-7.18 (m, 3H), 7.29-7.35 (m, 2H).

Example 122

(Z)-8-(2-cyclopropyl-5,7-dimethyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 122)

[step 1] (Z)-[8-(2-Cyclopropyl-5,7-dimethyl-3H-imidazo[4,5-b]pyridin-3-yl)methyl-6,11-dihydrodibenzo[b,e]oxepin-11-ylidene]acetonitrile (126 mg, 34%) was obtained in the same manner as in step 1 of Example 118, using 2-cyclopropyl-5,7-dimethyl-3H-imidazo[4,5-b]pyridine (159 mg, 0.85 mmol) instead of 2-ethyl-5,7-dimethyl-3H-imidazo[4,5-b]pyridine.

ESI-MS m/z: 433 $(M+H)^+$; $^1$H-NMR ($CDCl_3$, δ): 0.95-1.01 (m, 2H), 1.14-1.19 (m, 2H), 1.81 (tt, J=8.2, 5.0 Hz, 1H), 2.56 (s, 3H), 2.58 (s, 3H), 5.09 (s, 2H), 5.46 (s, 1H), 5.57 (s, 2H), 6.87 (s, 1H), 6.90 (dd, J=8.3, 1.0 Hz, 1H), 7.00-7.05 (m, 1H), 7.15 (s, 1H), 7.19 (dd, J=7.9, 1.7 Hz, 1H), 7.23 (d, J=7.9 Hz, 1H), 7.28-7.34 (m, 1H), 7.70 (dd, J=7.9, 1.5 Hz, 1H).

[step 2] The title compound (compound 122, 117 mg, 82%) was obtained in the same manner as in step 3 of Example 1, using (Z)-[8-(2-cyclopropyl-5,7-dimethyl-3H-imidazo[4,5-b]pyridin-3-yl)methyl-6,11-dihydrodibenzo[b,e]oxepin-11-ylidene]acetonitrile (126 mg, 0.29 mmol) obtained in step 1.

ESI-MS m/z: 492 $(M+H)^+$; $^1$H-NMR ($CDCl_3$, δ): 0.95-1.01 (m, 2H), 1.13-1.19 (m, 2H), 1.76-1.87 (m, 1H), 2.56 (s, 3H), 2.57 (s, 3H), 5.13 (br s, 2H), 5.56 (s, 2H), 6.30 (s, 1H), 6.87 (s, 1H), 6.93-7.00 (m, 2H), 7.10-7.13 (m, 2H), 7.21-7.36 (m, 3H).

Example 123

(Z)-8-(2-cyclopropyl-7-methyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 123)

[step 1] (Z)-[8-(2-Cyclopropyl-7-methyl-3H-imidazo[4,5-b]pyridin-3-yl)methyl-6,11-dihydrodibenzo[b,e]oxepin-11-ylidene]acetonitrile (104 mg, 21%) was obtained in the same manner as in step 1 of Example 118, using 2-cyclopropyl-7-methyl-3H-imidazo[4,5-b]pyridine (203 mg, 1.17 mmol) instead of 2-ethyl-5,7-dimethyl-3H-imidazo[4,5-b]pyridine.

ESI-MS m/z: 419 $(M+H)^+$; $^1$H-NMR ($CDCl_3$, δ): 1.00-1.07 (m, 2H), 1.19-1.29 (m, 2H), 1.85-1.90 (m, 1H), 2.64 (s, 3H), 5.09 (s, 2H), 5.45 (s, 1H), 5.59 (s, 2H), 6.89 (dd, J=8.3, 1.2 Hz, 1H), 7.01-7.03 (m, 2H), 7.17-7.34 (m, 4H), 7.69 (dd, J=7.8, 1.7 Hz, 1H), 8.16 (d, J=5.0 Hz, 1H).

[step 2] The title compound (compound 123, 89 mg, 75%) was obtained in the same manner as in step 3 of Example 1, using (Z)-[8-(2-cyclopropyl-7-methyl-3H-imidazo[4,5-b]pyridin-3-yl)methyl-6,11-dihydrodibenzo[b,e]oxepin-11-ylidene]acetonitrile (103 mg, 0.25 mmol) obtained in step 1.

ESI-MS m/z: 478 $(M+H)^+$; $^1$H-NMR ($CDCl_3$, δ): 1.00-1.07 (m, 2H), 1.19-1.24 (m, 2H), 1.83-1.92 (m, 1H), 2.62 (s, 3H), 5.04 (br s, 2H), 5.57 (s, 2H), 6.22 (s, 1H), 6.89-7.00 (m, 3H), 7.08-7.11 (m, 2H), 7.22 (dd, J=7.8, 1.7 Hz, 1H), 7.27-7.34 (m, 2H), 8.05 (d, J=5.1 Hz, 1H).

Example 124

(Z)-8-(2-ethoxy-5,7-dimethyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 124)

[step 1] (Z)-[8-(2-Ethoxy-5,7-dimethyl-3H-imidazo[4,5-b]pyridin-3-yl)methyl-6,11-dihydrodibenzo[b,e]oxepin-11-ylidene]acetonitrile (450 mg, 49%) was obtained in the same manner as in step 1 of Example 118, using 2-ethoxy-5,7-dimethyl-3H-imidazo[4,5-b]pyridine (400 mg, 2.09 mmol) instead of 2-ethyl-5,7-dimethyl-3H-imidazo[4,5-b]pyridine.

ESI-MS m/z: 437 $(M+H)^+$; $^1$H-NMR ($CDCl_3$, δ): 1.42 (t, J=7.2 Hz, 3H), 2.50 (s, 3H), 2.54 (s, 3H), 4.58 (q, J=7.2 Hz, 2H), 5.10 (s, 2H), 5.23 (s, 2H), 5.45 (s, 1H), 6.80 (s, 1H), 6.89 (dd, J=8.3, 1.3 Hz, 1H), 7.02 (ddd, J=8.3, 6.9, 1.0 Hz, 1H), 7.21 (d, J=7.6 Hz, 1H), 7.27-7.35 (m, 3H), 7.69 (dd, J=7.9, 1.7 Hz, 1H).

[step 2] The title compound (compound 124, 353 mg, 70%) was obtained in the same manner as in step 3 of Example 1, using (Z)-[8-(2-ethoxy-5,7-dimethyl-3H-imidazo[4,5-b]pyridin-3-yl)methyl-6,11-dihydrodibenzo[b,e]oxepin-11-ylidene]acetonitrile (442 mg, 1.01 mmol) obtained in step 1.

ESI-MS m/z: 496 $(M+H)^+$; $^1$H-NMR ($CDCl_3$, δ): 1.42 (t, J=7.1 Hz, 3H), 2.49 (s, 3H), 2.52 (s, 3H), 4.56 (q, J=7.1 Hz, 2H), 5.15 (br s, 2H), 5.23 (s, 2H), 6.23 (s, 1H), 6.80 (s, 1H), 6.88-6.94 (m, 2H), 7.10 (dd, J=7.9, 1.6 Hz, 1H), 7.25-7.35 (m, 4H).

Example 125

(Z)-8-(2-ethoxy-7-methyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 125)

[step 1] (Z)-[8-(2-Ethoxy-7-methyl-3H-imidazo[4,5-b]pyridin-3-yl)methyl-6,11-dihydrodibenzo[b,e]oxepin-11-ylidene]acetonitrile (374 mg, 26%) was obtained in the same manner as in step 1 of Example 118, using 2-ethoxy-7-methyl-3H-imidazo[4,5-b]pyridine (592 mg, 3.34 mmol) instead of 2-ethyl-5,7-dimethyl-3H-imidazo[4,5-b]pyridine.

ESI-MS m/z: 423 $(M+H)^+$; $^1$H-NMR ($CDCl_3$, δ): 1.46 (t, J=7.1 Hz, 3H), 2.55 (s, 3H), 4.63 (q, J=7.1 Hz, 2H), 5.10 (s, 2H), 5.26 (s, 2H), 5.45 (s, 1H), 6.87-7.04 (m, 3H), 7.21-7.36 (m, 4H), 7.69 (dd, J=7.9, 1.3 Hz, 1H), 8.03 (d, J=5.3 Hz, 1H).

[step 2] The title compound (compound 125, 268 mg, 64%) was obtained in the same manner as in step 3 of Example 1, using (Z)-[8-(2-ethoxy-7-methyl-3H-imidazo[4,5-b]pyridin-3-yl)methyl-6,11-dihydrodibenzo[b,e]oxepin-11-ylidene]acetonitrile (369 mg, 0.88 mmol) obtained in step 1.

ESI-MS m/z: 482 $(M+H)^+$; $^1$H-NMR ($CDCl_3$, δ): 1.45 (t, J=7.1 Hz, 3H), 2.55 (s, 3H), 4.62 (q, J=7.1 Hz, 2H), 5.08 (br s, 2H), 5.25 (s, 2H), 6.25 (s, 1H), 6.91-6.99 (m, 3H), 7.09 (dd, J=7.7, 1.8 Hz, 1H), 7.24 (d, J=1.1 Hz, 1H), 7.29-7.37 (m, 3H), 7.96 (d, J=5.1 Hz, 1H).

Example 126

(Z)-8-(7-chloro-2-ethyl-3H-imidazo[4,5-b]pyridin-3-yl)methyl-11-(5-oxo-4,5-dihydro-1,2,4-oxadiazol-3-yl)methylene-6,11-dihydrodibenzo[b,e]oxepine (Compound 126)

[step 1] (Z)-[8-(7-Chloro-2-ethyl-3H-imidazo[4,5-b]pyridin-3-yl)methyl-6,11-dihydrodibenzo[b,e]oxepin-11- ylidene]acetonitrile (177 mg, 36%) was obtained in the same manner as in step 1 of Example 118, using 7-chloro-2-ethyl-3H-imidazo[4,5-b]pyridine (209 mg, 1.15 mmol) instead of 2-ethyl-5,7-dimethyl-3H-imidazo[4,5-b]pyridine.

ESI-MS m/z: 427 $(M+H)^+$; $^1$H-NMR ($CDCl_3$, δ): 1.39 (t, J=7.5 Hz, 3H), 2.85 (q, J=7.5 Hz, 2H), 5.09 (s, 2H), 5.46 (s, 1H), 5.50 (s, 2H), 6.90 (dd, J=8.3, 1.0 Hz, 1H), 7.03 (ddd, J=8.2, 7.0, 1.0 Hz, 1H), 7.09-7.15 (m, 2H), 7.23-7.34 (m, 3H), 7.70 (dd, J=7.9, 1.5 Hz, 1H), 8.22 (d, J=5.3 Hz, 1H).

[step 2] The title compound (compound 126, 127 mg, 77%) was obtained in the same manner as in step 3 of Example 1, using (Z)-[8-(7-chloro-2-ethyl-3H-imidazo[4,5-b]pyridin-3-yl)methyl-6,11-dihydrodibenzo[b,e]oxepin-11-ylidene]acetonitrile (146 mg, 0.34 mmol) obtained in step 1.

ESI-MS m/z: 486 $(M+H)^+$; $^1$H-NMR ($CDCl_3$, δ): 1.38 (t, J=7.5 Hz, 3H), 2.84 (q, J=7.5 Hz, 2H), 5.12 (br s, 2H), 5.49 (s, 2H), 6.30 (s, 1H), 6.92-7.00 (m, 2H), 7.05 (d, J=1.5 Hz, 1H), 7.10 (dd, J=7.8, 1.7 Hz, 1H), 7.17 (dd, J=7.8, 1.7 Hz, 1H), 7.25-7.35 (m, 3H), 8.20 (d, J=5.3 Hz, 1H).

Example 127

(Z)-8-(2-ethyl-5,7-dimethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 127)

[step 1] (Z)-2-[8-(2-Ethyl-5,7-dimethyl-3H-imidazo[4,5-b]pyridin-3-yl)methyl-6,11-dihydrodibenzo[b,e]oxepin-11-ylidene]propiononitrile (158 mg, 57%) was obtained in the same manner as in step 1 of Example 104, using (Z)-2-(8-hydroxymethyl-6,11-dihydrodibenzo[b,e]oxepin-11-ylidene)propiononitrile (178 mg, 0.64 mmol) obtained in Reference Example 31 and 2-ethyl-5,7-dimethyl-3H-imidazo[4,5-b]pyridine (169 mg, 0.96 mmol).

ESI-MS m/z: 435 $(M+H)^+$; $^1$H-NMR ($CDCl_3$, δ): 1.32 (t, J=7.5 Hz, 3H), 1.98 (s, 3H), 2.58 (s, 3H), 2.64 (s, 3H), 2.77 (q, J=7.5 Hz, 2H), 4.73 (d, J=12.6 Hz, 1H), 5.41 (d, J=12.6 Hz, 1H), 5.46 (s, 2H), 6.80 (dd, J=8.3, 1.2 Hz, 1H), 6.91 (s, 1H), 6.95 (td, J=7.6, 1.2 Hz, 1H), 7.07-7.14 (m, 2H), 7.16 (s, 1H), 7.21-7.27 (m, 1H), 7.49 (dd, J=7.9, 1.6 Hz, 1H).

[step 2] The title compound (compound 127, 85 mg, 56%) was obtained in the same manner as in step 3 of Example 1, using (Z)-2-[8-(2-ethyl-5,7-dimethyl-3H-imidazo[4,5-b]pyridin-3-yl)methyl-6,11-dihydrodibenzo[b,e]oxepin-11-ylidene]propiononitrile (133 mg, 0.31 mmol) obtained in step 1.

ESI-MS m/z: 494 $(M+H)^+$; $^1$H-NMR ($CDCl_3$, δ): 1.23 (t, J=7.5 Hz, 3H), 2.06 (s, 3H), 2.54 (s, 3H), 2.58 (s, 3H), 2.68 (q, J=7.5 Hz, 2H), 4.51 (d, J=12.6 Hz, 1H), 5.28 (d, J=12.6 Hz, 1H), 5.44 (s, 2H), 6.65 (dd, J=8.3, 1.1 Hz, 1H), 6.80 (td, J=7.5, 1.1 Hz, 1H), 6.90 (s, 1H), 7.01 (dd, J=7.8, 1.7 Hz, 1H), 7.06 (s, 1H), 7.11-7.15 (m, 1H), 7.17 (br s, 2H).

Example 128

(Z)-8-(2-ethyl-7-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 128)

[step 1] (Z)-2-[8-(2-Ethyl-7-methyl-3H-imidazo[4,5-b]pyridin-3-yl)methyl-6,11-dihydrodibenzo[b,e]oxepin-11-ylidene]propiononitrile (181 mg, 18%) was obtained in the same manner as in step 1 of Example 127, using 2-ethyl-7-methyl-3H-imidazo[4,5-b]pyridine (392 mg, 2.43 mmol) instead of 2-ethyl-5,7-dimethyl-3H-imidazo[4,5-b]pyridine.

ESI-MS m/z: 421 $(M+H)^+$; $^1$H-NMR ($CDCl_3$, δ): 1.35 (t, J=7.6 Hz, 3H), 1.98 (s, 3H), 2.70 (s, 3H), 2.83 (q, J=7.5 Hz, 2H), 4.73 (d, J=12.7 Hz, 1H), 5.40 (d, J=12.7 Hz, 1H), 5.49 (s, 2H), 6.79 (dd, J=8.3, 1.1 Hz, 1H), 6.92-7.27 (m, 6H), 7.48 (dd, J=7.8, 1.7 Hz, 1H), 8.20 (d, J=5.0 Hz, 1H).

[step 2] The title compound (compound 128, 118 mg, 67%) was obtained in the same manner as in step 3 of Example 1, using (Z)-2-[8-(2-ethyl-7-methyl-3H-imidazo[4,5-b]pyridin-3-yl)methyl-6,11-dihydrodibenzo[b,e]oxepin-11-ylidene]propiononitrile (153 mg, 0.36 mmol) obtained in step 1.

ESI-MS m/z: 480 $(M+H)^+$; $^1$H-NMR ($CDCl_3$, δ): 1.35 (t, J=7.6 Hz, 3H), 2.08 (s, 3H), 2.68 (s, 3H), 2.83 (q, J=7.6 Hz, 2H), 4.74 (d, J=12.7 Hz, 1H), 5.46 (d, J=12.7 Hz, 1H), 5.49 (s, 2H), 6.81-6.91 (m, 2H), 6.99 (dd, J=7.6, 1.6 Hz, 1H), 7.04 (dd, J=4.9, 0.8 Hz, 1H), 7.15-7.29 (m, 4H), 8.20 (d, J=4.8 Hz, 1H).

Example 129

(Z)-8-(7-chloro-2-ethyl-5-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 129)

[step 1] (Z)-2-[8-(7-Chloro-2-ethyl-5-methyl-3H-imidazo[4,5-b]pyridin-3-yl)methyl-6,11-dihydrodibenzo[b,e]oxepin-11-ylidene]propiononitrile (374 mg, 51%) was obtained in the same manner as in step 1 of Example 127, using 7-chloro-2-ethyl-5-methyl-3H-imidazo[4,5-b]pyridine (317 mg, 1.62 mmol) instead of 2-ethyl-5,7-dimethyl-3H-imidazo[4,5-b]pyridine.

ESI-MS m/z: 455 $(M+H)^+$; $^1$H-NMR ($CDCl_3$, δ): 1.35 (t, J=7.5 Hz, 3H), 1.99 (s, 3H), 2.60 (s, 3H), 2.80 (q, J=7.5 Hz, 2H), 4.74 (d, J=12.6 Hz, 1H), 5.42 (d, J=12.6 Hz, 1H), 5.47 (s, 2H), 6.81 (dd, J=8.3, 1.2 Hz, 1H), 6.93-6.98 (m, 1H), 7.11-7.13 (m, 3H), 7.17 (s, 1H), 7.22-7.29 (m, 1H), 7.49 (dd, J=7.8, 1.7 Hz, 1H).

[step 2] The title compound (compound 129, 283 mg, 75%) was obtained in the same manner as in step 3 of Example 1, using (Z)-2-[8-(7-chloro-2-ethyl-5-methyl-3H-imidazo[4,5-b]pyridin-3-yl)methyl-6,11-dihydrodibenzo[b,e]oxepin-11-ylidene]propiononitrile (334 mg, 0.73 mmol) obtained in step 1.

ESI-MS m/z: 514 $(M+H)^+$; $^1$H-NMR ($CDCl_3$, δ): 1.34 (t, J=7.5 Hz, 3H), 2.10 (s, 3H), 2.61 (s, 3H), 2.79 (q, J=7.6 Hz, 2H), 4.76 (d, J=12.8 Hz, 1H), 5.47 (s, 2H), 5.48 (d, J=10.8 Hz, 1H), 6.82-6.92 (m, 2H), 7.00 (dd, J=7.7, 1.6 Hz, 1H), 7.13-7.30 (m, 5H).

Example 130

(Z)-8-(2-cyclopropyl-5,7-dimethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 130)

[step 1] (Z)-2-[8-(2-Cyclopropyl-5,7-dimethyl-3H-imidazo[4,5-b]pyridin-3-yl)methyl-6,11-dihydrodibenzo[b,e]oxepin-11-ylidene]propiononitrile (241 mg, 33%) was obtained in the same manner as in step 1 of Example 127, using 2-cyclopropyl-5,7-dimethyl-3H-imidazo[4,5-b]pyridine (304 mg, 1.62 mmol) instead of 2-ethyl-5,7-dimethyl-3H-imidazo[4,5-b]pyridine.

ESI-MS m/z: 447 $(M+H)^+$; $^1$H-NMR ($CDCl_3$, δ): 0.94-1.00 (m, 2H), 1.13-1.18 (m, 2H), 1.77-1.86 (m, 1H), 1.99 (s, 3H), 2.57 (s, 3H), 2.58 (d, J=0.5 Hz, 3H), 4.74 (d, J=12.8 Hz,

1H), 5.42 (d, J=12.8 Hz, 1H), 5.57 (s, 2H), 6.80 (dd, J=8.3, 1.0 Hz, 1H), 6.88 (s, 1H), 6.92-6.98 (m, 1H), 7.10 (d, J=7.9 Hz, 1H), 7.17-7.28 (m, 3H), 7.49 (dd, J=7.9, 1.5 Hz, 1H).

[step 2] The title compound (compound 130, 191 mg, 85%) was obtained in the same manner as in step 3 of Example 1, using (Z)-2-[8-(2-cyclopropyl-5,7-dimethyl-3H-imidazo[4,5-b]pyridin-3-yl)methyl-6,11-dihydrodibenzo[b,e]oxepin-11-ylidene]propiononitrile (200 mg, 0.45 mmol) obtained in step 1.

ESI-MS m/z: 506 (M+H)$^+$; $^1$H-NMR ($CDCl_3$, δ): 0.93-0.99 (m, 2H), 1.12-1.17 (m, 2H), 1.77-1.86 (m, 1H), 2.10 (s, 3H), 2.57 (d, J=0.5 Hz, 3H), 2.57 (s, 3H), 4.74 (d, J=12.8 Hz, 1H), 5.45 (d, J=12.5 Hz, 1H), 5.57 (s, 2H), 6.82-6.91 (m, 3H), 7.01 (dd, J=7.7, 1.6 Hz, 1H), 7.17-7.29 (m, 4H).

Example 131

(Z)-8-(2-cyclopropyl-7-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 131)

[step 1] (Z)-2-[8-(2-Cyclopropyl-7-methyl-3H-imidazo[4,5-b]pyridin-3-yl)methyl-6,11-dihydrodibenzo[b,e]oxepin-11-ylidene]propiononitrile (205 mg, 19%) was obtained in the same manner as in step 1 of Example 127, using 2-cyclopropyl-7-methyl-3H-imidazo[4,5-b]pyridine (422 mg, 2.43 mmol) instead of 2-ethyl-5,7-dimethyl-3H-imidazo[4,5-b]pyridine.

ESI-MS m/z: 433 (M+H)$^+$; $^1$H-NMR ($CDCl_3$, δ): 0.99-1.06 (m, 2H), 1.18-1.24 (m, 2H), 1.84-1.93 (m, 1H), 1.98 (s, 3H), 2.64 (s, 3H), 4.74 (d, J=12.7 Hz, 1H), 5.41 (d, J=12.9 Hz, 1H), 5.60 (s, 2H), 6.80 (dd, J=8.3, 1.0 Hz, 1H), 6.92-7.02 (m, 2H), 7.10 (d, J=7.8 Hz, 1H), 7.18-7.28 (m, 3H), 7.48 (dd, J=7.8, 1.7 Hz, 1H), 8.16 (d, J=4.8 Hz, 1H).

[step 2] The title compound (compound 131, 104 mg, 56%) was obtained in the same manner as in step 3 of Example 1, using (Z)-2-[8-(2-cyclopropyl-7-methyl-3H-imidazo[4,5-b]pyridin-3-yl)methyl-6,11-dihydrodibenzo[b,e]oxepin-11-ylidene]propiononitrile (164 mg, 0.38 mmol) obtained in step 1.

ESI-MS m/z: 492 (M+H)$^+$; $^1$H-NMR ($CDCl_3$, δ): 1.01-1.06 (m, 2H), 1.19-1.23 (m, 2H), 1.85-1.96 (m, 1H), 2.09 (s, 3H), 2.63 (s, 3H), 4.76 (d, J=12.6 Hz, 1H), 5.47 (d, J=12.8 Hz, 1H), 5.60 (s, 2H), 6.82-6.91 (m, 2H), 6.98-7.01 (m, 2H), 7.18-7.29 (m, 4H), 8.16 (d, J=4.9 Hz, 1H).

Example 132

(Z)-8-(2-ethoxy-5,7-dimethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 132)

[step 1] (Z)-2-[8-(2-Ethoxy-5,7-dimethyl-3H-imidazo[4,5-b]pyridin-3-yl)methyl-6,11-dihydrodibenzo[b,e]oxepin-11-ylidene]propiononitrile (454 mg, 47%) was obtained in the same manner as in step 1 of Example 127, using 2-ethoxy-5,7-dimethyl-3H-imidazo[4,5-b]pyridine (414 mg, 2.16 mmol) instead of 2-ethyl-5,7-dimethyl-3H-imidazo[4,5-b]pyridine.

ESI-MS m/z: 451 (M+H)$^+$; $^1$H-NMR ($CDCl_3$, δ): 1.41 (t, J=7.1 Hz, 3H), 1.99 (s, 3H), 2.50 (s, 3H), 2.54 (s, 3H), 4.58 (q, J=7.1 Hz, 2H), 4.77 (d, J=12.5 Hz, 1H), 5.23 (s, 2H), 5.42 (d, J=12.6 Hz, 1H), 6.78-6.81 (m, 2H), 6.94 (td, J=7.6, 1.1 Hz, 1H), 7.09 (d, J=7.7 Hz, 1H), 7.20-7.26 (m, 1H), 7.31-7.37 (m, 2H), 7.48 (dd, J=7.9, 1.6 Hz, 1H).

[step 2] The title compound (compound 132, 311 mg, 60%) was obtained in the same manner as in step 3 of Example 1, using (Z)-2-[8-(2-ethoxy-5,7-dimethyl-3H-imidazo[4,5-b]pyridin-3-yl)methyl-6,11-dihydrodibenzo[b,e]oxepin-11-ylidene]propiononitrile (454 mg, 1.01 mmol) obtained in step 1.

ESI-MS m/z: 510 (M+H)$^+$; $^1$H-NMR ($CDCl_3$, δ): 1.41 (t, J=7.1 Hz, 3H), 2.10 (s, 3H), 2.49 (s, 3H), 2.54 (s, 3H), 4.56 (q, J=7.1 Hz, 2H), 4.78 (d, J=12.5 Hz, 1H), 5.23 (s, 2H), 5.48 (d, J=12.5 Hz, 1H), 6.80-6.91 (m, 3H), 6.99 (dd, J=7.7, 1.8 Hz, 1H), 7.16-7.28 (m, 2H), 7.35-7.38 (m, 2H).

Example 133

(Z)-8-(2-ethoxy-7-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 133)

[step 1] (Z)-2-[8-(2-Ethoxy-7-methyl-3H-imidazo[4,5-b]pyridin-3-yl)methyl-6,11-dihydrodibenzo[b,e]oxepin-11-ylidene]propiononitrile (329 mg, 25%) was obtained in the same manner as in step 1 of Example 127, using 2-ethoxy-7-methyl-3H-imidazo[4,5-b]pyridine (579 mg, 3.03 mmol) instead of 2-ethyl-5,7-dimethyl-3H-imidazo[4,5-b]pyridine.

ESI-MS m/z: 437 (M+H)$^+$; $^1$H-NMR ($CDCl_3$, δ): 1.45 (t, J=7.1 Hz, 3H), 1.99 (s, 3H), 2.56 (s, 3H), 4.63 (q, J=7.1 Hz, 2H), 4.77 (d, J=12.8 Hz, 1H), 5.26 (s, 2H), 5.42 (d, J=12.6 Hz, 1H), 6.79 (dd, J=8.3, 1.2 Hz, 1H), 6.91-6.97 (m, 2H), 7.09 (d, J=7.7 Hz, 1H), 7.16-7.53 (m, 4H), 8.04 (d, J=5.1 Hz, 1H).

[step 2] The title compound (compound 133, 216 mg, 58%) was obtained in the same manner as in step 3 of Example 1, using (Z)-2-[8-(2-ethoxy-7-methyl-3H-imidazo[4,5-b]pyridin-3-yl)methyl-6,11-dihydrodibenzo[b,e]oxepin-11-ylidene]propiononitrile (329 mg, 0.75 mmol) obtained in step, 1.

ESI-MS m/z: 496 (M+H)$^+$; $^1$H-NMR ($CDCl_3$, δ): 1.45 (t, J=7.1 Hz, 3H), 2.09 (s, 3H), 2.55 (s, 3H), 4.62 (q, J=7.2 Hz, 2H), 4.78 (d, J=12.8 Hz, 1H), 5.26 (s, 2H), 5.48 (d, J=12.5 Hz, 1H), 6.81-7.00 (m, 4H), 7.17-7.28 (m, 2H), 7.35-7.38 (m, 2H), 8.03 (d, J=5.1 Hz, 1H).

Example 134

(Z)-8-(2-ethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 134)

[step 1] (Z)-2-[8-(2-Ethyl-3H-imidazo[4,5-b]pyridin-3-yl)methyl-6,11-dihydrodibenzo[b,e]oxepin-11-ylidene]propiononitrile (659 mg, 41%) was obtained in the same manner as in step 1 of Example 127, using 2-ethyl-3H-imidazo[4,5-b]pyridine (584 mg, 3.97 mmol) instead of 2-ethyl-5,7-dimethyl-3H-imidazo[4,5-b]pyridine.

ESI-MS m/z: 407 (M+H)$^+$; $^1$H-NMR ($CDCl_3$, δ): 1.41 (t, J=7.5 Hz, 3H), 1.99 (s, 3H), 2.83 (q, J=7.5 Hz, 2H), 4.74 (d, J=12.8 Hz, 1H), 5.42 (d, J=12.8 Hz, 1H), 5.50 (s, 2H), 6.80 (dd, J=8.4, 1.1 Hz, 1H), 6.92-6.98 (m, 1H), 7.09-7.16 (m, 2H), 7.20-7.26 (m, 3H), 7.49 (dd, J=7.9, 1.6 Hz, 1H), 8.04 (dd, J=8.1, 1.5 Hz, 1H), 8.34 (dd, J=4.8, 1.5 Hz, 1H).

[step 2] The title compound (compound 134, 385 mg, 75%) was obtained in the same manner as in step 3 of Example 1, using (Z)-2-[8-(2-ethyl-3H-imidazo[4,5-b]pyridin-3-yl)methyl-6,11-dihydrodibenzo[b,e]oxepin-11-ylidene]propiononitrile (448 mg, 1.10 mmol) obtained in step 1.

ESI-MS m/z: 466 $(M+H)^+$; $^1$H-NMR ($CDCl_3$, δ): 1.39 (t, J=7.5 Hz, 3H), 2.09 (s, 3H), 2.82 (q, J=7.5 Hz, 2H), 4.72 (d, J=12.8 Hz, 1H), 5.45 (d, J=12.8 Hz, 1H), 5.50 (s, 2H), 6.80 (d, J=8.4 Hz, 1H), 6.87 (t, J=7.7 Hz, 1H), 7.00 (dd, J=7.7, 1.5 Hz, 1H), 7.16-7.26 (m, 5H), 8.01 (d, J=7.7 Hz, 1H), 8.34 (d, J=4.8 Hz, 1H).

Example 135

(Z)-8-(2-ethoxy-3H-imidazo[4,5-b]pyridin-3-yl) methyl-11-[1-(5-oxo-4,5-dihydro-1,2,4-oxadiazol-3-yl)ethylidene]-6,11-dihydrodibenzo[b,e]oxepine (Compound 135)

[step 1] (Z)-2-[8-(2-Ethoxy-3H-imidazo[4,5-b]pyridin-3-yl)methyl-6,11-dihydrodibenzo[b,e]oxepin-11-ylidene]propiononitrile (387 mg, 29%) was obtained in the same manner as in step 1 of Example 127, using 2-ethoxy-3H-imidazo[4,5-b]pyridine (518 mg, 3.17 mmol) instead of 2-ethyl-5,7-dimethyl-3H-imidazo[4,5-b]pyridine.

ESI-MS m/z: 423 $(M+H)^+$; $^1$H-NMR ($CDCl_3$, δ): 1.47 (t, J=7.1 Hz, 3H), 1.99 (s, 3H), 4.63 (q, J=7.1 Hz, 2H), 4.78 (d, J=12.6 Hz, 1H), 5.28 (s, 2H), 5.43 (d, J=12.6 Hz, 1H), 6.80 (dd, J=25=8.3, 1.2 Hz, 1H), 6.92-6.97 (m, 1H), 7.10-7.15 (m, 2H), 7.20-7.26 (m, 1H), 7.35-7.41 (m, 2H), 7.48 (dd, J=7.8, 1.7 Hz, 1H), 7.76 (dd, J=7.8, 1.4 Hz, 1H), 8.17 (dd, J=5.0, 1.4 Hz, 1H).

[step 2] The title compound (compound 135, 324 mg, 73%) was obtained in the same manner as in step 3 of Example 1, using (Z)-2-[8-(2-ethoxy-3H-imidazo[4,5-b]pyridin-3-yl) methyl-6,11-dihydrodibenzo[b,e]oxepin-11-ylidene]propiononitrile (380 mg, 0.92 mmol) obtained in step 1.

ESI-MS m/z: 482 $(M+H)^+$; $^1$H-NMR ($CDCl_3$, δ): 1.47 (t, J=7.1 Hz, 3H), 2.10 (s, 3H), 4.62 (q, J=7.1 Hz, 2H), 4.80 (d, J=12.8 Hz, 1H), 5.28 (s, 2H), 5.50 (d, J=12.8 Hz, 1H), 6.81-6.89 (m, 2H), 6.99 (dd, J=7.9, 1.6 Hz, 1H), 7.13 (dd, J=7.9, 4.9 Hz, 1H), 7.18-7.27 (m, 2H), 7.38-7.40 (m, 2H), 7.75 (dd, J=7.9, 1.3 Hz, 1H), 8.17 (dd, J=4.9, 1.3 Hz, 1H).

Example 136

(Z)-8-(2-cyclopropyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 136)

[step 1] (Z)-2-[8-(2-Cyclopropyl-3H-imidazo[4,5-b]pyridin-3-yl)methyl-6,11-dihydrodibenzo[b,e]oxepin-11-ylidene]propiononitrile (402 mg, 30%) was obtained in the same manner as in step 1 of Example 127, using 2-cyclopropyl-3H-imidazo[4,5-b]pyridine (505 mg, 3.17 mmol) instead of 2-ethyl-5,7-dimethyl-3H-imidazo[4,5-b]pyridine.

ESI-MS m/z: 419 $(M+H)^+$; $^1$H-NMR ($CDCl_3$, δ): 1.05-1.09 (m, 2H), 1.23-1.28 (m, 2H), 1.88-1.96 (m, 1H), 1.99 (s, 3H), 4.76 (d, J=12.6 Hz, 1H), 5.43 (d, J=12.6 Hz, 1H), 5.62 (s, 2H), 6.80 (dd, J=8.3, 1.2 Hz, 1H), 6.93-6.98 (m, 1H), 7.12 (J, J=7.9 Hz, 1H), 7.19-7.28 (m, 4H), 7.49 (dd, J=7.8, 1.7 Hz, 1H), 7.94 (dd, J=8.0, 1.4 Hz, 1H), 8.31 (dd, J=4.9, 1.4 Hz, 1H).

[step 2] The title compound (compound 136, 377 mg, 82%) was obtained in the same manner as in step 3 of Example 1, using (Z)-2-[8-(2-cyclopropyl-3H-imidazo[4,5-b]pyridin-3-yl)methyl-6,11-dihydrodibenzo[b,e]oxepin-11-ylidene]propiononitrile (400 mg, 0.96 mmol) obtained in step 1.

ESI-MS m/z: 478 $(M+H)^+$; $^1$H-NMR ($CDCl_3$, δ): 1.04-1.10 (m, 2H), 1.22-1.28 (m, 2H), 1.88-1.97 (m, 1H), 2.10 (s, 3H), 4.77 (d, J=12.6 Hz, 1H), 5.49 (d, J=12.6 Hz, 1H), 5.62 (s, 2H), 6.83 (dd, J=8.4, 1.1 Hz, 1H), 6.88 (td, J=7.4, 1.1 Hz, 1H), 7.00 (dd, J=7.7, 1.8 Hz, 1H), 7.18-7.28 (m, 5H), 7.93 (dd, J=8.1, 1.5 Hz, 1H), 8.30 (dd, J=4.8, 1.5 Hz, 1H).

Example 137

(Z)-8-(7-chloro-2-ethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 137)

[step 1] (Z)-2-[8-(7-Chloro-2-ethyl-3H-imidazo[4,5-b]pyridin-3-yl)methyl-6,11-dihydrodibenzo[b,e]oxepin-11-ylidene]propiononitrile (442 mg, 41%) was obtained in the same manner as in step 1 of Example 127, using 7-chloro-2-ethyl-3H-imidazo[4,5-b]pyridine (442 mg, 2.43 mmol) instead of 2-ethyl-5,7-dimethyl-3H-imidazo[4,5-b]pyridine.

ESI-MS m/z: 441 $(M+H)^+$; $^1$H-NMR ($CDCl_3$, δ): 1.38 (t, J=7.5 Hz, 3H), 1.98 (s, 3H), 2.86 (q, J=7.5 Hz, 2H), 4.74 (d, J=12.7 Hz, 1H), 5.41 (d, J=12.6 Hz, 1H), 5.50 (s, 2H), 6.80 (dd, J=8.3, 1.2 Hz, 1H), 6.92-6.98 (m, 1H), 7.12-7.30 (m, 5H), 7.49 (dd, J=7.8, 1.7 Hz, 1H), 8.22 (d, J=5.4 Hz, 1H).

[step 2] The title compound (compound 137, 191 mg, 42%) was obtained in the same manner as in step 3 of Example 1, using (Z)-2-[8-(7-chloro-2-ethyl-3H-imidazo[4,5-b]pyridin-3-yl)methyl-6,11-dihydrodibenzo[b,e]oxepin-11-ylidene] propiononitrile (400 mg, 0.91 mmol) obtained in step 1.

ESI-MS m/z: 500 $(M+H)^+$; $^1$H-NMR ($CDCl_3$, δ): 1.27 (t, J=7.4 Hz, 3H), 1.96 (s, 3H), 2.90 (q, J=7.5 Hz, 2H), 4.87 (d, J=12.6 Hz, 1H), 5.56 (s, 2H), 5.59 (d, J=13.7 Hz, 1H), 6.72-6.80 (m, 2H), 6.93 (dd, J=7.7, 1.6 Hz, 1H), 7.13-7.22 (m, 2H), 7.30-7.42 (m, 3H), 8.25 (d, J=5.1 Hz, 1H).

Example 138

(Z)-8-(7-chloro-2-ethoxy-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 138)

[step 1] (Z)-2-[8-(7-Chloro-2-ethoxy-3H-imidazo[4,5-b]pyridin-3-yl)methyl-6,11-dihydrodibenzo[b,e]oxepin-11-ylidene]propiononitrile (40 mg, 32%) was obtained in the same manner as in step 1 of Example 127, using 7-chloro-2-ethoxy-3H-imidazo[4,5-b]pyridine (53 mg, 0.27 mmol) instead of 2-ethyl-5,7-dimethyl-3H-imidazo[4,5-b]pyridine.

ESI-MS m/z: 457 $(M+H)^+$; $^1$H-NMR ($CDCl_3$, δ): 1.47 (t, J=7.2 Hz, 3H), 1.99 (s, 3H), 4.70 (q, J=7.2 Hz, 2H), 4.78 (d, J=12.6 Hz, 1H), 5.27 (s, 2H), 5.43 (d, J=12.6 Hz, 1H), 6.80 (dd, J=8.3, 1.0 Hz, 1H), 6.94 (td, J=7.6, 1.1 Hz, 1H), 7.10-7.16 (m, 2H), 7.21-7.23 (m, 1H), 7.33-7.39 (m, 2H), 7.48 (dd, J=7.6, 1.7 Hz, 1H), 8.05 (d, J=5.6 Hz, 1H).

[step 2] The title compound (compound 138, 15 mg, 34%) was obtained in the same manner as in step 3 of Example 1, using (Z)-2-[8-(7-chloro-2-ethoxy-3H-imidazo[4,5-b]pyridin-3-yl)methyl-6,11-dihydrodibenzo[b,e]oxepin-11-ylidene]propiononitrile (39 mg, 0.087 mmol) obtained in step 1.

ESI-MS m/z: 516 $(M+H)^+$; $^1$H-NMR ($CDCl_3$, δ): 1.46 (t, J=7.0 Hz, 3H), 2.09 (s, 3H), 4.66 (q, J=7.0 Hz, 2H), 4.77 (d, J=12.6 Hz, 1H), 5.27 (s, 2H), 5.48 (d, J=12.6 Hz, 1H), 6.78-6.89 (m, 2H), 6.98 (dd, J=7.7, 1.8 Hz, 1H), 7.15 (d, J=5.5 Hz, 1H), 7.19-7.23 (m, 2H), 7.36-7.39 (m, 2H), 8.06 (d, J=5.5 Hz, 1H).

Example 139

(Z)-8-(7-chloro-2-cyclopropyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Compound 139)

[step 1] (Z)-2-[8-(7-Chloro-2-cyclopropyl-3H-imidazo[4,5-b]pyridin-3-yl)methyl-6,11-dihydrodibenzo[b,e]oxepin-11-ylidene]propiononitrile (376 mg, 32%) was obtained in the same manner as in step 1 of Example 127, using 7-chloro-2-cyclopropyl-3H-imidazo[4,5-b]pyridine (494 mg, 2.55 mmol) instead of 2-ethyl-5,7-dimethyl-3H-imidazo[4,5-b]pyridine.

ESI-MS m/z: 453 $(M+H)^+$; $^1$H-NMR ($CDCl_3$, δ): 1.05-1.12 (m, 2H), 1.29-1.34 (m, 2H), 1.87-1.95 (m, 1H), 1.99 (s, 3H), 4.76 (d, J=12.6 Hz, 1H), 5.43 (d, J=12.8 Hz, 1H), 5.60 (s, 2H), 6.80 (dd, J=8.2, 1.1 Hz, 1H), 6.95 (td, J=7.6, 1.0 Hz, 1H), 7.12 (d, J=7.9 Hz, 1H), 7.19-7.27 (m, 4H), 7.49 (dd, J=7.8, 1.7 Hz, 1H), 8.18 (d, J=5.3 Hz, 1H).

[step 2] The title compound (compound 139, 214 mg, 56%) was obtained in the same manner as in step 3 of Example 1, using (Z)-2-[8-(7-chloro-2-cyclopropyl-3H-imidazo[4,5-b]pyridin-3-yl)methyl-6,11-dihydrodibenzo[b,e]oxepin-11-ylidene]propiononitrile (335 mg, 0.74 mmol) obtained in step 1.

ESI-MS m/z: 512 $(M+H)^+$; $^1$H-NMR ($CDCl_3$, δ): 1.04-1.13 (m, 4H), 1.97 (s, 3H), 2.28-2.37 (m, 1H), 4.88 (d, J=12.6 Hz, 1H), 5.61 (d, J=12.3 Hz, 1H), 5.69 (s, 2H), 6.72-6.81 (m, 2H), 6.93 (dd, J=7.8, 1.7 Hz, 1H), 7.14-7.19 (m, 1H), 7.25-7.44 (m, 4H), 8.21 (d, J=5.3 Hz, 1H).

Example 140

(Z)-8-(2-ethyl-4,6-dimethylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 140)

[step 1] (Z)-2-(8-Hydroxymethyl-6,11-dihydrodibenzo[b,e]oxepin-11-ylidene)propiononitrile (150 mg, 0.54 mmol) was dissolved in THF (5.5 mL), and the solution was added with 2,6-lutidine (0.378 mL, 3.25 mmol), lithium bromide (282 mg, 3.25 mmol) and methanesulfonic anhydride (236 mg, 1.35 mmol), followed by stirring at room temperature for 16 hr. Ethyl acetate was added to the mixture, and the organic layer was washed with brine. The organic layer was dried over anhydrous magnesium sulfate, and concentrated under reduced pressure to give a residue. The obtained residue and 2-ethyl-4,6-dimethylbenzimidazole (123 mg, 0.71 mmol) were dissolved in DMF (3.0 mL) and the solution was added with lithium hydroxide (24 mg, 0.98 mmol) at 0° C., followed by stirring at room temperature for 2 hr. Ethyl acetate was added to the mixture, and the organic layer was washed with brine, dried over anhydrous magnesium sulfate, and concentrated under reduced pressure. The residue was purified by silica gel column chromatography (hexane/ethyl acetate=7/3-6/4) to give (Z)-2-[8-(2-ethyl-4,6-dimethylbenzimidazol-1-yl)methyl-6,11-dihydrodibenzo[b,e]oxepin-11-ylidene]propiononitrile (219 mg, 93%).

ESI-MS m/z: 434 $(M+H)^+$; $^1$H-NMR ($CDCl_3$, δ): 1.34 (t, J=7.6 Hz, 3H), 1.99 (s, 3H), 2.38 (s, 3H), 2.65 (s, 3H), 2.84 (q, J=7.6 Hz, 2H), 4.74 (d, J=12.5 Hz, 1H), 5.30 (s, 2H), 5.42 (d, J=12.5 Hz, 1H), 6.78-6.83 (m, 2H), 6.89 (s, 1H), 6.93-7.01 (m, 2H), 7.09-7.11 (m, 2H), 7.22-7.28 (m, 1H), 7.49 (dd, J=7.6, 1.6 Hz, 1H).

[step 2] The title compound (compound 140, 38 mg, 15%) was obtained in the same manner as in step 3 of Example 1, using (Z)-2-[8-(2-ethyl-4,6-dimethylbenzimidazol-1-yl)methyl-6,11-dihydrodibenzo[b,e]oxepin-11-ylidene]propiononitrile (217 mg, 0.50 mmol) obtained in step 1.

ESI-MS m/z: 493 $(M+H)^+$; $^1$H-NMR (DMSO-$d_6$, δ): 1.24 (t, J=7.4 Hz, 3H), 1.95 (s, 3H), 2.31 (s, 3H), 2.47 (s, 3H), 2.79 (q, J=7.4 Hz, 2H), 4.86 (d, J=12.6 Hz, 1H), 5.45 (s, 2H), 5.59 (d, J=12.6 Hz, 1H), 6.70-6.80 (m, 3H), 6.91 (dd, J=7.6, 1.7 Hz, 1H), 7.00-7.05 (m, 2H), 7.12-7.18 (m, 1H), 7.26 (d, J=1.3 Hz, 1H), 7.30 (d, J=7.9 Hz, 1H).

Example 141

(Z)-8-(4-methyl-2-propylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 141)

[step 1] (Z)-2-[8-(4-Methyl-2-propylbenzimidazol-1-yl)methyl-6,11-dihydrodibenzo[b,e]oxepin-11-ylidene]propiononitrile (301 mg, 74%) was obtained in the same manner as in step 1 of Example 140, using 4-methyl-2-propylbenzimidazole (163 mg, 0.94 mmol) instead of 2-ethyl-4,6-dimethylbenzimidazole.

ESI-MS m/z: 434 $(M+H)^+$; $^1$H-NMR ($CDCl_3$, δ): 0.99 (t, J=7.4 Hz, 3H), 1.77-1.83 (m, 2H), 1.99 (s, 3H), 2.69 (s, 3H), 2.83 (t, J=7.9 Hz, 2H), 4.74 (d, J=12.6 Hz, 1H), 5.35 (s, 2H), 5.41 (d, J=12.6 Hz, 1H), 6.81 (dd, J=8.2, 1.0 Hz, 1H), 6.93-7.12 (m, 7H), 7.23-7.27 (m, 1H), 7.49 (dd, J=7.9, 1.6 Hz, 1H).

[step 2] The title compound (compound 141, 63 mg, 22%) was obtained in the same manner as in step 3 of Example 1, using (Z)-2-[8-(4-methyl-2-propylbenzimidazol-1-yl)methyl-6,11-dihydrodibenzo[b,e]oxepin-11-ylidene]propiononitrile (248 mg, 0.57 mmol) obtained in step 1.

ESI-MS m/z: 493 $(M+H)^+$; $^1$H-NMR (DMSO-$d_6$, δ): 0.91 (t, J=7.5 Hz, 3H), 1.66-1.77 (m, 2H), 1.94 (s, 3H), 2.51 (s, 3H), 2.81 (t, J=7.5 Hz, 2H), 4.85 (d, J=12.5 Hz, 1H), 5.50 (s, 2H), 5.58 (d, J=12.5 Hz, 1H), 6.71-6.78 (m, 2H), 6.91 (dd, J=7.9, 1.6 Hz, 1H), 6.95 (d, J=7.0 Hz, 1H), 6.99-7.08 (m, 2H), 7.12-7.18 (m, 1H), 7.23 (d, J=7.7 Hz, 1H), 7.28-7.31 (m, 2H).

Example 142

(Z)-8-(2-propylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 142)

[step 1] (Z)-2-[8-(2-Propylbenzimidazol-1-yl)methyl-6,11-dihydrodibenzo[b,e]oxepin-11-ylidene]propiononitrile (256 mg, 87%) was obtained in the same manner as in step 1 of Example 140, using 2-propylbenzimidazole (114 mg, 0.71 mmol) instead of 2-ethyl-4,6-dimethylbenzimidazole.

ESI-MS m/z: 420 $(M+H)^+$; $^1$H-NMR ($CDCl_3$, δ): 1.01 (t, J=7.6 Hz, 3H), 1.81-1.95 (m, 2H), 1.99 (s, 3H), 2.80 (t, J=7.6 Hz, 2H), 4.74 (d, J=12.6 Hz, 1H), 5.36 (s, 2H), 5.42 (d, J=12.6 Hz, 1H), 6.81 (dd, J=8.4, 1.2 Hz, 1H), 6.95-7.01 (m, 2H), 7.10-7.29 (m, 6H), 7.49 (dd, J=7.9, 1.6 Hz, 1H), 7.77-7.79 (m, 1H).

[step 2] The title compound (compound 142, 67 mg, 23%) was obtained in the same manner as in step 3 of Example 1, using (Z)-2-[8-(2-propylbenzimidazol-1-yl)methyl-6,11-dihydrodibenzo[b,e]oxepin-11-ylidene]propiononitrile (256 mg, 0.61 mmol) obtained in step 1.

ESI-MS m/z: 479 $(M+H)^+$; $^1$H-NMR (DMSO-$d_6$, δ): 0.91 (t, J=7.4 Hz, 3H), 1.69-1.79 (m, 2H), 1.94 (s, 3H), 2.81 (t, J=7.4 Hz, 2H), 4.85 (d, J=12.6 Hz, 1H), 5.52 (s, 2H), 5.59 (d,

J=12.6 Hz, 1H), 6.70-6.79 (m, 2H), 6.91 (dd, J=7.6, 1.7 Hz, 1H), 7.07-7.18 (m, 4H), 7.29-7.32 (m, 2H), 7.43-7.45 (m, 1H), 7.56-7.59 (m, 1H).

Example 143

(Z)-8-(2-ethoxy-4-methylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 143)

[step 1] (Z)-2-[8-(2-Ethoxy-4-methylbenzimidazol-1-yl)methyl-6,11-dihydrodibenzo[b,e]oxepin-11-ylidene]propiononitrile (653 mg, 76%) was obtained in the same manner as in step 1 of Example 140, using 2-ethoxy-4-methylbenzimidazole (349 mg, 1.98 mmol), obtained in Reference Example 27, instead of 2-ethyl-4,6-dimethylbenzimidazole.

ESI-MS m/z: 436 $(M+H)^+$; $^1H$-NMR ($CDCl_3$, δ): 1.45 (t, J=7.2 Hz, 3H), 1.99 (s, 3H), 2.58 (s, 3H), 4.65 (q, J=7.2 Hz, 2H), 4.76 (d, J=12.6 Hz, 1H), 5.15 (s, 2H), 5.42 (d, J=12.6 Hz, 1H), 6.80 (dd, J=8.3, 1.3 Hz, 1H), 6.88-7.00 (m, 4H), 7.10 (d, J=7.9 Hz, 1H), 7.19-7.26 (m, 3H), 7.48 (dd, J=7.9, 1.7 Hz, 1H).

[step 2] The title compound (compound 143, 288 mg, 42%) was obtained in the same manner as in step 3 of Example 1, using (Z)-2-[8-(2-ethoxy-4-methylbenzimidazol-1-yl)methyl-6,11-dihydrodibenzo[b,e]oxepin-11-ylidene]propiononitrile (600 mg, 0.61 mmol) obtained in step 1.

ESI-MS m/z: 495 $(M+H)^+$; $^1H$-NMR (DMSO-$d_6$, δ): 1.38 (t, J=7.1 Hz, 3H), 1.94 (s, 3H), 2.42 (s, 3H), 4.57 (q, J=7.1 Hz, 2H), 4.86 (d, J=12.5 Hz, 1H), 5.23 (s, 2H), 5.59 (d, J=12.5 Hz, 1H), 6.68-7.44 (m, 10H).

Example 144

(Z)-8-(2-cyclopropyl-4-methylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 144)

[step 1] (Z)-2-[8-(2-Cyclopropyl-4-methylbenzimidazol-1-yl)methyl-6,11-dihydrodibenzo[b,e]oxepin-11-ylidene]propiononitrile (764 mg, 89%) was obtained in the same manner as in step 1 of Example 140, using 2-cyclopropyl-4-methylbenzimidazole (342 mg, 1.98 mmol), obtained in Reference Example 28, instead of 2-ethyl-4,6-dimethylbenzimidazole.

ESI-MS m/z: 432 $(M+H)^+$; $^1H$-NMR ($CDCl_3$, δ): 1.00-1.04 (m, 2H), 1.19-1.22 (m, 2H), 1.85-1.90 (m, 1H), 1.99 (s, 3H), 2.65 (s, 3H), 4.74 (d, J=12.8 Hz, 1H), 5.42 (d, J=12.8 Hz, 1H), 5.46 (s, 2H), 6.79-6.83 (m, 1H), 6.92-7.18 (m, 7H), 7.23-7.27 (m, 1H), 7.49 (dd, J=7.9, 1.6 Hz, 1H).

[step 2] The title compound (compound 144, 290 mg, 39%) was obtained in the same manner as in step 3 of Example 1, using (Z)-2-[8-(2-cyclopropyl-4-methylbenzimidazol-1-yl)methyl-6,11-dihydrodibenzo[b,e]oxepin-11-ylidene]propiononitrile (662 mg, 1.53 mmol) obtained in step 1.

ESI-MS m/z: 491 $(M+H)^+$; $^1H$-NMR (DMSO-$d_6$, δ): 0.92-1.10 (m, 4H), 1.94 (s, 3H), 2.22 (m, 1H), 2.45 (s, 3H), 4.86 (d, J=12.3 Hz, 1H), 5.61 (s, 2H), 5.60 (d, J=12.3 Hz, 1H), 6.68-7.40 (m, 10H).

Example 145

(Z)-8-(4-chloro-2-ethylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 145)

[step 1] (Z)-2-[8-(4-Chloro-2-ethylbenzimidazol-1-yl)methyl-6,11-dihydrodibenzo[b,e]oxepin-11-ylidene]propiononitrile (816 mg, 60%) was obtained in the same manner as in step 1 of Example 140, using 4-chloro-2-ethylbenzimidazole (559 mg, 3.09 mmol), obtained in Reference Example 29, instead of 2-ethyl-4,6-dimethylbenzimidazole.

ESI-MS m/z: 440 $(M+H)^+$; $^1H$-NMR ($CDCl_3$, δ): 1.40 (t, J=7.6 Hz, 3H), 1.99 (s, 3H), 2.90 (q, J=7.6 Hz, 2H), 4.74 (d, J=12.6 Hz, 1H), 5.36 (s, 2H), 5.42 (d, J=12.6 Hz, 1H), 6.81 (dd, J=8.3, 1.0 Hz, 1H), 6.93-7.15 (m, 6H), 7.23-7.29 (m, 2H), 7.49 (dd, J=7.9, 1.7 Hz, 1H).

[step 2] The title compound (compound 145, 244 mg, 31%) was obtained in the same manner as in step 3 of Example 1, using (Z)-2-[8-(4-chloro-2-ethylbenzimidazol-1-yl)methyl-6,11-dihydrodibenzo[b,e]oxepin-11-ylidene]propiononitrile (697 mg, 1.58 mmol) obtained in step 1.

ESI-MS m/z: 499 $(M+H)^+$; $^1H$-NMR ($CDCl_3$, δ): 1.37 (t, J=7.6 Hz, 3H), 2.10 (s, 3H), 2.86 (q, J=7.6 Hz, 2H), 4.69 (d, J=12.5 Hz, 1H), 5.36 (s, 2H), 5.46 (d, J=12.5 Hz, 1H), 6.75-7.33 (m, 10H).

Example 146

(Z)-8-(4-chloro-2-ethoxybenzimidazol-1-yl)methyl-11-[1-(5-oxo-4,5-dihydro-1,2,4-oxadiazol-3-yl)ethylidene]-6,11-dihydrodibenzo[b,e]oxepine (Compound 146)

[step 1] (Z)-2-[8-(4-Chloro-2-ethoxybenzimidazol-1-yl)methyl-6,11-dihydrodibenzo[b,e]oxepin-11-ylidene]propiononitrile (294 mg, 33%) was obtained in the same manner as in step 1 of Example 140, using 4-chloro-2-ethoxybenzimidazole (389 mg, 1.98 mmol), obtained in Reference Example 25, instead of 2-ethyl-4,6-dimethylbenzimidazole.

ESI-MS m/z: 456 $(M+H)^+$; $^1H$-NMR ($CDCl_3$, δ): 1.47 (t, J=7.2 Hz, 3H), 1.99 (s, 3H), 4.72 (q, J=7.2 Hz, 2H), 4.77 (d, J=12.8 Hz, 1H), 5.17 (s, 2H), 5.43 (d, J=12.8 Hz, 1H), 6.81 (dd, J=8.4, 1.2 Hz, 1H), 6.92-7.28 (m, 8H), 7.49 (dd, J=7.9, 1.6 Hz, 1H).

[step 2] The title compound (compound 146, 200 mg, 60%) was obtained in the same manner as in step 3 of Example 1, using (Z)-2-[8-(4-chloro-2-ethoxybenzimidazol-1-yl)methyl-6,11-dihydrodibenzo[b,e]oxepin-11-ylidene]propiononitrile (293 mg, 0.64 mmol) obtained in step 1.

ESI-MS m/z: 515 $(M+H)^+$; $^1H$-NMR (DMSO-$d_6$, δ): 1.37 (t, J=7.0 Hz, 3H), 1.93 (s, 3H), 4.58 (q, J=7.0 Hz, 2H), 4.86 (d, J=12.6 Hz, 1H), 5.26 (s, 2H), 5.58 (d, J=12.6 Hz, 1H), 6.66-7.48 (m, 10H).

Example 147

(Z)-8-(4-chloro-2-cyclopropylbenzimidazol-1-yl)methyl-11-[1-(5-oxo-4,5-dihydro-1,2,4-oxadiazol-3-yl)ethylidene]-6,11-dihydrodibenzo[b,e]oxepine (Compound 147)

[step 1] (Z)-2-[8-(4-Chloro-2-cyclopropylbenzimidazol-1-yl)methyl-6,11-dihydrodibenzo[b,e]oxepin-11-ylidene]propiononitrile (710 mg, 79%) was obtained in the same manner as in step 1 of Example 140, using 4-chloro-2-cyclopropylbenzimidazole (382 mg, 1.98 mmol), obtained in Reference Example 26, instead of 2-ethyl-4,6-dimethylbenzimidazole.

ESI-MS m/z: 452 $(M+H)^+$; $^1H$-NMR ($CDCl_3$, δ): 1.03-1.32 (m, 4H), 1.85-1.92 (m, 1H), 2.00 (s, 3H), 4.75 (d, J=12.9 Hz, 1H), 5.43 (d, J=12.9 Hz, 1H), 5.48 (s, 2H), 6.81 (dd, J=8.0, 1.3 Hz, 1H), 6.96 (td, J=7.6, 1.1 Hz, 1H), 7.05-7.27 (m, 7H), 7.50 (dd, J=7.6, 1.7 Hz, 1H).

[step 2] The title compound (compound 147, 176 mg, 26%) was obtained in the same manner as in step 3 of Example 1, using (Z)-2-[8-(4-chloro-2-cyclopropylbenzimidazol-1-yl)methyl-6,11-dihydrodibenzo[b,e]oxepin-11-ylidene]propiononitrile (600 mg, 1.33 mmol) obtained in step 1.

ESI-MS m/z: 511 $(M+H)^+$; $^1$H-NMR (DMSO-$d_6$, δ): 1.01-1.26 (m, 4H), 2.02 (s, 3H), 2.36 (m, 1H), 4.94 (d, J=12.3 Hz, 1H), 5.66 (d, J=12.3 Hz, 1H), 5.74 (s, 2H), 6.72-7.60 (m, 10H).

Example 148

(Z)-8-(2-ethyl-5,7-dimethyl-3H-imidazo[4,5-b]pyridin-3-yl)methyl-11-[1-(1H-tetrazol-5-yl)ethylidene]-6,11-dihydrodibenzo[b,e]oxepine (Compound 148)

The title compound (compound 148, 12 mg, 54%) was obtained in the same manner as in Example 22, using (Z)-2-[8-(2-ethyl-5,7-dimethyl-3H-imidazo[4,5-b]pyridin-3-yl)methyl-6,11-dihydrodibenzo[b,e]oxepin-11-ylidene]propiononitrile (20 mg, 0.046 mmol) obtained in step 1 of Example 127.

ESI-MS m/z: 478 $(M+H)^+$; $^1$H-NMR ($CDCl_3$, δ): 1.10 (t, J=7.6 Hz, 3H), 2.15 (s, 3H), 2.34 (s, 3H), 2.58 (q, J=7.6 Hz, 2H), 2.60 (s, 3H), 4.20 (d, J=12.5 Hz, 1H), 5.05 (d, J=12.5 Hz, 1H), 5.42 (d, J=16.4 Hz, 1H), 5.49 (d, J=16.4 Hz, 1H), 6.45 (d, J=8.2 Hz, 1H), 6.61 (t, J=7.5 Hz, 1H), 6.72 (d, J=7.7 Hz, 1H), 6.91 (s, 1H), 6.93 (s, 1H), 7.00 (t, J=7.7 Hz, 1H), 7.30 (br s, 2H).

Example 149

(Z)-8-(2-ethyl-7-methyl-3H-imidazo[4,5-b]pyridin-3-yl)methyl-11-[1-(1H-tetrazol-5-yl)ethylidene]-6,11-dihydrodibenzo[b,e]oxepine (Compound 149)

The title compound (compound 149, 8.8 mg, 29%) was obtained in the same manner as in Example 22, using (Z)-2-[8-(2-ethyl-7-methyl-3H-imidazo[4,5-b]pyridin-3-yl)methyl-6,11-dihydrodibenzo[b,e]oxepin-11-ylidene]propiononitrile (28 mg, 0.07 mmol) obtained in step 1 of Example 128.

ESI-MS m/z: 464 $(M+H)^+$; $^1$H-NMR ($CDCl_3$, δ): 1.23 (t, J=7.5 Hz, 3H), 2.17 (s, 3H), 2.53 (s, 3H), 2.73 (q, J=7.6 Hz, 2H), 4.37 (d, J=12.3 Hz, 1H), 5.22 (d, J=12.5 Hz, 1H), 5.48 (s, 2H), 6.59-6.75 (m, 3H), 7.03-7.11 (m, 3H), 7.24-7.30 (m, 2H), 8.19 (d, J=4.9 Hz, 1H).

Example 150

(Z)-8-(7-chloro-2-ethyl-5-methyl-3H-imidazo[4,5-b]pyridin-3-yl)methyl-11-[1-(1H-tetrazol-5-yl)ethylidene]-6,11-dihydrodibenzo[b,e]oxepine (Compound 150)

The title compound (compound 150, 27 mg, 62%) was obtained in the same manner as in Example 22, using (Z)-2-[8-(7-chloro-2-ethyl-5-methyl-3H-imidazo[4,5-b]pyridin-3-yl)methyl-6,11-dihydrodibenzo[b,e]oxepin-11-ylidene]propiononitrile (41 mg, 0.09 mmol) obtained in step 1 of Example 129.

ESI-MS m/z: 498 $(M+H)^+$; $^1$H-NMR ($CDCl_3$, δ): 1.21 (t, J=7.5 Hz, 3H), 2.23 (s, 3H), 2.62 (s, 3H), 2.68 (q, J=7.5 Hz, 2H), 4.50 (d, J=12.6 Hz, 1H), 5.34 (d, J=12.6 Hz, 1H), 5.43 (d, J=16.2 Hz, 1H), 5.52 (d, J=16.3 Hz, 1H), 6.64-6.80 (m, 3H), 7.03 (s, 1H), 7.09-7.16 (m, 2H), 7.22-7.31 (m, 2H).

Example 151

(Z)-8-(2-cyclopropyl-5,7-dimethyl-3H-imidazo[4,5-b]pyridin-3-yl)methyl-11-[1-(1H-tetrazol-5-yl)ethylidene]-6,11-dihydrodibenzo[b,e]oxepine (Compound 151)

The title compound (compound 151, 22.3 mg, 49%) was obtained in the same manner as in Example 22, using (Z)-2-[8-(2-cyclopropyl-5,7-dimethyl-3H-imidazo[4,5-b]pyridin-3-yl)methyl-6,11-dihydrodibenzo[b,e]oxepin-11-ylidene]propiononitrile (41.5 mg, 0.09 mmol) obtained in step 1 of Example 130.

ESI-MS m/z: 490 $(M+H)^+$; $^1$H-NMR ($CDCl_3$, δ): 0.79-0.85 (m, 2H), 0.98-1.03 (m, 2H), 1.66-1.72 (m, 1H), 2.18 (s, 3H), 2.32 (s, 3H), 2.60 (s, 3H), 4.26 (d, J=12.6 Hz, 1H), 5.03 (d, J=12.4 Hz, 1H), 5.56 (d, J=3.5 Hz, 2H), 6.56 (d, J=8.1 Hz, 1H), 6.69 (t, J=6.9 Hz, 1H), 6.80 (dd, J=7.8, 1.7 Hz, 1H), is 6.88 (s, 1H), 7.04-7.12 (m, 2H), 7.27-7.37 (m, 2H).

Example 152

(Z)-8-(2-cyclopropyl-7-methyl-3H-imidazo[4,5-b]pyridin-3-yl)methyl-11-[1-(1H-tetrazol-5-yl)ethylidene]-6,11-dihydrodibenzo[b,e]oxepine (Compound 152)

The title compound (compound 152, 4 mg, 9%) was obtained in the same manner as in Example 22, using (Z)-2-[8-(2-cyclopropyl-7-methyl-3H-imidazo[4,5-b]pyridin-3-yl)methyl-6,11-dihydrodibenzo[b,e]oxepin-11-ylidene]propiononitrile (41.3 mg, 0.10 mmol) obtained in step 1 of Example 131.

ESI-MS m/z: 476 $(M+H)^+$; $^1$H-NMR ($CDCl_3$, δ): 0.86-0.96 (m, 2H), 1.07-1.12 (m, 2H), 1.75-1.84 (m, 1H), 2.16 (s, 3H), 2.43 (s, 3H), 4.31 (d, J=12.5 Hz, 1H), 5.12 (d, J=12.5 Hz, 1H), 5.57 (s, 2H), 6.57 (d, J=8.2 Hz, 1H), 6.68 (t, J=7.3 Hz, 1H), 6.76 (dd, J=7.8, 1.6 Hz, 1H), 7.01 (d, J=5.1 Hz, 1H), 7.05-7.10 (m, 2H), 7.23-7.38 (m, 2H), 8.15 (d, J=4.9 Hz, 1H).

Example 153

Tablet (Compound S16)

Tablets having the following composition are prepared by a conventional method. Compound S16 (40 g), lactose (286.8 g) and potato starch (60 g) are mixed, and a 10% aqueous solution (120 g) of hydroxypropylcellulose is added thereto. According to a conventional method, the obtained mixture is kneaded, granulated, dried and sieved to give granules for tableting. Magnesium stearate (1.2 g) is added thereto and mixed therewith. The mixture is tableted by a tableting machine (RT-15, manufactured by KIKUSUI SEISAKUSHO LTD.) with a punch having a diameter of 8 mm to give tablets containing 20 mg of the active ingredient per tablet.

TABLE 36

| | | |
|---|---|---|
| Formulation | compound S16 | 20 mg |
| | lactose | 143.4 mg |
| | potato starch | 30 mg |
| | hydroxypropylcellulose | 6 mg |
| | magnesium stearate | 0.6 mg |
| | | 200 mg |

Example 154

Injection (Compound S13)

Injections having the following composition are prepared by a conventional method. Compound S13 (1 g) is added to distilled water for injection and mixed therewith. Hydrochloric acid and aqueous sodium hydroxide solution are further added to adjust pH of the mixture to 7, and distilled water for injection is added to make the total amount 1000 mL. The obtained mixture is aseptically filled in glass vials by 2 mL to give injections containing 2 mg of the active ingredient per vial.

TABLE 37

| | | |
|---|---|---|
| formulation | compound S13 | 2 mg |
| | hydrochloric acid | q.s. |
| | aqueous sodium hydroxide solution | q.s. |
| | distilled water for injection | q.s. |
| | | 2.00 mL |

INDUSTRIAL APPLICABILITY

According to the present invention, a PPARγ agonist comprising a tricyclic compound as an active ingredient and the like can be provided.

In addition, a novel tricyclic compound or a pharmaceutically acceptable salt thereof having a PPARγ agonistic activity or the like can be provided.

The invention claimed is:

1. A tricyclic compound represented by the formula (IA-C)

(IA-C)

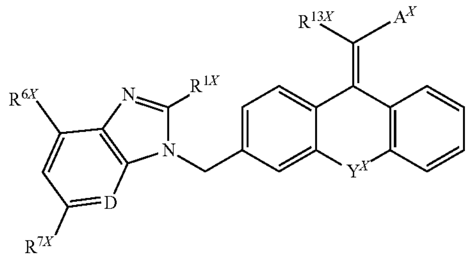

wherein

D is CH or N, $R^{1X}$ is methyl, ethyl, propyl, cyclopropyl, cyclobutyl, cyclopentyl, cyclohexyl, methoxy, ethoxy, or propoxy, $R^{6X}$ is hydrogen, fluoro, chloro, bromo, methyl, ethyl, propyl, or isopropyl, $R^{7X}$ is hydrogen, fluoro, chloro, bromo, methyl, ethyl, propyl, or isopropyl, $Y^X$ is $CH_2CH_2$ or $CH_2O$, $R^{13X}$ is $C_{1-6}$ alkyl, and $A^X$ is formula (b3)

(b3)

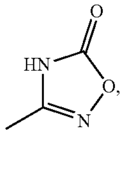

or a pharmaceutically acceptable salt thereof.

2. A pharmaceutical composition comprising the tricyclic compound or the pharmaceutically acceptable salt thereof recited in claim 1 as an active ingredient.

3. A method of activating PPARγ, which comprises administering an effective amount of the tricyclic compound or the pharmaceutically acceptable salt thereof recited in claim 1 to a human in need of activation of PPARγ.

4. A method of activating PPARγ and antagonizing an angiotensin II receptor, which comprises administering an effective amount of the tricyclic compound or the pharmaceutically acceptable salt thereof recited in claim 1 to a human in need of activation of PPARγ and antagonization of an angiotensin II receptor.

5. The method according to claim 3, wherein the method of activating PPARγ is a method for treating a disease related to PPARγ.

6. The method according to claim 5, wherein the disease related to PPARγ is a disease further related to an angiotensin II receptor.

7. The method according to claim 5, wherein the disease related to PPARγ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

8. A method of antagonizing an angiotensin II receptor, which comprises administering an effective amount of the tricyclic compound or the pharmaceutically acceptable salt thereof recited in claim 1 to a human in need of antagonization of an angiotensin II receptor.

9. The method according to claim 8, wherein the method of antagonizing an angiotensin II receptor is a method for treating a disease related to an angiotensin II receptor.

10. The method according to claim 9, wherein the method for treating a disease related to an angiotensin II receptor is a method for treating hypertension.

11. A tricyclic compound selected from the group consisting of (E)-2-(2-ethyl-7-methyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene;

(E)-2-(4-methyl-2-propylbenzimidazol-1-yl)methyl-5-[1-(5-oxo-4,5-dihydro-1,2,4-oxadiazol-3-yl)ethylidene]-10,11-dihydro-5H-dibenzo[a,d]cycloheptene;

(E)-2-(2-ethoxy-5,7-dimethyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene;

(E)-2-(2-ethoxy-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene;

(E)-2-(7-chloro-2-cyclopropyl-3H-imidazo[4,5-b]pyridin-3-yl)methyl-5-[1-(5-oxo-4,5-dihydro-1,2,4-oxadiazol-3-yl)ethylidene]-10,11-dihydro-5H-dibenzo[a,d]cycloheptene;

(E)-3-(2-cyclopropyl-5,7-dimethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine;

(Z)-8-(7-chloro-2-ethyl-5-methyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine;

(Z)-8-(7-chloro-2-ethyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine;

(Z)-8-(7-chloro-2-ethoxy-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine;

(Z)-8-(7-chloro-2-cyclopropyl-3H-imidazo[4,5-b]pyridin-3-yl)methyl-11-[1-(5-oxo-4,5-dihydro-1,2,4-oxadiazol-3-yl)ethylidene]-6,11-dihydrodibenzo[b,e]oxepine (Example 139);

(Z)-8-(4-chloro-2-ethoxybenzimidazol-1-yl)methyl-11-[1-(5-oxo-4,5-dihydro-1,2,4-oxadiazol-3-yl)ethylidene]-6,11-dihydrodibenzo[b,e]oxepine; and (Z)-8-(4-chloro-2-cyclopropylbenzimidazol-1-yl)methyl-11-[1-(5-oxo-4,5-dihydro-1,2,4-oxadiazol-3-yl)ethylidene]-6,11-dihydrodibenzo[b,e]oxepine, or a pharmaceutically acceptable salt thereof.

12. A pharmaceutical composition comprising the tricyclic compound or the pharmaceutically acceptable salt thereof recited in claim 11 as an active ingredient.

13. A method of activating PPARγ, which comprises administering an effective amount of the tricyclic compound or the pharmaceutically acceptable salt thereof recited in claim 11 to a human in need of activation of PPARγ.

14. A method of activating PPARγ and antagonizing an angiotensin II receptor, which comprises administering an effective amount of the tricyclic compound or the pharmaceutically acceptable salt thereof recited in claim 11 to a human in need of activation of PPARγ and antagonization of an angiotensin II receptor.

15. The method according to claim 13, wherein the method of activating PPARγ is a method for treating a disease related to PPARγ.

16. The method according to claim 15, wherein the disease related to PPARγ is a disease further related to an angiotensin II receptor.

17. The method according to claim 15, wherein the disease related to PPARγ is a disease selected from the group consisting of type 2 diabetes, impaired glucose tolerance, insulin resistance syndrome, hypertension, hyperlipidemia, metabolic syndrome, visceral obesity, obesity and hypertriglyceridemia.

18. A method of antagonizing an angiotensin II receptor, which comprises administering an effective amount of the tricyclic compound or the pharmaceutically acceptable salt thereof recited in claim 11 to a human in need of antagonization of an angiotensin II receptor.

19. The method according to claim 18, wherein the method of antagonizing an angiotensin II receptor is a method for treating a disease related to an angiotensin II receptor.

20. The method according to claim 19, wherein the method for treating a disease related to an angiotensin II receptor is a method for treating hypertension.

* * * * *

UNITED STATES PATENT AND TRADEMARK OFFICE

CERTIFICATE OF CORRECTION

PATENT NO. : 8,242,151 B2
APPLICATION NO. : 12/162119
DATED : August 14, 2012
INVENTOR(S) : Yanagisawa et al.

It is certified that error appears in the above-identified patent and that said Letters Patent is hereby corrected as shown below:

*In the Claims*

Claim 11, column 183, line 7:

"epine (Example 139);" should read -- epine; --

Signed and Sealed this
Fourteenth Day of May, 2013

Teresa Stanek Rea
*Acting Director of the United States Patent and Trademark Office*